US006716829B2

(12) United States Patent
Rocha et al.

(10) Patent No.: US 6,716,829 B2
(45) Date of Patent: Apr. 6, 2004

(54) ALDOSTERONE ANTAGONIST AND CYCLOOXYGENASE-2 INHIBITOR COMBINATION THERAPY TO PREVENT OR TREAT INFLAMMATION-RELATED CARDIOVASCULAR DISORDERS

(75) Inventors: Ricardo Rocha, Gurnee, IL (US); Marc Zack, Evanston, IL (US); Ellen McMahon, Sunset Hills, MO (US); Eileen R. Blasi, St. Louis, MO (US)

(73) Assignee: Pharmacia Corporation, Chicago, IL (US)

( * ) Notice: Subject to any disclaimer, the term of this patent is extended or adjusted under 35 U.S.C. 154(b) by 0 days.

(21) Appl. No.: 09/915,784

(22) Filed: Jul. 26, 2001

(65) Prior Publication Data

US 2003/0125312 A1 Jul. 3, 2003

Related U.S. Application Data

(60) Provisional application No. 60/261,497, filed on Jan. 12, 2001, provisional application No. 60/261,352, filed on Jan. 12, 2001, now abandoned, and provisional application No. 60/221,364, filed on Jul. 27, 2000.

(51) Int. Cl.$^7$ ........................ A61K 31/56; A61K 31/585; A61K 31/35; A61K 31/38
(52) U.S. Cl. ........................ 514/171; 514/173; 514/175; 514/456; 514/432
(58) Field of Search .......................... 514/171, 173, 514/175, 456, 432

(56) References Cited

U.S. PATENT DOCUMENTS

| | | | |
|---|---|---|---|
| 3,013,012 A | 12/1961 | Ceila et al. | 260/239.57 |
| 3,257,390 A | 6/1966 | Patchett | 260/239.55 |
| 4,129,564 A | 12/1978 | Wiechert et al. | 260/239.57 |
| 4,559,332 A | 12/1985 | Grob et al. | 514/175 |
| 4,789,668 A | 12/1988 | Nickisch et al. | 514/173 |
| 5,145,684 A | 9/1992 | Liversidge et al. | 424/489 |
| 5,318,767 A | 6/1994 | Liversidge et al. | 424/5 |
| 5,344,991 A | 9/1994 | Reitz et al. | 568/34 |
| 5,380,738 A | 1/1995 | Norman et al. | 514/374 |
| 5,384,124 A | 1/1995 | Courteille et al. | 424/430 |
| 5,393,790 A | 2/1995 | Reitz et al. | 514/709 |
| 5,434,178 A | 7/1995 | Talley et al. | 514/406 |
| 5,466,823 A | 11/1995 | Talley et al. | 548/377.1 |
| 5,474,995 A | 12/1995 | Ducharme et al. | 514/241 |
| 5,510,368 A | 4/1996 | Lau et al. | 514/419 |
| 5,747,001 A | 5/1998 | Wiedmann et al. | 424/45 |
| 6,034,256 A | 3/2000 | Carter et al. | 549/456 |
| 6,077,850 A | 6/2000 | Carter et al. | 514/311 |

FOREIGN PATENT DOCUMENTS

| CA | WO94/20480 | 9/1994 |
|---|---|---|
| CA | WO94/26731 | 11/1994 |
| CA | WO95/00501 | 1/1995 |
| CA | WO96/06840 | 1/1995 |
| CA | WO94/13635 | 3/1996 |
| CA | WO96/19469 | 6/1996 |
| DE | 2652761 | 11/1976 |
| DE | 1550568 | 8/1979 |
| US | WO94/15932 | 7/1994 |
| US | WO94/27980 | 12/1994 |
| US | WO9515166 | 6/1995 |
| US | WO95/15316 | 6/1995 |
| US | WO96/03387 | 2/1996 |
| US | WO96/03388 | 2/1996 |
| US | WO96/25405 | 8/1996 |
| US | WO9640255 | 12/1996 |
| US | WO9721720 | 6/1997 |
| US | WO9825948 | 6/1998 |
| US | WO0010552 | 3/2000 |
| US | WO0023433 | 4/2000 |
| US | WO0024719 | 5/2000 |

OTHER PUBLICATIONS

Ridker et al., *The New England Journal of Medicine*, 336:973–9 (Apr. 3, 1997).
J.J. Boyle, *Journal of Pathology*, 181:93–9 (1997).
Uusimaa et al., *International Journal of Cardiology*, 69:5–14 (1999).
Bonafede et al., *Journal of the American Chemical Society*, vol. 117, No. 30:7853–61 (Aug. 2, 1995).
Saruta T., *Journal of Clinical Therapuetic Medicine*, 13:4024–9 (1997).
Shimamoto K., *Nihon Rinsyo*, Clinical Medicine in Japan, 58 (Suppl 593–6), (2000).
Nakagawa H. et al., *Human Hypertension*, 13(11):735–41 (Nov. 1999).
Kobayshi Y. et al., *Japanese Circulation Journal*, 47:268–75 (2000).
Ogihara T. et al., *Nippon Ronen Igakka Zasshi*, 33(12):945–75 (1996).
Mizushima S., *Clinical and Experimental Pharmacology and Physiology*, 26:573 (1999).
Eisner GM., *American Journal of Kidney Diseases*, vol. XVI, No. 4(Suppl 1):35–40 (Oct. 1990).
Svetkey LP et al., *Hypertension*, 28:854–8 (1996).
Flack JM, *Journal of the Association for Academic Minority Physicians*, 2:143–50 (1991).
Flack JM, *Hypertension*, 17 (suppl 1):1115–21 (1991).
Ferri et al., *Diabetes*, 48:1623–30 (Aug. 1999).
Di Gennaro C. et al., *Hypertension*, 35(4):869–874 (2000).
Bonner, *MMW Fortschritte der Medizin*, 46:34–6 (Nov. 18, 1999).
Dimsdale et al., *American Journal of Hypertension*, 3:429–35 (1990).
Falkner B. et al., *American Journal of Clinical Nutrition*, 65 (suppl):618S–21S (1997).
Rocchini AP. et al., *The American Journal of the Medical Sciences*, 307 (Suppl 1):S75–80 (1994).

(List continued on next page.)

Primary Examiner—Theodore J. Criares
(74) Attorney, Agent, or Firm—Philip B. Polster, II; Joseph R. Schuh

(57) ABSTRACT

Combinations of aldosterone blockers and Cyclooxygenase-2 inhibitors useful in the treatment of inflammation are disclosed.

68 Claims, 55 Drawing Sheets

OTHER PUBLICATIONS

Roselear et al., *Arterioscelrosis, Thrombosis, and Vascular Biology*, 16:1013–18 (1996).

Stehbens, *Progress in Cardiovascular Disease*, vol. XXIX, No. 2:107–28 (Sep./Oct. 1986).

Rales 003 Study, *American Journal of Cardiology*, 78:902–907 (1996).

Pitt, et al., Rales 004 Study, *New England Journal of Medicine*, 341:709–717 (1999).

Cangiano J L, et al., *Journal of Pharmacological Experimental Therapy*, 206:310–313 (1979).

Zhang, et al., *Science;* 258: 468–471 (1992).

Ward, et al., *Circulation;* 104 (4): 467–472 (Jul. 2001).

Van Belle, et al., *Cardiovascular Research;* 29 (1): 27–32 (Jan. 1995).

Van Belle, et al., *European Heart Journal;* , 15: 116 (1994).

Klauber, et al., *Circulation;* 94 (10): 2566–2571 (1996).

Epstein, et al., *Journal of the American Society of Nephrology;* 9: 322A—333A (Sep. 1998).

Epstein, et al., *Circulation;* 98 (17): 198–199 (Oct. 1998).

Rabasseda et al., *Drugs of the Future;* 24 (5): 488–501 (1999).

Slight, et al., *Journal of Molecular and Cellular Cardiology;* 31 (6): 1175–1184 (Jun. 1999).

Benetos, et al., *Arteriosclerosis, Thrombosis, and Vascular Biology;* 17 (6): 1152–1156 (Jun. 1997).

Rocha, et al., *Hypertension;* 31 (1, part 2): 451–458 (1998).

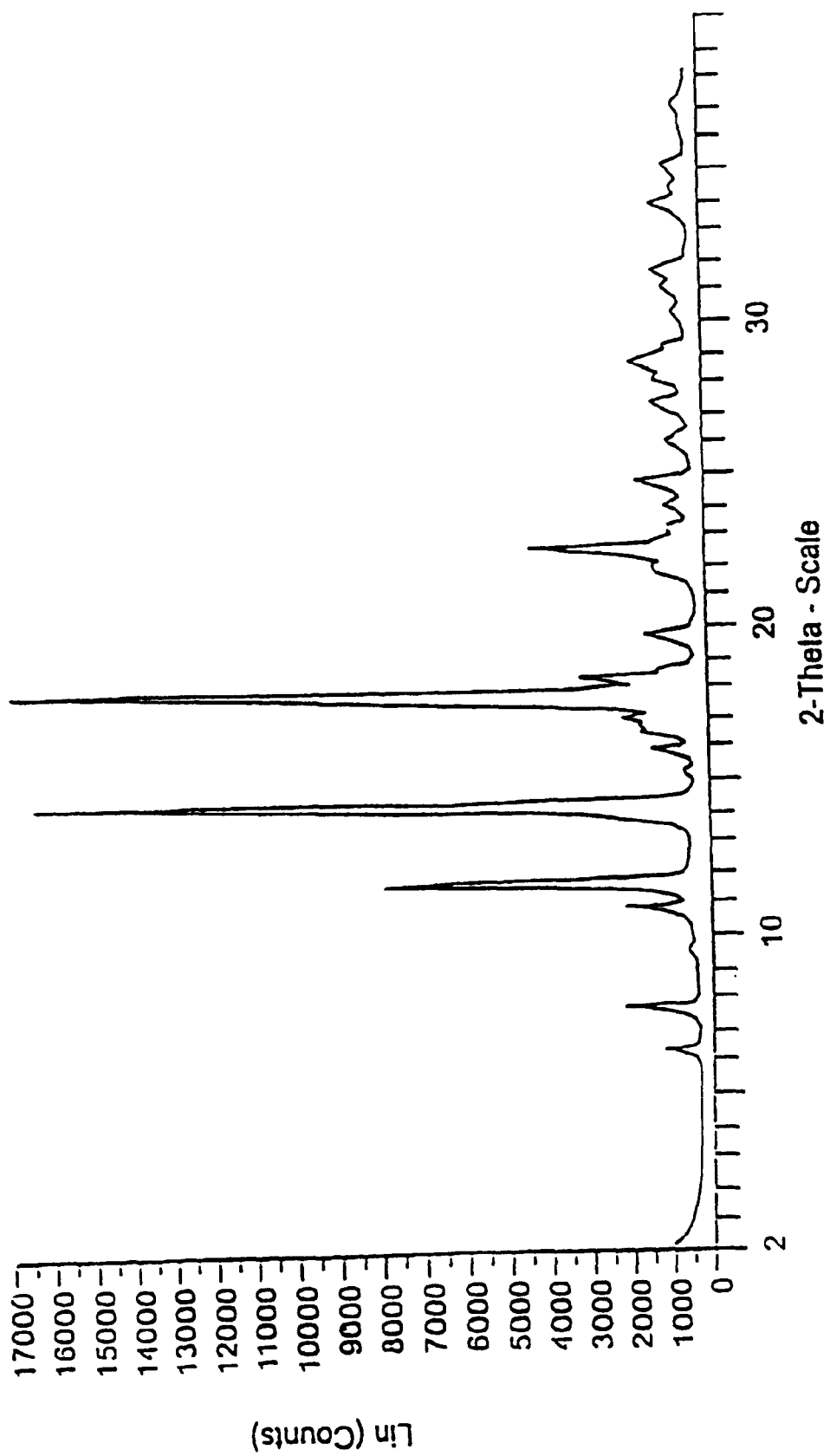
Fig. 1-A

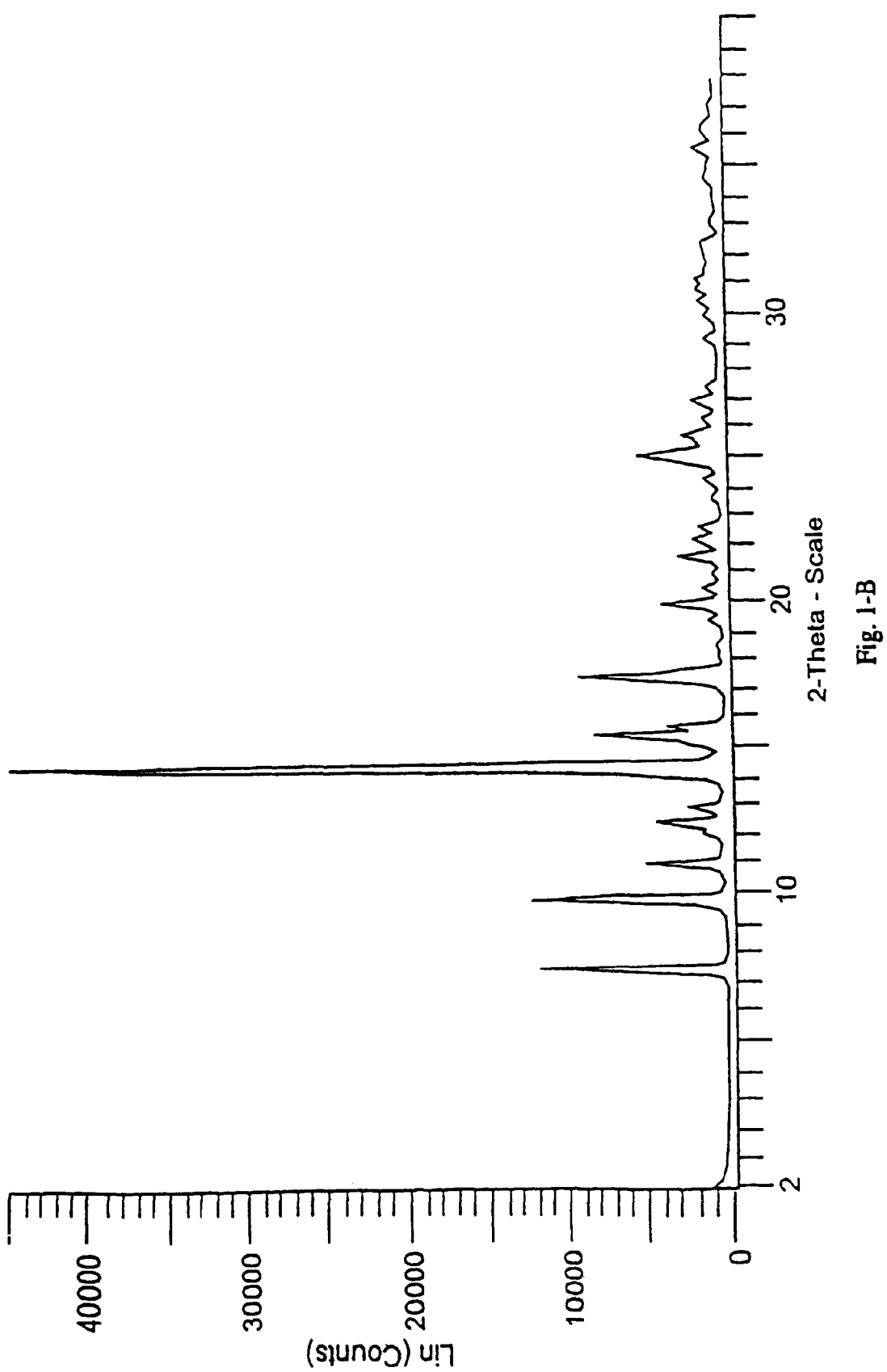
Fig. 1-B

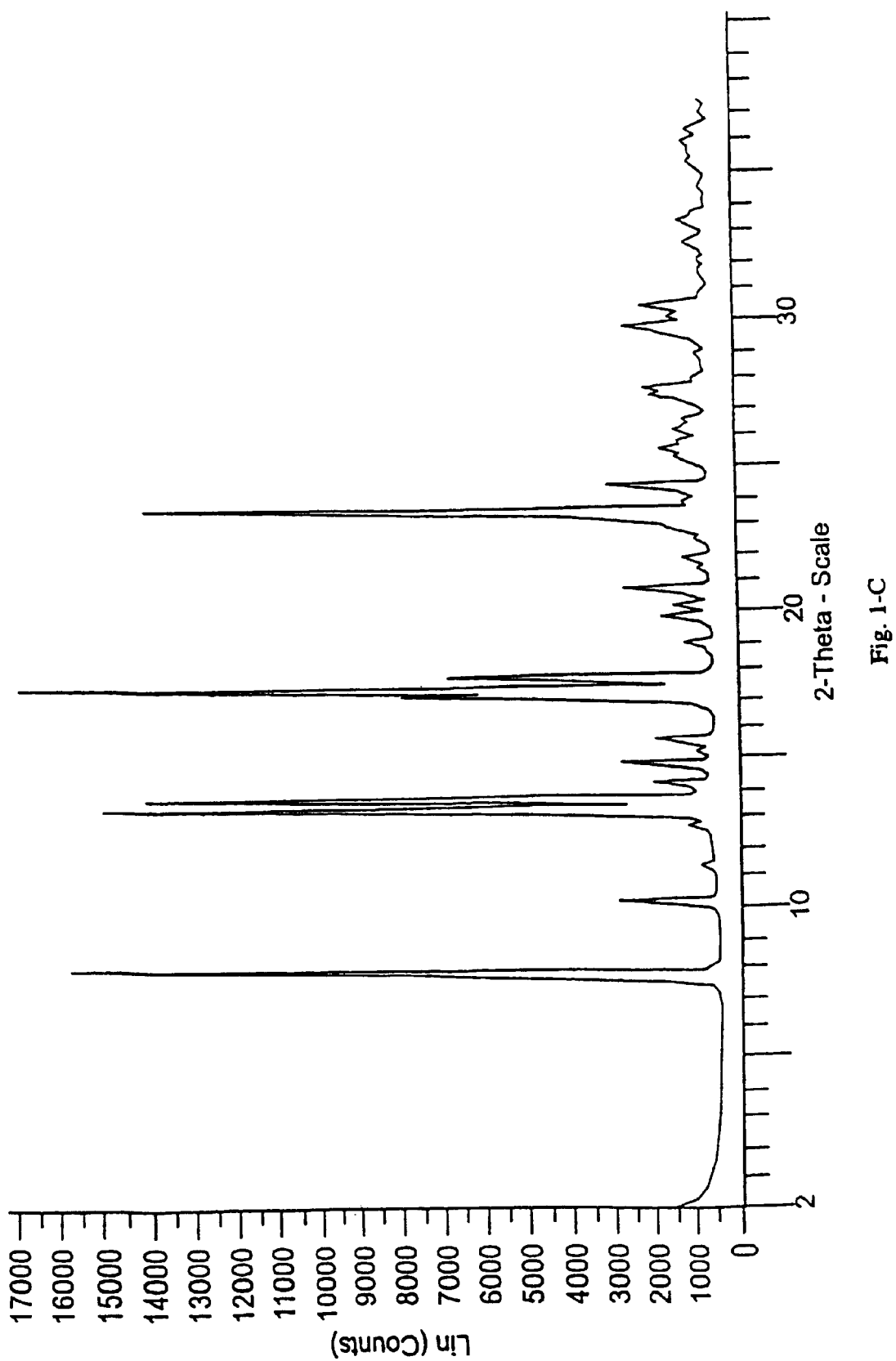
Fig. 1-C

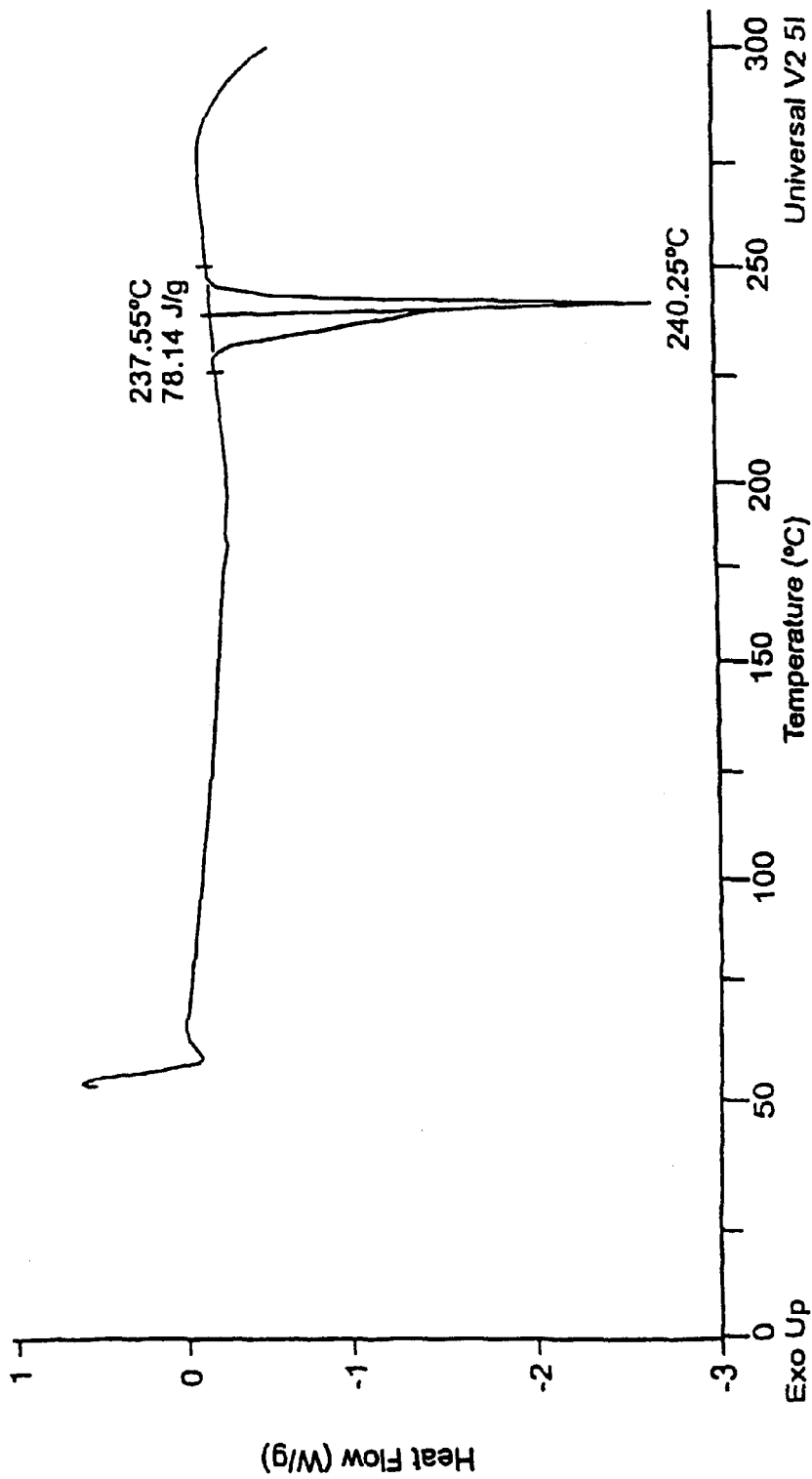
Fig. 2-A

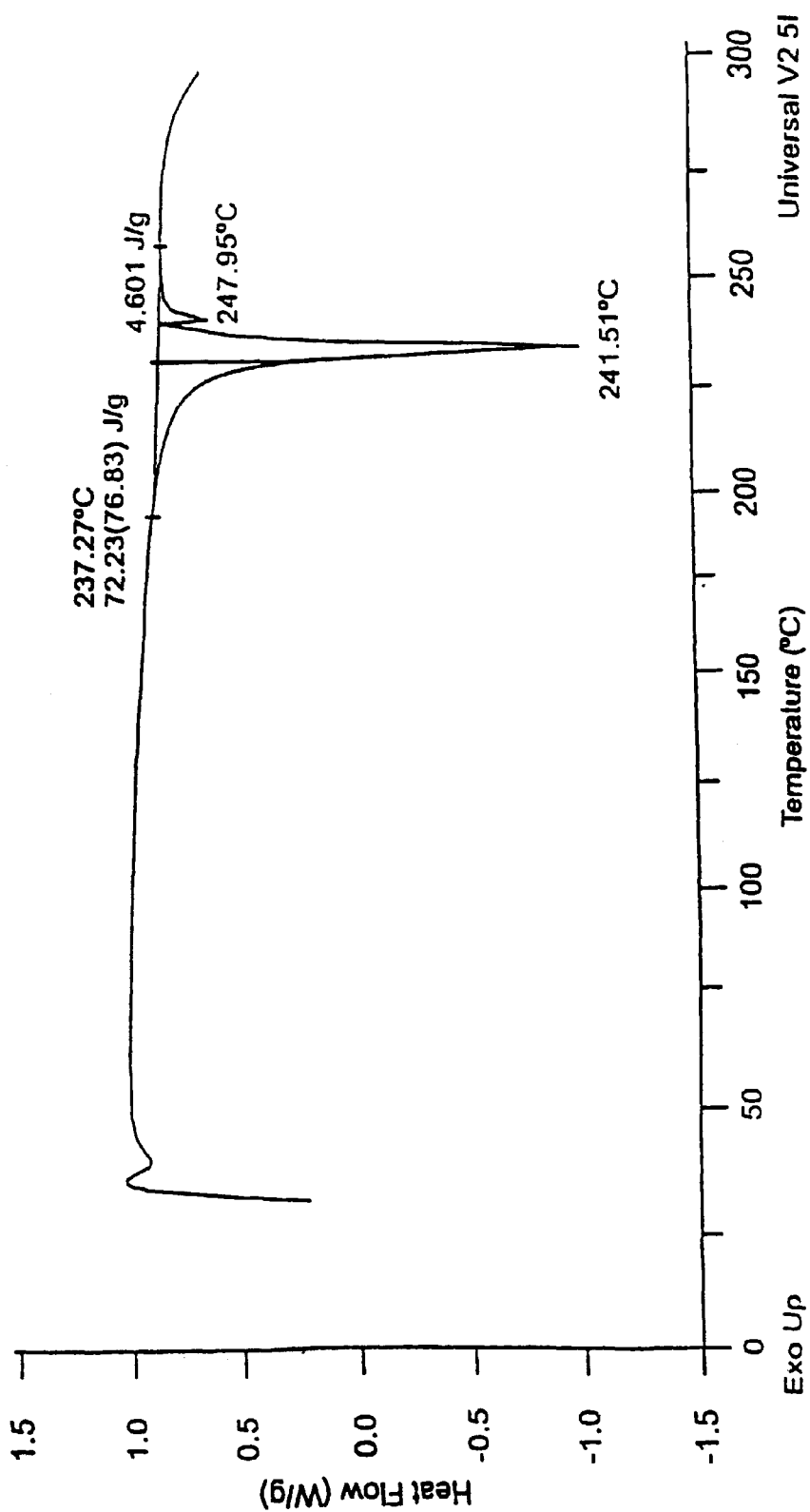
Fig. 2-B

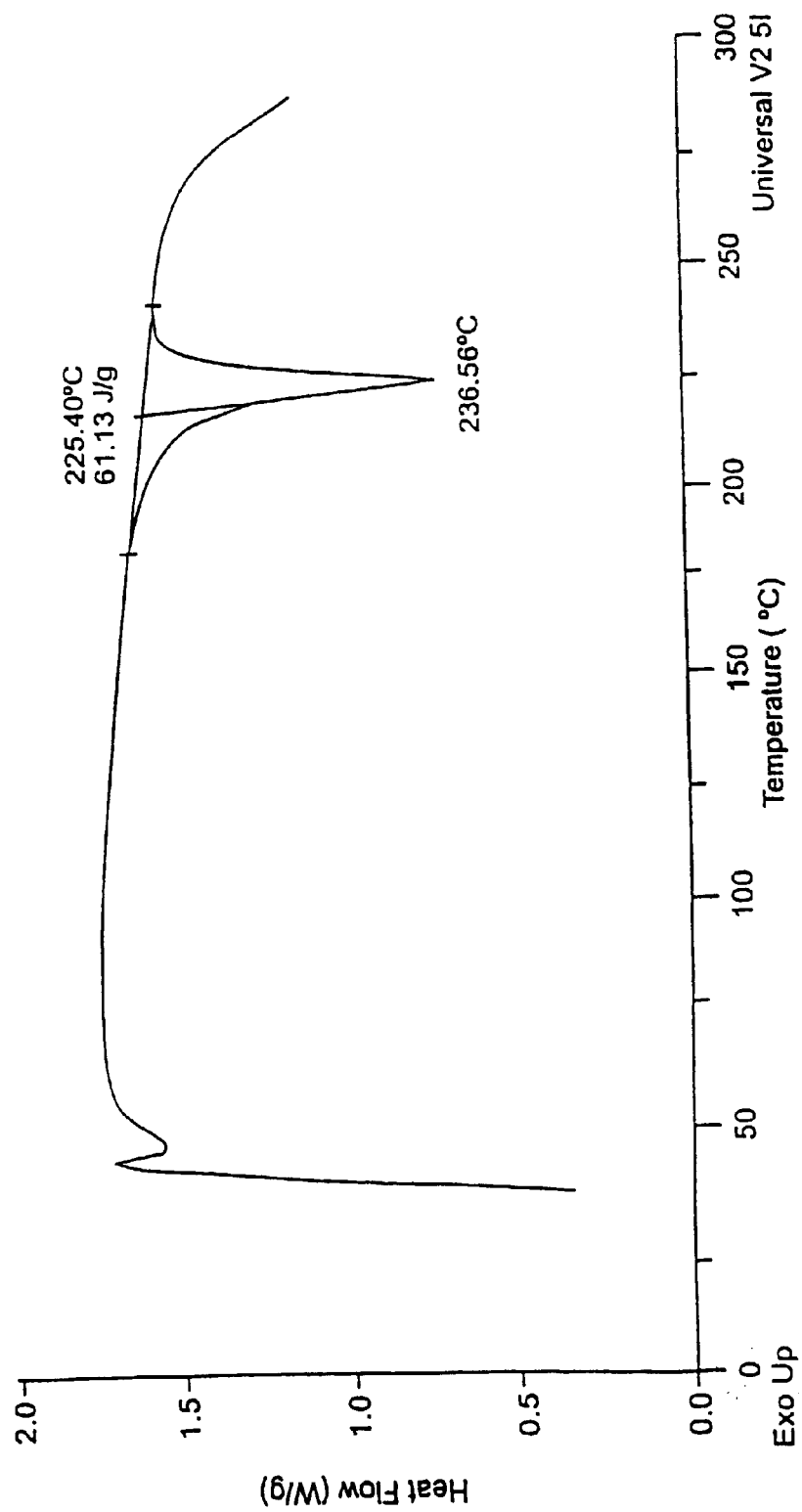
Fig. 2-C

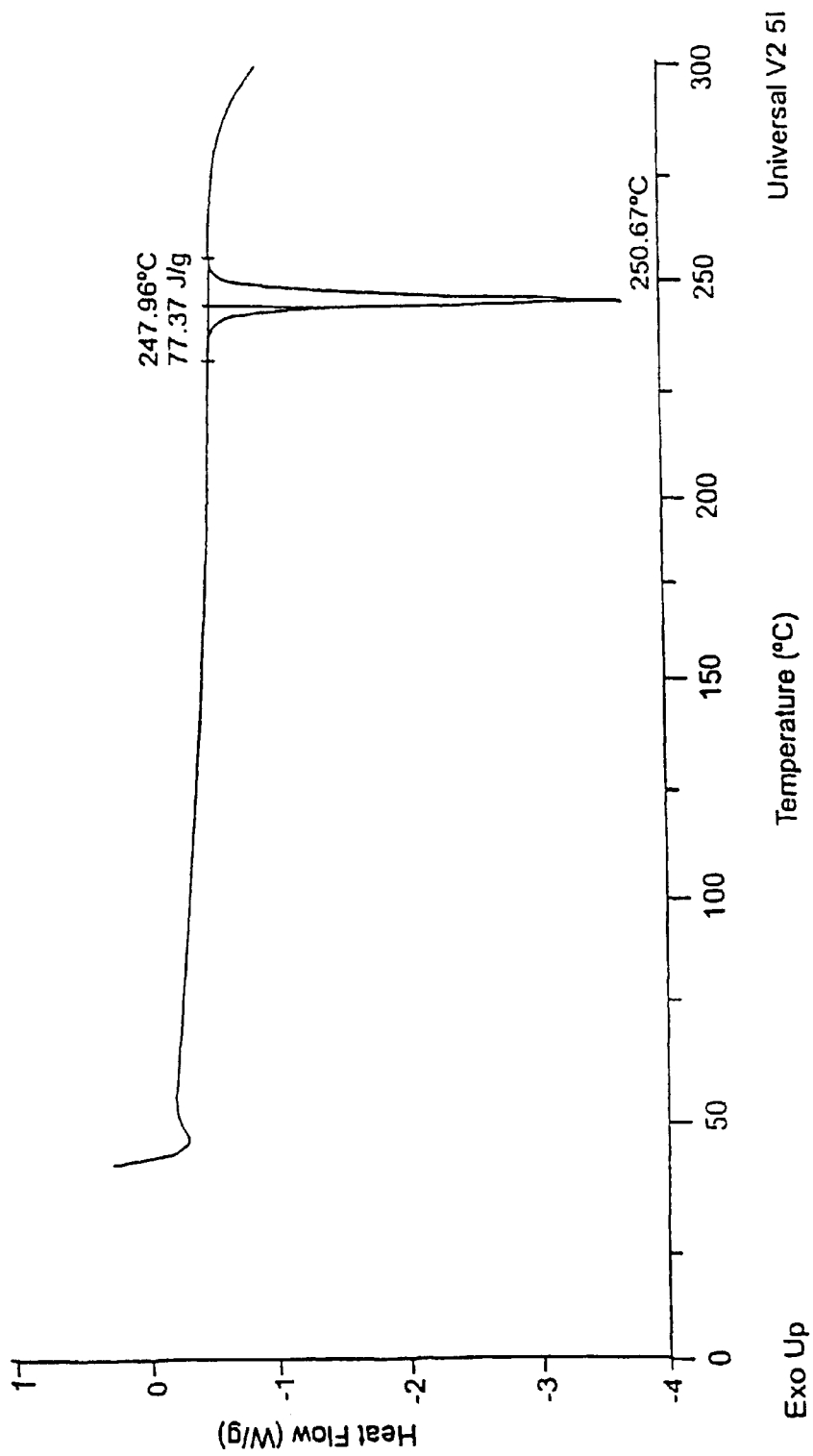
Fig. 2-D

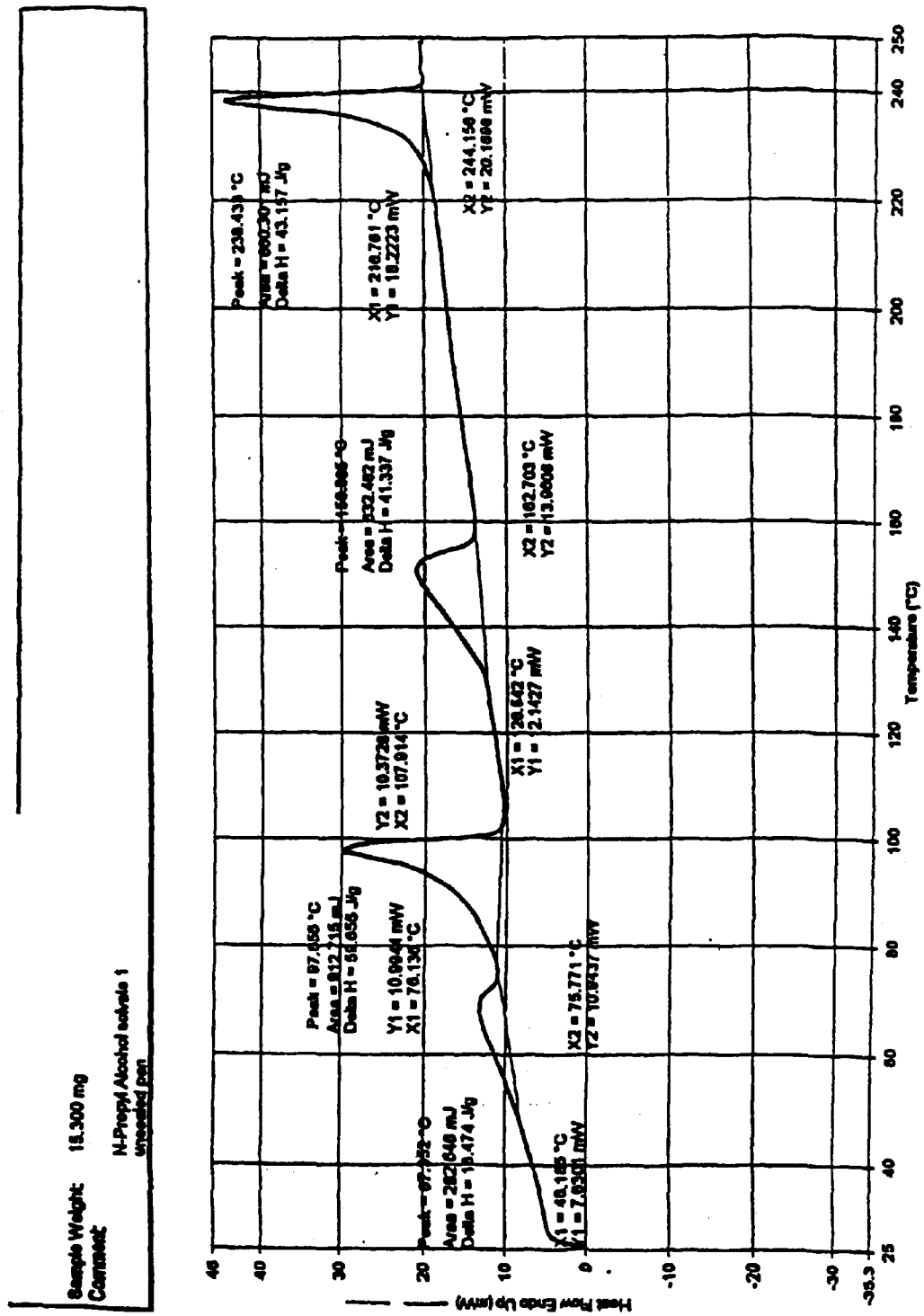
Fig. 2-E

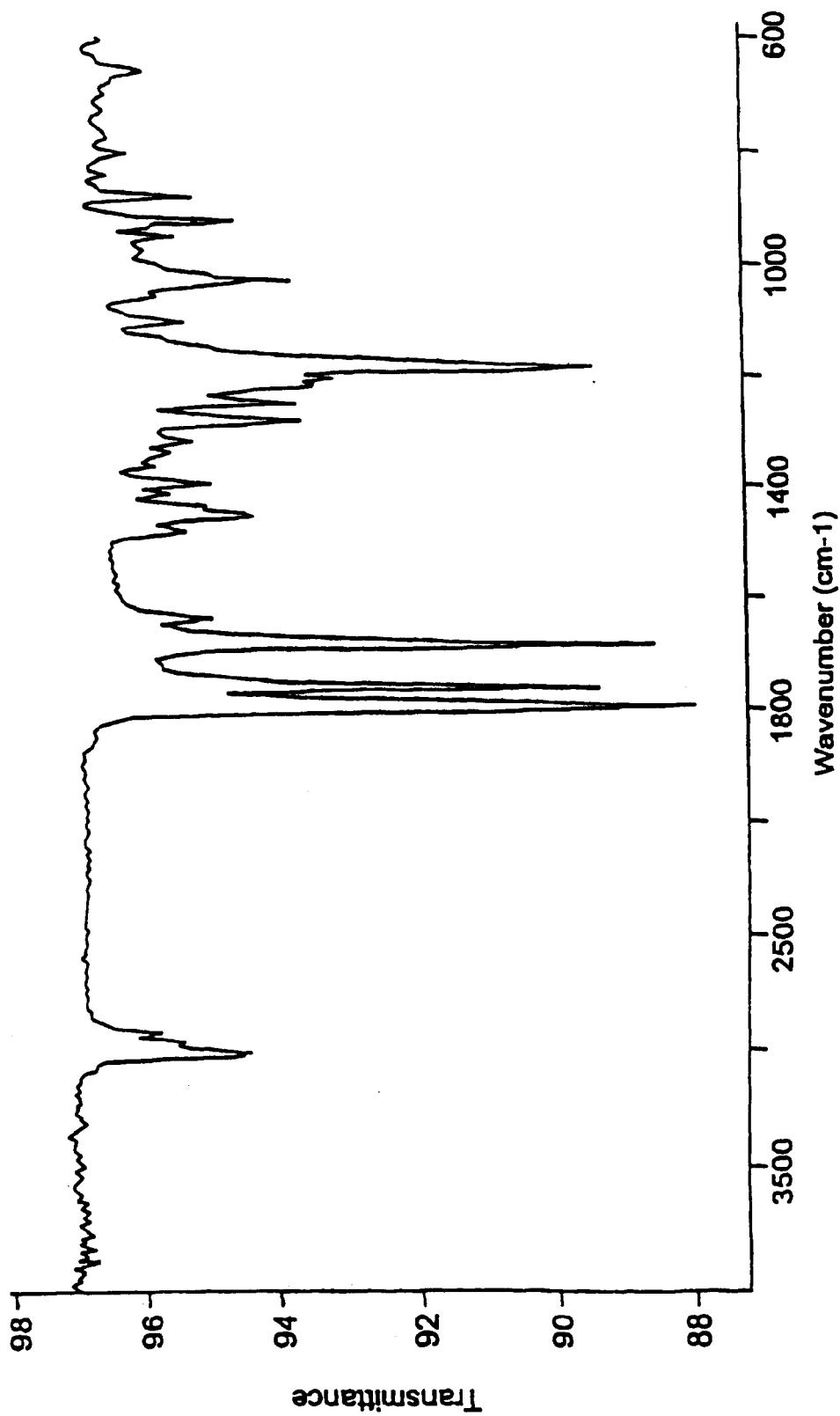
Fig. 3-A

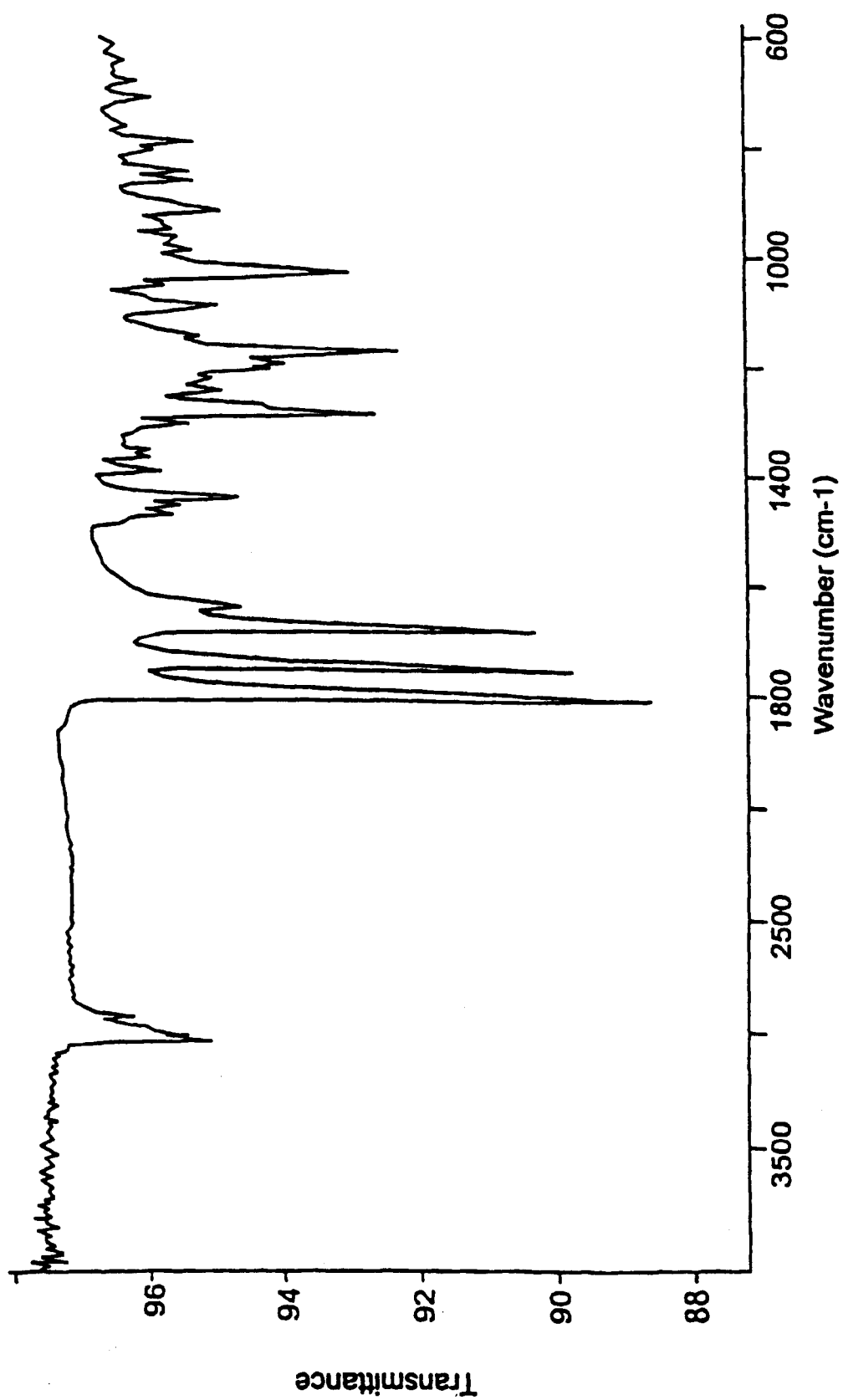
Fig. 3-B

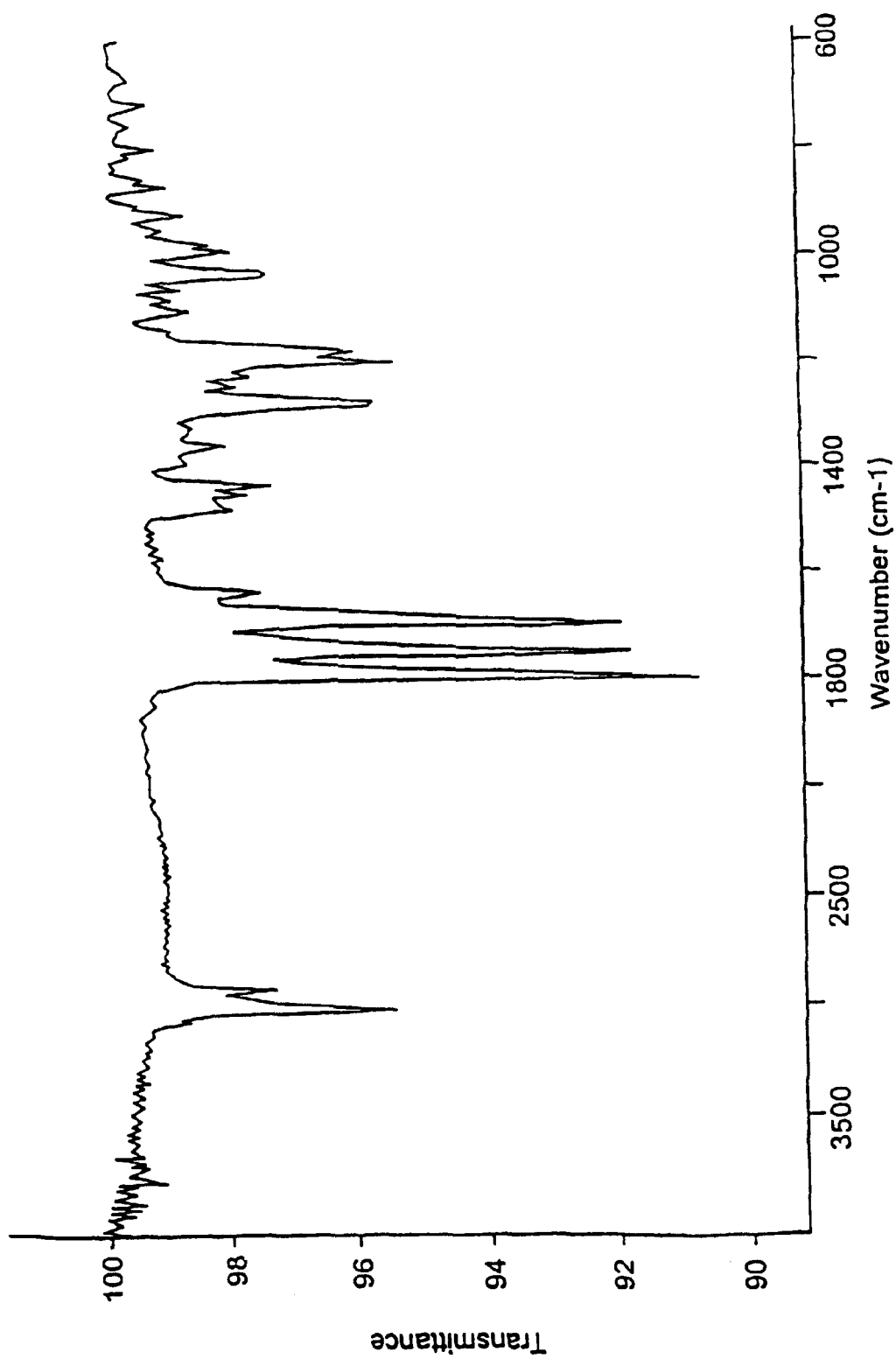
Fig. 3-C

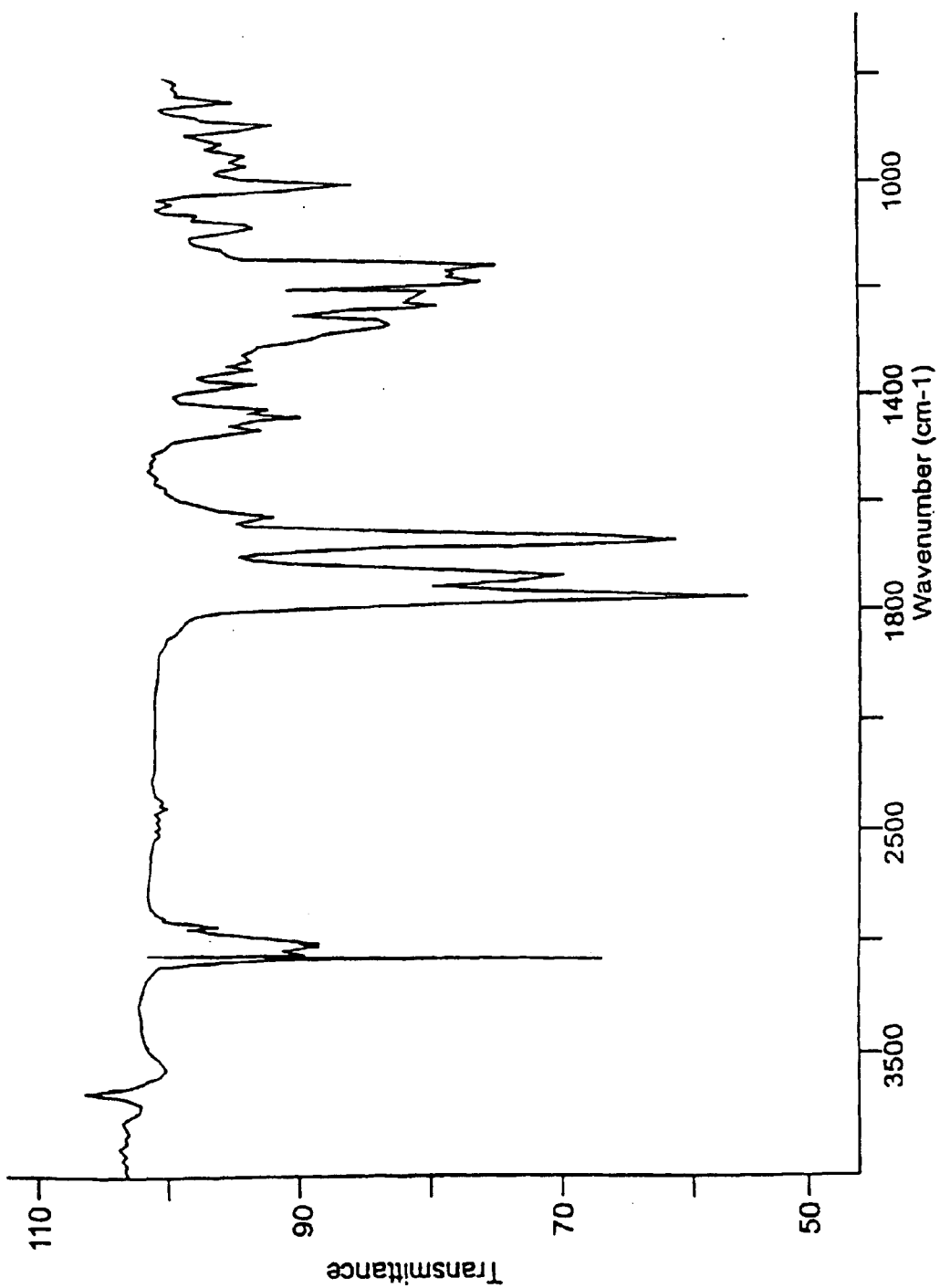
Fig. 3-D

Fig. 6-A

Eplerenone Prevents the Vascular Inflammatory Lesions in Angiotensin II/Salt Hypertensive Rats COX-2 is Not Expressed in the Heart of 1% NaCl-Drinking Rats 1% NaCl Osteopontin is Not Expressed in the Normal Heart Saline-Drinking Control

Histopathologic Scores for Renal Injury in Saline-Drinking Stroke-Prone SHR

| | Vehicle (n=8) | Capt (n=10) | Capt ALDO (n=7) | Capt Ang II (n=7) | Capt+Ang II+ Eplerenone (n=7) |
|---|---|---|---|---|---|
| Renal arteriopathy (lesions/100 glom.) | 18±3** | 0±0 | 15±1** | 16±2** | 3.6±1**, ## |
| Glomerular damage (lesions/100 glom.) | 24±3** | 0±0 | 26±1** | 15±3** | 3.2±1**, ## |

\*\* $P<.001$ vs Captopril
\#\# $P<.001$ vs Captopril & Ang II

FIGURE 36

ALDOSTERONE ANTAGONIST AND CYCLOOXYGENASE-2 INHIBITOR COMBINATION THERAPY TO PREVENT OR TREAT INFLAMMATION-RELATED CARDIOVASCULAR DISORDERS

This application claims the benefit of U.S. Provisional Application Ser. No. 60/221,364, filed Jul. 27, 2000 and U.S. Provisional Application Ser. No. 60/261,352, filed Jan. 12, 2001 and U.S. Provisional Ser. No. 60/261,497 filed Jan. 12, 2001.

FIELD OF THE INVENTION

This invention is in the field of preventing or treating cardiovascular disorders. More specifically, this invention relates to the use of aldosterone antagonist and cyclooxygenase-2 inhibitor combination therapy in preventing or treating cardiovascular disease including atherosclerosis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAID's) that are active in reducing the prostaglandin-induced pain and swelling associated with the inflammation process are also active in affecting other prostaglandin-regulated processes not associated with the inflammation process. Thus, use of high doses of most common NSAID's can produce severe side effects, including life threatening ulcers, that limit their therapeutic potential. An alternative to NSAID's is the use of corticosteroids, which also produce severe adverse effects, especially when long term therapy is involved.

NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

Recently, the role of inflammation in cardiovascular diseases is becoming more understood. Ridker et al. (*New Eng. J. Med.*, 336, 973–9 (1997)) describes a possible role of inflammation in cardiovascular disease. J. Boyle (*J. Path.*, 181, 93–9 (1997)) describes the association of plaque rupture and atherosclerotic inflammation.

Compounds which selectively inhibit cyclooxygenase-2 have been described in U.S. Pat. Nos. 5,380,738, 5,344,991, 5,393,790, 5,434,178, 5,474,995, 5, 510,368 and WO documents WO96/06840, WO96/03388, WO96/03387, WO96/19469, WO96/25405, WO95/15316, WO94/15932, WO94/27980, WO95/00501, WO94/13635, WO94/20480, and WO94/26731.

[Pyrazol-1-yl]benzenesulfonamides have been described as inhibitors of cyclooxygenase-2 and have shown promise in the treatment of inflammation, arthritis, and pain, with minimal side effects in pre-clinical and clinical trials. Their use for treating inflammation in vascular disease has been described in U.S. Pat. No. 5,466,823.

The present invention is directed to the use of aldosterone antagonist and cyclooxygenase-2 inhibitor combination therapy for the prevention or treatment of inflammation related cardiovascular disorders. More specifically, this invention relates to the use of aldosterone antagonist and cyclooxygenase-2 inhibitor combination therapy in preventing cardiovascular disease.

BRIEF DESCRIPTION OF THE DRAWINGS

FIG. 1-A shows X-ray powder diffraction patterns of Form H eplerenone;

FIG. 1-B shows X-ray powder diffraction patterns of Form L eplerenone;

FIG. 1-C shows X-ray powder diffraction patterns of the methyl ethyl ketone solvate of eplerenone;

FIG. 2-A shows a differential scanning calorimetry (DSC) thermogram of non-milled Form L directly crystallized from methyl ethyl ketone;

FIG. 2-B shows a differential scanning calorimetry (DSC) thermogram of non-milled Form L prepared by desolvation of a solvate obtained by crystallization of a high purity eplerenone from methyl ethyl ketone;

FIG. 2-C shows a differential scanning calorimetry (DSC) thermogram of Form L prepared by crystallizing a solvate from a solution of high purity eplerenone in methyl ethyl ketone, desolvating the solvate to yield Form L, and milling the resulting Form;

FIG. 2-D shows a differential scanning calorimetry (DSC) thermogram of non-milled Form H prepared by desolvation of a solvate obtained by digestion of low purity eplerenone from appropriate solvents;

FIG. 2-E shows a DSC thermogram for the methyl ethyl ketone solvate;

FIG. 3-A shows the infrared spectra (diffuse reflectance, DRIFTS) of Form H eplerenone;

FIG. 3-B shows the infrared spectra (diffuse reflectance, DRIFTS) of Form L eplerenone;

FIG. 3-C shows the infrared spectra (diffuse reflectance, DRIFTS) of the methyl ethyl ketone solvate of eplerenone;

FIG. 3-D shows the infrared spectra (diffuse reflectance, DRIFTS) of eplerenone in chloroform solution;

FIG. 36 shows reduction in histopathological scores for renal injury with eplerenone treatment in angiotensin II infused, captopril treated stroke prone spontaneously hypertensive rats.

DETAILED DESCRIPTION OF THE INVENTION

Figure 4:
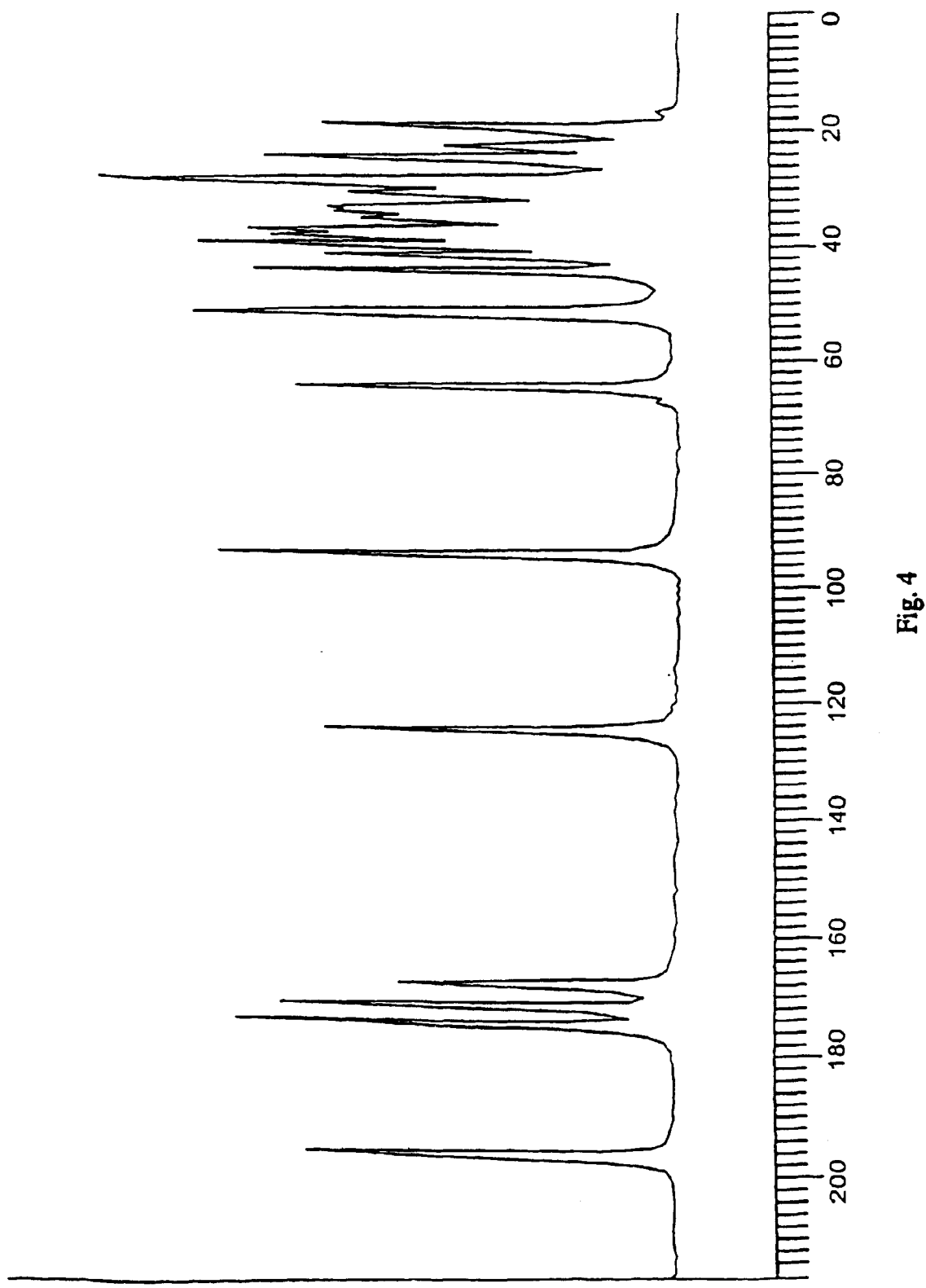
FIG. 4 shows $^{13}C$ NMR spectra for Form H of eplerenone.

The present invention provides a method for preventing or treating cardiovascular disorders in a subject in need thereof. The method comprises treating the subject with a therapeutically effective amount of an aldosterone receptor antagonist or derivative or pharmaceutically-acceptable salt thereof in combination with a cyclooxygenase-2 inhibitor or derivative or a pharmaceutically acceptable salt thereof.

The method above would be useful for, but not limited to, preventing or treating inflammation-related disorders in a subject, including but not limited to inflammation-related disorders of the heart, kidney and brain, particularly vascular inflammation-related disorders. The method would be useful for prevention or treatment of coronary artery disease, aneurysm, arteriosclerosis, atherosclerosis including cardiac transplant atherosclerosis, myocardial infarction, embolism, stroke, thrombosis, including venous thrombosis, angina including unstable angina, calcification (such as vascular calcification and valvar calcification), Kawasaki disease and inflammation (such as coronary plaque inflammation, bacterial-induced inflammation including Chlamydia-induced inflammation and viral induced inflammation). The method is useful for treating or preventing conditions by altering the expression of one or more expression products that directly or indirectly regulate inflammation. Inflammation-related cardiovascular disorders may be mediated, in whole or in part, by one or more expression products, which may undergo increased or decreased expression. Said expression products may include but are not limited to organic molecules, proteins, DNA-based or RNA-based molecules, and networks or aggregates of such products, acting together or alone, to directly or indirectly produce an effect. Changes in patterns of expression of said expression products may occur sequentially or simultaneously, involving two or more expression products. These expression products may have direct or indirect affects on the tissues or organs of the subject, inducing or amplifying a pathological effect induced by other molecules or expression products. These expression products may produce pro-inflammatory effects by increased expression or decreased expression, depending on their function as pro-inflammatory or anti-inflammatory expression products, respectively.

The method is particularly useful for treating or preventing conditions by moderating the upregulation of pro-inflammatory components found in affected tissues, including cyclooxygenase-2 and osteopontin, while also inhibiting the activity of cyclooxygenase-2 in the kidney, particularly the macula densa where aldosterone antagonism can induce expression of cyclooxygenase-2. While the use of an aldosterone antagonist leads to a reduction in cyclooxygenase-2 expression induced by an inflammation-related disorder, it may not completely prevent cyclooxygenase-2 activity. The co-action of adding an inhibitor of cyclooxygenase-2 will also lead to a reduction in inflammation of the affected tissue or organ. It is also known that the use of an aldosterone antagonist can induce upregulation of cyclooxygenase-2 in the macula densa and cortical thick ascending limb (CTAL) of Henle's loop in the kidney. In the kidney, prostaglandins, the product of cyclooxygenase, are involved in the regulation of renal hemodynamics and salt/water homeostasis. As a result the non-inflammatory aldosterone antagonist induction of cyclooxygenase-2 in the macula densa and CTAL region of the kidney can lead to pathological effects such as increased blood pressure and retention of salt and water. Accordingly, co-administration of a cyclooxygenase-2 inhibitor with an aldosterone antagonist, will slow, stop, or reverse the progression of the pathological renal response to the aldosterone antagonist induction of cyclooxygenase-2 in the kidney.

In the method above, cardiovascular disorder includes, but is not limited to, those disorders which are known to have an inflammation component and those that may be mediated by aldosterone or cyclooxygenase-2 or both. The method above also includes treatment of patients with an aldosterone antagonist and cyclooxygenase-2 inhibitor combination requiring moderation of the upregulated expression of cyclooxygenase-2 or osteopontin. In tissues, including but not limited to the kidney, heart, and brain, the isoform cyclooxygenase-2, may be induced resulting in upregulated expression of this pro-inflammatory enzyme, which can cause mild to severe tissue and organ damage. In the method above, administration of an aldosterone antagonist and cyclooxygenase-2 inhibitor combination is used to moderate the upregulated expression of cyclooxygenase-2. The method above would also be useful for preventing or treating conditions which may arise in tissues, including but not limited to the kidney, heart, and brain, wherein the upregulated expression of the pro-inflammatory protein osteopontin, may be induced, resulting in mild to severe tissue and organ damage. In the method above, administration of an aldosterone antagonist and cyclooxygenase-2 inhibitor combination is used to moderate the upregulated expression of osteopontin.

In another embodiment, the present invention would be useful in preventing or treating conditions in tissues and organs, including but not limited to the kidney, heart and brain, wherein the upregulated expression of any one of the pro-inflammatory expression products MCP-1, IL-1, IL-6, VCAM-1 and ICAM-1 may occur, resulting in mild to severe tissue and organ damage. In the method above, administration of an aldosterone antagonist and cyclooxygenase-2 inhibitor combination is used to moderate the upregulated expression of any one of MCP-1, IL-1, IL-6, VCAM-1 and ICAM-1.

Figure 34:
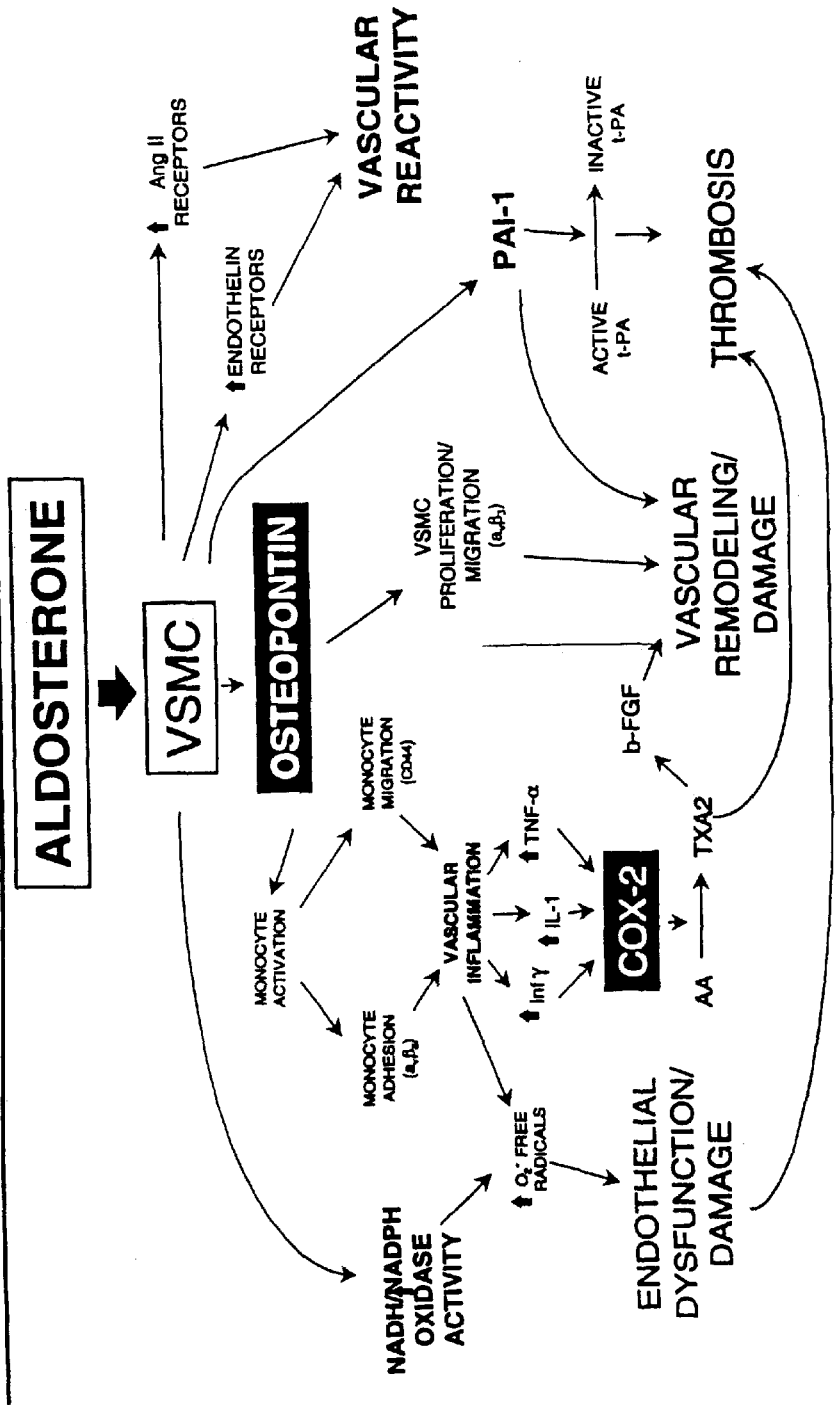
FIG. 34 shows some of the mechanisms for aldosterone-induced vascular inflammation and injury.
Figure 35:
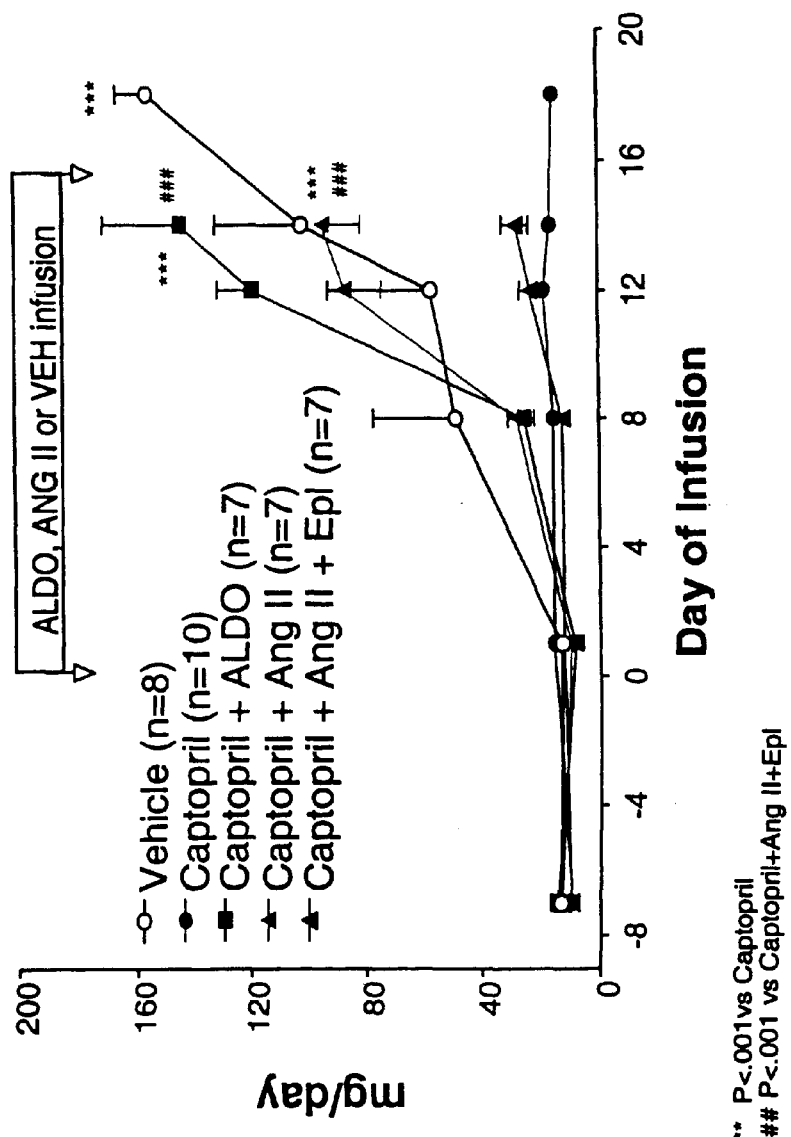
FIG. 35 shows inhibition of increased urinary protein excretion by eplerenone treatment in angiotensin II infused, captopril treated stroke prone spontaneously hypertensive rats.
Figure 37:
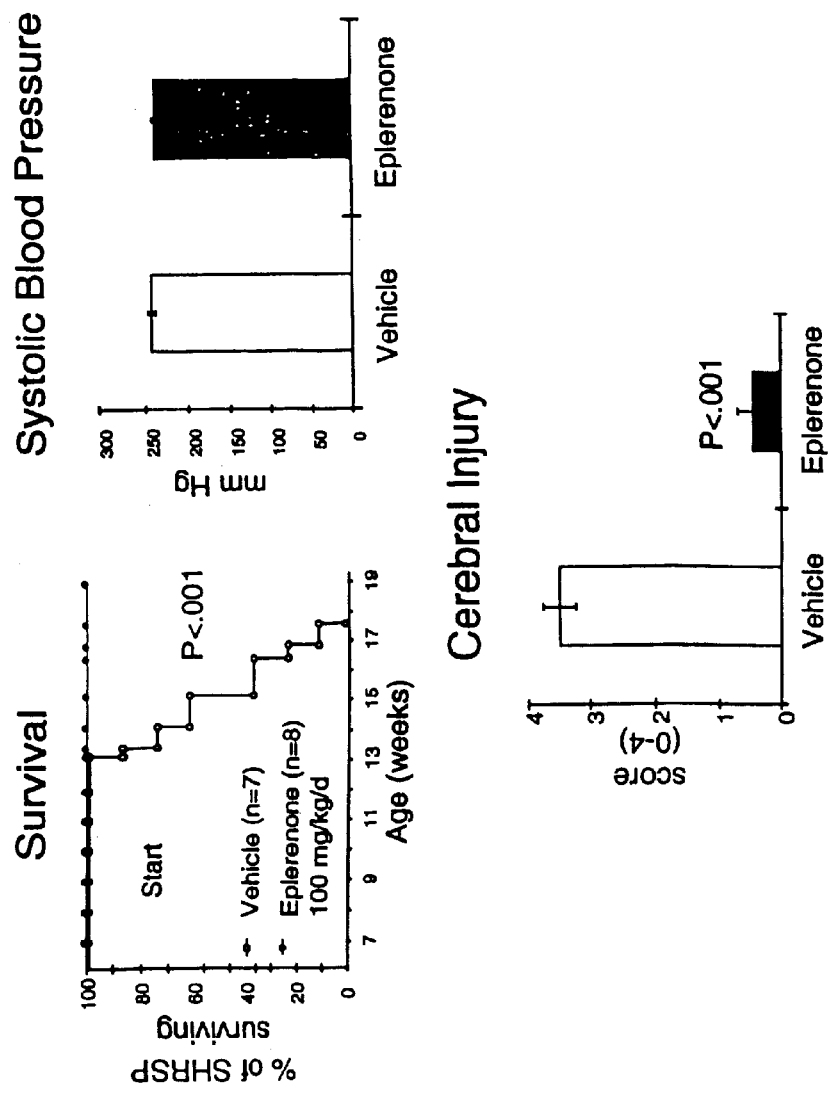
FIG. 37 shows increased survival and reduced cerebral injury with eplerenone treatment in stroke-prone spontaneously hypertensive rats.
Figure 38:
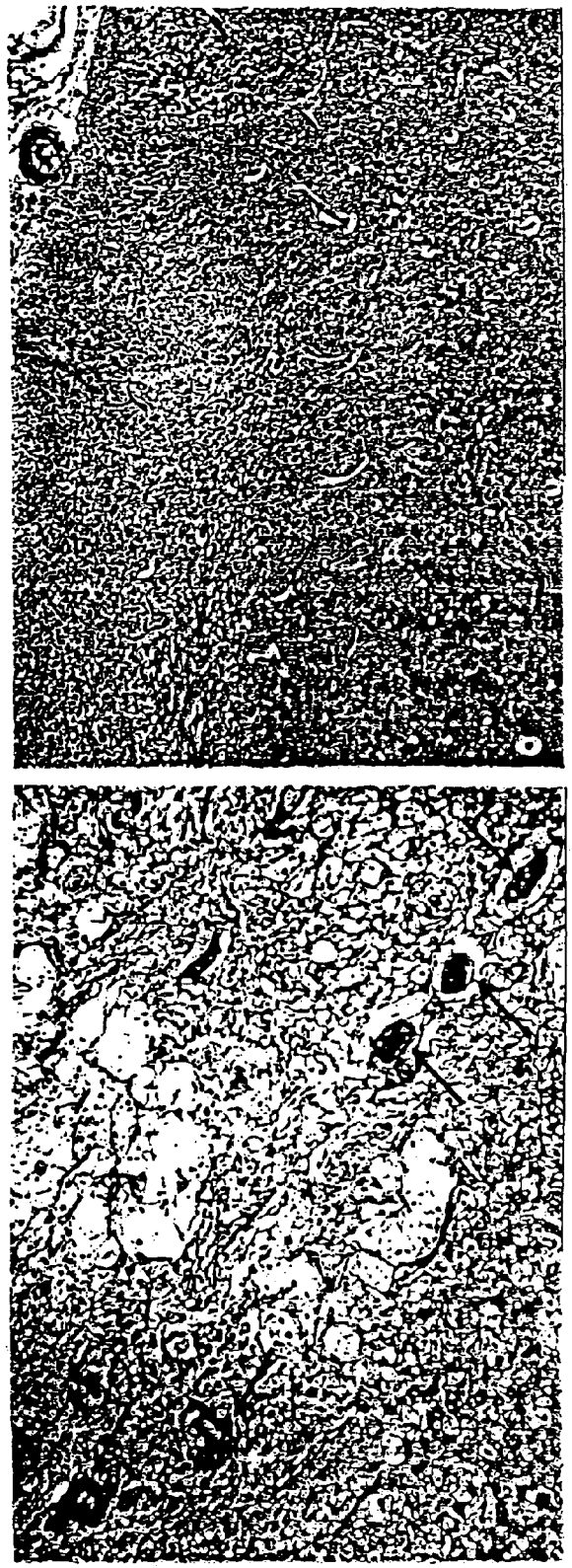
FIG. 38 shows decrease in cerebral injury with eplerenone treatment in stroke-prone spontaneously hypertensive rats.

Non-limiting examples of expression products, whose expression can be moderated to reduce inflammation-related cardiovascular disease by treatment with an aldosterone antagonist and cyclooxygenase-2 inhibitor combination, are shown in FIG. 34 and include upregulation of one or more of the following:

(a) receptors for angiotensin II and endothelin,
(b) monocyte activating molecules $\alpha v\beta 3$ (adhesion, proliferation, migration) and CD44 (migration),
(c) mediators of vascular inflammation interferon-$\gamma$ (Inf-$\gamma$), interleukin-1 (IL-1) and tumor necrosis factor-a (TNF-a),
(d) NADH/NADPH oxidase to produce tissue damaging superoxide radicals and
(e) prothrombotic plasminogen activator inhibitor-1 (PAI-1) causing a decrease in active tissue plasminogen activator (t-PA).

In another embodiment of the present invention, non-limiting examples of expression products, whose expression can be moderated to reduce inflammation-related cardiovascular disease by treatment with an aldosterone antagonist and cyclooxygenase-2 inhibitor combination, include one or more of the following:

acute phase reactants like C-reactive protein (CRP),
pleiotropic cytokines like interleukin-6 (IL-6), IL-10, IL-12, soluble intracellular adhesion molecule-1 (sICAM-1),
troponin T or I, heat shock protein 65 (HSP65), amyloid, phospholipase A2, fibrinogen, CD40/CD40L signaling pathway
and adhesion mediators like collagen-binding integrins $a1\beta 1$ (mesenchymal cells) and $a2\beta 1$ (epithelial cells).

Inhibitors of the cyclooxygenase pathway in the metabolism of arachidonic acid used in the prevention of cardiovascular disorder may inhibit enzyme activity through a variety of mechanisms. By the way of example, the inhibitors used in the methods described herein may inhibit expression of the enzyme activity. Blocking expression of cyclooxygenase-2, at the site of inflammatory damage, using an aldosterone antagonist, is highly advantageous in that it minimizes the gastric side effects that can occur with non-selective NSAID's, especially where prolonged prophylactic treatment is expected.

Dosages and Treatment Regimen

The amount of aldosterone blocker that is administered and the dosage regimen for the methods of this invention depend on a variety of factors, including the age, weight, sex and medical condition of the subject, the severity of the pathogenic effect, the route and frequency of administration, and the particular aldosterone blocker employed, and thus may vary widely. A daily dose administered to a subject of about 0.001 to 30 mg/kg body weight, preferably between about 0.005 and about 20 mg/kg body weight, more preferably between about 0.01 and about 15 mg/kg body weight, still more preferably between about 0.05 and about 10 mg/kg body weight, and most preferably between about 0.01 to 5 mg/kg body weight, may be appropriate. The amount of asldosterone antagonist that is administered to a human subject typically will range from about 0.1 to about 2000 mg. In one embodiment of the present invention, the dosage range is from about 0.5 to about 500 mg. In another embodiment of the present invention, the dosage range is from about 0.75 to about 250 mg. In a further embodiment of the present invention, the dosage range is from about 1 to about 100 mg. In another embodiment of the present invention, the dosage range is from about 10 to 100 mg. In a further embodiment of the present invention, the dosage range is from about 25 to about 100 mg. In another embodiment of the present invention, the dosage range is from about 25 to about 75 mg. A daily dose of aldosterone blocker that produces no substantial diuretic and/or anti-hypertensive effect in a subject is specifically embraced by the present method. The daily dose can be administered in one to four doses per day.

Dosing of the aldosterone blocker can be determined and adjusted based on measurement of blood pressure or appropriate surrogate markers (such as natriuretic peptides, endothelins, and other surrogate markers discussed below). Blood pressure and/or surrogate marker levels after administration of the aldosterone blocker can be compared against the corresponding baseline levels prior to administration of the aldosterone blocker to determine efficacy of the present method and titrated as needed. Non-limiting examples of surrogate markers useful in the method are surrogate markers for renal and cardiovascular disease.

Prophylatic Dosing

It is beneficial to administer the aldosterone blocker prophylatically, prior to a diagnosis of said inflammation-related cardiovascular disorders, and to continue administration of the aldosterone blocker during the period of time the subject is susceptible to the inflammation-related cardiovascular disorders. Individuals with no remarkable clinical presentation but that are nonetheless susceptible to pathologic effects therefore can be placed upon a prophylatic dose of an aldosterone blocking compound. Such prophylactic doses of the aldosterone blocker may, but need not, be lower than the doses used to treat the specific pathogenic effect of interest.

Cardiovascular Pathology Dosing

Dosing to treat pathologies of cardiovascular function can be determined and adjusted based on measurement of blood concentrations of natriuretic peptides. Natriuretic peptides are a group of structurally similar but genetically distinct peptides that have diverse actions in cardiovascular, renal, and endocrine homeostasis. Atrial natriuretic peptide ("ANP") and brain natriuretic peptide ("BNP") are of myocardial cell origin and C-type natriuretic peptide ("CNP") is of endothelial origin. ANP and BNP bind to the natriuretic peptide-A receptor ("NPR-A"), which, via 3',5'-cyclic guanosine monophosphate (cGMP), mediates natriuresis, vasodilation, renin inhibition, antimitogenesis, and lusitropic properties. Elevated natriuretic peptide levels in the blood, particularly blood BNP levels, generally are observed in subjects under conditions of blood volume expansion and after vascular injury such as acute myocardial infarction and remain elevated for an extended period of time after the infarction. (Uusimaa et al.: *Int. J. Cardiol* 1999; 69: 5–14).

A decrease in natriuretic peptide level relative to the baseline level measured prior to administration of the aldosterone blocker indicates a decrease in the pathologic effect of aldosterone and therefore provides a correlation with inhibition of the pathologic effect.

Blood levels of the desired natriuretic peptide level therefore can be compared against the corresponding baseline level prior to administration of the aldosterone blocker to determine efficacy of the present method in treating the patologic effect. Based upon such natriuretic peptide level measurements, dosing of the aldosterone blocker can be adjusted to reduce the cardiovascular pathologic effect.

Similarly, cardiac pathologies can also be identified, and the appropriate dosing determined, based on circulating and urinary cGMP Levels. An increased plasma level of cGMP parallels a fall in mean arterial pressure. Increased urinary excretion of cGMP is correlated with the natriuresis.

Cardiac pathologies also can be identified by a reduced ejection fraction or the presence of myocardial infarction or heart failure or left ventricular hypertrophy. Left ventricular hypertrophy can be identified by edho-cardiogram or magnetic resonance imaging and used to monitor the progress of the treatment and appropriateness of the dosing.

In another embodiment of the invention, therefore, the methods of the present invention can be used to reduce natriuretic peptide levels, particularly BNP levels, thereby also treating related cardiovascular pathologies.

Renal Pathology Dosing

Dosing to treat pathologies of renal function can be determined and adjusted based on measurement of proteinuria, microalbuminuria, decreased glomerular filtration rate (GFR), or decreased creatinine clearance. Proteinuria is identified by the presence of greater than 0.3 g of urinary protein in a 24 hour urine collection. Microalbuminuria is identified by an increase in immunoassayable urinary albumin. Based upon such measurements, dosing of the aldosterone blocker can be adjusted to reduce the renal pathologic effect.

Neuropathy Pathology Dosing

Neuropathy, especially peripheral neuropathy, can be identified by and dosing adjustments based on, neurologic exam of sensory deficit or sensory motor ability.

Retinopathy Pathology Dosing Retinopathy can be identified by, and dosing adjustments based on, opthamologic exam.

Inflammation Markers

Certain markers may be indicative of or responsible for inflammation, or pre-inflammatory conditions. Measurement of these markers may be useful in determination of an appropriate dosage of aldosterone blocker to be administered, or determination of an efficatious dose of an aldosterone blocker after administration. Non-limiting examples of such markers are: osteopontin; acute phase reactants such as C reactive protein (CRP), fibrinogen, Factor VIII, serum copper (carrier protein ceruloplasmin), serum iron (carrier. protein ferritin), Plasminogen activator Inhibitor-1 (PAI-1) and lipoprotein(a); natriuretic peptides; endothelins; VCAM-1; ICAM-1; IL-1β; TNF-α; IL-6; COX-2; fractalkine; MCP-1; and triglyceride.

The present invention is further directed to combinations comprising an aldosterone antagonist and a cyclooxygenase-2 inhibitor. In one embodiment, the combination is a pharmaceutical composition comprising and aldosterone antagonist and a cyclooxygenase-2 inhibitor. One illustrative, nonlimiting example is a pharmaceutical composition comprising eplerenone and celecoxib.

A class of selective cyclooxygenase-2 inhibiting agents useful in the present invention include compounds of Formula 1:

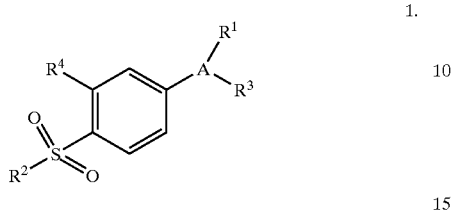

1.

wherein A is a 5- or 6-member ring substituent selected from partially unsaturated or unsaturated heterocyclo and carboxcyclic rings, wherein A is optionally substituted with one or more radicals selected from alkyl, halo, oxo, and alkoxy;

wherein $R^1$ is selected from cyclohexyl, pyridinyl, and phenyl, wherein cyclohexyl, pyridinyl, or phenyl are optionally substituted with one or more radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, halo, alkoxy, and alkylthio;

wherein $R^2$ is selected from alkyl and amino;

wherein $R^3$ is a radical selected from halo, alkyl, alkenyl, alkynyl, aryl, heteroaryl, oxo, cyano, carboxyl, cyanoalkyl, heterocyclyloxy, alkyloxy, alkylthio, alkylcarbonyl, cycloalkyl, phenyl, haloalkyl, heterocyclo, cycloalkenyl, phenylalkyl, heterocyclylalkyl, alkylthioalkyl, hydroxyalkyl, alkoxycarbonyl, phenylcarbonyl, phenylalkylcarbonyl, phenylalkenyl, alkoxyalkyl, phenylthioalkyl, phenyloxyalkyl, alkoxyphenylalkoxyalkyl, alkoxycarbonylalkyl, aminocarbonyl, aminocarbonylalkyl, alkylaminocarbonyl, N-phenylaminocarbonyl, N-alkyl-N-phenylaminocarbonyl, alkylaminocarbonylalkyl, carboxyalkyl, alkylamino, N-arylamino, N-arylkylamino, N-alkyl-N-arylkylamino, N-alkyl-N-arylamino, aminoalkyl, alkylaminoalkyl, N-phenylaminoalkyl, N-phenylalkylaminoalkyl, N-alkyl-N-phenylalkylaminoalkyl, N-alkyl-N-phenylaminoalkyl, phenyloxy, phenylalkoxy, phenylthio, phenylalkylthio, alkylsulfinyl, alkylsulfonyl, aminosulfonyl, alkylaminosulfonyl, N-phenylaminosulfonyl, phenylsulfonyl, and N-alkyl-N-phenylaminosulfonyl; and wherein $R^4$ is selected from hydrido and halo;

or a pharmaceutically-acceptable salt thereof.

The present invention preferably includes compounds which selectively inhibit cyclooxygenase-2 over cyclooxygenase-1. In one embodiment, the compounds have a selectivity ratio of cyclooxygenase-2 inhibition over cyclooxygenase-1 inhibition of at least 50, and in another embodiment have a selectivity ratio of at least 100. Such selectivity ratios may indicate an ability to reduce the incidence of common NSAID-induced side effects.

Within Formula 1 there is a subclass of compounds of particular interest wherein A is selected from thienyl, oxazolyl, furyl, furanone, pyrrolyl, thiazolyl, imidazolyl, benzofuryl, indenyl, benzithienyl, isoxazolyl, pyrazolyl, cyclopentenyl, cyclopentadienyl, benzindazolyl, cyclopentenone, benzopyranopyrazolyl, phenyl, and pyridyl;

wherein $R^1$ is selected from cyclohexyl, pyridinyl, and phenyl, wherein cyclohexyl, pyridinyl, or phenyl is substituted with one or more radicals selected from $C_{1-2}$ alkyl, $C_{1-2}$ haloalkyl, cyano, carboxyl, $C_{1-2}$ alkoxycarbonyl, hydroxyl, $C_{1-2}$ hydroxyalkyl, $C_{1-2}$ haloalkoxy, amino, $C_{1-2}$ alkylamino, phenylamino, nitro, $C_{1-2}$ alkoxy-$C_{1-2}$-alkyl, $C_{1-2}$ alkylsulfinyl, $C_{1-2}$ alkoxy, halo, alkoxy, and $C_{1-2}$ alkylthio;

wherein $R^2$ is selected from alkyl and amino;

wherein $R^3$ is a radical selected from halo, $C_{1-2}$ alkyl, $C_{2-3}$ alkenyl, $C_{2-3}$ alkynyl, aryl, heteroaryl, oxo, cyano, carboxyl, cyano-$C_{1-3}$-alkyl, heterocyclyloxy, $C_{1-3}$ alkyloxy, alkylthio, alkylcarbonyl, cycloalkyl, phenyl, $C_{1-3}$ haloalkyl, heterocyclo, cycloalkenyl, phenyl-$C_{1-3}$-alkyl, heterocyclyl-$C_{1-3}$-alkyl, $C_{1-3}$ alkylthio-$C_{1-3}$-alkyl, $C_{1-3}$ hydroxyalkyl, $C_{1-3}$ alkoxycarbonyl, phenylcarbonyl, phenyl-$C_{1-3}$-alkylcarbonyl, phenyl-$C_{2-3}$-alkenyl, $C_{1-3}$ alkoxy-$C_{1-3}$-alkyl, phenylthio-$C_{1-3}$-alkyl, phenyloxyalkyl, alkoxyphenylalkoxyalkyl, alkoxycarbonylalkyl, aminocarbonyl, aminocarbonyl-$C_{1-3}$-alkyl, $C_{1-3}$ alkylaminocarbonyl, N-phenylaminocarbonyl, N—$C_{1-3}$ alkyl-N-phenylaminocarbonyl, $C_{1-3}$ alkylaminocarbonyl-$C_{1-3}$-alkyl, carboxy-$C_{1-3}$-alkyl, $C_{1-3}$ alkylamino, N-arylamino, N-arylkylamino, N—$C_{1-3}$ alkyl-N-arylkylamino, N—$C_{1-3}$ alkyl-N-arylamino, amino-$C_{1-3}$-alkyl, $C_{1-3}$ alkylaminoalkyl, N-phenylamino-$C_{1-3}$-alkyl, N-phenyl-$C_{1-3}$-alkylaminoalkyl, N—$C_{1-3}$ alkyl-N-phenyl-$C_{1-3}$-alkylamino-$C_{1-3}$-alkyl, N—$C_{1-3}$ alkyl-N-phenylamino-$C_{1-3}$-alkyl, phenyloxy, phenylalkoxy, phenylthio, phenyl-$C_{1-3}$-alkylthio, $C_{1-3}$ alkylsulfinyl, $C_{1-3}$ alkylsulfonyl, aminosulfonyl, $C_{1-3}$ alkylaminosulfonyl, N-phenylaminosulfonyl, phenylsulfonyl, and N—$C_{1-3}$ alkyl-N-phenylaminosulfonyl; and wherein $R^4$ is selected from hydrido and halo;

or a pharmaceutically-acceptable salt thereof.

Another class of compounds within Formula 1 of even more interest include compounds wherein A is substituted with one or more radicals selected from alkyl, halo, oxo, and alkoxy;

wherein $R^1$ is selected from pyridyl, cyclohexyl, and phenyl, wherein pyridyl, cyclohexyl, or phenyl is optionally substituted with one or more radicals selected from alkyl, halo, and alkoxy;

wherein $R^2$ is $C_{1-2}$ alkyl or amino;

wherein $R^3$ is a radical selected from halo, $C_{1-2}$ alkyl, cyano, carboxyl, $C_{1-2}$ alkyloxy, phenyl, C1–2 haloalkyl, and $C_{1-2}$ hydroxyalkyl; and wherein $R^4$ is selected from hydrido and fluoro;

or a pharmaceutically-acceptable salt thereof.

A family of specific compounds within Formula 1 of particular interest include compounds and pharmaceutically-acceptable salts thereof, as follows:

C1)

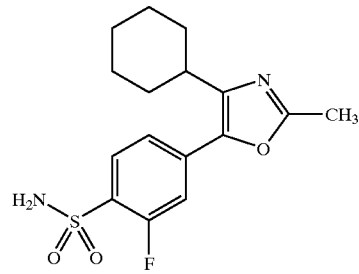

4-(4-cyclohexyl-2-methyloxazol-5-yl)-2-fluorobenzenesulfonamide;

C2)
   5-chloro-3-(4-(methylsulfonyl)phenyl)-2-(methyl-5-pyridinyl)pyridine;
C3)
   2-(3,5-difluorophenyl)-3-4-(methylsulfonyl)phenyl)-2-cyclopenten-1-one;
C4)

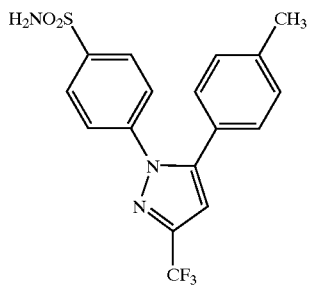

4-[5-(4-methylphenyl)-3-(trifluoromethyl)-1H-pyrazol-1-yl]-benzenesulfonamide;
C5)

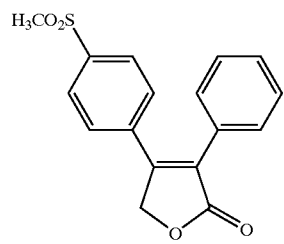

4-(4-(methylsulfonyl)phenyl]-3-phenyl-2(5H)-furanone;
C6)

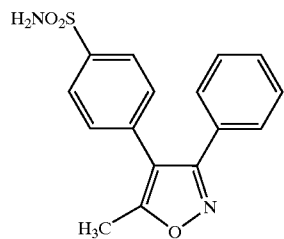

4-(5-methyl-3-phenylisoxazol-4-yl)benzenesulfonamide;
C7)
   N-[[4-(5-methyl-3-phenylisoxazol-4ylphenyl]sulfonyl]propanamide;
C8)

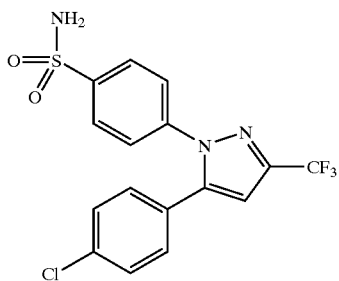

4-[5-(4-chorophenyl)-3-(trifluoromethyl)-1H-pyrazole-1-yl]benzenesulfonamide;

C9)

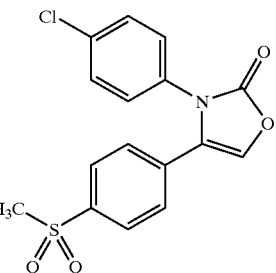

3-(4-chlorophenyl)-4-[4-(methylsulfonyl)phenyl]-2(3H)-oxazolone;
C10)

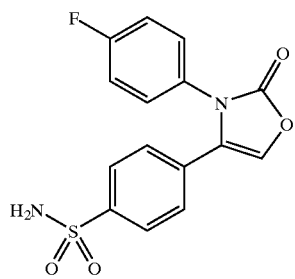

4-[3-(4-fluorophenyl)-2,3-dihydro-2-oxo-4-oxazolyl]benzenesulfonamide;
C11)

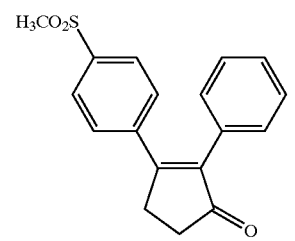

3-[4-(methylsulfonyl)phenyl]-2-phenyl-2-cyclopenten-1-one;
C12)

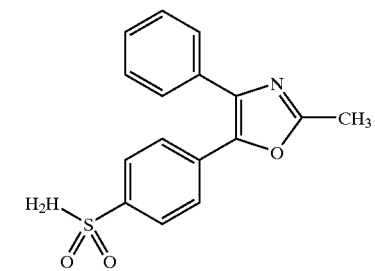

4-(2-methyl-4-phenyl-5-oxazolyl)benzenesulfonamide;

C13)

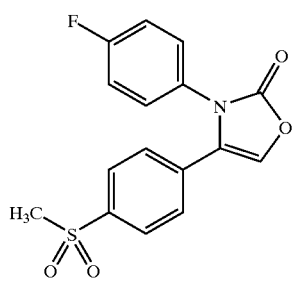

3-(4-fluorophenyl)-4-[4-(methylsulfonyl)phenyl]-2(3H)-oxazolone;

C14)

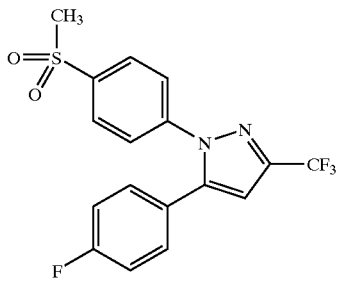

5-(4-fluorophenyl)-1-[4-(methylsulfonyl)phenyl]-3-(trifluoromethyl)-1H-pyrazole;

C15)

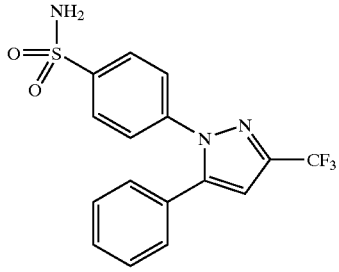

4-[5-phenyl)-3-(trifluoromethyl)-1H-pyrazol-1-yl)benzenesulfonamide;

C16)

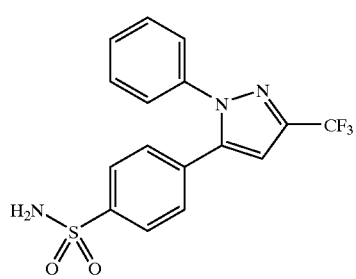

4-[1-phenyl-3-(trifluoromethyl)-1H-pyrazol-5-yl]benzenesulfonamide;

C17)

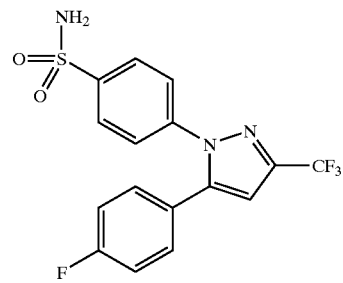

4-[5-(4-fluorophenyl)-3-(trifluoromethyl)-1H-pyrazol-1-yl]benzenesulfonamide;

C18)

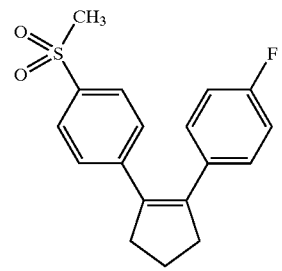

1-fluoro-4-[2-[4-(methylsulfonyl)phenyl]cyclopenten-1-yl]benzene;

C19)

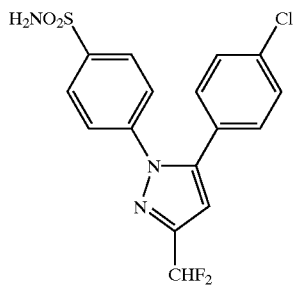

4-[5-(4-chlorophenyl)-3-(difluoromethyl)-1H-pyrazol-1-yl]benzenesulfonamide;

C20)

3-[1-[4-(methylsulfonyl)phenyl]-4-(trifluoromethyl)-1H-imidazol-2-yl]pyridine;

C21)
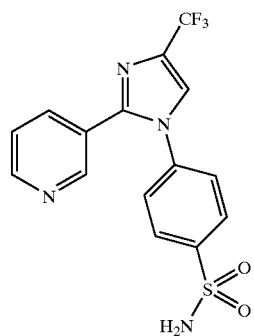
4-[2-(3-pyridinyl)-4-(trifluoromethyl)-1H-imidazol-1-yl]benzenesulfonamide;
C22)
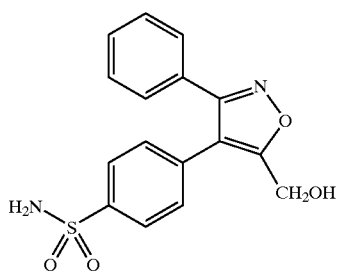
4-[5-(hydroxymethyl)-3-phenylisoxazol-4-yl]benzenesulfonamide;
C23)
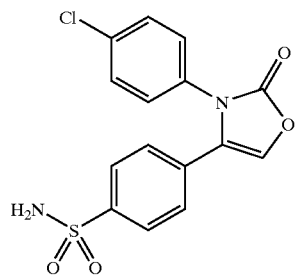
4-[3-(4-chlorophenyl)-2,3-dihydro-2-oxo-4-oxazolyl]benzenesulfonamide;
C24)
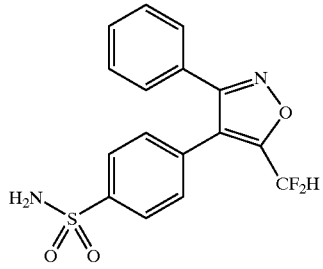
4-[5-(difluoromethyl)-3-phenylisoxazol-4-yl]benzenesulfonamide;
C25)
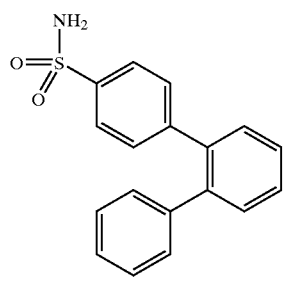
[1,1':2',1''-terphenyl]-4-sulfonamide;
C26)
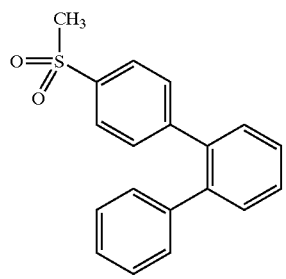
4-(methylsulfonyl)-1,1',2',1''-terphenyl;
C27)
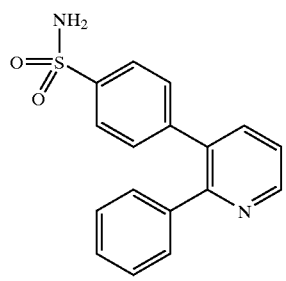
4-(2-phenyl-3-pyridinyl)benzenesulfonamide;
C28)
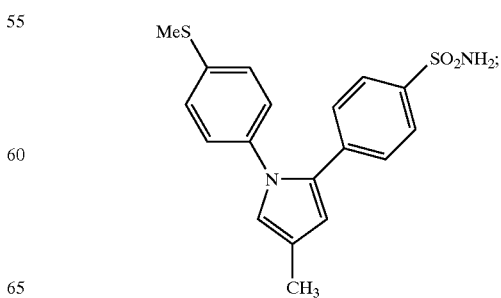

C29)

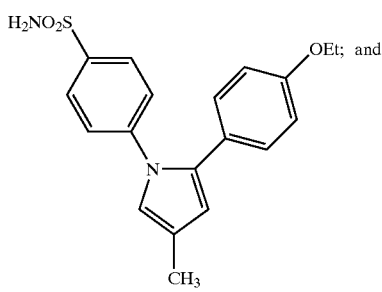

C30)
2-(6-methylpyrid-3-yl)-3-(4-methylsulfinylphenyl)-5-chloropyridine.

Additional specific compounds of particular interest within Formula I include each of the compounds and pharmaceutically-acceptable salts thereof as follows:
4-(4-cyclohexyl-2-methyloxazol-5-yl)-2-fluorobenzenesulfonamide,
4-(4-(methylsulfonyl)phenyl]-3-phenyl-2(5H)-furanone,
2-(6-methylpyrid-3-yl)-3-(4-methylsulfinylphenyl)-5-chloropyridine:

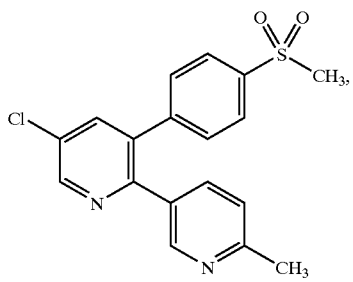

4-[5-(4-methylphenyl)-3-(trifluoromethyl)-1H-pyrazol-1-yl]-benzenesulfonamide,
4-(4-(methylsulfonyl)phenyl]-3-phenyl-2(5H)-furanone,
4-[5-(4-chorophenyl)-3-(trifluoromethyl)-1H-pyrazole-1-yl]benzenesulfonamide,
4-(4-cyclohexyl-2-methyloxazol-5-yl)-2-fluorobenzenesulfonamide,
5-chloro-3-(4-(methylsulfonyl)phenyl)-2-(methyl-5-pyridinyl)pyridine,
2-(3,5-difluorophenyl)-3–4-(methylsulfonyl)phenyl)-2-cyclopenten-1-one,
4-(4-(methylsulfonyl)phenyl]-3-phenyl-2(5H)-furanone,
4-[5-methyl-3-phenyl-isoxazol-4-yl]benzenesulfonamide, and
N-[[4-(5-methyl-3-phenylisoxazol-4-yl]phenyl]sulfonyl] propanamide.

In another embodiment of the invention the cyclooxygenase-2 selective inhibitor is preferably of the chromene structural class that is a substituted benzopyran or a substituted benzopyran analog, and even more preferably selected from the group consisting of substituted benzothiopyrans, dihydroquinolines, or dihydronaphthalenes having the general Formula II shown below and possessing, by way of example and not limitation, the structures disclosed in Table 3, including the diastereomers, enantiomers, racemates, tautomers, salts, esters, amides and prodrugs thereof. Furthermore, benzopyran COX-2 selective inhibitors useful in the practice of the present invention are described in International publication WO/00/23433, U.S. Pat. Nos. 6,034,256 and 6,077,850 herein incorporated by reference.

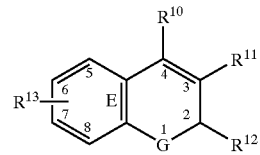

II wherein G is selected from the group consisting of O or S or NR$^a$; wherein R$^a$ is alkyl;

wherein R$^{10}$ is selected from the group consisting of H and aryl wherein R$^{11}$ is selected-from the group consisting of carboxyl, aminocarbonyl, alkylsulfonylaminocarbonyl and alkoxycarbonyl;

wherein R$^{12}$ is selected from the group consisting of haloalkyl, alkyl, aralkyl, cycloalkyl and aryl optionally substituted with one or more radicals selected from alkylthio, nitro and alkylsulfonyl; or wherein R$^{13}$ is selected from the group consisting of one or more radicals selected from H, halo, alkyl, aralkyl, alkoxy, aryloxy, heteroaryloxy, aralkyloxy, heteroaralkyloxy, haloalkyl, haloalkoxy, alkylamino, arylamino, aralkylamino, heteroarylamino, heteroarylalkylamino, nitro, amino, aminosulfonyl, alkylaminosulfonyl, arylaminosulfonyl, heteroarylaminosulfonyl, aralkylaminosulfonyl, heteroaralkylaminosulfonyl, heterocyclosulfonyl, alkylsulfonyl, hydroxyarylcarbonyl, nitroaryl, optionally substituted aryl, optionally substituted heteroaryl, aralkylcarbonyl, heteroarylcarbonyl, arylcarbonyl, aminocarbonyl, and alkylcarbonyl;

or wherein R$^{13}$ together with ring E forms a naphthyl radical; or an isomer or pharmaceutically acceptable salt thereof, such as, for example the compounds shown in table 3:

TABLE 3

Examples of Chromene COX-2 Selective Inhibitors as Embodiments

| Compound Number | Structural Formula |
|---|---|
| C-31 | 6-Nitro-2-trifluoromethyl-2H-1-benzopyran-3-carboxylic acid |
| C-32 | 6-Chloro-8-methyl-2-trifluoromethyl-2H-1-benzopyran-3-carboxylic acid |

TABLE 3-continued

Examples of Chromene COX-2 Selective Inhibitors as Embodiments

| Compound Number | Structural Formula |
|---|---|
| C-33 | 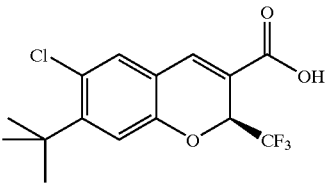<br>((S)-6-Chloro-7-(1,1-dimethylethyl)-2-(trifluoro-methyl-2H-1-benzopyran-3-carboxylic acid |
| C-34 | 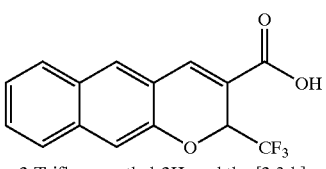<br>2-Trifluoromethyl-2H-naphtho [2,3-b] pyran-3-carboxylic acid |
| C-35 | 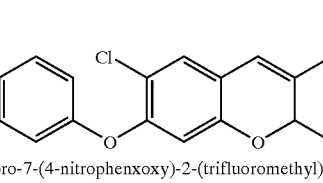<br>6-Chloro-7-(4-nitrophenxoxy)-2-(trifluoromethyl)-2H-1-benzopyran-3-carboxylic acid |
| C-36 | 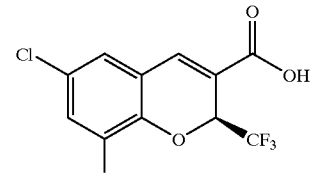<br>((S)-6,8-Dichloro-2-(trifluoromethyl)-2H-1-benzopyran-3-carboxylic acid |
| C-37 | 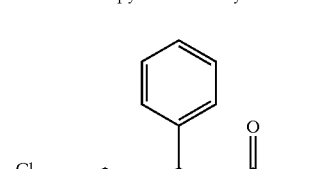<br>6-Chloro-2-(trifluoromethyl)-4-phenyl-2H-1-benzopyran-3-carboxylic acid |
| C-38 | 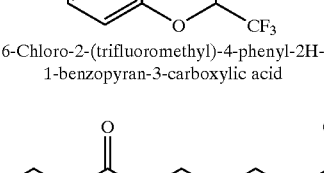<br>6-(4-Hydroxybenzoyl)-2-(trifluoromethyl)-2H-1-benzopyran-3-carboxylic acid |
| C-39 | 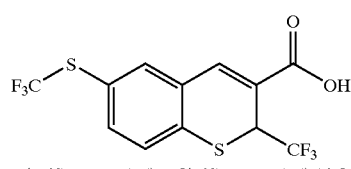<br>2-(Trifluoromethyl)-6-[(trifluoromethyl)thio]-2H-1-benzothiopyran-3-carboxylic acid |
| C-40 | 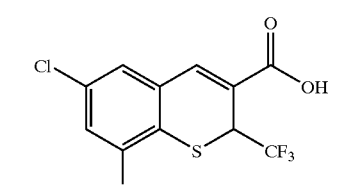<br>6,8-Dichloro-2-trifluoromethyl-2H-1-benzothiopyran-3-carboxylic acid |
| C-41 | 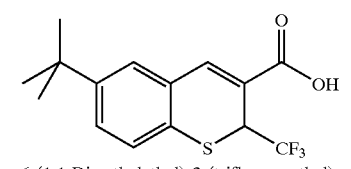<br>6-(1,1-Dimethylethyl)-2-(trifluoromethyl)-2H-1-benzothiopyran-3-carboxylic acid |
| C-42 | 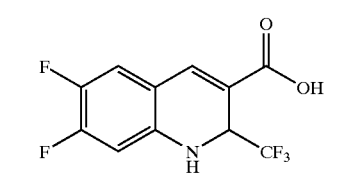<br>6,7-Difluoro-1,2-dihydro-2-(trifluoromethyl)-3-quinolinecarboxylic acid |
| C-43 | 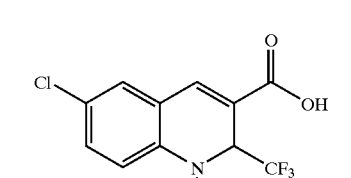<br>6-Chloro-1,2-dihydro-1-methyl-2-(trifluoromethyl)-3-quinolinecarboxylic acid |
| C-44 | 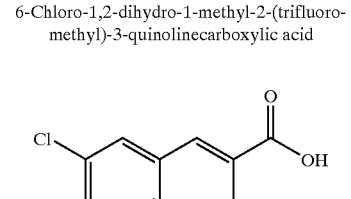<br>6-Chloro-2-(trifluoromethyl)-1,2-dihydro [1,8]naphthyridine-3-carboxylic acid |

TABLE 3-continued

Examples of Chromene COX-2 Selective Inhibitors as Embodiments

| Compound Number | Structural Formula |
|---|---|
| C-45 | 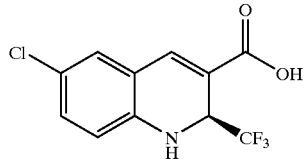<br>((S)-6-Chloro-1,2-dihydro-2-(trifluoromethyl)-3-quinolinecarboxylic acid |
| C-46 | 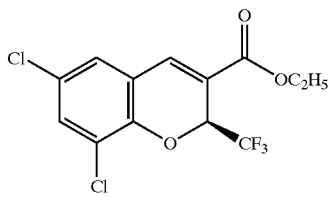<br>6,8-Dichloro-2-(trifluoromethyl)-2H-1 benzopyran-3-ethyl acetate |
| C-47 | 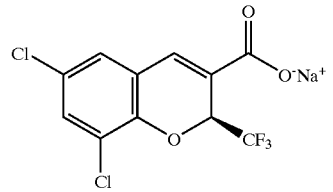<br>Sodium 6,8-Dichloro-2-(trifluoromethyl)-2H-1 benzopyran-3-carboxylate |
| C-48 | 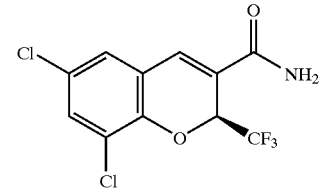<br>6,8-Dichloro-2-(trifluoromethyl)-2H-1 benzopyran-3-carboxamide |

Additional Cyclooxygenase-2 selective inhibitors advantageously employed in the combination therapy of the present invention include:

C-49)

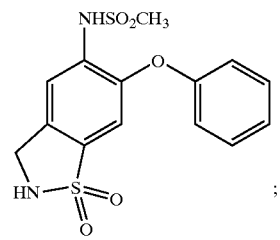

;

C-50)

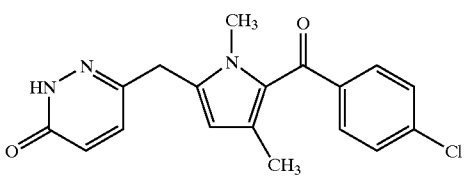

RS 57067, 6-[[5-(4-chlorobenzoyl)-1,4-dimethyl-1H-pyrrol-2-yl]methyl]-3(2H)-pyridazinone, (CAS registry number 179382-91-3);

C-51)

N-(4-nitro-2-phenoxyphenyl)methanesulfonamide;

C-52)

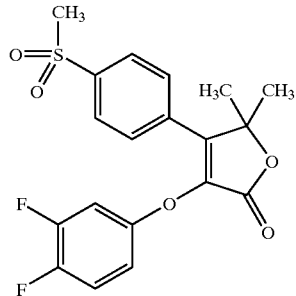

3-(3,4-difluorophenoxy)-5,5-dimethyl-4-[4-(methylsulfonyl)phenyl]-2(5H)-furanone;

C-53)

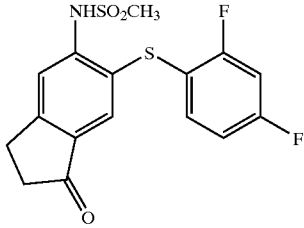

N-[6-[(2,4-difluorophenyl)thio]-2,3-dihydro-1-oxo-1H-inden-5-yl]methanesulfonamide;

C-54)

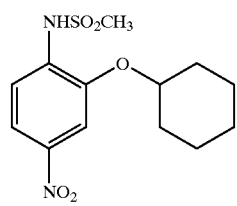

N-[2-(cyclohexyloxy)-4-nitrophenyl]
methanesulfonamide;

C-55)

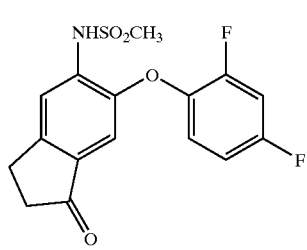

N-[6-(2,4-difluorophenoxy)-2,3-dihydro-1-oxo-1H-
inden-5-yl]methanesulfonamide;

C-56)

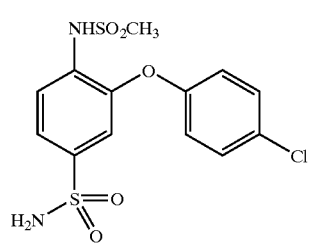

3-(4-chlorophenoxy)-4-[(methylsulfonyl)amino]
benzenesulfonamide;

C-57)

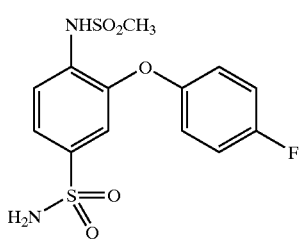

3-(4-fluorophenoxy)-4-[(methylsulfonyl)amino]
benzenesulfonamide;

C-58)

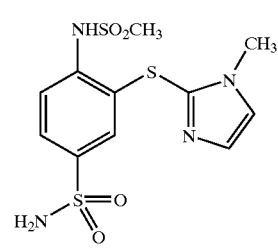

3-[(1-methyl-1H-imidazol-2-yl)thio]-4[(methylsulfonyl)
amino]benzenesulfonamide;

C-59)

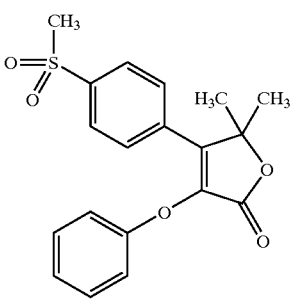

5,5-dimethyl-4-[4-(methylsulfonyl)phenyl]-3-phenoxy-2
(5H)-furanone;

C-60)

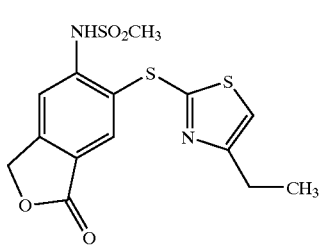

N-[6-[(4-ethyl-2-thiazolyl)thiol-1,3-dihydro-1-oxo-5-
isobenzofuranyl]methanesulfonamide;

C-61)

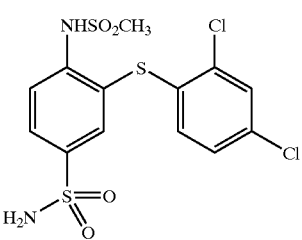

3-[(2,4-dichlorophenyl)thio]-4-[(methylsulfonyl)amino]
benzenesulfonamide;

C-62)

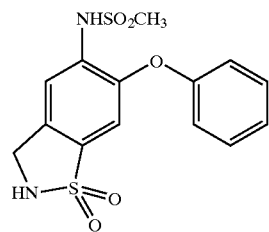

N-(2,3-dihydro-1,1-dioxido-6-phenoxy-1,2-benzisothiazol-5-yl)methanesulfonamide;

C-63)

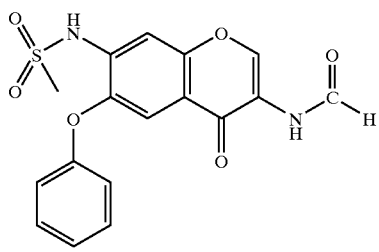

N-[3-(formylamino)-4-oxo-6-phenoxy-4H-1-benzopyran-7-yl]methanesulfonamide; and

C-64)

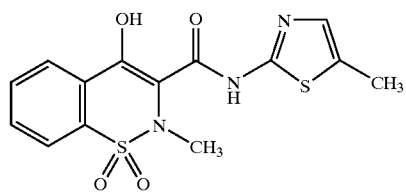

Meloxicam, (CAS registry number 71125-38-7)

In another embodiment of the invention, the compound ABT-963 having the formula C-66 that has been previously described in International Publication number WO 00/24719 (which is herein incorporated by reference), is another tricyclic cyclooxygenase-2 selective inhibitor which may be advantageously employed in the combination therapy of the present invention.

C-66)

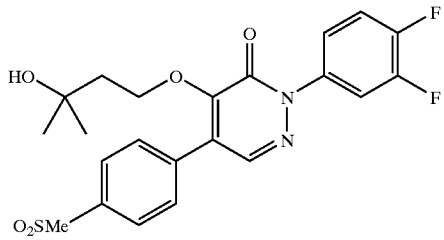

In another embodiment of the present invention, the Cyclooxygenase-2 selective inhibitor is COX-189, Novartis AG, Basel, Switzerland, formula C-67:

C-67)

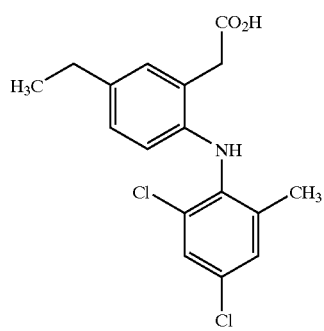

Derivatives are intended to encompass any compounds which are structurally related to the cyclooxygenase-2 inhibitors or which possess the substantially equivalent biologic activity. By way of example, such inhibitors may include, but are not limited to, prodrugs thereof.

The term "aldosterone antagonist" denotes a compound capable of binding to an aldosterone receptor, as a competitive inhibitor of the action of aldosterone itself at the receptor site, so as to modulate the receptor-mediated activity of aldosterone.

Aldosterone Antagonists

The aldosterone antagonists used in the methods of the present invention generally are spirolactone-type steroidal compounds. The term "spirolactone-type" is intended to characterize a structure comprising a lactone moiety attached to a steroid nucleus, typically at the steroid "D" ring, through a spiro bond configuration. A subclass of spirolactone-type aldosterone antagonist compounds consists of epoxy-steroidal aldosterone antagonist compounds such as eplerenone. Another subclass of spirolactone-type antagonist compounds consists of non-epoxy-steroidal aldosterone antagonist compounds such as spironolactone.

The epoxy-steroidal aldosterone antagonist compounds used in the method of the present invention generally have a steroidal nucleus substituted with an epoxy-type moiety. The term "epoxy-type" moiety is intended to embrace any moiety characterized in having an oxygen atom as a bridge between two carbon atoms, examples of which include the following moieties:

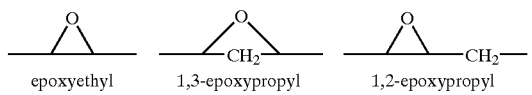

epoxyethyl    1,3-epoxypropyl    1,2-epoxypropyl

The term "steroidal", as used in the phrase "epoxy-steroidal", denotes a nucleus provided by a cyclopentenophenanthrene moiety, having the conventional "A", "B", "C" and "D" rings. The epoxy-type moiety may be attached to the cyclopentenophenanthrene nucleus at any attachable or substitutable positions, that is, fused to one of the rings of the steroidal nucleus or the moiety may be substituted on a ring member of the ring system. The phrase "epoxy-steroidal" is intended to embrace a steroidal nucleus having one or a plurality of epoxy-type moieties attached thereto.

Epoxy-steroidal aldosterone antagonists suitable for use in the present methods include a family of compounds having an epoxy moiety fused to the "C" ring of the steroidal nucleus. Especially preferred are 20-spiroxane compounds characterized by the presence of a 9α,11α-substituted epoxy moiety. Compounds 1 through 11, Table 1 below, are illustrative 9α,11α-epoxy-steroidal compounds that may be used in the present methods. These epoxy steroids may be prepared by procedures described in Grob et al., U.S. Pat. No. 4,559,332. Additional processes for the preparation of 9,11-epoxy steroidal compounds and their salts are disclosed in Ng et al., WO97/21720 and Ng et al., WO98/25948.

TABLE I

Aldosterone Receptor Antagonist

| Compound # | Structure and Name |
|---|---|
| 1 | Pregn-4-ene-7,21-dicarboxylic acid, 9,11-epoxy-17-hydroxy-3-oxo-, γ-lactone, methyl ester, (7α, 11α, 17α)- |
| 2 | Pregn-4-ene-7,21-dicarboxylic acid, 9,11-epoxy-17-hydroxy-3-oxo-, dimethyl ester, (7α, 11α, 17β)- |
| 3 | 3′H-cyclopropa[6,7]pregna-4,6-diene-21-carboxylic acid, 9,11-epoxy-6,7-dihydro-17-hydroxy-3-oxo-, γ-lactone, (6β, 7β, 11α, 17β)- |
| 4 | Pregn-4-ene-7,21-dicarboxylic acid, 9,11-epoxy-17-hydroxy-3-oxo-, 7-(1-methylethyl) ester, monopotassium salt, (7α, 11α, 17β)- |
| 5 | Pregn-4-ene-7,21-dicarboxylic acid, 9,11-epoxy-17-hydroxy-3-oxo-, 7-methylethyl) ester, monopotassium salt, (7α, 11α, 17β)- |
| 6 | 3′H-cyclopropa[6,7]pregna-1,4,6-triene-21-carboxylic acid, 9,11-epoxy-6,7-dihydro-17-hydroxy-3-oxo-, γ-lactone, (6β, 7β, 11α)- |
| 7 | 3′H-cyclopropa[6,7]pregna-4,6-diene-21-carboxylic acid, 9,11-epoxy-6,7-dihydro-17-hydroxy-3-oxo-, methyl ester, (6β, 7β, 11α, 17β)- |
| 8 | 3′H-cyclopropa[6,7]pregna-4,6-diene-21-carboxylic acid, 9,11-epoxy-6,7-dihydro-17-hydroxy-3-oxo-, monopotassium salt, (6β, 7β, 11α, 17β)- |

TABLE I-continued

Aldosterone Receptor Antagonist

| Compound # | Structure and Name |
|---|---|
| 9 | 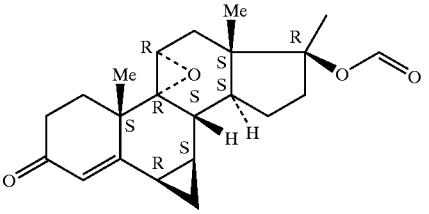<br>3'H-cyclopropa[6,7]pregna-1,4,6-triene-21-carboxylic acid, 9,11-epoxy-6,7-dihydro-17-hydroxy-3-oxo-, γ-lactone (6β, 7β, 11α, 17β)- |
| 10 | 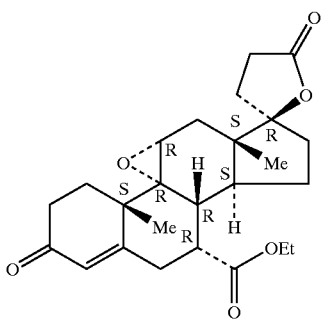<br>Pregn-4-ene-7,21-dicarboxylic acid, 9,11-epoxy-17-hydroxy-3-oxo-, γ-lactone, ethyl ester, (7α, 11α, 17β)- |
| 11 | 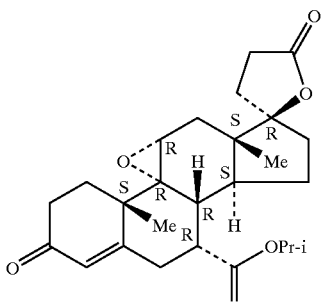<br>Pregn-4-ene-7,21-dicarboxylic acid, 9,11-epoxy-17-hydroxy-3-oxo-, γ-lactone, 1-methylethyl ester, (7α, 11α, 17β)- |

Of particular interest is the compound eplerenone (also known as epoxymexrenone) which is compound 1 as shown above. Eplerenone is an aldosterone receptor antagonist and has a higher specificity for aldosterone receptors than does, for example, spironolactone. Selection of eplerenone as the aldosterone antagonist in the present method would be beneficial to reduce certain side-effects such as gynecomastia that occur with use of aldosterone antagonists having less specificity.

Non-epoxy-steroidal aldosterone antagonists suitable for use in the present methods include a family of spirolactone-type compounds defined by Formula I:

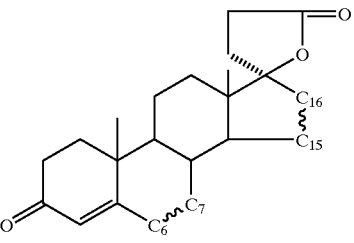

wherein $C_6 \sim C_7$ is 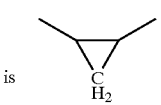 or H—SCOR, wherein R is lower alkyl of up to 5 carbon atoms, and wherein $C_{15} \sim C_{16}$ is 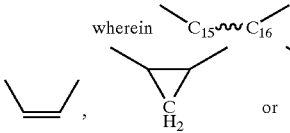.

Lower alkyl residues include branched and unbranched groups, preferably methyl, ethyl and n-propyl.

Specific compounds of interest within Formula I are the following:

7α-acetylthio-3-oxo-4,15-androstadiene-[17(β-1')-spiro-5'] perhydrofuran-2'-one;

3-oxo-7α-propionylthio-4,15-androstadiene-[17((β-1')-spiro-5']perhydrofuran-2'-one;

6β,7β-methylene-3-oxo4,15-androstadiene-[17((β-1')-spiro-5']perhydrofuran-2'-one;

15α,16α-methylene-3-oxo-4,7α-propionylthio-4-androstene[17(β-1')-spiro-5']perhydrofuran-2'-one;

6β,7β,15α,16α-dimethylene-3-oxo-4-androstene[17(β-1')-spiro-5']-perhydrofuran-2'-one;

7α-acetylthio-15β,16β-Methylene-3-oxo-4-androstene-[17(β-1')-spiro-5']perhydrofuran-2'-one;

15β,16β-methylene-3-oxo-7β-propionylthio-4-androstene-[17(β(β-1')-spiro-5']perhydrofuran-2'-one; and 6β,7β,15β,16β-dimethylene-3-oxo-4-androstene-[17(β-1')-spiro-5']perhydrofuran-2'-one.

Methods to make compounds of Formula I are described in U.S. Pat. No. 4,129,564 to Wiechart et al. issued on Dec. 12, 1978.

Another family of non-epoxy-steroidal compounds of interest is defined by Formula II:

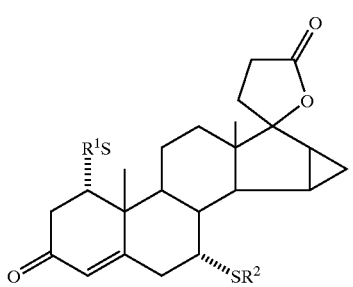

wherein $R^1$ is $C_{1-3}$-alkyl or $C_{1-3}$ acyl and $R^2$ is H or $C_{1-3}$-alkyl.

Specific compounds of interest within Formula II are the following:

1α-acetylthio-15β,16β-methylene-7α-methylthio-3-oxo-17α-pregn-4-ene-21,17-carbolactone; and 15β,16β-methylene-1α,7α-dimethylthio-3-oxo-17α-pregn-4-ene-21,17-carbolactone.

Methods to make the compounds of Formula II are described in U.S. Pat. No. 4,789,668 to Nickisch et al. which issued Dec. 6, 1988.

Yet another family of non-epoxy-steroidal compounds of interest is defined by a structure of Formula III:

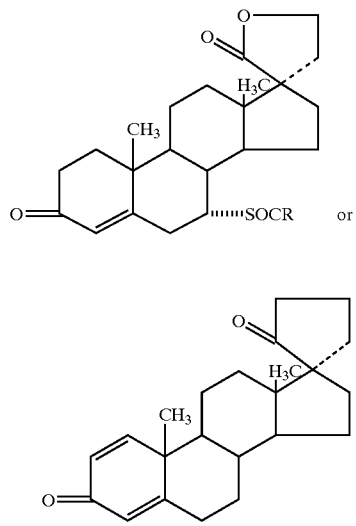

(III)

wherein R is lower alkyl, with preferred lower alkyl groups being methyl, ethyl, propyl and butyl. Specific compounds of interest include:

3β,21-dihydroxy-17α-pregna-5,15-diene-17-carboxylic acid γ-lactone;

3β,21-dihydroxy-17α-pregna-5,15-diene-17-carboxylic acid γ-lactone 3-acetate;

3β,21-dihydroxy-17α-pregn-5-ene-17-carboxylic acid γ-lactone;

3β,21-dihydroxy-17α-pregn-5-ene-17-carboxylic acid γ-lactone 3-acetate;

21-hydroxy-3-oxo-17α-pregn-4-ene-17-carboxylic acid γ-lactone;

21-hydroxy-3-oxo-17α-pregna-4,6-diene-17-carboxylic acid γ-lactone;

21-hydroxy-3-oxo-17α-pregna-1,4-diene-17-carboxylic acid γ-lactone;

7α-acylthio-21-hydroxy-3-oxo-17α-pregn-4-ene-17-carboxylic acid γlactone; and

7α-acetylthio-21-hydroxy-3-oxo-17α-pregn-4-ene-17-carboxylic acid γ-lactone.

Methods to make the compounds of Formula III are described in U.S. Pat. No. 3,257,390 to Patchett which issued Jun. 21, 1966.

Still another family of non-epoxy-steroidal compounds of interest is represented by Formula IV:

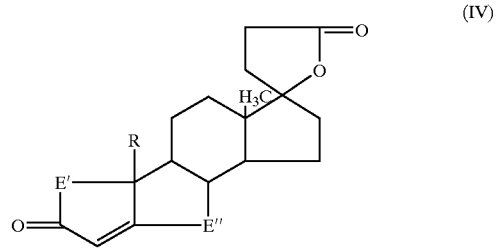

(IV)

wherein E' is selected from the group consisting of ethylene, vinylene and (lower alkanoyl)thioethylene radicals, E" is selected from the group consisting of ethylene, vinylene, (lower alkanoyl)thioethylene and (lower alkanoyl)thiopropylene radicals; R is a methyl radical except when E' and E" are ethylene and (lower alkanoyl) thioethylene radicals, respectively, in which case R is selected from the group consisting of hydrogen and methyl radicals; and the selection of E' and E" is such that at least one (lower alkanoyl)thio radical is present.

A preferred family of non-epoxy-steroidal compounds within Formula IV is represented by Formula V:

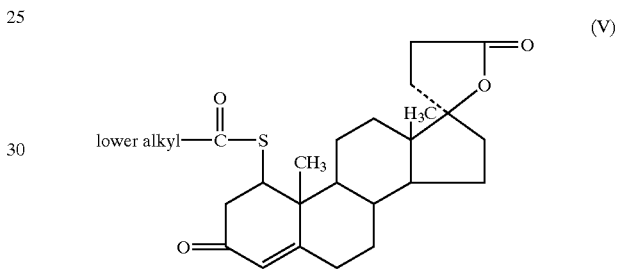

(V)

A more preferred compound of Formula V is 1-acetylthio-17α-(2-carboxyethyl)-17β-hydroxy-androst-4-en-3-one lactone.

Another preferred family of non-epoxy-steroidal compounds within Formula IV is represented by Formula VI:

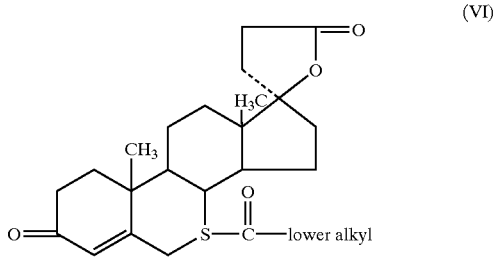

(VI)

More preferred compounds within Formula VI include the following:

7α-acetylthio-17α-(2-carboxyethyl)-17β-hydroxy-androst-4-en-3-one lactone;

7β-acetylthio-17α-(2-carboxyethyl)-17β-hydroxy-androst-4-en-3-one lactone;

1α,7α-diacetylthio-17α-(2-carboxyethyl)-17β-hydroxy-androsta-4,6-dien-3-one lactone;

7α-acetylthio-17α-(2-carboxyethyl)-17β-hydroxy-androsta-1,4-dien-3-one lactone;

7α-acetylthio-17α-(2-carboxyethyl)-17β-hydroxy-19-norandrost-4-en-3-one lactone; and 7α-acetylthio-17α-(2-carboxyethyl)-17β-hydroxy-6α-methylandrost-4-en-3-one lactone;

In Formulae IV–VI, the term "alkyl" is intended to embrace linear and branched alkyl radicals containing one to about eight carbons. The term "(lower alkanoyl)thio" embraces radicals of the formula lower alkyl

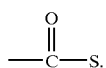

Of particular interest is the compound spironolactone having the following structure and formal name:

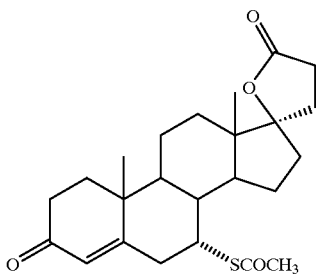

"spironolactone": 17-hydroxy-7α-mercapto-3-oxo-17α-pregn-4-ene-21-carboxylic acid γ-lactone acetate.

Methods to make compounds of Formulae IV–VI are described in U.S. Pat. No. 3,013,012 to Cella et al. which issued Dec. 12, 1961. Spironolactone is sold by G.D. Searle & Co., Skokie, Ill., under the trademark "ALDACTONE", in tablet dosage form at doses of 25 mg, 50 mg and 10.0 mg per tablet.

Another family of steroidal aldosterone antagonists is exemplified by drospirenone, [6R-(6alpha, 7alpha, 8beta, 9alpha, 10beta, 13beta, 14alpha, 15alpha, 16alpha, 17beta)]-1,3',4',6,7,8,9,10,11,12,13,14,15,16,20,21-hexadecahydro-10,13-dimethylspiro[17H-dicyclopropa[6,7:15,16]cyclopenta[a]phenanthrene-17,2'(5'H)-furan]-3,5'(2H)-dione, CAS registration number 67392-87-4. Methods to make and use drospirenone are described in patent GB 1550568 1979, priority DE 2652761 1976.

Definitions

The term "treatment" or "treating" includes the administration, to a person in need, of an amount of an aldosterone antagonist and cyclooxygenase-2 inhibitor combination which will inhibit or reverse development of a pathological cardiovascular condition.

The term "prevention" or "preventing" includes either preventing the onset of clinically evident cardiovascular disorders altogether or preventing the onset of a preclinically evident stage of cardiovascular disorder in individuals. This includes prophylactic treatment of those at risk of developing a cardiovascular disorder.

The phrase "therapeutically-effective" is intended to qualify the amount of the two agents given in combination which will achieve the goal of improvement in disorder severity and the frequency of incidence, while avoiding adverse side effects.

The term "subject" for purposes of treatment includes any human or animal subject who is susceptible to or suffering from a cardiovascular disorders, and preferably is a human subject. The subject, for example, may be at risk due to diet, exposure to bacterial or viral infection, having common markers present, being genetically predisposed to the cardiovascular disorders, and the like.

The terms "aldosterone antagonist" and "aldosterone receptor antagonist" include a compound that inhibits the binding of aldosterone to mineralocorticoid receptors thereby blocking the biological effects of aldosterone.

The term "pro-inflammmatory" characterizes molecules produced in the body to induce, activate or enhance an inflammatory response in a tissue or organ.

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkenyl" embraces linear or branched radicals having at least one carbon-carbon double bond of two to about twenty carbon atoms or, preferably, two to about twelve carbon atoms. More preferred alkyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl", "lower alkenyl", embrace radicals having "cis" and "trans" orientations, or alternatively, "E" and "Z" orientations. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl, cyclopentadienyl, and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl., dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclyl" embraces saturated, partially unsaturated and unsaturated heteroatom-containing ring-shaped radicals, where the heteroatoms may be selected from nitrogen, sulfur and oxygen. Examples of saturated heterocyclyl radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. The term "heteroaryl" embraces unsaturated heterocyclyl radicals. Examples of unsaturated heterocyclyl radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b] pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term also embraces radicals where heterocyclyl radicals are fused with aryl radicals. Examples of such fused bicyclic radicals include benzofuran, benzothiophene, and the like. Said "heterocyclyl group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote NH$_2$O$_2$S—. The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl. The term "carbonyl", whether used alone or with other terms, such as "alkoxycarbonyl", denotes —(C=O)—. The term "aroyl" embraces aryl radicals with a carbonyl radical as defined above. Examples of aroyl include benzoyl, naphthoyl, and the like and the aryl in said aroyl may be additionally substituted. The terms "carboxy" or "carboxyl", whether used alone or with other terms, such as "carboxyalkyl", denotes —CO$_2$H. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl porions having 1 to 6 carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined above, attached to a carbonyl radical. Examples of such radicals include substituted or unsubstituted methylcarbonyl, ethylcarbonyl, phenylcarbonyl and benzylcarbonyl. The term "aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heterocyclylalkyl" embraces saturated and partially unsaturated heterocyclyl-substituted alkyl radicals, such as pyrrolidinylmethyl, and heteroaryl-substituted alkyl radicals, such as pyridylmethyl, quinolylmethyl, thienylmethyl, furylethyl, and quinolyl-ethyl. The heteroaryl in said heteroaralkyl may be additionally substituted with halo, alkyl, alkoxy, halkoalkyl and haloalkoxy. The term "aralkoxy" embraces aralkyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "aminoalkyl" embraces alkyl radicals substituted with one or more amino radicals. More preferred are "lower aminoalkyl" radicals. Examples of such radicals include aminomethyl, aminoethyl, and the like. The term "alkylamino" denotes amino groups which have been substituted with one or two alkyl radicals. Preferred are "lower N-alkylamino" radicals having alkyl portions having 1 to 6 carbon atoms. Suitable lower alkylamino may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an amino nitrogen atom to other radicals. The terms "N-arylaminoalkyl" and "N-aryl-N-alkyl-aminoalkyl" denote amino groups which have been substituted with one aryl radical or one aryl and one alkyl radical, respectively, and having the amino group attached to an alkyl radical. Examples of such radicals include N-phenylaminomethyl and N-phenyl-N-methylaminomethyl. The term "aminocarbonyl" denotes an amide group of the formula —C(=O)NH$_2$. The term "alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined above. The term "alkylaminoalkyl" embraces radicals having one or more alkyl radicals attached to an aminoalkyl radical. The term "aryloxyalkyl" embraces radicals having an aryl radical attached to an alkyl radical through a divalent oxygen atom. The term "arylthioalkyl" embraces radicals having an aryl radical attached to an alkyl radical through a divalent sulfur atom.

The compounds utilized in the methods of the present invention may be present in the form of free bases or pharmaceutically acceptable acid addition salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, b-hydroxybutyric, salicylic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, for example, the appropriate acid or base with the compound.

The present invention comprises a pharmaceutical composition for the prevention of cardiovascular disorders, comprising a therapeutically-effective amount of an aldosterone antagonist and cyclooxygenase-2 inhibitor combination in association with at least one pharmaceutically-acceptable carrier, adjuvant or diluent (collectively referred to herein as "carrier" materials) and, if desired, other active ingredients. The active compounds of the present invention may be administered by any suitable route known to those-skilled in the art, preferably in the form of a pharmaceutical composition adapted to such a route, and in a dose effective for the treatment intended. The active compounds and composition may, for example, be administered orally, intravascularly, intraperitoneally, intranasally, intrabronchially, subcutaneously, intramuscularly or topically (including aerosol).

Administration of aldosterone antagonist and cyclooxygenase-2 inhibitor combination may take place sequentially in separate formulations, or may be accomplished by simultaneous administration in a single formulation or separate formulations. Administration may be accomplished by oral route, or by intravenous, intramuscular or subcutaneous injections. The formulation may be in the form of a bolus, or in the form of aqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropyl-methyl cellulose, together with one or more of a lubricant, preservative, surface-active or dispersing agent.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of each active ingredient from about 1 to 250 mg, preferably from about 25 to 150 mg. A suitable daily dose for a mammal may vary widely depending on the condition of the patient and other factors. However, a dose of from about 0.01 to 30 mg/kg body weight, particularly from about 1 to 15 mg/kg body weight, may be appropriate.

The active ingredients may also be administered by injection as a composition wherein, for example, saline, dextrose or water may be used as a suitable carrier. A suitable daily dose of each active component is from about 0.01 to 15 mg/kg body weight injected per day in multiple doses depending on the disease being treated. A preferred daily dose would be from about 1 to 10 mg/kg body weight. Compounds indicated for prophylactic therapy will preferably be administered in a daily dose generally in a range from about 0.1 mg to about 15 mg per kilogram of body weight per day. A more preferred dosage will be a range from about 1 mg to about 15 mg per kilogram of body weight. Most preferred is a dosage in a range from about 1 to about 10 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

In combination therapy, the aldosterone receptor antagonist may be present in an amount in a range from about 5 mg to about 400 mg, and the cyclooxygenase-2 inhibitor may be present in an amount in a range from about 1 mg to about 200 mg, which represents aldosterone antagonist-to-cyclooxygenase-2 inhibitor ratios ranging from about 400:1 to about 1:40.

In a preferred combination therapy, the aldosterone receptor antagonist may be present in an amount in a range from about 10 mg to about 200 mg, and the cyclooxygenase-2 inhibitor may be present in an amount in a range from about 5 mg to about 100 mg, which represents aldosterone antagonist-to-cyclooxygenase-2 inhibitor ratios ranging from about 40:1 to about 1:10.

In a more preferred combination therapy, the aldosterone receptor antagonist may be present in an amount in a range from about 20 mg to about 100 mg, and cyclooxygenase-2 inhibitor may be present in an amount in a range from about 10 mg to about 80 mg, which represents aldosterone antagonist-to-cyclooxygenase-2 inhibitor ratios ranging from about 10:1 to about 1:4.

The dosage regimen for treating a disease condition with the combination therapy of this invention is selected in accordance with a variety of factors, including the type, age, weight, sex and medical condition of the patient, the severity of the disease, the route of administration, and the particular compound employed, and thus may vary widely.

For therapeutic purposes, the active components of this combination therapy invention are ordinarily combined with one or more adjuvants appropriate to the indicated route of administration. If administered per os, the components may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The components may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The present invention further comprises kits that are suitable for use in performing the methods of treatment and/or prophylaxis described above. In one embodiment, the kit contains a first dosage form comprising one or more of the epoxy-steroidal aldosterone antagonists previously identified and a second dosage form comprising a beta-adrenergic antagonist identified in Table 2 in quantities sufficient to carry out the methods of the present invention. Preferably, the first dosage form and the second dosage form together comprise a therapeutically effective amount of the inhibitors.

Solid State Forms of Epoxy-Steroidal Aldosterone Antagonists

The methods of the present invention encompass the administration of a therapeutically-effective amount of eplerenone in any of its solid state forms, either as one or more solid state forms per se or in the form of a pharmaceutical composition comprising one or more solid state forms of eplerenone. These novel solid state forms include, but are not limited to, solvated crystalline eplerenone, non-solvated crystalline eplerenone, and amorphous eplerenone.

In one embodiment, the eplerenone administered in accordance with the methods of the present invention is a non-solvated crystalline form of eplerenone having the X-ray powder diffraction pattern set forth in Table 1A below (referred to herein as the "higher melting point polymorph" or "Form H").

In another embodiment, the eplerenone is administered in the form of a pharmaceutical composition wherein the entire amount of eplerenone contained in the composition is present as phase pure Form H.

In another embodiment, the eplerenone is administered in the form of a pharmaceutical composition wherein the entire amount of eplerenone contained in the composition is present as phase pure Form L. In another embodiment, the eplerenone is administered in the form of a pharmaceutical composition wherein the entire amount of eplerenone contained in the composition is present as a phase pure solvated crystalline eplerenone.

In another embodiment, the eplerenone is administered in the form of a pharmaceutical composition wherein the entire amount of eplerenone contained in the composition is present as amorphous eplerenone.

In another embodiment, the eplerenone is administered in the form of a pharmaceutical composition wherein the composition comprises a first solid state form of eplerenone and a second solid state form of eplerenone, and the first and second solid state forms of eplerenone are selected from Form H, Form L, solvated eplerenone and amorphous eplerenone. In general, the weight ratio of said first solid state form to said second solid state form preferably is at least about 1:9, preferably about 1:1, more preferably at least about 2:1, more preferably at least about 5:1, and still more preferably at least about 9:1.

In another embodiment, the eplerenone is administered in the form of a pharmaceutical composition wherein the composition comprises both Form H and Form L. The ratio of the amount of Form L to Form H in the composition generally is between about 1:20 to about 20:1. In other embodiments, for example, this ratio is between about 10:1 to about 1:10; about 5:1 to about 1:5; about 2:1 to about 1:2; or about 1:1.

Although each of the above embodiments can embrace the administration of a solid state form of eplerenone over a broad range of eplerenone particle sizes, it has been discovered that coupling the selection of the solid state form of eplerenone with a reduction of the eplerenone particle size can improve the bioavailability of unformulated eplerenone and pharmaceutical compositions comprising that solid state form of eplerenone.

In one such embodiment, the $D_{90}$ particle size of the unformulated eplerenone or the eplerenone used as a starting material in the pharmaceutical composition generally is less than about 400 microns, preferably less than about 200 microns, more preferably less than about 150 microns, still more preferably less than about 100 microns, and still more preferably less than about 90 microns. In another embodiment, the $D_{90}$ particle size is between about 40 microns to about 100 microns. In another embodiment, the $D_{90}$ particle size is between about 30 microns to about 50 microns. In another embodiment, the $D_{90}$ particle size is between about 50 microns to about 150 microns. In another embodiment, the $D_{90}$ particle size is between about 75 microns to about 125 microns.

In another such embodiment, the $D_{90}$ particle size of the unformulated eplerenone or the eplerenone used as a starting material in the pharmaceutical composition generally is less than about 15 microns, preferably less than about 1 micron, more preferably less than about 800 nm, still more preferably less than about 600 nm, and still more preferably less than about 400 nm. In another embodiment, the $D_{90}$ particle size is between about 10 nm to about 1 micron. In another embodiment, the $D_{90}$ particle size is between about 100 nm to about 800 nm. In another embodiment, the $D_{90}$ particle size is between about 200 nm to about 600 nm. In another embodiment, the $D_{90}$ particle size is between about 400 nm to about 800 nm.

Solid state forms of eplerenone having a particle size less than about 15 microns can be prepared in accordance with applicable particle size reduction techniques known in the art. Such techniques include, but are not limited to those described in U.S. Pat. Nos. 5,145,684, 5,318,767, 5,384,124 and 5,747,001. U.S. Pat. Nos. 5,145,684, 5,318,767, 5,384,124 and 5,747,001 are expressly incorporated by reference as if fully set forth at length. In accordance with the method of U.S. Pat. No. 5,145,684, for example, particles of suitable size are prepared by dispersing the eplerenone in a liquid dispersion medium and wet-grinding the mixture in the presence of grinding media to reduce the particles to the desired size. If necessary or advantageous, the particles can be reduced in size in the presence of a surface modifier.

Definitions

The term "amorphous" as applied to eplerenone refers to a solid state wherein the eplerenone molecules are present in a disordered arrangement and do not form a distinguishable crystal lattice or unit cell. When subjected to X-ray powder diffraction, amorphous eplerenone does not produce any characteristic crystalline peaks.

Where reference is made in this application to the "boiling point" of a substance or solution, the term "boiling point" means the boiling point of the substance or solution under the applicable process conditions.

The term "crystalline form" as applied to eplerenone refers to a solid state form wherein the eplerenone molecules are arranged to form a distinguishable crystal lattice (i) comprising distinguishable unit cells, and (ii) yielding diffraction peaks when subjected to X-ray radiation.

The term "crystallization" as used throughout this application can refer to crystallization and/or recrystallization depending upon the applicable circumstances relating to the preparation of the eplerenone starting material.

The term "digestion" means a process in which a slurry of solid eplerenone in a solvent or mixture of solvents is heated at the boiling point of the solvent or mixture of solvents under the applicable process conditions.

The term "direct crystallization" as used herein refers to the crystallization of eplerenone directly from a suitable solvent without the formation and desolvation of an intermediate solvated crystalline solid state form of eplerenone.

The term "particle size" as used herein refers to particle size as measured by conventional particle size measuring techniques well known in the art, such as laser light scattering, sedimentation field flow fractionation, photon correlation spectroscopy, or disk centrifugation. The term "$D_{90}$ particle size" means the particle size of at least 90% of the particles as measured by such conventional particle size measuring techniques.

The term "purity" means the chemical purity of eplerenone according to conventional HPLC assay. As used herein, "low purity eplerenone" generally means eplerenone that contains an effective amount of a Form H growth promoter and/or a Form L growth inhibitor. As used herein, "high purity eplerenone" generally means eplerenone that does not contain, or contains less than an effective amount of, a Form H growth promoter and/or a Form L growth inhibitor.

The term "phase purity" means the solid state purity of eplerenone with regard to a particular crystalline or amorphous form of the eplerenone as determined by the infrared spectroscopy analytical methods described herein.

The term "XPRD" means X-ray powder diffraction.

The term "$T_m$" means melting temperature.

Characterization of Solid State Form
1. Molecular Conformation

Single crystal X-ray analysis indicates that the eplerenone molecular conformation differs between Form H and Form L, particularly with respect to the orientation of the ester group at the 7-position of the steroid ring. The orientation of the ester group can be defined by the C8-C7-C23-02 torsion angle.

In the Form H crystal lattice, the eplerenone molecule adopts a conformation in which the methoxy group of the ester is approximately aligned with the C—H bond at the 7-position and the carbonyl group is approximately positioned over the center of the B-steroid ring. The C8-C7-C23-02 torsion angle is approximately −73.0° in this conformation. In this orientation, the carbonyl oxygen atom of the ester group (01) is in close contact with the oxygen atom of the 9,11-epoxide ring (04). The 01–04 distance is about 2.97 Å, which is just below the van der Waal's contact distance of 3.0 Å (assuming van der Waal's radii of 1.5 Å for the oxygen).

In the Form L crystal lattice, the eplerenone molecule adopts a conformation in which the ester group is rotated approximately 1500 relative to that of Form H and has a C8-C7-C23-02 torsion angle of approximately +76.90. In this orientation, the methoxy group of the ester is directed toward the 4,5-alkene segment of the A-steroid ring. In this orientation, the distance between either oxygen atom of the ester group (01,02) and the oxygen atom of the 9,11-epoxide ring is increased relative to the distance determined for Form H. The 02–04 distance is approximately 3.04 Å, falling just above the van der Waal's contact distance. The 01–04 distance is about 3.45 Å.

The eplerenone molecule appears to adopt a conformation characteristic of Form L in the solvated crystalline forms analyzed by single crystal X-ray diffraction to date.

2. X-Ray Powder Diffraction

The various crystalline forms of eplerenone were analyzed with either a Siemens D5000 powder diffractometer or an Inel Multipurpose Diffractometer. For the Siemens D500 powder diffractometer, the raw data was measured for 2q values from 2 to 50, with steps of 0.020 and step periods of two seconds. For the Inel Multipurpose Diffractometer, samples were placed in an aluminum sample holder and raw data was collected for 30 minutes at all two theta values simultaneously.

Tables 1A, 1B and 1C set out the significant parameters of the main peaks in terms of 2q values and intensities for the Form H (prepared by desolvation of the ethanol solvate obtained by digestion of low purity eplerenone), Form L (prepared by desolvation of the methyl ethyl ketone solvate obtained by recrystallization of high purity eplerenone), and methyl ethyl ketone solvate (prepared by room temperature slurry conversion of high purity eplerenone in methyl ethyl ketone) crystalline forms of eplerenone, respectively (X-ray radiation at a wavelength of 1.54056 Angstroms).

Minor shifts in peak positioning may be present in the diffraction patterns of Form H and Form L as a result of imperfections in the spacing of the crystal diffraction planes due to the route of manufacture of Form H and Form L (i.e. desolvation of a solvate). In addition, Form H is isolated from a solvate prepared by digestion of crude eplerenone. This method results in a lower overall chemical purity (approximately 90%) of the Form H. Finally, the solvated forms of eplerenone are expected to show some shifting in the positioning of the diffraction peaks due to the increased mobility of the solvent molecules within the solvent channels in the crystal lattice.

TABLE 1A

FORM H DATA

| Angle 2-theta | d-spacing Angstrom | Intensity | Intensity % |
|---|---|---|---|
| 6.994 | 12.628 | 1188 | 7.2 |
| 8.291 | 10.655 | 2137 | 13 |
| 10.012 | 8.827 | 577 | 3.5 |
| 11.264 | 7.849 | 1854 | 11.3 |
| 12.04 | 7.344 | 7707 | 46.8 |
| 14.115 | 6.269 | 3121 | 19 |
| 14.438 | 6.13 | 15935 | 96.8 |
| 15.524 | 5.703 | 637 | 3.9 |
| 16.169 | 5.477 | 1349 | 8.2 |
| 16.699 | 5.305 | 1663 | 10.1 |
| 16.94 | 5.23 | 1692 | 10.3 |
| 17.147 | 5.167 | 2139 | 13 |
| 17.66 | 5.018 | 6883 | 41.8 |
| 17.91 | 4.949 | 16455 | 100 |
| 18.379 | 4.823 | 3106 | 18.9 |
| 18.658 | 4.752 | 1216 | 7.4 |
| 19.799 | 4.48 | 1499 | 9.1 |
| 20.235 | 4.385 | 383 | 2.3 |
| 21.707 | 4.091 | 1267 | 7.7 |

TABLE 1A-continued

FORM H DATA

| Angle 2-theta | d-spacing Angstrom | Intensity | Intensity % |
|---|---|---|---|
| 21.8 | 4.073 | 1260 | 7.7 |
| 21.959 | 4.044 | 1279 | 7.8 |
| 22.461 | 3.955 | 4264 | 25.9 |
| 23.191 | 3.832 | 1026 | 6.2 |
| 23.879 | 3.723 | 1000 | 6.1 |
| 24.599 | 3.616 | 1688 | 10.3 |
| 25.837 | 3.445 | 931 | 5.7 |
| 26.034 | 3.42 | 686 | 4.2 |
| 26.868 | 3.316 | 912 | 5.5 |
| 27.093 | 3.288 | 1322 | 8 |
| 27.782 | 3.209 | 1236 | 7.5 |
| 28.34 | 3.147 | 1845 | 11.2 |
| 28.861 | 3.091 | 957 | 5.8 |
| 29.866 | 2.9892 | 745 | 4.5 |
| 30.627 | 2.9166 | 992 | 6 |
| 31.108 | 2.8726 | 1205 | 7.3 |
| 33.215 | 2.6951 | 1287 | 7.8 |
| 33.718 | 2.656 | 802 | 4.9 |
| 34.434 | 2.6024 | 914 | 5.6 |

TABLE 1B

FORM L DATA

| Angle 2-theta | d-spacing Angstrom | Intensity Cps | Intensity % |
|---|---|---|---|
| 7.992 | 11.054 | 11596 | 26.6 |
| 10.044 | 8.799 | 12048 | 27.6 |
| 11.206 | 7.889 | 4929 | 11.3 |
| 12.441 | 7.109 | 1747 | 4 |
| 12.752 | 6.936 | 4340 | 9.9 |
| 13.257 | 6.673 | 2444 | 5.6 |
| 14.705 | 6.019 | 43646 | 100 |
| 15.46 | 5.727 | 2670 | 6.1 |
| 15.727 | 5.63 | 7982 | 18.3 |
| 16.016 | 5.529 | 3519 | 8.1 |
| 17.671 | 5.015 | 8897 | 20.4 |
| 17.9 | 4.951 | 2873 | 6.6 |
| 18.352 | 4.83 | 612 | 1.4 |
| 18.703 | 4.74 | 689 | 1.6 |
| 19.524 | 4.543 | 1126 | 2.6 |
| 20.103 | 4.413 | 3753 | 8.6 |
| 20.63 | 4.302 | 1451 | 3.3 |
| 21.067 | 4.214 | 876 | 2 |
| 21.675 | 4.097 | 2760 | 6.3 |
| 22.232 | 3.995 | 1951 | 4.5 |
| 22.652 | 3.922 | 1657 | 3.8 |
| 23.624 | 3.763 | 827 | 1.9 |
| 24.279 | 3.663 | 1242 | 2.8 |
| 25.021 | 3.556 | 5144 | 11.8 |
| 25.485 | 3.492 | 1702 | 3.9 |
| 25.707 | 3.463 | 2493 | 5.7 |
| 26.251 | 3.392 | 1371 | 3.1 |
| 26.85 | 3.318 | 1970 | 4.5 |
| 27.319 | 3.262 | 1029 | 2.4 |
| 27.931 | 3.192 | 440 | 1 |
| 27.969 | 3.187 | 440 | 1 |
| 28.937 | 3.083 | 1128 | 2.6 |
| 29.703 | 3.005 | 1211 | 2.8 |
| 30.173 | 2.9594 | 1506 | 3.5 |
| 30.584 | 2.9206 | 1602 | 3.7 |
| 30.885 | 2.8928 | 1550 | 3.6 |
| 31.217 | 2.8628 | 1068 | 2.4 |
| 31.605 | 2.8285 | 1038 | 2.4 |
| 32.059 | 2.7895 | 1211 | 2.8 |
| 32.64 | 2.7412 | 684 | 1.6 |
| 32.747 | 2.7324 | 758 | 1.7 |
| 33.46 | 2.6759 | 506 | 1.2 |

TABLE 1B-continued

FORM L DATA

| Angle 2-theta | d-spacing Angstrom | Intensity Cps | Intensity % |
|---|---|---|---|
| 34.194 | 2.6201 | 1085 | 2.5 |
| 34.545 | 2.5943 | 915 | 2.1 |

TABLE 1C

METHYL ETHYL KETONE DATA

| Angle 2-theta | d-spacing Angstrom | Intensity Cps | Intensity % |
|---|---|---|---|
| 7.584 | 11.648 | 5629 | 32.6 |
| 7.753 | 11.393 | 15929 | 92.3 |
| 10.151 | 8.707 | 2877 | 16.7 |
| 11.31 | 7.817 | 701 | 4.1 |
| 12.646 | 6.994 | 1027 | 5.9 |
| 13.193 | 6.705 | 15188 | 88 |
| 13.556 | 6.526 | 14225 | 82.4 |
| 14.074 | 6.287 | 1966 | 11.4 |
| 14.746 | 6.002 | 2759 | 16 |
| 15.165 | 5.837 | 801 | 4.6 |
| 15.548 | 5.694 | 1896 | 11 |
| 17.031 | 5.202 | 7980 | 46.2 |
| 17.28 | 5.127 | 17267 | 100 |
| 17.706 | 5.005 | 6873 | 39.8 |
| 18.555 | 4.778 | 545 | 3.2 |
| 18.871 | 4.699 | 1112 | 6.4 |
| 19.766 | 4.488 | 1704 | 9.9 |
| 20.158 | 4.401 | 1396 | 8.1 |
| 20.725 | 4.282 | 2644 | 15.3 |
| 21.787 | 4.076 | 1127 | 6.5 |
| 22.06 | 4.026 | 451 | 2.6 |
| 22.864 | 3.886 | 1542 | 8.9 |
| 23.412 | 3.796 | 14185 | 82.2 |
| 23.75 | 3.743 | 1154 | 6.7 |
| 24.288 | 3.662 | 3063 | 17.7 |
| 25.253 | 3.524 | 1318 | 7.6 |
| 25.503 | 3.49 | 1736 | 10.1 |
| 25.761 | 3.455 | 1225 | 7.1 |
| 26.176 | 3.402 | 1346 | 7.8 |
| 26.548 | 3.355 | 1098 | 6.4 |
| 27.357 | 3.257 | 1944 | 11.3 |
| 27.605 | 3.229 | 2116 | 12.3 |
| 27.9 | 3.195 | 858 | 5 |
| 28.378 | 3.142 | 583 | 3.4 |
| 28.749 | 3.103 | 763 | 4.4 |
| 29.3 | 3.046 | 1182 | 6.8 |
| 29.679 | 3.008 | 2606 | 15.1 |
| 30.402 | 2.9377 | 2184 | 12.6 |
| 30.739 | 2.9063 | 648 | 3.8 |

Graphical examples of the x-ray diffraction patterns for Form H, Form L, and the methyl ethyl ketone solvate crystalline forms of eplerenone are shown in FIGS. 1-A, 1-B, and 1-C, respectively. Form H shows distinguishing peaks at 7.0±0.2, 8.3±0.2, and 12.0±0.2 degrees two theta. Form L shows distinguishing peaks at 8.0±0.2, 12.4±0.2, 12.8±0.2, and 13.3±0.2 degrees two theta. The methyl ethyl ketone solvated crystalline form shows distinguishing peaks at 7.6±0.2, 7.8±0.2, and 13.6±0.2 degrees two theta.

3. Melting/Decomposition Temperature

The temperatures of melting and/or decomposition of non-solvated eplerenone crystalline forms were determined using a TA Instruments 2920 differential scanning calorimeter. Each sample (1–2 mg) was placed in either a sealed or unsealed aluminum pan and heated at 10° C./minute. Melting/decomposition ranges were defined from the extrapolated onset to the maximum of the melting/decomposition endotherm.

The melting of the non-solvated eplerenone crystals forms (Form H and Form L) was associated with chemical decomposition and loss of trapped solvent from the crystal lattice. The melting/decomposition temperature also was affected by the manipulation of the solid prior to analysis. For example, non-milled Form L (approximate $D_{90}$ particle size of about 180–450 microns) prepared by direct crystallization from an appropriate solvent or from desolvation of a solvate obtained from crystallization of high purity eplerenone in an appropriate solvent or mixture of solvents generally had a melting range of about 237–242° C. Milled Form L (approximate $D_{90}$ particle size of about 80–100 microns) (Form L prepared by crystallizing a solvate from a solution of high purity eplerenone in an appropriate solvent or mixture of solvents, desolvating the solvate to yield Form L, and milling the resulting Form L) generally had a lower and broader melting/decomposition range of about 223–234° C. Non-milled Form H (approximate $D_{90}$ particle size of about 180–450 microns) prepared by desolvation of a solvate obtained by digestion of low purity eplerenone generally had a higher melting/decomposition range of about 247–251° C. Examples of the DSC thermograms of (a) non-milled Form L directly crystallized from methyl ethyl ketone, (b) non-milled Form L prepared by desolvation of a solvate obtained by crystallization of a high purity eplerenone from methyl ethyl ketone, (c) Form L prepared by milling a desolvated solvate obtained by crystallization of high purity eplerenone from methyl ethyl ketone, and (d) non-milled Form H prepared by desolvation of a solvate obtained by digestion of low purity eplerenone from methyl ethyl ketone are given in FIGS. 2-A, 2-B, 2-C and 2-D, respectively.

DSC thermograms of solvated forms of eplerenone were determined using a Perkin Elmer Pyris 1 differential scanning calorimeter. Each sample (1–10 mg) was placed in an unsealed aluminum pan and heated at 10° C./minute. One or more endothermal events at lower temperatures were associated with enthalpy changes that occurred as solvent was lost from the solvate crystal lattice. The highest temperature endotherm or endotherms were associated with the melting/decomposition of Form L or Form H eplerenone. An example of the DSC thermogram for the methyl ethyl ketone solvated crystalline form of eplerenone is shown in FIG. 2-E.

4. Infrared Absorption Spectroscopy

Infrared absorption spectra of the non-solvated forms of eplerenone (Form H and Form L) were obtained with a Nicolet DRIFT (diffuse reflectance infrared fourier transform) Magna System 550 spectrophotometer. A Spectra-Tech Collector system and a microsample cup were used. Samples (5%) were analyzed in potassium bromide and scanned from 400–4000 cm$^{-1}$. Infrared absorption spectra of eplerenone in dilute chloroform solution (3%) or in the solvated crystal forms were obtained with a Bio-rad FTS-45 spectrophotometer. Chloroform solution samples were analyzed using a solution cell of 0.2 mm path length with sodium chloride salt plates. Solvate FTIR spectra were collected using an IBM micro-MIR (multiple internal reflectance) accessory. Samples were scanned from 400–4000 cm$^{-1}$. Examples of the infrared absorption spectra of (a) Form H, (b) Form L, (c) the methyl ethyl ketone solvate, and (d) eplerenone in chloroform solution are shown in FIGS. 3-A, 3-B, 3-C and 3-D, respectively.

Table 2 discloses illustrative absorption bands for eplerenone in the Form H, Form L, and methyl ethyl ketone solvate crystal forms. Illustrative absorption bands for eplerenone in chloroform solution are also disclosed for comparison. Differences between Form H and either Form L or the methyl ethyl ketone solvate were observed, for example, in the carbonyl region of the spectrum. Form H has an ester carbonyl stretch of approximately 1739 cm$^{-1}$ while both Form L and the methyl ethyl ketone solvate.have the corresponding stretch at approximately 1724 and 1722 cm$^{-1}$, respectively. The ester carbonyl stretch occurs at approximately 1727 cm$^{-1}$ in the eplerenone in chloroform solution. The change in stretching frequency of the ester carbonyl between Form H and Form L reflects the change in orientation of the ester group between the two crystal forms. In addition, the stretch of the ester of the conjugated ketone in the A-steroid ring shifts from approximately 1664–1667 cm$^{-1}$ in either Form H or the methyl ethyl ketone solvate to approximately 1655 cm$^{-1}$ in Form L. The corresponding carbonyl stretch occurs at approximately 1665 cm$^{-1}$ in dilute solution.

Another difference between Form H and Form L was seen in the C—H bending region. Form H has an absorption at approximately 1399 cm$^{-1}$ which is not observed in Form L, the methyl ethyl ketone solvate, or the eplerenone in chloroform solution. The 1399 cm$^{-1}$ stretch occurs in the region of CH$_2$ scissoring for the C2 and C21 methylene groups adjacent to carbonyl groups.

TABLE 2

| Absorption Region | Form H (cm$^{-1}$) | Form L (cm$^{-1}$) | Methyl Ethyl Ketone Solvate (cm$^{-1}$) | Eplerenone in Chloroform (cm$^{-1}$) |
|---|---|---|---|---|
| ν C=O (lactone) | 1773 | 1775 | 1767 | 1768 |
| ν C=O (ester) | 1739 | 1724 | 1722 | 1727 |
| ν C=O (3keto) | 1664 | 1655 | 1667 | 1665 |
| ν C=C (3,4-olefin) | 1619 | 1619 | 1622 | 1623 |
| δ$_{as}$CH3, δCH2, δCH2 (α to carbonyl) | 1460, 1444, 1426 | 1467, 1438, 1422, 1399 | 1467, 1438, 1422 | 1464, 1438, 1422 |
| δ$_s$CH3 | 1380 | 1381 | ~1380 | 1378 |

Figure 5:
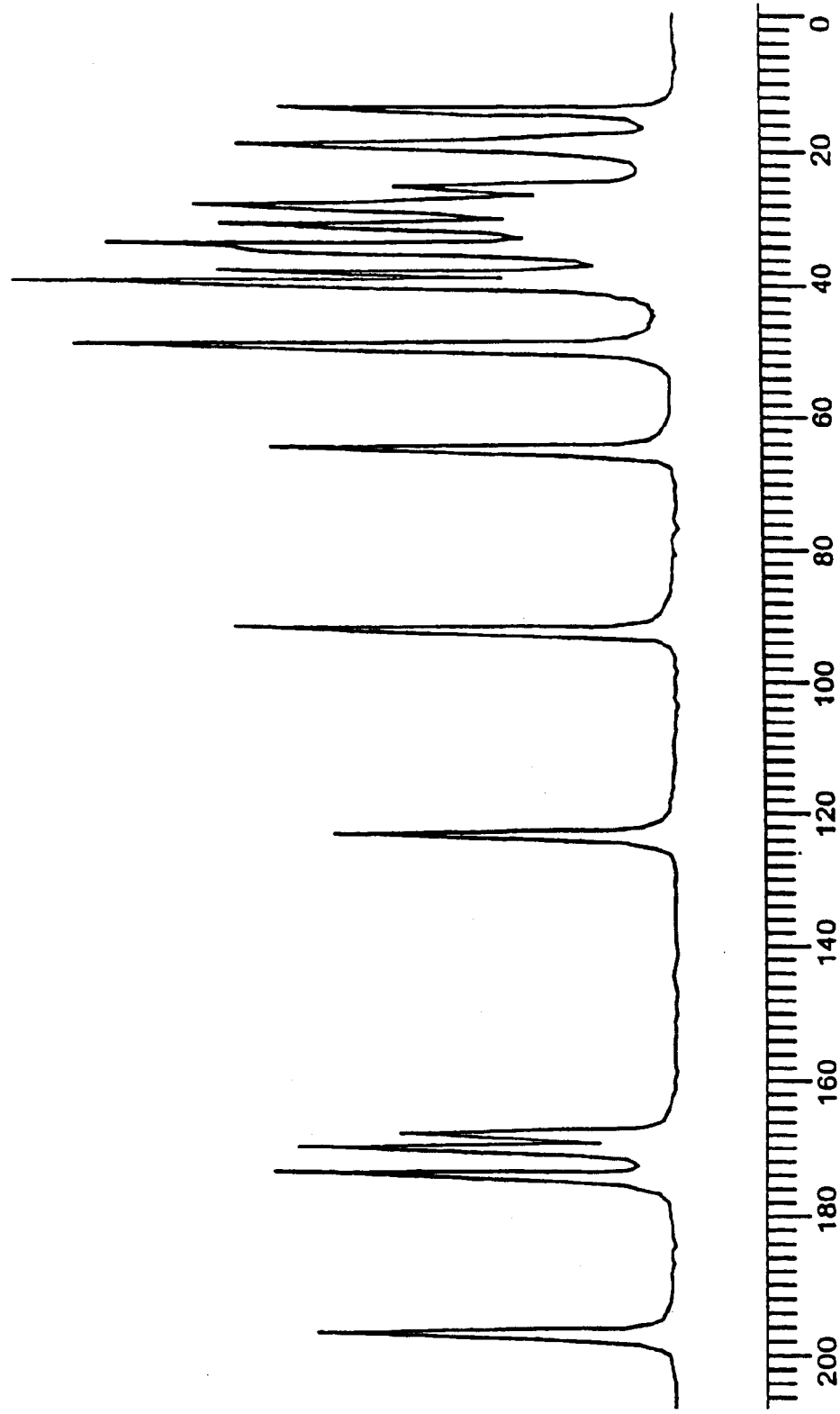
FIG. 5 shows $^{13}C$ NMR spectra for Form L of eplerenone.

5. Nuclear Magnetic Resonance $^{13}$C NMR spectra were obtained at a field of 31.94 MHz. Examples of the $^{13}$C NMR spectra of Form H and Form L eplerenone are shown in FIGS. 4 and 5, respectively. The Form H eplerenone analyzed to obtain the data reflected in FIG. 4 was not phase pure and included a small amount of Form L eplerenone. Form H is most clearly distinguished by the carbon resonances at around 64.8 ppm, 24.7 ppm and 19.2 ppm. Form L is most clearly distinguished by the carbon resonances at around 67.1 ppm and 16.0 ppm.

6. Thermogravimetry

Figure 6:
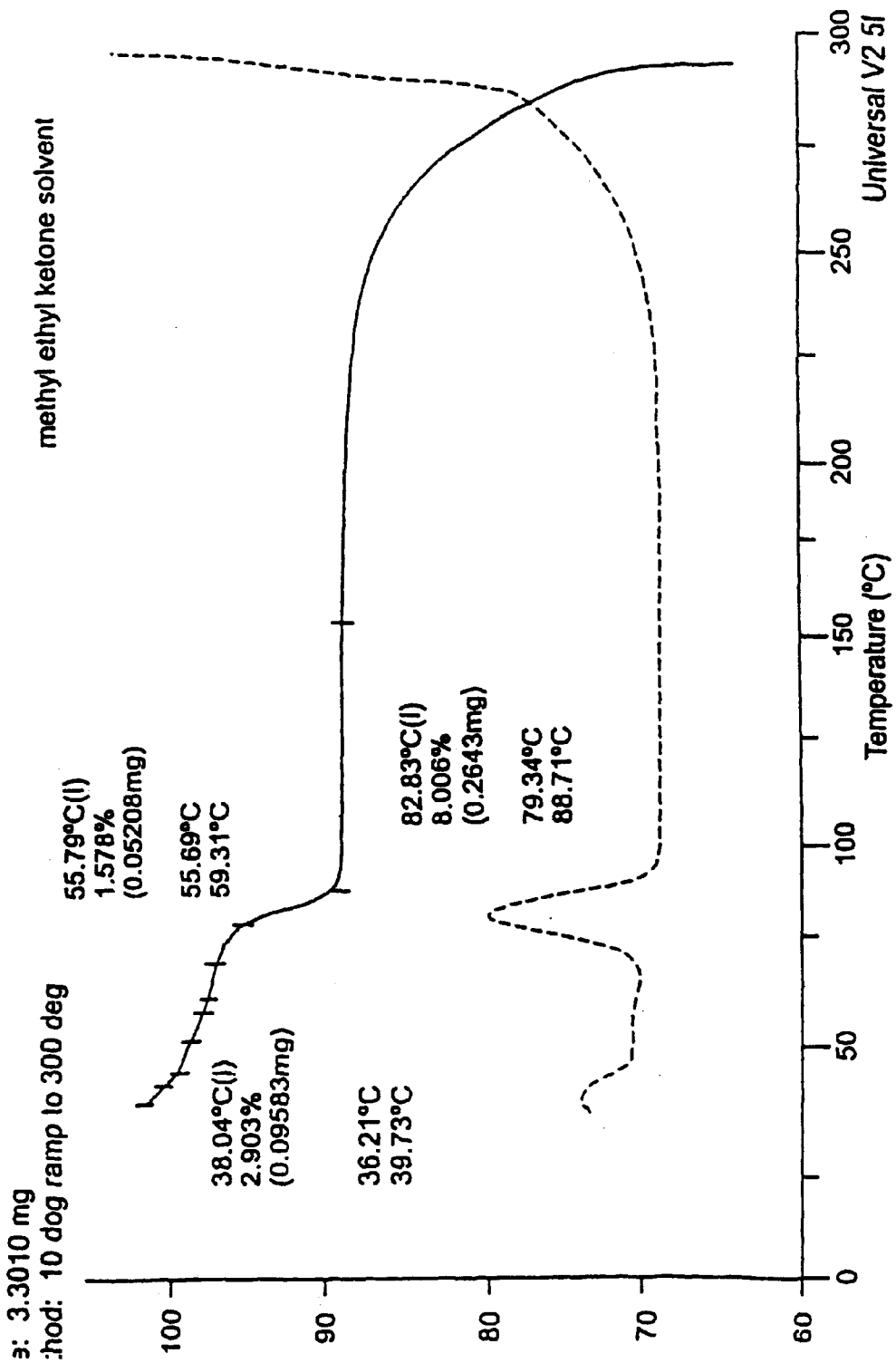
FIG. 6-A shows the thermogravimetry analysis profile for the methyl ethyl ketone solvate.
Figure 7:
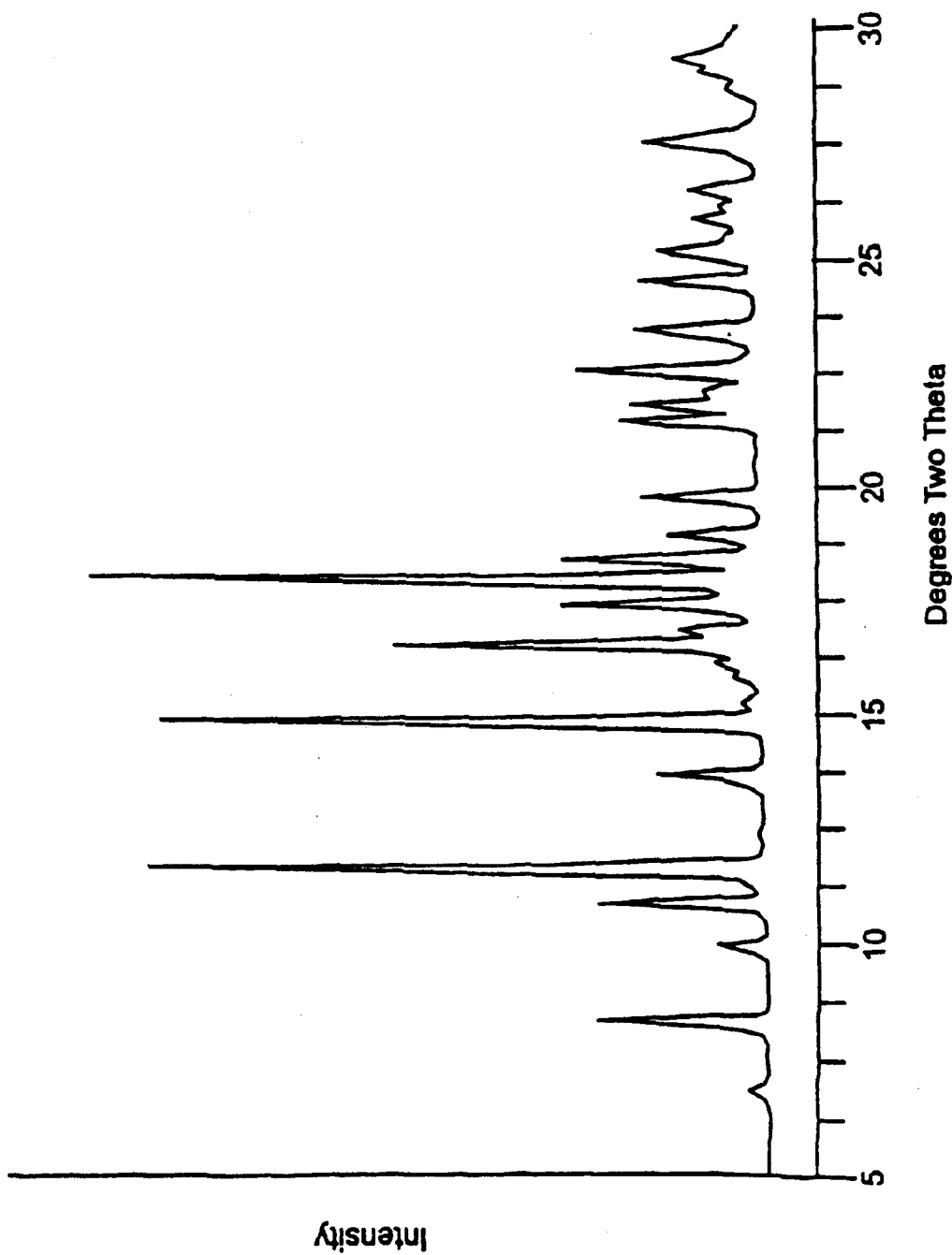
FIG. 7 shows an X-ray powder diffraction pattern of a crystalline form of 7-methyl hydrogen 4α,5α:9α,11α-diepoxy-17-hydroxy-3-oxo-17α-pregnane-7α,21-dicarboxylate, γ-lactone isolated from methyl ethyl ketone.
Figure 8:
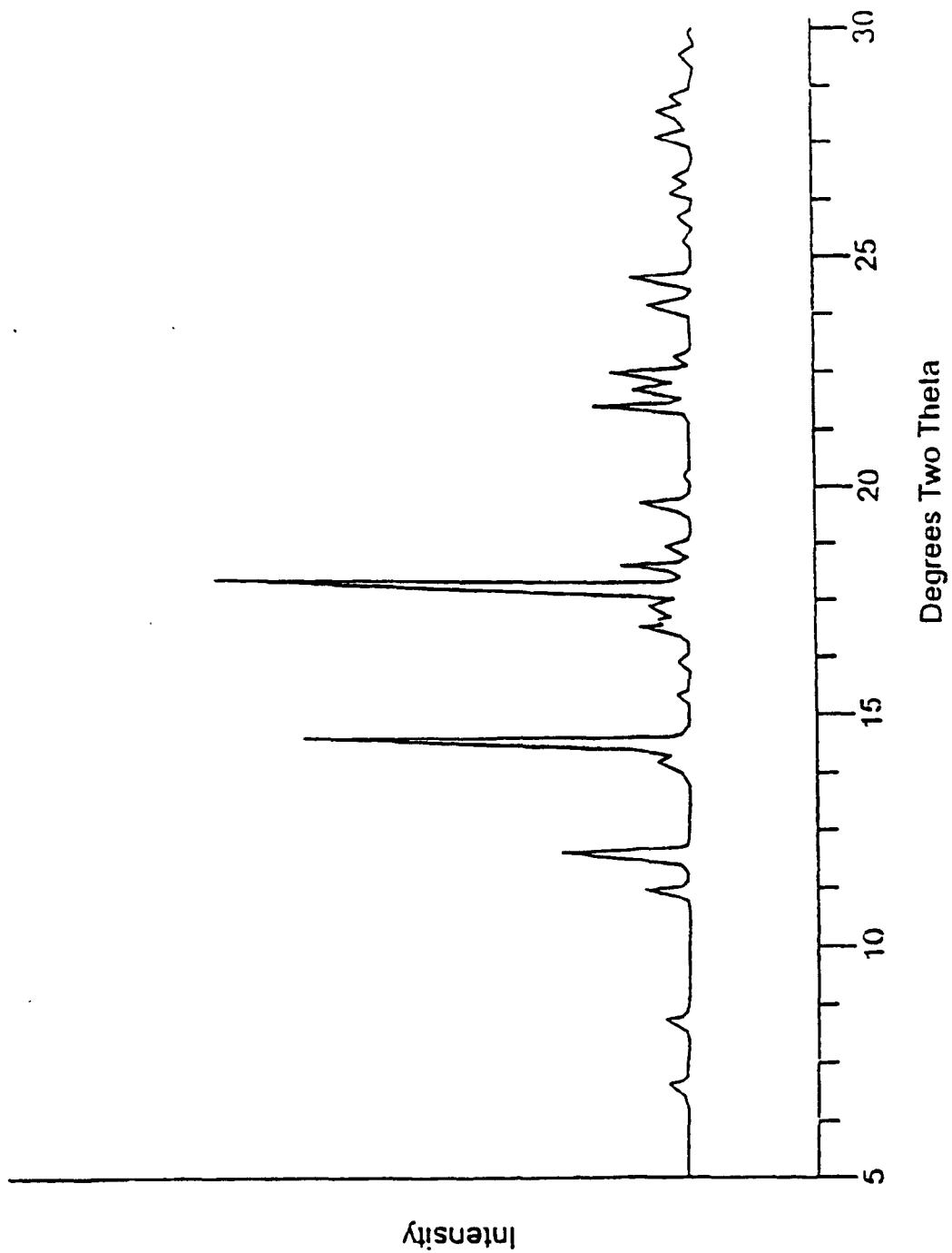
FIG. 8 shows an X-ray powder diffraction pattern of the crystalline form of 7-methyl hydrogen 11α,12α-epoxy-17-hydroxy-3-oxo-17α-pregn-4-ene-7α,21-dicarboxylate, γ-lactone isolated from isopropanol.

Thermogravimetric analysis of solvates was performed using a TA Instruments TGA 2950 thermogravimetric analyzer. Samples were placed in an unsealed aluminum pan under nitrogen purge. Starting temperature was 25° C. with the temperature increased at a rate of about 10° C./minute. An example of the thermogravimetry analysis profile for the methyl ethyl ketone solvate is shown in FIG. 6-A.

7. Unit Cell Parameters

Tables 3A, 3B and 3C below summarize the unit cell parameters determined for Form H, Form L, and several solvated crystalline forms.

TABLE 3A

| Parameter | Form H | Form L | Methyl ethyl ketone Solvate |
|---|---|---|---|
| Crystal system | Orthorhombic | Monoclinic | Orthorhombic |
| Space group | P2$_1$2$_1$2$_1$ | P2$_1$ | P2$_1$2$_1$2$_1$ |
| a | 21.22 Å | 8.78 Å | 23.53 Å |
| b | 15.40 Å | 11.14 Å | 8.16 Å |
| c | 6.34 Å | 11.06 Å | 13.08 Å |
| α | 90° | 90° | 90° |
| β | 90° | 93.52° | 90° |
| γV | 90° | 90° | 90° |
| Z | 4 | 2 | 4 |
| Volume (Å) | 2071.3 | 1081.8 | 2511.4 |
| ρ (calculated) | 1.329 g/cm$^3$ | 1.275 g/cm$^3$ | 1.287 g/cm$^3$ |
| R | 0.0667 | 0.062 | 0.088 |

TABLE 3B

| Parameter | Acetone Solvate | Toluene Solvate | Butyl Acetate Solvate[1] |
|---|---|---|---|
| Crystal system | Orthorhombic | Orthorhombic | Orthorhombic |
| Space group | P2$_1$2$_1$2$_1$ | P2$_1$2$_1$2$_1$ | P2$_1$2$_1$2$_1$ |
| a | 23.31 Å | 23.64 Å | 23.07 Å |
| b | 13.13 Å | 13.46 Å | 13.10 Å |
| c | 8.28 Å | 8.16 Å | 8.24 Å |
| α | 90° | 90° | 90° |
| β | 90° | 90° | 90° |
| γ | 90° | 90° | 90° |
| Z | 4 | 4 | 4 |
| Volume (Å) | 2533.7 | 2596.6 | 2490.0 |
| ρ (calculated) | 1.239 g/cm$^3$ | 1.296 g/cm$^3$ | 1.334 g/cm$^3$ |
| R | 0.058 | 0.089 | 0.093 |

[1]The solvate molecules were note completely refined due to disorder of the solvent molecules in the channels.

TABLE 3C

| Parameter | Isobutyl Acetate Solvate[1] | Isopropanol Solvate[1] | Ethanol Solvate[1] |
|---|---|---|---|
| Crystal system | Orthorhombic | Orthorhombic | Orthorhombic |
| Space group | P2$_1$2$_1$2$_1$ | P2$_1$2$_1$2$_1$ | P2$_1$2$_1$2$_1$ |
| a | 23.19 Å | 23.15 Å | 23.51 Å |
| b | 12.95 Å | 12.73 Å | 13.11 Å |
| c | 8.25 Å | 8.2S Å | 8.27 Å |
| α | 90° | 90° | 90° |
| β | 90° | 90° | 90° |
| γ | 90° | 90° | 90° |
| Z | 4 | 4 | 4 |
| Volume (Å) | 2476.4 | 2433.2 | 2548.6 |
| ρ (calculated) | 1.337 g/cm$^3$ | 1.296 g/cm$^3$ | 1.234 g/cm$^3$ |
| R | 0.098 | 0.152 | 0.067 |

[1]The solvate molecules were not refined completely due to disorder of the solvent molecules in the channels.

Additional information on selected solvated crystalline forms of eplerenone is reported in Table 4 below. The unit cell data reported in Table 3A above for the methyl ketone solvate also are representative of the unit cell parameters for many of these additional eplerenone crystalline solvates. Most of the eplernone crystalline solvates tested are substantially isostructural to each other. While there may be some minor shifting in the X-ray powder diffraction peaks from one solvated crystalline form to the next due to the size of the incorporated solvent molecule, the overall diffraction patterns are substantially the same and the unit cell parameters and molecular positions are substantially identical for most of the solvates tested.

TABLE 4

| Solvent | Stoichiometry (Solvent: Eplerenone) | Isostructural to Methyl Ethyl ketone Solvate? | Desolvation Temperature[1] (° C.) |
|---|---|---|---|
| Methyl Ethyl Ketone | 1:1 | N/A | 89 |
| 2-Pentanone | — | — | — |
| Acetic Acid | 1:2 | Yes | 203 |
| Acetone | 1:1 | Yes | 117 |
| Butyl Acetate | 1:2 | Yes | 108 |
| Chloroform | — | Yes | 125 |
| Ethanol | 1:1 | Yes | 166 |
| Isobutanol | — | — | — |
| Isobutyl Acetate | 1:2 | Yes | 112 |
| Isopropanol | 1:1 | Yes | 121 |
| Methyl Acetate | 1:1 | Yes | 103 |
| Ethyl Propionate | 1:1 | Yes | 122 |
| n-Butanol | 1:1 | Yes | 103 |
| n-Octanol | — | Yes | 116 |
| n-Propanol | 1:1 | Yes | 129 |
| Propyl Acetate | 1:1 | Yes | 130 |
| Propylene Glycol | — | Yes | 188 |
| t-Butanol | — | — | — |
| Tetrahydrofuran | 1:1 | Yes | 136 |
| Toluene | 1:1 | Yes | 83 |
| t-Butyl Acetate | — | Yes | 109 |

[1]Defined as the extrapolated desolvation temperature from the final solvent weight loss step as determined by thermogravimetric analysis at a heating rate of 10° C./minute under nitrogen purge. Desolvation temperatures, however, can be affected by the method of manufacture of the solvate. Different methods can produce different numbers of nucleation sites capable of initiating desolvation in the solvate at lower temperatures.

The unit cell of the solvate is composed of four eplerenone molecules. The stoichiometry of the eplerenone molecules and solvent molecules in the unit cell is also reported in Table 4 above for a number of solvates. The unit cell of Form H is composed of four eplerenone molecules. The unit cell of Form L is composed of two eplerenone molecules. The solvate unit cells are converted during desolvation into Form H and/or Form L unit cells when the eplerenone molecules undergo translation and rotation to fill the spaces left by the solvent molecules. Table 4 also reports the desolvation temperatures for a number of different solvates.

8. Crystal Properties of Impurity Molecules

Selected impurities in eplerenone can induce the formation of Form H during the desolvation of the solvate. In particular, the effect of the following two impurity molecules was evaluated: 7-methyl hydrogen 4α,5α:9α,11α-diepoxy-17-hydroxy-3-oxo-17α-pregnane-7α,21-dicarboxylate, γ-lactone 3 (the "diepoxide"); and 7-methyl hydrogen 11α,12α-epoxy-17-hydroxy-3-oxo-17α-pregn-4-ene-7α,21-dicarboxylate, γ-lactone 4 (the "11,12-epoxide").

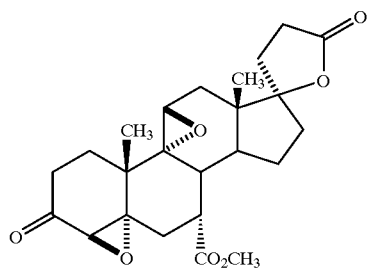

3

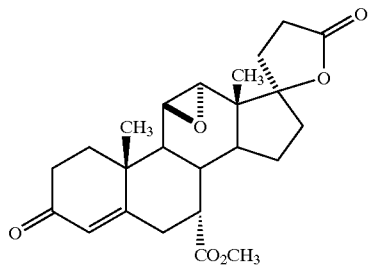

4

The effect of these impurity molecules on the eplerenone crystalline form resulting from desolvation is described in greater detail in the examples of this application.

Given the similarity in single crystal structure of 7-methyl hydrogen 17-hydroxy-3-oxo-17α-pregna-4,9(11)-diene-7α, 21-dicarboxylate, γ-lactone 5 (the "9,11-olefin") and Form H, it is hypothesized that the 9,11-olefin also can induce the formation of Form H during the desolvation of the solvate.

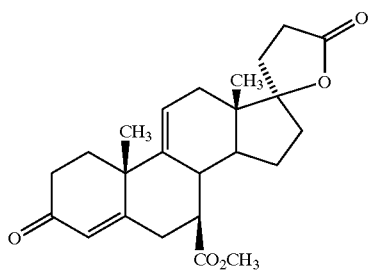

5

The diepoxide, 11,12-olefin and 9,11-olefin can be prepared as set forth, for example, in Examples 47C, 47B and 37H of Ng et al., WO98/25948, respectively.

Figure 9:
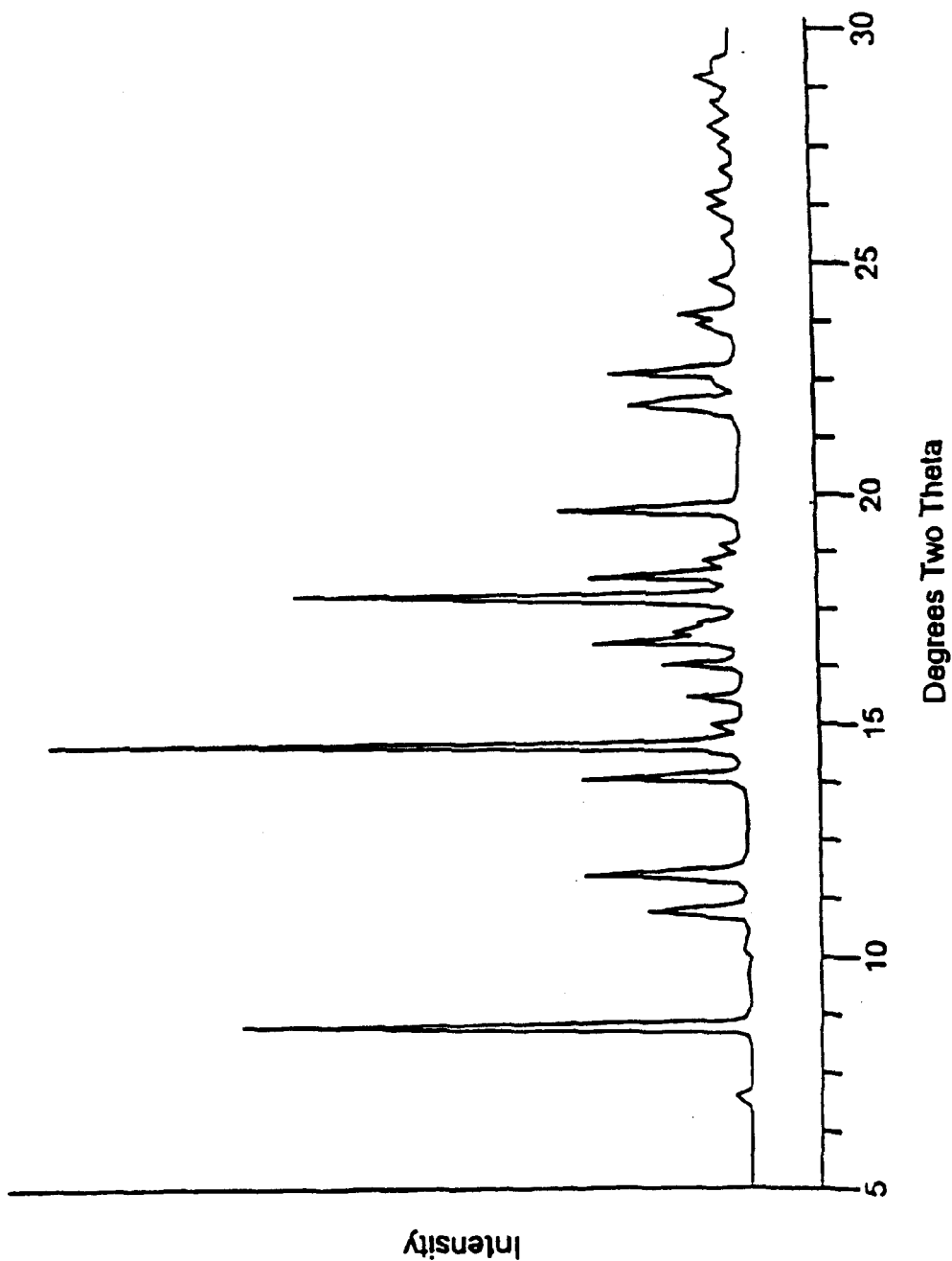
FIG. 9 shows an X-ray powder diffraction pattern of the crystalline form of 7-methyl hydrogen 17-hydroxy-3-oxo-17α-pregna-4,9(11)-diene-7α,21-dicarboxylate, γ-lactone isolated from n-butanol.
Figure 10:
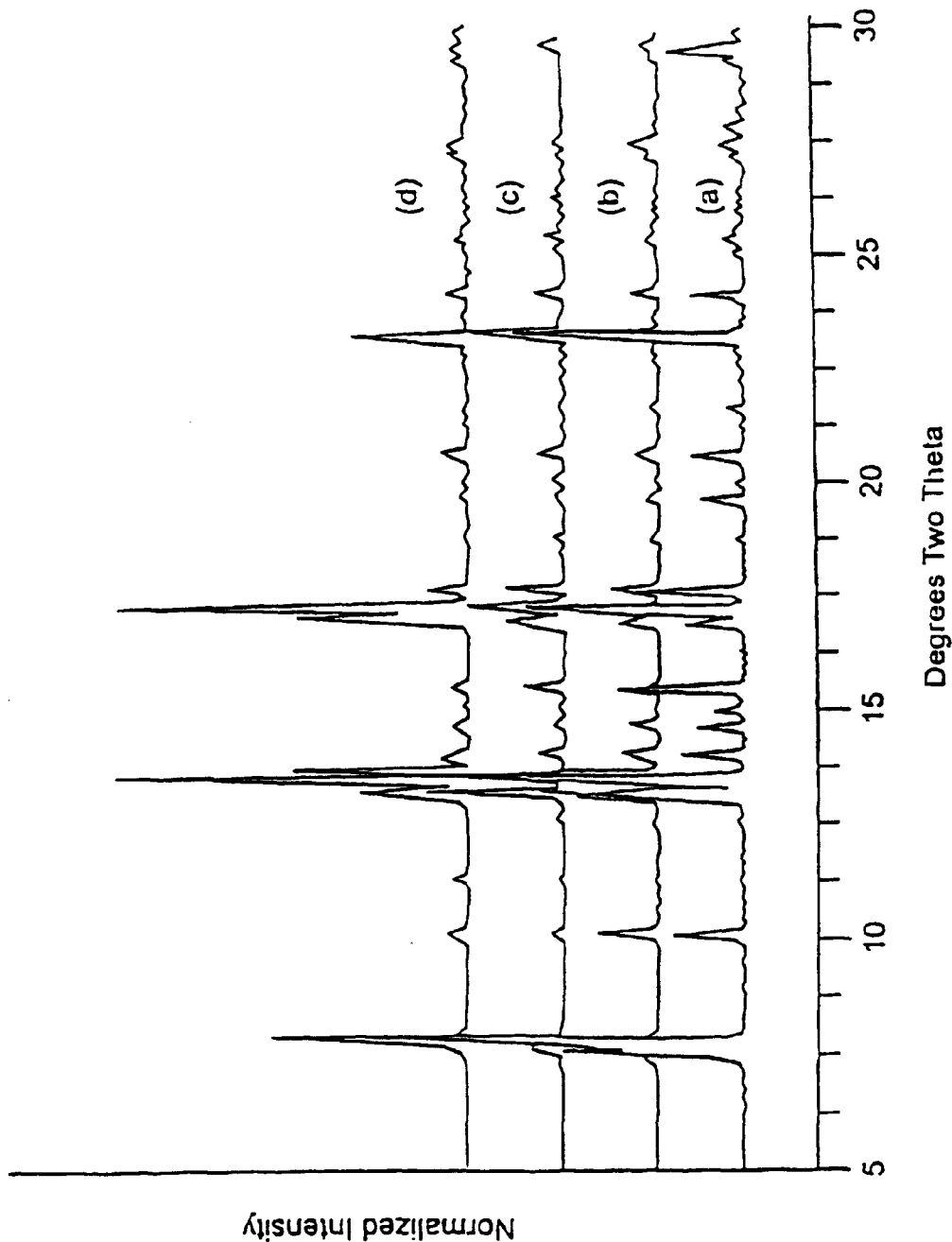
FIG. 10 shows the X-ray powder diffraction patterns for the wet cake (methyl ethyl ketone solvate) obtained from (a) 0%, (b) 1%, (c) 3%, and (d) 5% diepoxide-doped methyl ethyl ketone crystallizations.
Figure 11:
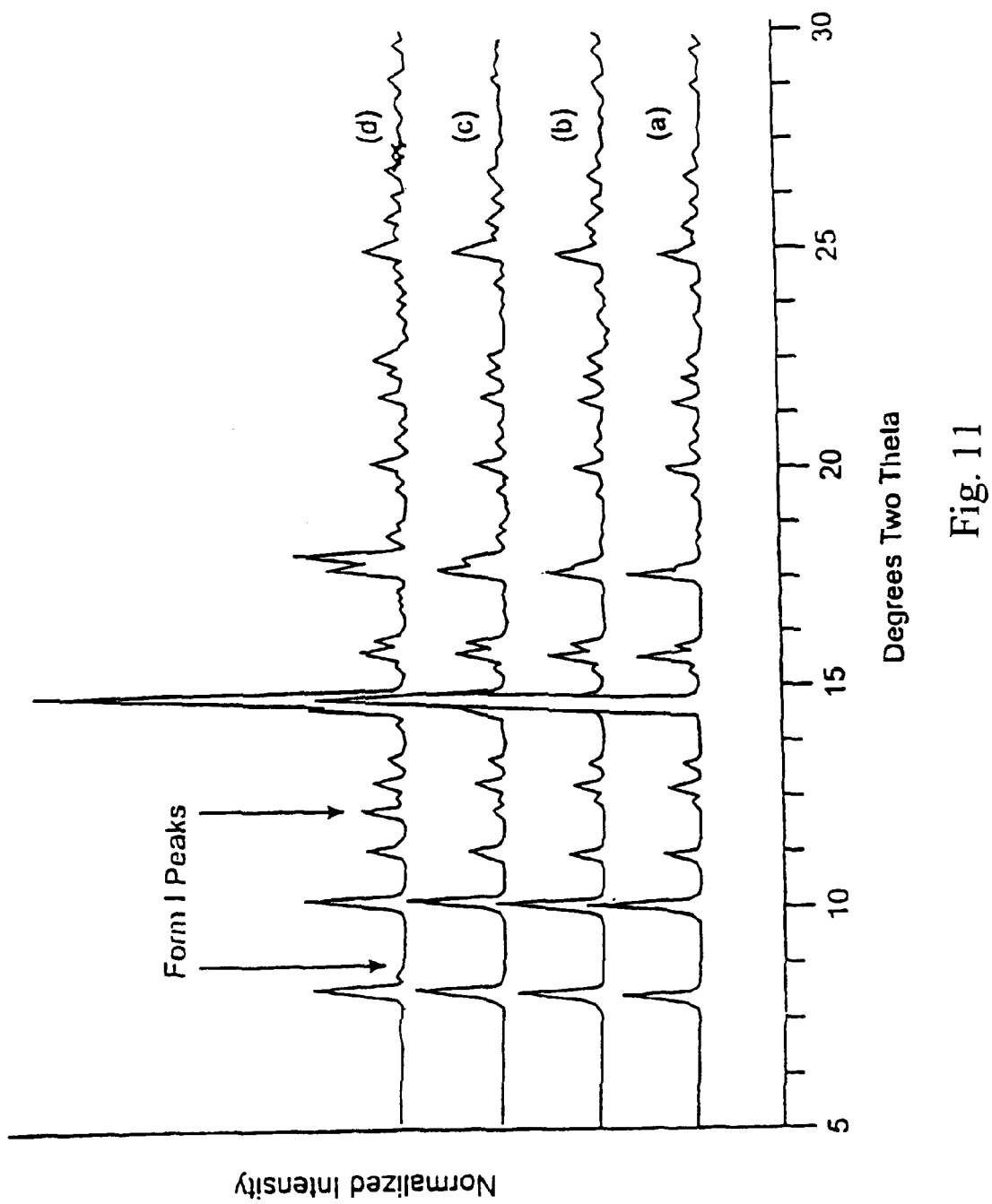
FIG. 11 shows the X-ray powder diffraction patterns for the dried solids obtained from (a) 0%, (b) 1%, (c) 3%, and (d) 5% diepoxide-doped methyl ethyl ketone crystallizations.
Figure 12:
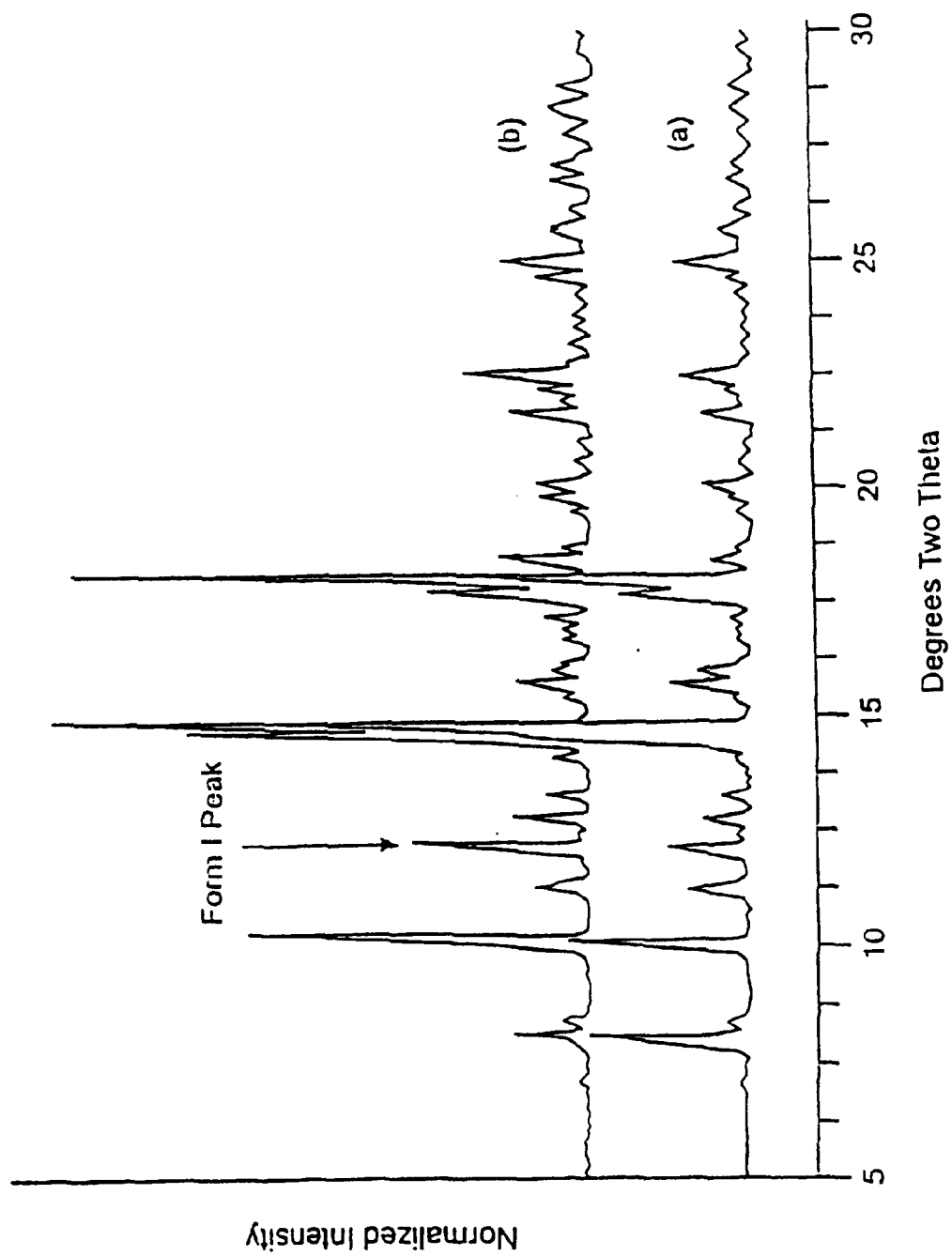
FIG. 12 shows the X-ray powder diffraction patterns for the dried solids from the methyl ethyl ketone crystallization with 3% doping of diepoxide (a) without grinding of the solvate prior to drying, and (b) with grinding of the solvate prior to drying.

A single crystal form was isolated for each impurity compound. Representative X-ray powder diffraction patterns for the crystal forms isolated for the diepoxide, 11,12-epoxide and 9,11-olefin are given in FIGS. 9, 10 and 11, respectively. The X-ray powder diffraction pattern of each impurity molecule is similar to the X-ray powder diffraction pattern of Form H, suggesting that Form H and the three impurity compounds have similar single crystal structures.

Single crystals of each impurity compound also were isolated and subjected to X-ray structure determination to verify that these three compounds adopt single crystal structures similar to that of Form H. Single crystals of the diepoxide were isolated from methyl ethyl ketone. Single crystals of the 11,12-epoxide were isolated from isopropanol. Single crystals of the 9,11-olefin were isolated from n-butanol. Crystal structure data determined for the crystalline form of each impurity compound are given in Table 5. The resulting crystal system and cell parameters were substantially the same for the Form H, diepoxide, 11,12-epoxide, and 9,11-olefin crystalline forms.

TABLE 5

| Parameter | Form H | Diepoxide | 11,12 Epoxide | 9,11 olefin |
|---|---|---|---|---|
| Crystal system | Ortho-rhombic | Ortho-rhombic | Ortho-rhombic | Ortho-rhombic |
| Space group | $P2_12_12_1$ | $P2_12_12_1$ | $P2_12_12_1$ | $P2_12_12_1$ |
| a | 21.22 Å | 21.328 Å | 20.90 Å | 20.90 Å |
| b | 15.40 Å | 16.16 Å | 15.55 Å | 15.74 Å |
| c | 6.34 Å | 6.15 Å | 6.38 Å | 6.29 Å |
| α | 90° | 90° | 90° | 90° |
| β | 90° | 90° | 90° | 90° |
| γ | 90° | 90° | 90° | 90° |
| Z | 4 | 4 | 4 | 4 |
| Volume (Å) | 2071.3 | 2119.0 | 2073.2 | 2069.3 |
| ρ (calculated) | 1.329 g/cm$^3$ | 1.349 g/cm$^3$ | 1.328 g/cm$^3$ | 1.279 g/cm$^3$ |
| R | 0.0667 | 0.0762 | 0.0865 | 0.0764 |

The four compounds reported in Table 5 crystallize into the same space group and have similar cell parameters (i.e., they are isostructural). It is hypothesized that the diepoxide, 11,12-epoxide and 9,11-olefin adopt a Form H conformation. The relative ease of isolation of a Form H packing (directly from solution) for each impurity compound, indicates that the Form H lattice is a stable packing mode for this series of structurally similar compounds.

Preparation of Eplerenone

The eplerenone starting material used to prepare the novel crystalline forms of the present invention can be prepared using the methods set forth in Ng et al., WO97/21720; and Ng et al., WO98/25948, particularly scheme 1 set forth in WO97/21720 and WO98/25948.

Preparation of Crystalline Forms
1. Preparation of Solvated Crystalline Form

The solvated crystalline forms of eplerenone can be prepared by crystallization of eplerenone from a suitable solvent or a mixture of suitable solvents. A suitable solvent or mixture of suitable solvents generally comprises an organic solvent or a mixture of organic solvents that solubilizes the eplerenone together with any impurities at an elevated temperature, but upon cooling, preferentially crystallizes the solvate. The solubility of eplerenone in such solvents or mixtures of solvents generally is about 5 to about 200 mg/mL at room temperature. The solvent or mixtures of solvents preferably are selected from those solvents previously used in the process to prepare the eplerenone starting material, particularly those solvents that would be pharmaceutically acceptable if contained in the final pharmaceutical composition comprising the eplerenone crystalline form. For example, a solvent system comprising methylene chloride that yields a solvate comprising methylene chloride generally is not desirable.

Each solvent used preferably is a pharmaceutically acceptable solvent, particularly a Class 2 or Class 3 solvent as defined in "Impurities: Guideline For Residual Solvents", International Conference On Harmonisation Of Technical Requirements For Registration Of Pharmaceuticals For Human Use (Recommended for Adoption at Step 4 of the ICH Process on Jul. 17, 1997 by the ICH Steering Committee). Still more preferably, the solvent or mixture of solvents is selected from the group consisting of methyl ethyl ketone, 1-propanol, 2-pentanone, acetic acid, acetone, butyl acetate, chloroform, ethanol, isobutanol, isobutyl acetate, ethyl acetate, ethyl propionate, n-butanol, n-octanol, isopropanol, propyl acetate, propylene glycol, t-butanol, tetrahydrofuran, toluene, methanol and t-butyl acetate. Still more preferably, the solvent is selected from the group consisting of methyl ethyl ketone and ethanol.

To prepare the solvated crystalline form of eplerenone, an amount of the eplerenone starting material is solubilized in a volume of the solvent and cooled until crystals form. The solvent temperature at which the eplerenone is added to the solvent generally will be selected based upon the solubility curve of the solvent or mixture of solvents. For most of the solvents described herein, for example, this solvent temperature typically is at least about 25° C., preferably from about 30° C. to the boiling point of the solvent, and more preferably from about 25° C. below the boiling point of the solvent to the boiling point of the solvent.

Alternatively, hot solvent may be added to the eplerenone and the mixture can be cooled until crystals form. The solvent temperature at the time it is added to the eplerenone generally will be selected based upon the solubility curve of the solvent or mixture of solvents. For most of the solvents described herein, for example, the solvent temperature typically is at least 25° C., preferably from about 50° C. to the boiling point of the solvent, and more preferably from about 15° C. below the boiling point of the solvent to the boiling point of the solvent.

The amount of the eplerenone starting material mixed with a given volume of solvent likewise will depend upon the solubility curve of the solvent or mixture of solvents. Typically, the amount of eplerenone added to the solvent will not completely solubilize in that volume of solvent at room temperature. For most of the solvents described herein, for example, the amount of eplerenone starting material mixed with a given volume of solvent usually is at least about 1.5 to about 4.0 times, preferably about 2.0 to about 3.5 times, and more preferably about 2.5 times, the amount of eplerenone that will solubilize in that volume of solvent at room temperature.

After the eplerenone starting material has completely solubilized in the solvent, the solution typically is cooled slowly to crystallize the solvated crystalline form of eplerenone. For most of the solvents described herein, for example, the solution is cooled at a rate slower than about 20° C./minute, preferably at a rate of about 10° C./minute or slower, more preferably at a rate of about 5° C./minute or slower, and still more preferably at a rate of about 1° C./minute or slower.

The endpoint temperature at which the solvated crystalline form is harvested will depend upon the solubility curve of the solvent or mixture of solvents. For most of the solvents described herein, for example, the endpoint temperature typically is less than about 25° C., preferably less than about 5° C., and more preferably less than about −5° C. Decreasing the endpoint temperature generally favors the formation of the solvated crystalline form.

Alternatively, other techniques may be used to prepare the solvate. Examples of such techniques include, but are not limited to, (i) dissolving the eplerenone starting material in one solvent and adding a co-solvent to aid in the crystallization of the solvate crystalline form, (ii) vapor diffusion growth of the solvate, (iii) isolation of the solvate by evaporation, such as rotary evaporation, and (iv) slurry converstion.

The crystals of the solvated crystalline form prepared as described above can be separated from the solvent by any suitable conventional means such as by filtration or centrifugation. Increased agitation of the solvent system during crystallization generally results in smaller crystal particle sizes.

2. Preparation of Form L From Solvate

Form L eplerenone can be prepared directly from the solvated crystalline form by desolvation. Desolvation can be accomplished by any suitable desolvation means such as, but not limited to, heating the solvate, reducing the ambient pressure surrounding the solvate, or combinations thereof. If the solvate is heated to remove the solvent, such as in an oven, the temperature of the solvate during this process typically does not exceed the enantiotropic transition temperature for Form H and Form L. This temperature preferably does not exceed about 150° C.

The desolvation pressure and time of desolvation are not narrowly critical. The desolvation pressure preferably is about one atmosphere or less. As the desolvation pressure is reduced, however, the temperature at which the desolvation can be carried out and/or the time of desolvation likewise is reduced. Particularly for solvates having higher desolvation temperatures, drying under vacuum will permit the use of lower drying temperatures. The time of desolvation need only be sufficient to allow for the desolvation, and thus the formation of Form L, to reach completion.

To ensure the preparation of a product that comprises substantially all Form L, the eplerenone starting material typically is a high purity eplerenone, preferably substantially pure eplerenone. The eplerenone starting material used to prepare Form L eplerenone generally is at least 90% pure, preferably at least 95% pure, and more preferably at least 99% pure. As discussed in greater detail elsewhere in this application, certain impurities in the eplerenone starting material can adversely affect the yield and Form L content of the product obtained from the process.

The crystallized eplerenone product prepared in this manner from a high purity eplerenone starting material generally comprises at least 10% Form L, preferably at least 50% Form L, more preferably at least 75% Form L, still more preferably at least 90% Form L, still more preferably at least about 95% Form L, and still more preferably substantially phase pure Form L.

3. Preparation of Form H From Solvate

A product comprising Form H can be prepared in substantially the same manner as set forth above for the preparation of Form L by (i) using a low purity eplerenone starting material instead of a high purity eplerenone starting material, (ii) seeding the solvent system with phase pure Form H crystals, or (iii) a combination of (i) and (ii).

A. Use Of Impurities As Growth Promoters and Inhibitors

The presence and amount of selected impurities in the eplerenone starting material, rather than the total amount of all impurities in the eplerenone starting material, affect the potential for Form H crystal formation during the desolvation of the solvate. The selected impurity generally is a Form H growth promoter or Form L growth inhibitor. It may be contained in the eplerenone starting material, contained in the solvent or mixture of solvents before the eplerenone starting material is added, and/or added to the solvent or mixture of solvents after the eplerenone starting material is added. Bonafede et al., "Selective Nucleation and Growth of an Organic Polymorph by Ledge-Directed Epitaxy on a Molecular Crystal Substate", *J. Amer. Chem. Soc.*, Vol. 117, No. 30 (Aug. 2, 1995) discusses the use of growth promoters and growth inhibitors in polymorph systems and is incorporated by reference herein. For the present invention, the impurity generally comprises a compound having a single crystal structure substantially identical to the single crystal structure of Form H. The impurity preferably is a compound having an X-ray powder diffraction pattern substantially identical to the X-ray powder diffraction pattern of Form H, and more preferably is selected from the group consisting of the diepoxide, the 11,12-epoxide, the 9,11-olefin and combinations thereof.

The amount of impurity needed to prepare Form H crystals typically can depend, in part, upon the solvent or mixture of solvents and the solubility of the impurity relative to eplerenone. In the crystallization of Form H from a methyl ethyl ketone solvent, for example, the weight ratio of diepoxide to low purity eplerenone starting material typically is at least about 1:100, preferably at least about 3:100, more preferably between about 3:100 and about 1:5, and still more preferably between about 3:100 and about 1:10. The 11,12-epoxide has a higher solubility in methyl ethyl ketone than the diepoxide and generally requires a larger amount of the 11,12-epoxide generally is necessary to prepare Form H crystals. Where the impurity comprises the 11,12-epoxide, the weight ratio of the diepoxide to the low purity eplerenone starting material typically is at least about 1:5, more preferably at least about 3:25, and still more preferably between about 3:25 and about 1:5. Where both the diexpoxide and the 11,12-epoxide impurities are used in the preparation of the Form H crystals, the weight ratio of each impurity to the eplerenone starting material may be lower than the corresponding ratio when only that impurity is used in the preparation of the Form H crystals.

A mixture of Form H and Form L is generally obtained when a solvate comprising the selected impurity is desolvated. The weight fraction of Form H in the product resulting from the initial desolvation of the solvate typically is less than about 50%. Further treatment of this product by crystallization or digestion, as discussed below, generally will increase the weight fraction of Form L in the product.

B. Seeding

Form H crystals also can be prepared by seeding the solvent system with phase pure Form H crystals (or a Form H growth promoter and/or Form L growth inhibitor as previously discussed above) prior to crystallization of the eplerenone. The eplerenone starting material can be either a low purity eplerenone or a high purity eplerenone. When the resulting solvate prepared from either starting material is desolvated, the weight fraction of Form H in the product typically is at least about 70% and may be as great as about 100%.

The weight ratio of Form H seed crystals added to the solvent system to the eplerenone starting material added to the solvent system generally is at least about 0.75:100, preferably between about 0.75:100 to about 1:20, and more preferably between about 1:100 to about 1:50. The Form H seed crystals can be prepared by any of the methods discussed in this application for the preparation of Form H crystals, particularly the preparation of Form H crystals by digestion as discussed below.

The Form H seed crystals may be added at one time, in multiple additions or substantially continually over a period of time. The addition of the Form H seed crystals, however, generally is completed before the eplerenone begins to crystallize from solution, i.e., the seeding is completed before the cloud point (the lower end of the metastable zone) is reached. Seeding typically is performed when the solution temperature ranges from about 0.5° C. above the cloud point to about 10° C. above the cloud point, preferably within about 2° C. to about 3° C. above the cloud point. As the temperature above the cloud point at which the seeds are added increases, the amount of seeding needed for crystallization of Form H crystals generally increases.

The seeding preferably occurs not only above the cloud point, but within the metastable zone. Both the cloud point and the metastable zone are dependent on the eplerenone solubility and concentration in the solvent or mixture of solvents. For a 12 volume dilution of methyl ethyl ketone, for example, the high end of the metastable zone generally is between about 70° C. to about 73° C. and the lower end of the metastable zone (i.e., the cloud point) is between about 57° C. and 63° C. For a concentration of 8 volumes of methyl ethyl ketone, the metastable zone is even narrower because the solution is supersaturated. At this concentration, the cloud point of the solution occurs at about 75° C. to about 76° C. Because the boiling point of methyl ethyl ketone is about 80° C. under ambient conditions, seeding for this solution typically occurs between about 76.5° C. and the boiling point.

An illustrative non-limiting example of seeding with Form H is set forth below in Example 7.

The crystallized eplerenone product obtained using a Form H growth promoter or Form L growth inhibitor, and/or Form H seeding generally comprises at least 2% Form H, preferably at least 5% Form H, more preferably at least 7% Form H, and still more preferably at least about 10% Form H. The remaining crystallized eplerenone product generally is Form L.

C. Form H Prepared By Grinding Eplerenone

In yet another alternative, it has been discovered that a small amount of Form H can be prepared by suitable grinding eplerenone. Concentrations of Form H in ground eplerenone as high as about 3% have been observed.

4. Preparation of Form L from Solvate Prepared from Low Purity Eplerenone

As discussed above, crystallization of low purity eplerenone to form a solvate followed by desolvation of the solvate generally yields a product comprising both Form H and Form L. A product having a greater Form L content can be prepared from low purity eplerenone in substantially the same manner as set forth above for the preparation of Form H by seeding the solvent system with phase pure Form L crystals, or by using a Form L growth promoter and/or Form H growth inhibitor. The seeding protocol and the weight ratio of the amount of Form L seed crystals added to the solvent system to the amount of the eplerenone starting material added to the solvent system generally are similar to those ratios previously discussed above for the preparation of Form H eplerenone by seeding with phase pure Form H crystals.

The crystallized eplerenone product prepared in this manner generally comprises at least 10% Form L, preferably at least 50% Form L, more preferably at least 75% Form L, more preferably at least 90% Form L, still more preferably at least about 95% Form L, and still more preferably substantially phase pure Form L.

The seeding protocols described in this section and in the prior section relating to the preparation of Form H eplerenone also may allow for improved control of the particle size of the crystallized eplerenone.

5. Crystallization of Form L Directly from Solution

Form L eplerenone also can be prepared by the direct crystallization of eplerenone from a suitable solvent or mixture of solvents without the formation of an intermediate solvate and the accompanying need for desolvation. Typically, (i) the solvent has a molecular size that is incompatible with the available channel space in the solvate crystal lattice, (ii) the eplerenone and any impurities are soluble in the solvent at elevated temperatures, and (iii) upon cooling, results in the crystallization of the non-solvated Form L eplerenone. The solubility of eplerenone in the solvent or mixture of solvents generally is about 5 to about 200 mg/mL at room temperature. The solvent or mixture of solvents preferably comprises one or more solvents selected from the group consisting of methanol, ethyl acetate, isopropyl acetate, acetonitrile, nitrobenzene, water and ethyl benzene.

To crystallize Form L eplerenone directly from solution, an amount of the eplerenone starting material is solubilized in a volume of the solvent and cooled until crystals form. The solvent temperature at which the eplerenone is added to the solvent generally will be selected based upon the solubility curve of the solvent or mixture of solvents. For most of the solvents described herein, for example, this solvent temperature typically is at least about 25° C., preferably from about 30° C. to the boiling point of the solvent, and more preferably from about 25° C. below the boiling point of the solvent to the boiling point of the solvent.

Alternatively, hot solvent may be added to the eplerenone and the mixture can be cooled until crystals form. The solvent temperature at the time it is added to the eplerenone generally will be selected based upon the solubility curve of the solvent or mixture of solvents. For most of the solvents described herein, for example, the solvent temperature typically is at least 25° C., preferably from about 50° C. to the boiling point of the solvent, and more preferably from about 15° C. below the boiling point of the solvent to the boiling point of the solvent.

The amount of the eplerenone starting material mixed with a given volume of solvent likewise will depend upon the solubility curve of the solvent or mixture of solvents. Typically, the amount of eplerenone added to the solvent will not completely solubilize in that volume of solvent at room temperature. For most of the solvents described herein, for example, the amount of eplerenone starting material mixed with a given volume of solvent usually is at least about 1.5 to about 4.0 times, preferably about 2.0 to about 3.5 times, and more preferably about 2.5 times, the amount of eplerenone that will solubilize in that volume of solvent at room temperature.

To ensure the preparation of a product that comprises substantially phase pure Form L, the eplerenone starting material generally is a high purity eplerenone. The eplerenone starting material preferably is at least 65% pure, more preferably at least 90% pure, still more preferably at least 98% pure, and still more preferably at least 99% pure.

After the eplerenone starting material has completely solubilized in the solvent, the solution typically is cooled slowly to crystallize the solvated crystalline form of eplerenone. For most of the solvents described herein, for example, the solution is cooled at a rate slower than about 1.0° C./minute, preferably at a rate of about 0.2° C./minute or slower, and more preferably at a rate between about 5° C./minute and about 0.1° C./minute.

The endpoint temperature at which the Form L crystals are harvested will depend upon the solubility curve of the solvent or mixture of solvents. For most of the solvents described herein, for example, the endpoint temperature typically is less than about 25° C., preferably less than about 5° C, and more preferably less than about −5° C.

Alternatively, other techniques may be used to prepare the Form L crystals. Examples of such techniques include, but are not limited to, (i) dissolving the eplerenone starting material in one solvent and adding a co-solvent to aid in the crystallization of Form L eplerenone, (ii) vapor diffusion growth of Form L eplerenone, (iii) isolation of Form L eplerenone by evaporation, such as rotary evaporation, and (iv) slurry conversion.

The crystals of the solvated crystalline form prepared as described above can be separated from the solvent by any suitable conventional means such as by filtration or centrifugation.

In addition, Form L eplerenone also can be prepared by digesting (as described below) a slurry of high purity eplerenone in methyl ethyl ketone and filtering the digested eplerenone at the boiling point of the slurry.

6. Preparation of Form H Directly from Solution

It is hypothesized that if the crystallization is performed above the enantiotropic transition temperature ($T_t$) for Form H and Form L, particularly if Form H growth promoters or Form L growth inhibitors are present or the solvent is seeded with phase pure Form H crystals, Form H should crystallize directly from solution since Form H is more stable at these higher temperatures. The solvent system used preferably comprises a high boiling solvent such as nitrobenzene. Suitable Form H growth promoters would include, but would not be limited to, the diepoxide and the 11,12-olefin.

7. Digestion of Eplerenone With a Solvent

The solvated crystalline forms, Form H and Form L of eplerenone also can be prepared by digestion of an eplerenone starting material in a suitable solvent or mixture of solvents. In the digestion process, a slurry of eplerenone is heated at the boiling point of the solvent or mixture of solvents. For example, an amount of eplerenone starting material is combined with a volume of solvent or mixture of solvents, heated to reflux, and the distillate is removed while an additional amount of the solvent is added simultaneously with the removal of the distillate. Alternatively, the distillate can be condensed and recycled without the addition of more solvent during the digestion process. Typically, once the original volume of solvent has been removed or condensed and recycled, the slurry is cooled and solvated crystals form. The solvated crystals can be separated from the solvent by any suitable conventional means such as by filtration or centrifugation. Desolvation of the solvate as previously described yields either Form H or Form L eplerenone depending upon the presence or absence of the selected impurities in the solvated crystals.

A suitable solvent or mixture of solvents generally comprises one or more of the solvents previously disclosed herein. The solvent may be selected, for example, from the group consisting of methyl ethyl ketone and ethanol.

The amount of eplerenone starting material added to the solvent used in the digestion process generally is sufficient to maintain a slurry (i.e., the eplerenone in the solvent or mixture of solvents is not completely solubilized) at the boiling point of the solvent or mixture of solvents. Illustrative values include, but are not limited to, about one gram of eplerenone per four mL methyl ethyl ketone and about one gram of eplerenone per eight mL ethanol.

The solution generally is cooled slowly once solvent turnover is complete to crystallize the solvated crystalline form of eplerenone. For the solvents tested, for example, the solution is cooled at a rate slower than about 20° C./minute, preferably about 10° C./minute or slower, more preferably about 5° C./minute or slower, and still more preferably about 1° C./minute or slower.

The endpoint temperature at which the solvated crystalline form is harvested will depend upon the solubility curve of the solvent or mixture of solvents. For most of the solvents described herein, for example, the endpoint temperature typically is less than about 25° C., preferably less than about 5° C., and more preferably less than about −5° C.

If a product comprising primarily or exclusively Form L is desired, a high purity eplerenone starting material typically is digested. The high purity eplerenone starting material preferably is at least 98% pure, more preferably at least 99% pure, and still more preferably at least 99.5% pure. The digested eplerenone product prepared in this manner generally comprises at least 10% Form L, preferably at least 50% Form L, more preferably at least 75% Form L, more preferably at least 90% Form L, still more preferably at least about 95% Form L, and still more preferably substantially phase pure Form L.

If a product comprising primarily or exclusively Form H is desired, a low purity eplerenone starting material typically is digested. The low purity eplerenone starting material generally contains only as much Form H growth promoter and/or Form L growth inhibitor as is needed to yield Form H. Preferably, the low purity eplerenone starting material is at least 65% pure, more preferably at least 75% pure, and still more preferably at least 80% pure. The digested eplerenone product prepared in this manner generally comprises at least 10% Form H, preferably at least 50% Form H, more preferably at least 75% Form H, more preferably at least 90% Form H, still more preferably at least about 95% Form H, and still more preferably substantially phase pure Form H.

8. Preparation of Amorphous Eplerenone

Amorphous eplerenone can be prepared in small quantities by suitable comminution of solid eplerenone, such as by crushing, grinding and/or micronizing. Phase pure amorphous eplerenone can be prepared, for example, by lyophilizing a solution of eplerenone, particularly an aqueous solution of eplerenone. These processes are illustrated in Examples 13 and 14 below.

WORKING EXAMPLES

The following examples contain detailed descriptions of the methods of preparation of the various solid state forms of eplerenone described in this application. These detailed descriptions fall within the scope, and serve to exemplify the invention. These detailed descriptions are presented for illustrative purposes only and are not intended as a restriction on the scope of the invention. All parts are by weight and temperatures are in degrees Centigrade unless otherwise indicated. The eplerenone starting material used in each of the following examples was prepared in accordance with scheme 1 set forth in Ng et al., WO98/25948.

Example 1

Preparation of (a) Methyl Ethyl Ketone Solvate from High Purity Eplerenone Starting Material and (b) Form L Crystalline Eplerenone from Resulting Solvate A. Preparation of Methyl Ethyl Ketone Solvate: High purity eplerenone (437 mg; greater than 99% purity with less than 0.2% diepoxide and 11,12 epoxide present) was dissolved in 10 mL of methyl ethyl ketone by heating to boiling on a hot plate with magnetic stirring at 900 rpm. The resulting solution was allowed to cool to room temperature with continuous magnetic stirring. Once at room temperature, the solution was transferred to a 1° C. bath with maintenance of the stirring for one hour. After one hour, the solid methyl ethyl ketone solvate was collected by vacuum filtration.

B. Preparation of Form L crystalline eplerenone: The solid methyl ethyl ketone solvate prepared in Step A above was dried in an oven at 100° C. for four hours at ambient pressure. The dried solid was determined to be pure Form L by DSC and XPRD analysis.

Example 2

Preparation of Additional Solvates from High Purity Eplerenone Starting Material Additional solvated crystalline forms were prepared by replacing methyl ethyl ketone with one of the following solvents: n-propanol, 2-pentanone, acetic acid, acetone, butyl acetate, chloroform, ethanol, isobutanol, isobutyl acetate, isopropanol, methyl acetate, ethyl propioriate, n-butanol, n-octanol, propyl acetate, propylene glycol, t-butanol, tetrahydrofuran, and toluene and carrying out the crystallization substantially as described above in Step A of Example 1. Form L eplerenone was formed from each of the solvates substantially as described in Step B of Example 1.

Example 3

Preparation of Methyl Ethyl Ketone Solvate by Vapor Diffusion Growth

Eplerenone (400 mg; greater than 99.9% purity) was dissolved in 20 mL of methyl ethyl ketone by warming on a hot plate to form a stock solution. An 8 mL amount of the stock solution was transferred to a first 20 mL scintillation vial and diluted to 10 mL with methyl ethyl ketone (80%). A 10 mL amount of the stock solution was transferred to a second 20 mL scintillation vial and diluted to 10 mL with methyl ethyl ketone (40%). The final 2 mL of the stock solution was diluted to 10 mL with methyl ethyl ketone (20%). The four vials containing the dilutions were transferred to a dessicator jar containing a small amount of hexane as an anti-solvent. The dessicator jar was sealed and the hexane vapor allowed to diffuse into the methyl ethyl ketone solutions. Methyl ethyl ketone solvate crystals grew in the 80% dilution sample by the next day.

Example 4

Preparation of Methyl Ethyl Ketone Solvate by Rotary Evaporation

About 400 mg of eplerenone (greater than 99.9% purity) is weighed into a 250 mL round bottom flask. Solvent (150 mL) is added to the flask and, if necessary, the solution is heated gently until the solid is dissolved. The resulting clear solution is placed on a Buchi rotary evaporator with a bath temperature of about 85° C. and the solvent is removed under vacuum. Solvent removal is stopped when approximately 10 mL of solvent remain in the round bottom flask. The resulting solids are analyzed by appropriate method (XPRD, DSC, TGA, microscopy, etc.) for determination of form.

Example 5

Slurry Conversion

Approximately 150 mg of Form L eplerenone and 150 mg of Form H eplerenone were added to 5 mL of ethyl acetate. The resulting slurry was allowed to stir at 300 rpm (magnetic stirring) overnight. The next day a sample of the solid was collected by filtration. Analysis of the sample by XPRD indicated that the sample was entirely composed of Form L eplerenone.

Example 6

Preparation of (a) Solvate from Low Purity Eplerenone Starting Material and (b) Form H Crystalline Eplerenone from Resulting Solvate Samples containing varying amounts of the impurity 7-methyl hydrogen 4α,5α:9α,11α-diepoxy-17-hydroxy-3-oxo-17α-pregnane-7α,21-dicarboxylate, γ-lactone (the "diepoxide") or the impurity 7-methyl hydrogen 11α,12α-epoxy-17-hydroxy-3-oxo-17α-pregn-4-ene-7α,21-dicarboxylate, γ-lactone (the "11,12-epoxide") were prepared by adding the desired amount of the impurity to a 7 mL scintillation vial together with an amount of eplerenone sufficient to provide a total sample mass of 100 mg. The weight percent of the diepoxide or 11,12-epoxide in each sample is given in Tables X-6A and X-6B, respectively. A micro-flea magnetic stirrer was added to each scintillation vial along with 1 mL of methyl ethyl ketone. The vials were loosely capped and the solid dissolved by heating to reflux on a hot plate with magnetic stirring. Once the solids were dissolved, the solutions were allowed to cool to room temperature on the hot plate. Magnetic stirring was maintained during the cooling period. After the solutions reached room temperature, the solids were collected by vacuum filtration and immediately analyzed by X-ray powder diffraction (XPRD). The solids were then placed in a 100° C. oven and dried for one hour at ambient pressure. The dried solids were analyzed by XPRD for Form H content by monitoring the area of the Form H diffraction peak at about 12.1 degrees two theta. All XPRD diffraction patterns were recorded using an Inel Multipurpose Diffractometer.

TABLE X-6A

| Weight Percent Diepoxide | Weight Eplerenone (mg) | Weight Diepoxide (mg) |
|---|---|---|
| 0% | 100.44 | — |
| 1% | 99.08 | 1.24 |
| 2% | 98.09 | 2.24 |
| 3% | 97.08 | 3.04 |
| 5% | 95.09 | 5.04 |

TABLE X-6B

| Weight Percent 11,12-Epoxide | Weight Eplerenone (mg) | Weight 11,12-Epoxide (mg) |
|---|---|---|
| 0% | 101.38 | 0 |
| 1% | 99.23 | 1.10 |
| 5% | 94.97 | 5.36 |
| 10% | 90.13 | 10.86 |

A. Diepoxide Results

Figure 13:
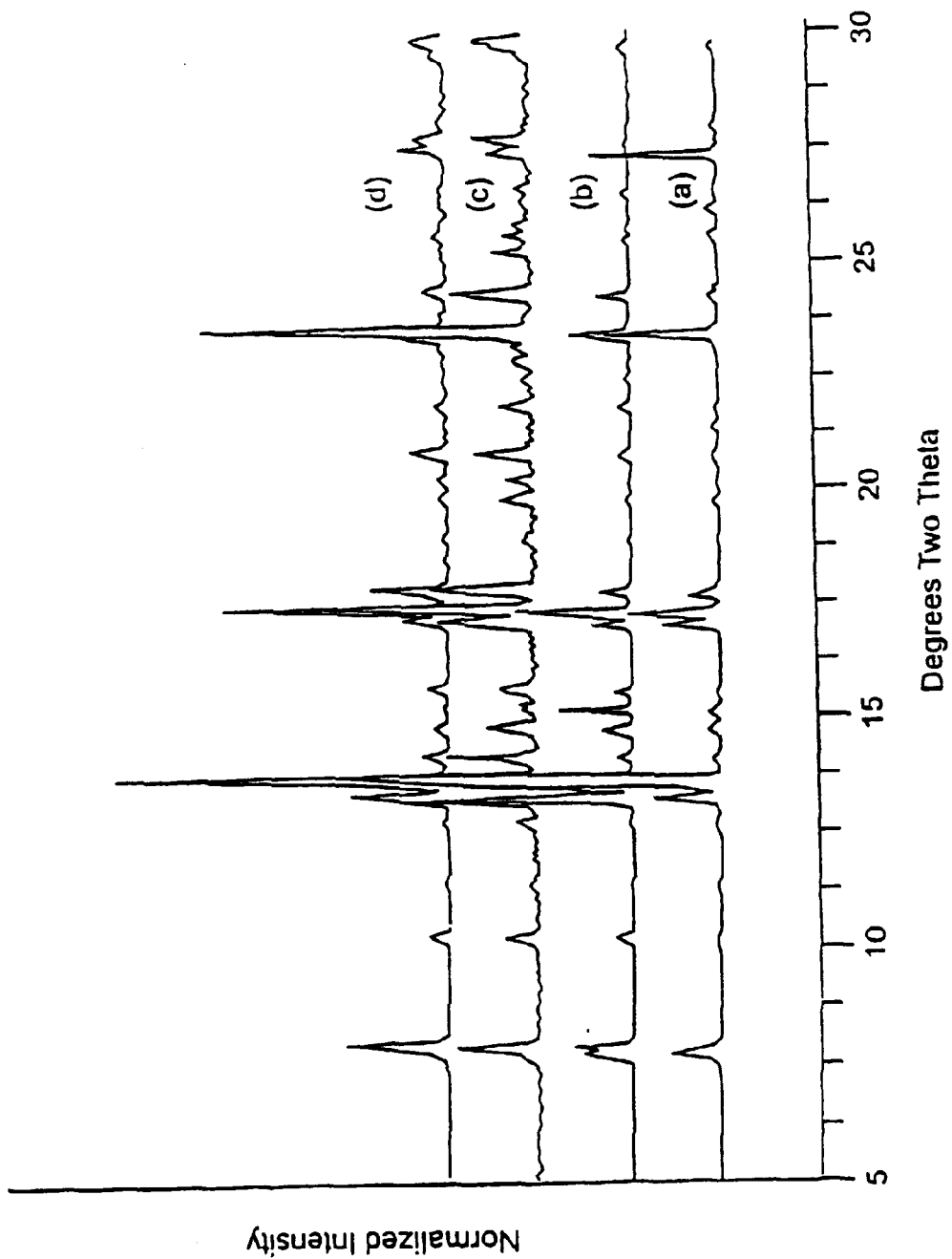
FIG. 13 shows the X-ray powder diffraction patterns for the wet cake (methyl ethyl ketone solvate) obtained from (a) 0%, (b) 1%, (c) 5%, and (d) 10% 11,12-epoxide-doped methyl ethyl ketone crystallizations.

FIG. 13 shows the X-ray powder diffraction patterns for the wet cake (methyl ethyl ketone solvate) obtained from the (a) 0%, (b) 1%, (c) 3%, and (d) 5% diepoxide-doped methyl ethyl ketone crystallizations. The peak intensities have been normalized for ease of comparison. No peaks characteristic of Form H or the diepoxide are present in the diffraction patterns. The patterns are characteristic of the methyl ethyl ketone solvate of eplerenone.

Figure 14:
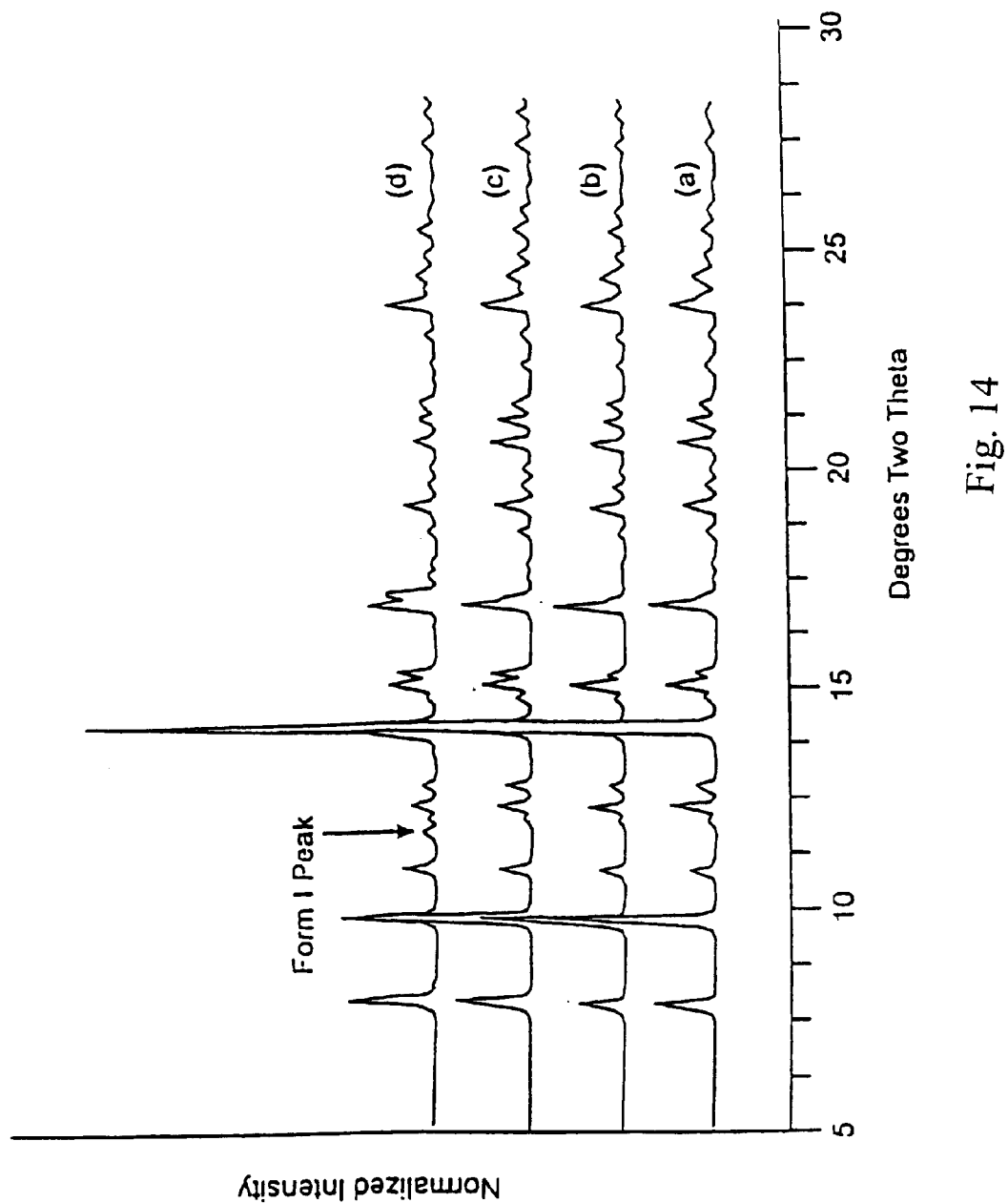
FIG. 14 shows the X-ray powder diffraction patterns for the dried solids obtained from (a) 0%, (b) 1%, (c) 5%, and (d) 10% 11,12-epoxide-doped methyl ethyl ketone crystallizations.

FIG. 14 shows the X-ray powder diffraction patterns for the dried solids obtained from the (a) 0%, (b) 1%, (c) 3%, and (d) 5% diepoxide-doped methyl ethyl ketone crystallizations. The peak intensities have been normalized for ease of comparison. No Form H was detected for the dried samples corresponding to the methyl ethyl ketone crystallizations performed at doping levels of 0 and 1%. Form H was detected in the dried samples corresponding to the methyl ethyl ketone crystallizations performed at doping levels of 3 and 5%. The area for the Form H diffraction peak at about 12.1 degrees two theta and the estimated Form H content for each sample are given in Table X-6C below.

TABLE X-6C

| Weight Percent of Diepoxide in Starting Eplerenone Mixture | Weight Percent of Diepoxide in Resulting Crystals (HPLC) | Form H Peak Area 12° Two Theta Peak | Estimated Weight Percent of Form H |
|---|---|---|---|
| 0% | — | None Detected | None Detected |
| 1% | 0.29% | None Detected | None Detected |
| 3% | 0.58% | 1168 | 10% |
| 5% | 1.05% | 4175 | 30% |

The results reported in Table X-6C confirm that the presence of the diepoxide affects the formation of Form H during the desolvation. These results indicate that the diepoxide is effective in inducing the formation of Form H eplerenone when it is incorporated into and/or adsorbed onto the methyl ethyl ketone solvate crystals.

Figure 15:
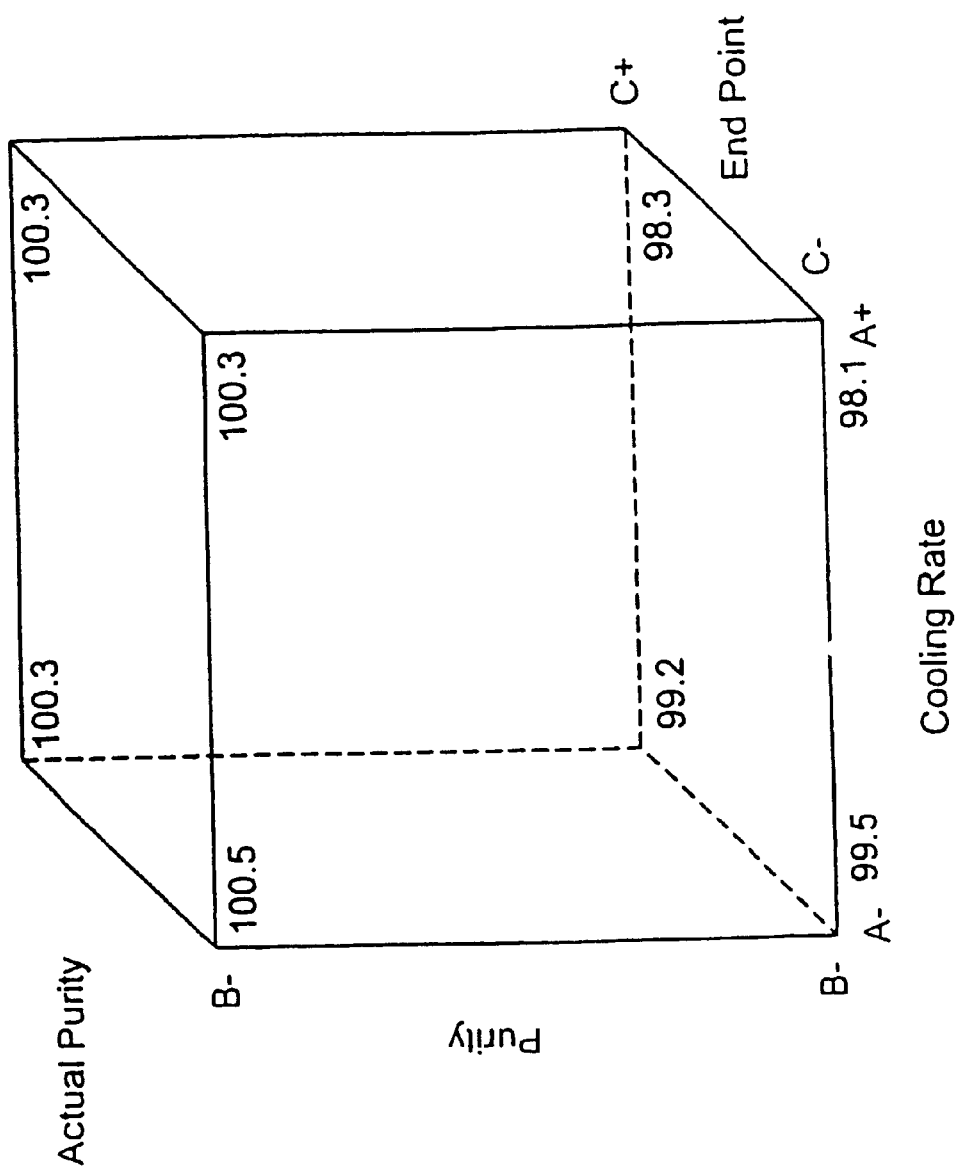
FIG. 15 shows a cube plot of product purity, starting material purity, cooling rate and endpoint temperature based on the data reported in Table X-7A.

The 3% diepoxide doping experiment was repeated to analyze the impact of the route of preparation on the amount of Form H formed during the desolvation. In this experiment, the methyl ethyl ketone solvate obtained from the doped crystallization was divided into two portions. The first portion was left untreated while the second portion was lightly ground in a mortar and pestle to induce a higher level of crystal defects. The two portions were both dried at 100° C. for one hour at ambient pressure. The dried solids were analyzed by XPRD. The XPRD patterns are given in FIG. 15 for the dried solids from the methyl ethyl ketone crystallization with 3% doping of diepoxide (a) without grinding of the solvate prior to drying, and (b) with grinding of the solvate prior to drying. The XPRD patterns indicated a greater amount of Form H in the ground sample relative to the unground sample. These results suggest that the conditions under which the methyl ethyl ketone solvate is isolated and handled can affect the crystal form that results from the desolvation.

B. 11,12-Epoxide Results

Figure 16:
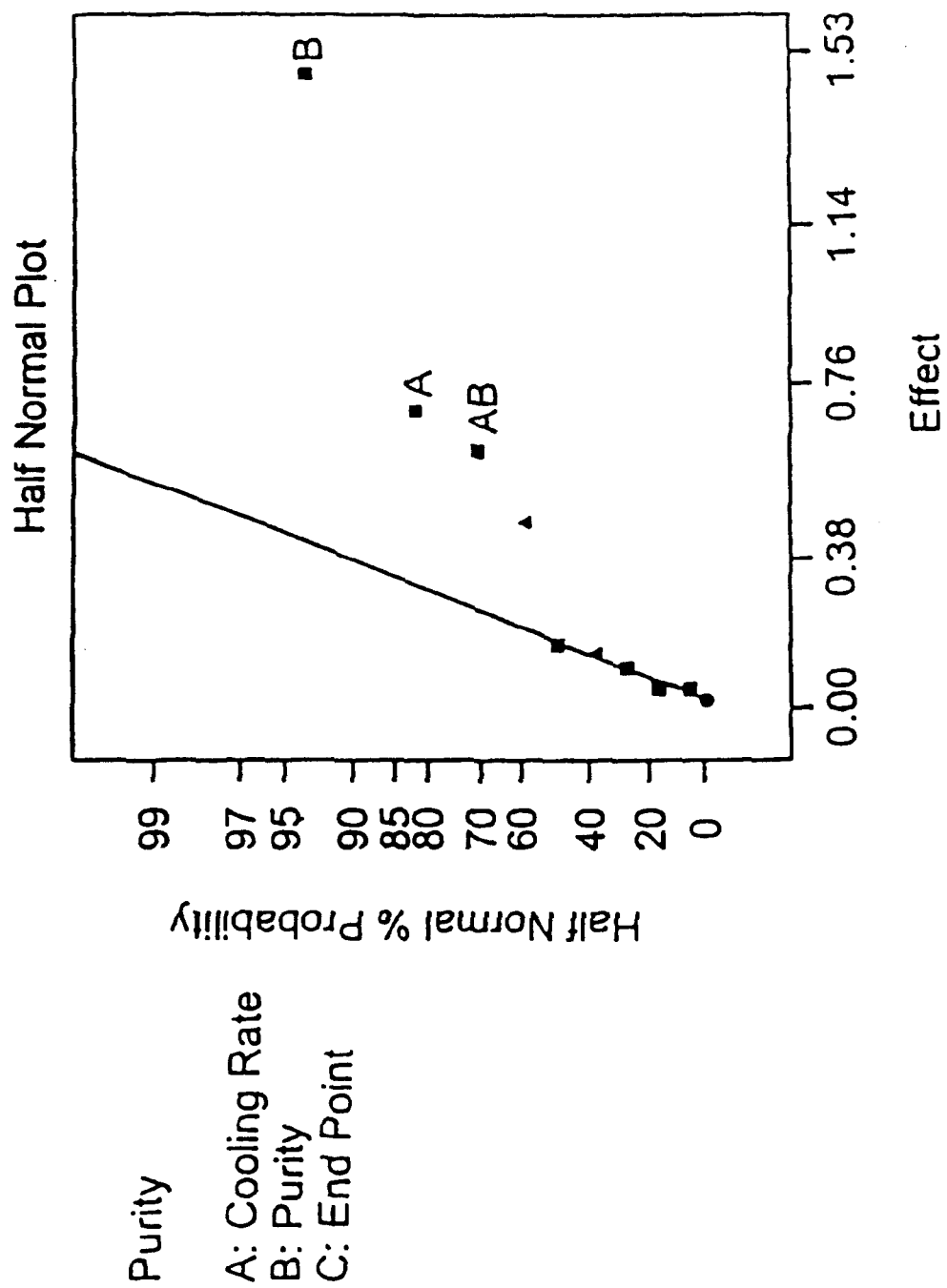
FIG. 16 shows a half normal plot prepared using the cube plot of FIG. 18 to determine those variables having a statistically significant effect on the purity of the final material.

FIG. 16 shows the X-ray powder diffraction patterns for the wet cake (methyl ethyl ketone solvate) obtained from the (a) 0%, (b) 1%, (c) 5%, and (d) 10% 11,12-epoxide-doped methyl ethyl ketone crystallizations. The peak intensities have been normalized for ease of comparison. No peaks characteristic of Form H or the 11,12-epoxide are present in the diffraction patterns. The patterns are characteristic of the methyl ethyl ketone solvate of eplerenone.

Figure 17:
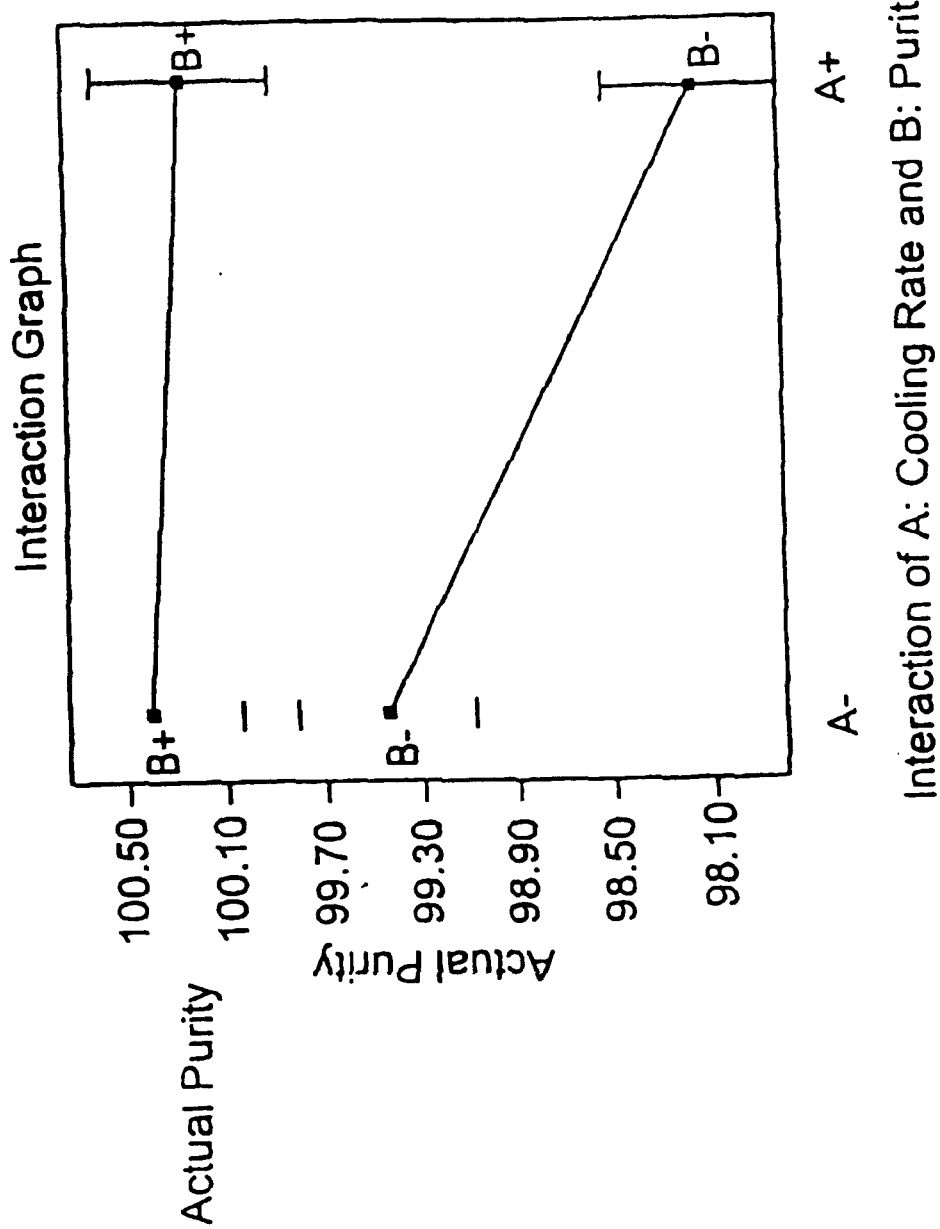
FIG. 17 is an interaction graph based on the results reported in Table X-7A showing the interaction between starting material purity and cooling rate on final material purity.

FIG. 17 shows the X-ray powder diffraction patterns for the dried solids obtained from the (a) 0%, (b) 1%, (c) 5%, and (d) 10% 11,12-epoxide-doped methyl ethyl ketone crystallizations. The peak intensities have been normalized for ease of comparison. No Form H was detected for the dried samples corresponding to the methyl ethyl ketone crystallizations performed at doping levels of 0, 1% and 5%. Form H was detected in the dried samples corresponding to the methyl ethyl ketone crystallization performed at a doping level of 10%. The area for the Form H diffraction peak at 12.1 degrees two theta and estimated Form H content for each sample are given in Table X-6D.

TABLE X-6D

| Weight Percent 11,12-Epoxide in Starting Eplerenone Mixture | Weight Percent 11,12-Epoxide in Resulting Crystals (HPLC) | Form H Peak Area 12° Two Theta Peak | Estimated Weight Percent of Form H |
|---|---|---|---|
| 0% | Not Available | None Detected | None Detected |
| 1% | Not Available | None Detected | None Detected |
| 5% | Not Available | None Detected | None Detected |
| 10% | Not Available | 1541 | 10–15% |

The results reported in Table X-6D confirm that the presence of the 11,12-epoxide impacts the formation of Form H during the desolvation. The percentage of impurity in the methyl ethyl ketone crystallization required to induce the formation of Form H eplerenone appears to be greater for the 11,12-epoxide than for the diepoxide.

Example 7

Effect of Crystallization and Drying on Final Crystal Form

The following four experiments analyzing the effect of crystallization and drying on the final crystal form were conducted: (i) methyl ethyl ketone crystallization of eplerenone ($2^3$+3 statistical design of experiment), (ii) crystallization of poor quality mother liquor residue, (iii) crystallization of high purity eplerenone with Form H seeding, and (iv) crystallization of low purity eplerenone with Form L seeding. Variables in the design of the experiments included cooling rate, starting material purity level, and end point temperature of crystallization. For purposes of this Example, high purity eplerenone was defined as ultra-pure milled eplerenone (HPLC analysis showed this material to be 100.8% pure) and low purity eplerenone was defined as 89% pure eplerenone. To prepare the low purity eplerenone, stripped-down mother liquors from the process for the preparation of eplerenone were analyzed and blended to yield a material that was 61.1% eplerenone, 12.8% diepoxide and 7.6% 11,12-epoxide. This material was then blended with a sufficient amount of high purity eplerenone to yield the 89% eplerenone.

A. Methyl Ethyl Ketone Crystallization

In the methyl ethyl ketone crystallization experiment, all runs were performed using 60 g of high purity eplerenone. High endpoint was defined as 45° C. and low endpoint was defined as 5° C. High cooling rate was defined as 3° C./minute cooling and low cooling rate was defined as 0.1° C./minute cooling. Center points were 1.5° C./minute cooling, 94.5% pure eplerenone, and a 25° C. endpoint.

After a background reading was taken with the FTIR, 250 mL of methyl ethyl ketone was charged to a 1 L Mettler RC-1, MP10 reactor and stirred at 100 rpm. After several scans, eplerenone was charged to the reactor followed by an additional 470 mL of methyl ethyl ketone. Agitation was increased to 500 rpm to suspend solids and the batch temperature was increased to 80° C. The batch temperature was held at 80° C. to ensure dissolution of the eplerenone. Black or white specks generally were visible in the resulting transparent solution. The batch temperature was then ramp cooled at the desired rate to the desired endpoint, where it was maintained for one hour before being pulled into a transfer flask and filtered. The vacuum was reactor, transfer flask and cake were then washed with 120 mL methyl ethyl ketone. Once the wash was pulled through the cake, the stopped. About 10 grams of each wet cake were dried in a vacuum oven under nominal conditions of 75° C. with a light nitrogen bleed. For the "high, high, high" and "low, low, low" experiments described below, fluid bed drying was operated under high and low conditions. High fluid bed drying was defined as 100° C. with a blower setting of "4" while low fluid bed drying was defined as 40° C. with a blower setting of "1".

B. Crystallization of Poor Quality Mother Liquor Residue

In the crystallization of poor quality mother liquor residue experiment, 60 g of the 61.1% pure material and 720 mL methyl ethyl ketone were charged directly to a 1 L Mettler RC-1, MP10 reactor. The 61.1% pure material was not blended with high purity eplerenone prior to being charged to the reactor. The resulting mixture was heated to 80° C. and was an opaque slurry at that temperature. The crystallization continued and the mixture was filtered at 45° C. under fast cooling conditions.

C. Form H Seeding

In the Form H seeding experiment, 60 g of pure (100.8%) eplerenone and 720 mL of methyl ethyl ketone were charged to a 1 L Mettler RC-1, MP10 reactor. The mixture was heated to 80° C. and then cooled to 25° C. at a rate of 1.5° C./minute. When the solution had cooled to 62° C., it was seeded with 3 g of phase pure Form H crystals to initiate crystallization. The Form H seed crystals were prepared by the digestion process described in Example 9 below.

D. Form L Seeding

In the Form L seeding experiment, 66.6 g of 89.3% eplerenone (prepared by mixing 48.3 g of 100% eplerenone with 18.3 g of 61.1% eplerenone) and 720 mL of methyl ethyl ketone were charged to a 1 L Mettler RC-1, MP10 reactor. The mixture was heated to 80° C. and then cooled to 25° C. at a rate of 1.5° C./minute. When the solution had cooled to 63° C., it was seeded with 3 g of phase pure Form L crystals to initiate crystallization. The Form L seed crystals were prepared by the crystallization and desolvation process described in Example 1 above.

Results from the experiments are reported in Table X-7A. In the n+1 crystallization experiment, Form H was detected only in the experiments employing low purity eplerenone where the product contained the diepoxide. Elevated levels of the diepoxide in the final product were also observed with higher cooling rates.

The crystallization of poor quality mother liquor residue experiment yielded poor quality material that appeared to be a mixture of the diepoxide and Form H when analyzed by X-ray powder diffraction.

The Form H seeding experiment (where high purity eplerenone was seeded with Form H) yielded a product that was 77% Form H based on X-ray powder diffraction analysis, but entirely Form H based on DSC. The X-ray powder diffraction model, however, had not been tested for linearity beyond about 15% Form H. This experiment was the only one of the four experiments of this Example where Form H was created in the absence of the diepoxide.

The Form L seeding experiment (where low purity eplerenone was seeded with Form L) yielded a product that was entirely Form L.

The data obtained for the high fluid bed drying of eplerenone appeared to correspond to the data obtained for the vacuum oven drying. The low fluid bed dryings yielded results that differed from those of the vacuum oven dryings.

TABLE X-7A

| Cooling Rate[1] | Cooling Endpoint[2] | Impurity Level[3] | Nucleation Temperature (° C.) | Weight Percent 11,12-Epoxide[4] | Weight Percent Diepoxide[4] | Assay For Desolvated Crystal | Percent Yield | Weight Percent Form H (XPRD) |
|---|---|---|---|---|---|---|---|---|
| + | + | − | 57.0 | ND | ND | 100.3 | 66.1 | ND |
| + | − | − | 54.9 | ND | ND | 100.3 | 98.1 | ND |
| − | + | − | 60.9 | ND | ND | 100.3 | | ND |
| − | − | − | 63.4 | ND | ND | 100.5 | 79.3 | ND |
| + | + | ++ | N/A | 4.8 | 36.6 | 43.3 | 27 | 100[5] |
| + | + | + | 52.2 | 0.49 | 0.88 | 98.3 | 62 | 29 |
| + | − | + | 53.3 | 0.56 | 1.0 | 98.1 | 87 | 9 |
| 0 | 0 | 0 | 59.0 | 0.18 | 0.36 | 99.4 | 75 | 5 |
| − | + | + | 63.3 | 0.20 | 0.44 | 99.4 | 36 | 31 |
| − | − | + | 61.4 | 0.18 | 0.40 | 99.5 | 87 | ND |
| 0 | 0 | 0 | 60.6 | 0.18 | 0.36 | 99.5 | 79.2 | ND |
| 0 | 0 | 0 | 55.9 | 0.38 | 0.80 | 98.6 | 80.5 | <3% |
| 0 | 0 | 100.8% eplerenone seeded with Form H | | 0.03 | ND | 100.4 | 82.2 | 77/100[6] |
| 0 | 0 | 89.3% eplerenone seeded with Form L | | 0.33 | 0.50 | 97.5 | 80.2 | ND |

[1]Cooling Rate: + = 3° C./min.; 0 = 1.5° C./min.; and − = 0.1° C./min.
[2]Cooling Endpoint: + = 45° C.; 0 = 25° C.; and − = 5° C.
[3]Impurity Level: : + = 89.3% purity eplerenone starting material; ++ = 61.1% purity eplerenone starting material; 0 = 100.8% purity eplerenone starting material; and − = 94.5% purity eplerenone starting material.
[4]Weight percent after drying solvate in a vacuum oven at 75° C.
[5]Appears to be mixture of Form H and diepoxide when analyzed by XPRD.
[6]Appears to be 77% Form H when analyzed by XPRD and 100% Form H when analyzed by DSC.

A. Material Purity

Figure 18:
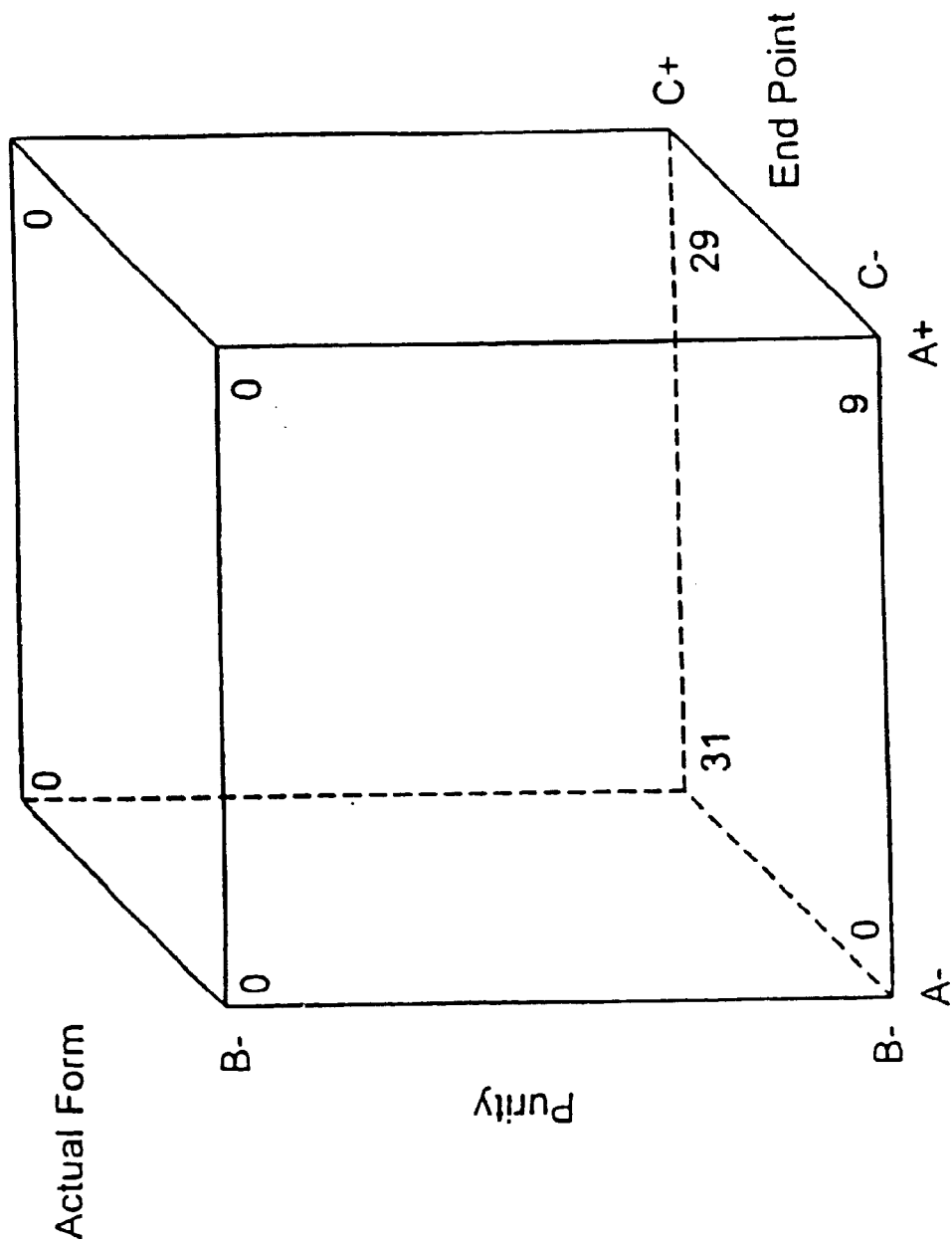
FIG. 18 shows a cube plot of Form H weight fraction, starting material purity, cooling rate and endpoint temperature based on the data reported in Table X-7A.

A cube plot of product purity, starting material purity, cooling rate and endpoint temperature based on the data reported in Table X-7A is shown in FIG. 18. The cube plot suggests that the use of a higher purity material at the start of crystallization will yield a higher purity product. The endpoint temperature of crystallization does not appear to greatly affect the product purity. The cooling rate, however, appears to have an effect with slightly less pure product resulting from a faster cooling rate. In fact, the level of diepoxide generally was higher with faster cooling rates.

Figure 19:
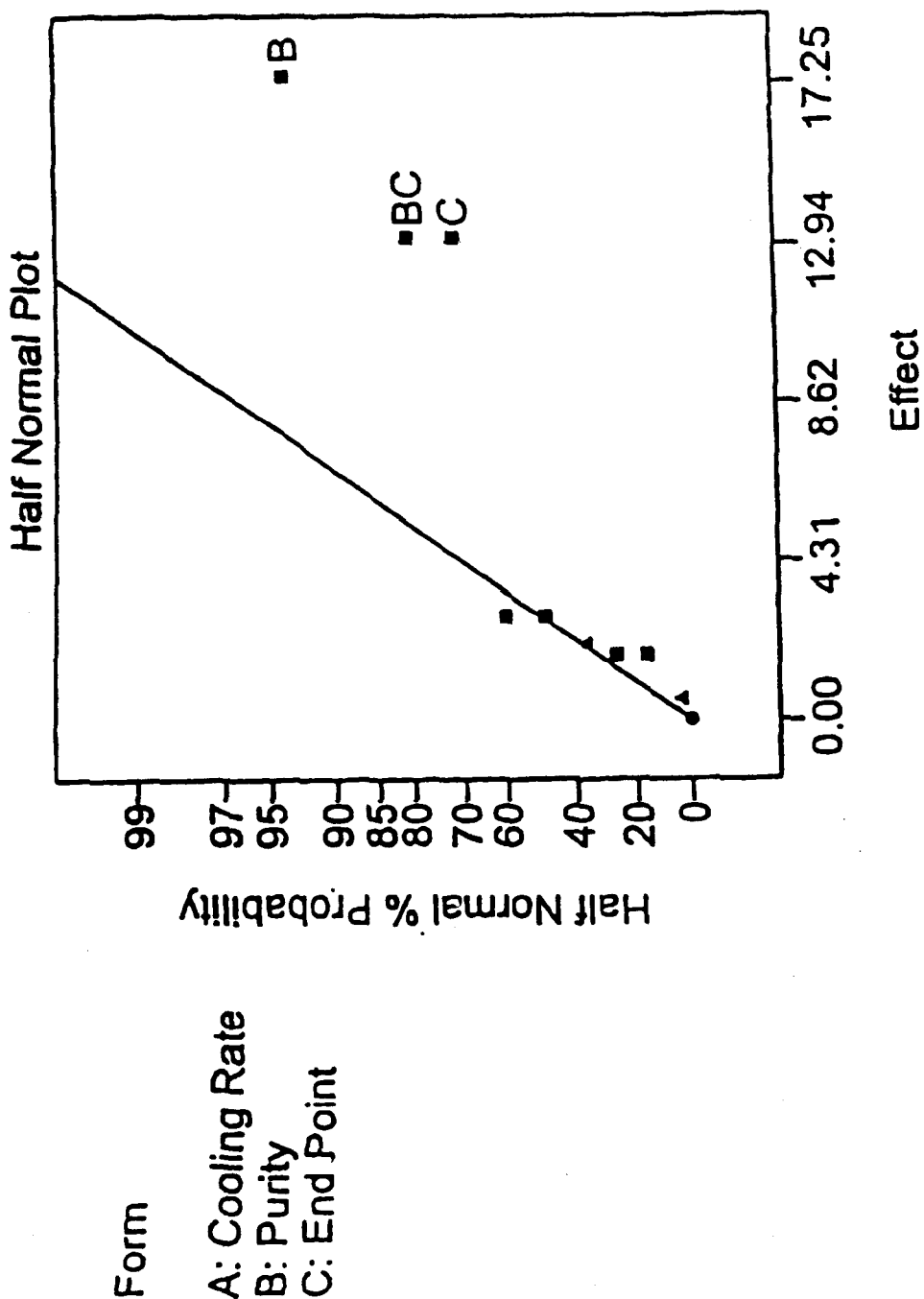
FIG. 19 shows a half normal plot prepared using the cube plot of FIG. 21 to determine those variables having a statistically significant effect on the purity of the final material.

FIG. 19 shows a half normal plot that was prepared using the results of cube plot to determine which variables, if any, had a statistically significant effect on the product purity. Starting material purity had the greatest statistically significant effect on product purity, although cooling rate and the interaction between cooling rate and starting material purity were also seen as statistically significant effects.

Figure 20:
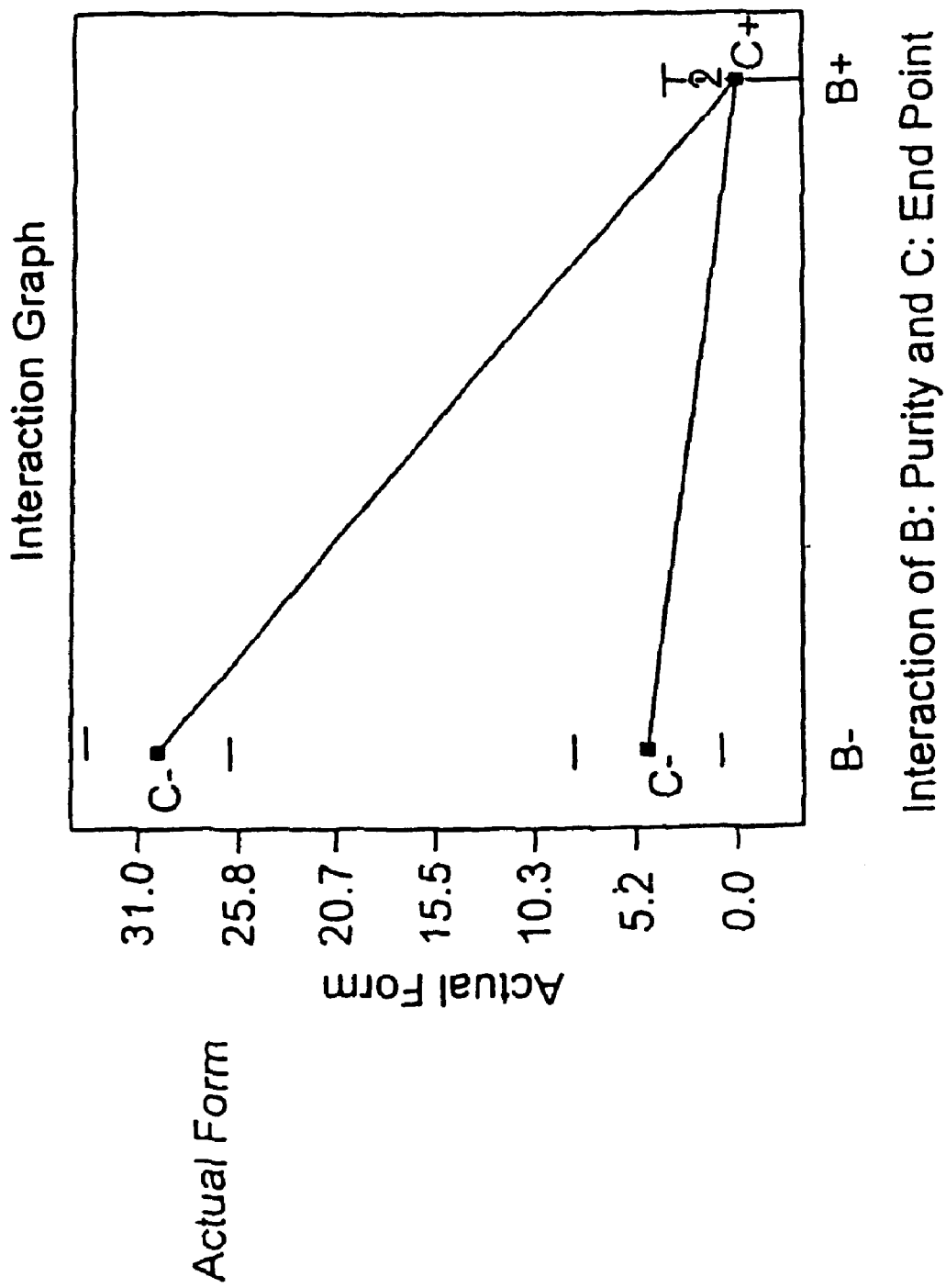
FIG. 20 is an interaction graph based on the results reported in Table X-7A showing the interaction between starting material purity and endpoint temperature on final material purity.

FIG. 20 is an interaction graph based on these results and showing the interaction between starting material purity and cooling rate on product purity. With the high purity eplerenone (100.8% eplerenone starting material) the cooling rate appears to have little or no effect on final purity. With the low purity eplerenone (89.3% eplerenone starting material), however, the product purity decreases as cooling rate increases. This result suggests that more impurities crystallize out in eplerenone crystallizations conducted at higher cooling rates.

B. Form H Content

Figure 21:
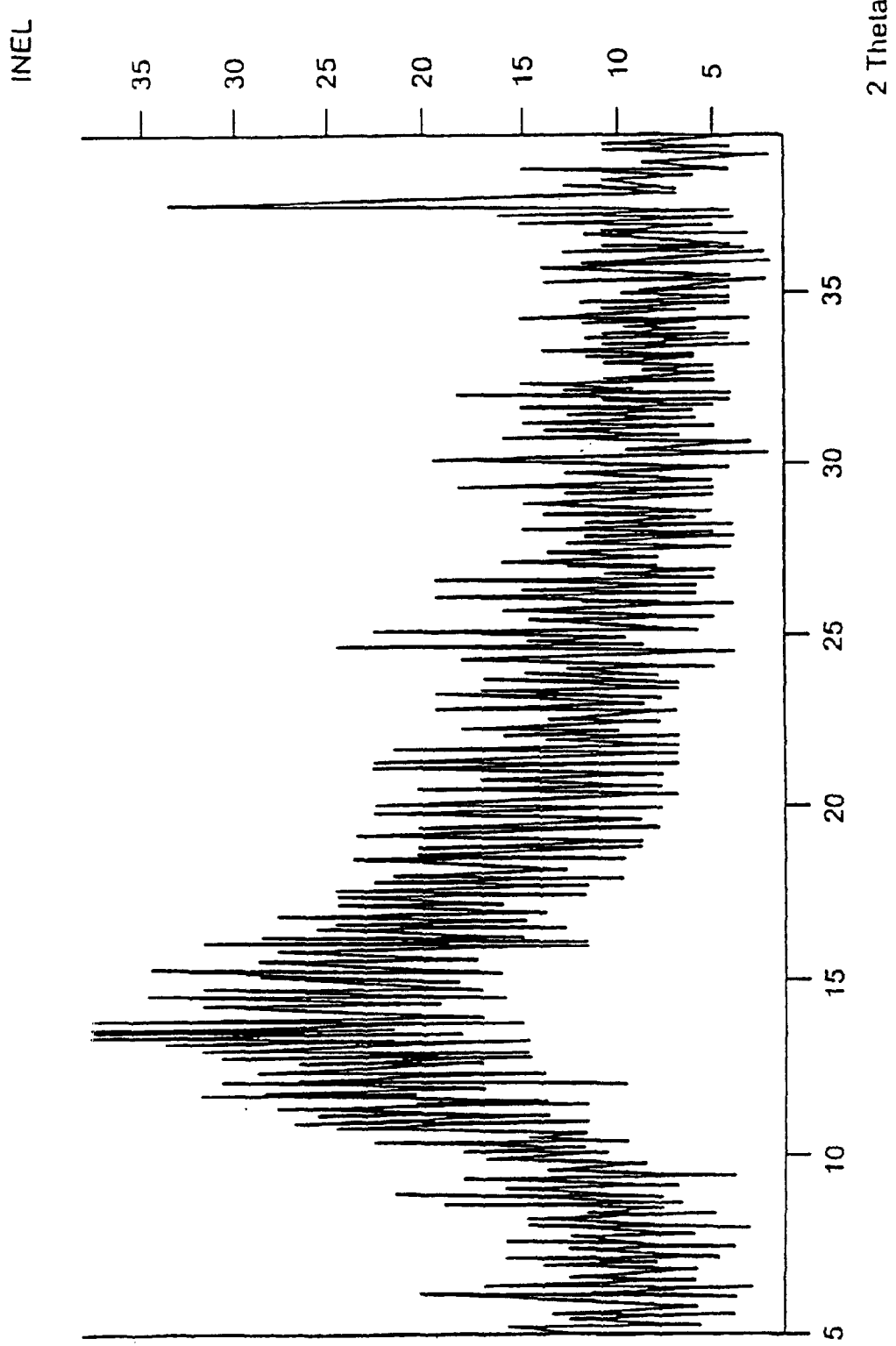
FIG. 21 shows an X-ray diffraction pattern of amorphous eplerenone.

A cube plot of Form H weight fraction, starting material product purity, cooling rate and endpoint temperature based on the data reported in Table X-7A is shown in FIG. 21. The cube plot suggests that the use of a higher purity eplerenone at the start of crystallization will yield a lower amount of Form H. The endpoint temperature of crystallization also appears to have an effect on the form of the final product. The cooling rate does not appear to greatly affect the formation of Form H although some Form H may result from faster cooling at the low endpoint temperature in the presence of impurities.

Figure 22:
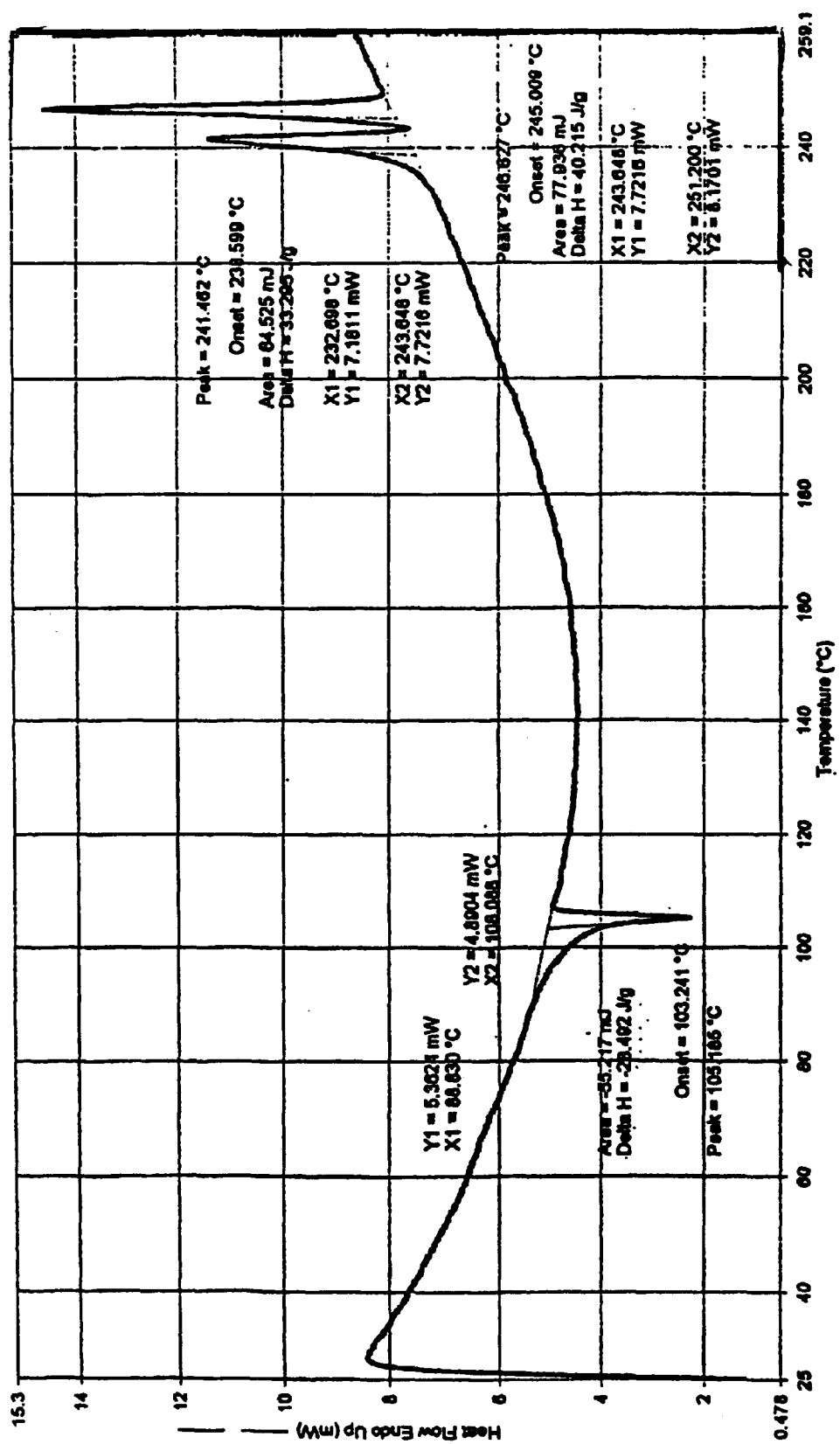
FIG. 22 shows a DSC thermogram of amorphous eplerenone.

FIG. 22 shows a half normal plot that was prepared using the results of the cube plot to determine which variables, if any, had a statistically significant effect on the amount of Form H in the final material. Starting material purity, endpoint temperature of the crystallization and the interaction between the two variables were seen as statistically significant effects.

Figure 23:
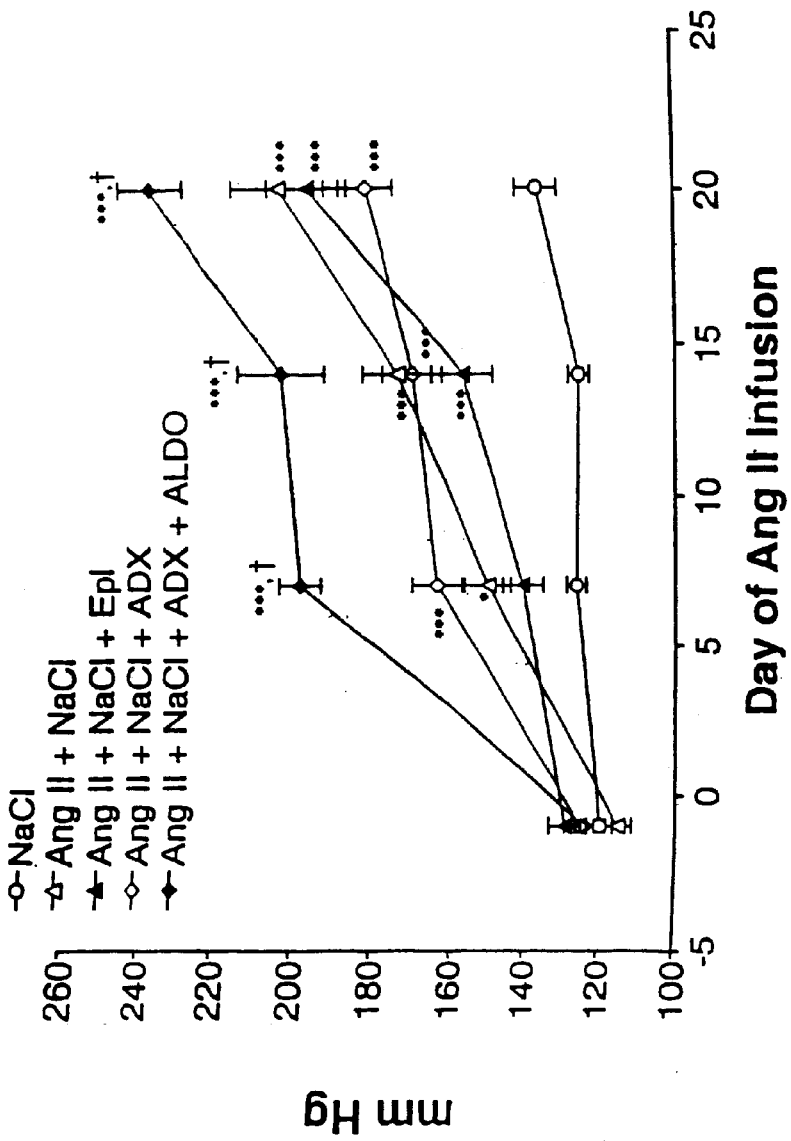
FIG. 23 shows changes in systolic blood pressure in angiotensin II infused rat study.

FIG. 23 is an interaction graph based on these results and showing the interaction between starting material purity and endpoint temperature on final Form H content. With the high purity eplerenone (100.8% eplerenone starting material), endpoint temperature appears to have little effect on Form H content. No Form H resulted in either case with pure eplerenone. With low purity eplerenone (89.3% eplerenone starting material), however, Form H was present in both cases, with significantly more Form H at higher endpoint temperatures.

Table X-7B reports the weight fraction of Form H measured in materials dried using either a fluid bed (LAB-LINE/P.R.L. Hi-Speed Fluid Bed Dryer, Lab-Line Instruments, Inc.) or a vacuum oven (Baxter Scientific Products Vacuum Drying Oven, Model DP-32). Similar Form H content was observed for comparable materials dried in either the high fluid bed or the vacuum oven. A difference was observed, however, for comparable materials dried in the low fluid bed relative to the vacuum oven.

TABLE X-7B

| Cooling Rate | End Point | Impurity Level | Drying Type | Weight Percent Form H |
|---|---|---|---|---|
| High | High | High | Vacuum Oven | 29% |
| High | High | High | High Fluid Bed | 25% |
| High | High | High | Low Fluid Bed | 4.7% |
| Low | Low | Low | Vacuum Oven | ND |
| Low | Low | Low | High Fluid Bed | ND |
| Low | Low | Low | Low Fluid Bed | 5.5% |

Example 8

Crystallization of a Mixture of Form H and Form L From Methyl Ethyl Ketone To Prepare a Solvate, and (b) Desolvation of the Solvate to Prepare Form L Form H eplerenone (10 g) was combined with 80 mL of methyl ethyl ketone. The mixture was heated to reflux (79° C.) and stirred at this temperature for about 30 minutes. The resulting slurry was then cooled with a stepwise, holdpoint protocol by maintaining the slurry at 65° C., 50° C., 35° C. and 25° C. for about 90 minutes at each temperature. The slurry was filtered and rinsed with about 20 mL methyl ethyl ketone. The isolated solid was initially dried on the filter and then in a vacuum oven at 40–50° C. The drying was completed in the vacuum oven at 90–100° C. The desolvated solid was obtained with an 82% recovery. XPRD, MIR and DSC confirmed that the solid had a Form L crystalline structure.

Example 9

Digestion of Low Purity Eplerenone Starting Material with a Solvent to Prepare Form H A. Digestion With Ethanol Solvent:

Low purity eplerenone (24.6 g; 64% by weight assay via HPLC) was combined with 126 mL of ethanol 3A. The slurry was heated to reflux and the distillate removed. An additional 126 mL of ethanol 3A was simultaneously added as 126 ml of solvent was removed via atmospheric distillation. Upon completion of the solvent turnover, the mixture was cooled to 25° C. and stirred for one hour. The solid was filtered and rinsed with ethanol 3A. The solid was air-dried to give the ethanol solvate. The solvate was further dried in a vacuum oven at 90–100° C. for six hours to obtain 14.9 g of Form H eplerenone.

B. Digestion with Methyl Ethyl Ketone Solvent

In an alternative digestion process, 1 gram of low purity eplerenone (about 65% pure) was digested in 4 mL of methyl ethyl ketone for two hours. After the two hours, the mixture was allowed to cool to room temperature. Once cooled, the solid was collected by vacuum filtration and determined to be the methyl ethyl ketone solvate by XPRD analysis. The solid was dried at 100° C. for 30 to 60 minutes. The dried solids were determined to be pure Form H by XPRD.

Example 10

Digestion of High Purity Eplerenone Starting Material with a Solvent to Prepare Form L A. Digestion with Ethanol Solvent:

High purity eplerenone (1 gram) was digested in 8 mL of ethanol for approximately two hours. The solution was then allowed to cool to room temperature and the solids were collected by vacuum filtration. Analysis of the solids by XPRD immediately after filtration indicated that the solids were a solvate (presumably the ethanol solvate). The solids were subsequently dried at 100° C. at atmospheric pressure for 30 minutes. The dried solid was analyzed by XPRD and determined to be predominately Form L (no Form H detected).

B. Digestion with Methyl Ethyl Ketone Solvent:

High purity eplerenone (1 gram) was digested in 4 mL of methyl ethyl ketone for two hours. After the two hours, the solution was allowed to cool to room temperature and the solids collected by vacuum filtration. The solid was immediately analyzed by XPRD and determined to be a solvate of eplerenone (presumably the methyl ethyl ketone solvate). The solvate was subsequently dried at 100° C. at ambient pressure for 30 to 60 minutes. The dried solids were analyzed by XPRD and determined to be primarily Form L with no diffraction peaks for Form H present.

Example 11

Crystallization of Form L Directly From Solution

Procedure A: Eplerenone (2.5 g) was dissolved in ethyl acetate by heating to 75° C. Once the eplerenone dissolved, the solution was held at 75° C. for 30 minutes to ensure complete dissolution. The solution was then cooled at 1° C./min to 13° C. Once at 13° C., the slurry was allowed to stir for two hours at 750 rpm with an overhead stirrer. The crystals were collected by vacuum filtration and dried in a vacuum oven at 40° C. for one hour. The XPRD pattern and DSC thermogram of the solid were characteristic of Form L eplerenone. Thermal gravimetric analysis (TGA) of the solid indicated no weight loss from the solid up to 200° C.

Procedure B: In an alternative procedure, 2 g of eplerenone was dissolved in 350 mL of 15/85% acetonitrile/water by heating on a hot plate with magnetic stirring. Once the eplerenone was dissolved, the solution was allowed to cool to room temperature overnight with magnetic stirring. The resulting solid was collected by vacuum filtration. The crystals were birefringent and had a triangular, plate-like crystal habit. The solid had an XPRD and DSC characteristic of Form L eplerenone. TGA indicated no weight loss up to 200° C.

Procedure C: In an alternative procedure, 640 mg of eplerenone was placed in a 50 mL flask with 20 mL of ethyl benzene. The resulting slurry was heated to 116° C. and became a clear solution. The clear solution was cooled to 25° C. over 30 minutes. Nucleation began at 84° C. during the cooling period. The resulting solids were filtered from the solution and air-dried to give 530 mg of solids (83% recovery). Hot-stage microscopy and XPRD confirmed that the solids were Form L crystals.

Procedure D: In an alternative procedure, 1.55 g of eplerenone was added to 2.0 mL of nitrobenzene and heated to 200° C. The resulting slurry was stirred overnight at 200° C. The solution was allowed to cool to room temperature (natural air convection) the following day and the solid was isolated. The solid was determined to be Form L eplerenone by XPRD and polarized light microscopy.

Procedure E: In an alternative procedure, 5.0 g of eplerenone (purity greater than 99%) was added to 82 g of methanol (104 mL). Under stirring action (210 rpm), the solution was heated to 60° C. and held at that temperature for 20 minutes to ensure complete dissolution. The solution was then cooled to −5° C. at a rate of 0.16° C./minute under stirring. The crystals were collected by filtration and dried in a vacuum oven at 40° C. for 20 hours. The dried solids were determined to be pure Form L eplerenone by DSC and XPRD analysis.

Procedure F: In an alternative procedure, 6.0 g of eplerenone (ethanol solvate containing 9% ethanol and having a corrected purity of 95.2%) was added to 82 g of methanol (104 mL). Under stirring action (210 rpm), the solution was heated to 60° C. and held at that temperature for 20 minutes to ensure complete dissolution. The solution was then cooled to 50° C. at a rate of 0.14° C./minute and then held at that temperature for about 2.5 hours. The solution was then cooled to −5° C. at a rate of 0.13° C./minute under stirring. The crystals were collected by filtration and dried in a vacuum oven at 40° C. for 16 hours. The dried solids were determined to be pure Form L eplerenone by DSC and XPRD analysis.

Example 12

Crystallization of Form E Directly From Solution 150.5 mg of the diepoxide and 2.85 g of eplerenone were added to 1.5 mL of nitrobenzene. The mixture was magnetically stirred at 200° C. for several hours. The slurry was then allowed to cool to room temperature by natural air convection. The sample was dried and analyzed by polarized light microscopy and XPRD. The XPRD indicated that the sample was a mixture of Form H and Form L. The crystals were translucent by microscopy, indicating that desolvation (and conversion to either Form H or Form L) did not occur.

Example 13

Preparation of Amorphous Eplerenone by Comminution

Approximately one-half of a steel Wig-L-Bug container was filled with about 60 g of eplerenone (greater than 99.9% purity). A steel ball and cap were placed on the sample container and agitated for 30 seconds by the Wig-L-Bug apparatus. The eplerenone was scraped off the surface of the Wig-L-Bug container and the container agitated for an additional 30 seconds. The resulting solid was analyzed by XPRD and DSC and determined to be a mixture of amorphous eplerenone and Form L crystalline eplerenone.

Example 14

Preparation of Amorphous by Lyophilization

Figure 24:
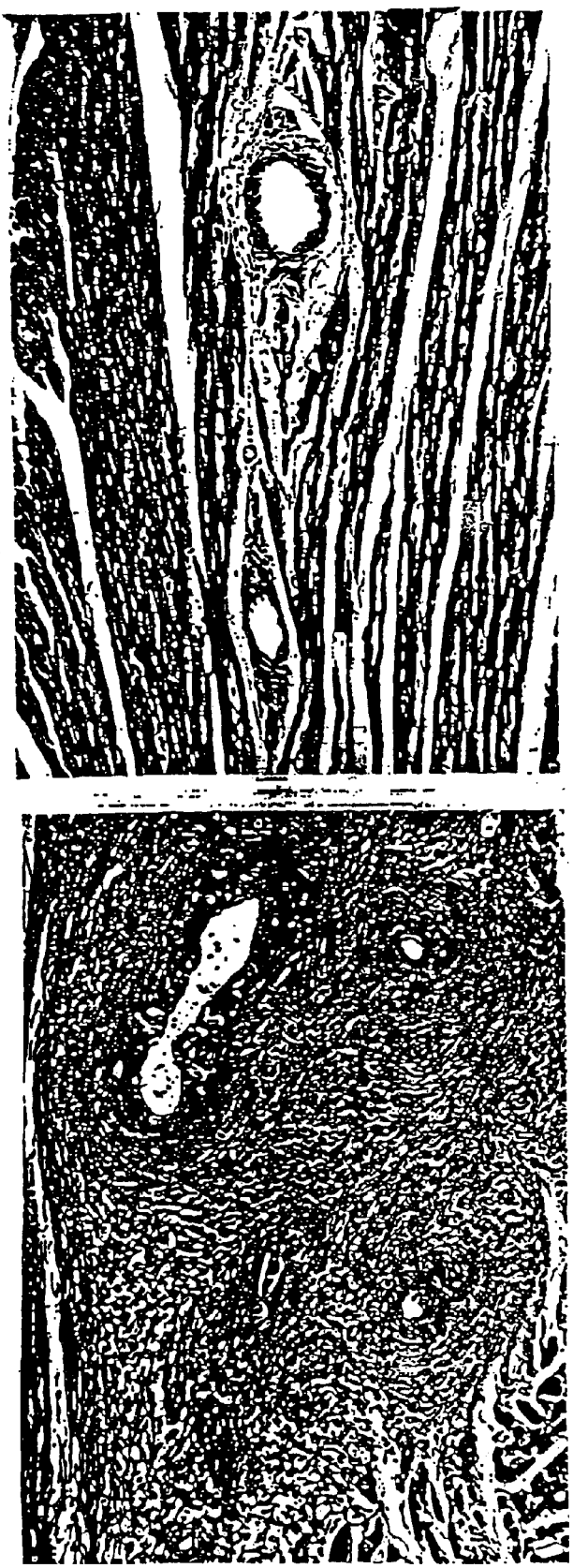
FIG. 24 shows prevention by eplerenone (epoxymexrenone) of vascular inflammation in the heart of angiotensin II infused rats.
Figure 25:
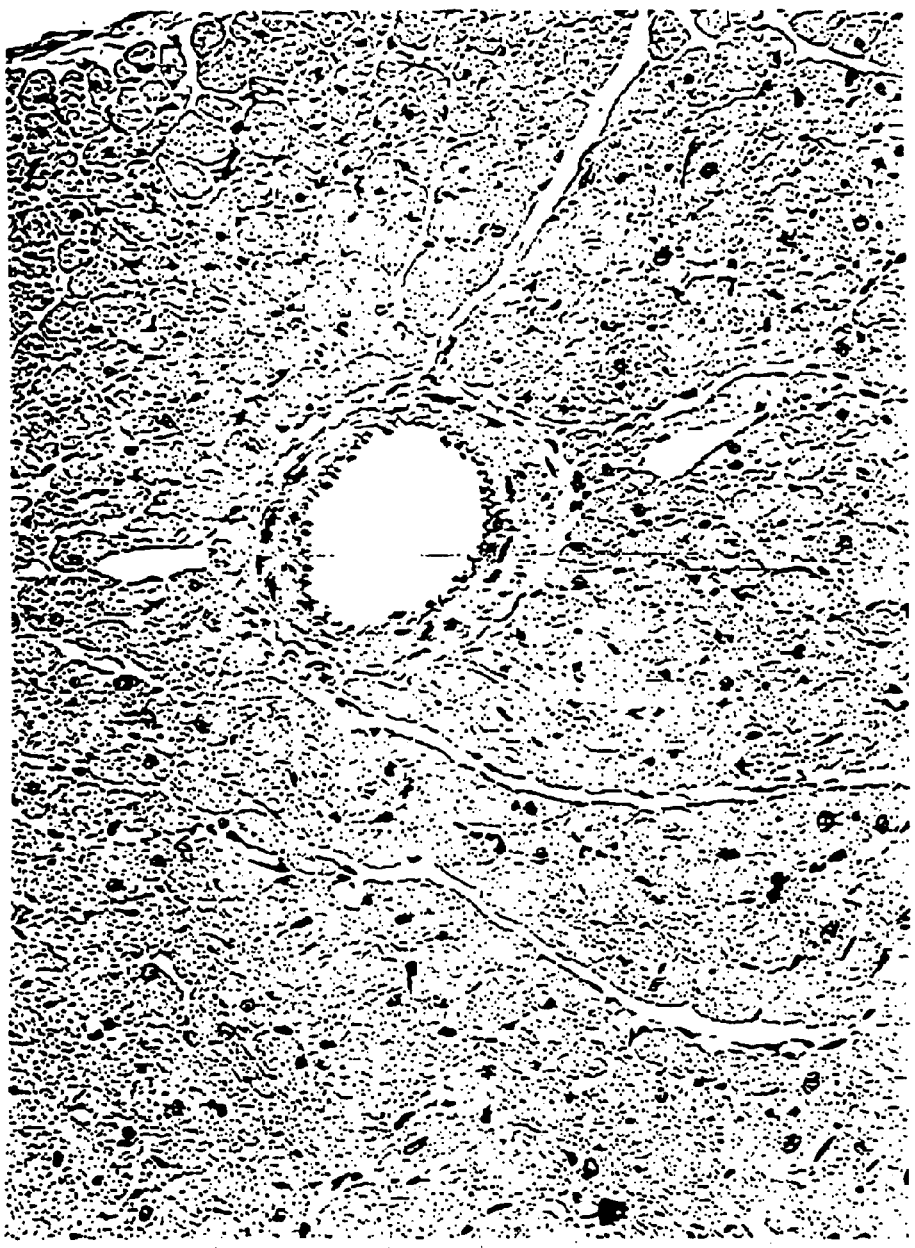
FIG. 25 shows lack of cyclooxygenase-2 (COX-2) expression in the heart of a vehicle infused rat.

Approximately 100 mg of crude eplerenone was weighed into a beaker containing 400 mL of water. The solution was heated slightly for five minutes, and then sonicated and heated with stirring for an additional five minutes. Approximately 350 mL of the eplerenone solution was filtered into a 1000 mL round bottom flask containing 50 mL of HPLC water. The solution was flashed frozen in a dry ice/acetone bath over a time period of one to two minutes. The flask was attached to a Labconco Freezone 4.5 freeze dryer and dried overnight. The solids in the flask were transferred to a small brown bottle. A small aliquot was observed under polarized light microscopy at 10×, 1.25× optivar in cargille oil (1.404) and observed to be at least 95% amorphous eplerenone. FIGS. 24 and 25 show the XPRD pattern and DSC thermogram obtained for the amorphous eplerenone. The peak observed at 39 degrees two theta in FIG. 24 is attributable to the aluminum sample container.

Example 15

Eplerenone Polymorph Composition

Tablets containing 25 mg, 50 mg, 100 mg and 200 mg doses of Form L eplerenone are prepared and have the following composition:

| Ingredient | Weight % of Tablet |
| --- | --- |
| Form L Eplerenone | 29.41 |
| Form H Eplerenone | Not Detected |
| Lactose Monohydrate (#310, NF) | 42.00 |
| Microcrystalline Cellulose (NF, Avicel PH101) | 18.09 |
| Croscarmellose Sodium (NF, Ac-Di-Sol) | 5.00 |
| Hydroxypropyl Methylcellulose (#2910, USP, Pharmacoat 603) | 3.00 |
| Sodium Lauryl Sulfate (NF) | 1.00 |
| Talc (USP) | 1.00 |
| Magnesium Stearate (NF) | 0.5 |
| Total | 100.00 |

Example 16

Eplerenone Polymorph Composition

Capsules (hard gelatin capsule, #0) are prepared containing a 100 mg dose of eplerenone and have the following composition:

| Ingredient | Amount (mg) |
| --- | --- |
| Form L Eplerenone | 90.0 |
| Form H Eplerenone | 10.0 |
| Lactose, Hydrous, NF | 231.4 |
| Microcrystalline Cellulose, NF | 45.4 |
| Talc, USP | 10.0 |
| Croscarmellose Sodium, NF | 8.0 |
| Sodium Lauryl Sulfate, NF | 2.0 |
| Colloidal Silicon Dioxide, NF | 2.0 |
| Magnesium Stearate, NF | 1.2 |
| Total Capsule Fill Weight | 400.0 |

Example 17

Eplerenone Polymorph Composition

Capsules (hard gelatin capsule, size #0) are prepared containing a 200 mg dose of eplerenone and have the following composition:

| Ingredient | Amount (mg) |
| --- | --- |
| Form L Eplerenone | 190.0 |
| Form H Eplerenone | 10.0 |
| Lactose, Hydrous, NF | 147.8 |
| Microcrystalline Cellulose, NF | 29.0 |
| Talc, USP | 10.0 |
| Croscarmellose Sodium, NF | 8.0 |
| Sodium Lauryl Sulfate, NF | 2.0 |
| Colloidal Silicon Dioxide, NF | 2.0 |
| Magnesium Stearate, NF | 1.2 |
| Total Capsule Fill Weight | 400.0 |

Example 18

Preparation of Milled Eplerenone

Dried methyl ethyl ketone solvate is first delumped by passing the solvate through a 20 mesh screen on a Fitzmill. The delumped solid is then pin milled using an Alpine Hosakawa stud disk pin mill operating under liquid nitrogen cooling at a feed rate of approximately 250 kilograms/hour. Pin milling produces milled eplerenone with a $D_{90}$ size of approximately 65–100 microns.

Subject Populations

Certain groups are more prone to disease modulating effects of aldosterone. Members of these groups that are sensitive to aldosterone are typically also salt sensitive, wherein individuals blood pressure generally rises and falls with increased and decreased sodium consumption, respectively. While the present invention is not to be construed as limited in practice to these groups, it is contemplated that these subject groups may be particularly suited for therapy with an anti-inflammatory dose of an aldosterone blocker of the present invention.

In an embodiment of the present invention, the subject preferably is a member, in whole or in part, of the Japanese ethnic group or the Black ethnic group. Hypertension in Japan is a significant problem. One recent estimate suggests that around 30 million Japanese adults suffer from hypertension. (Saruta T. *J Clin Ther Med* 1997;13:4024–9). While blood pressure control status has recently improved in Japan, hypertension management is still considered to be insufficient. (Shimamoto; K. Japanese Cases. Nihon Rinsyo (Clinical Medicine in Japan), 2000;58 (Suppl):593–6). Trends in blood pressure and urinary sodium and potassium excretion in Japan: reinvestigation in the 8th year after the Intersalt Study. Nakagawa H, et al.: *Hum Hypertens* 1999 November;13(11):735–41, recommended that the Japanese population increase dietary potassium and decrease dietary sodium.

Sodium restriction regimens in Japan, however, are confounded by poor compliance. A Japanese study by Kobayashi et. al. prescribed a diet restricted to 5–8 grams/day yet failed also to achieve good compliance. (Kobayashi, Y et al.: *Jpn Circ J* 1983;47:268–75). The Ministry of Health and Welfare of Japan has recommended that sodium restricted to less than 10 grams/day (Guidelines on treatment of hypertension in the elderly, 1995—a tentative plan for comprehensive research projects on aging and health—Members of the Research Group for "Guidelines on Treatment of Hypertension in the Elderly", Comprehensive Research Projects on Aging and Health, the Ministry of Health and Welfare of Japan). Ogihara T, et al.: *Nippon Ronen Igakkai Zasshi.* 1996;33(12):945–75). Despite 10 years of initiatives to educate the public, there still remains a high rate of non-compliance (estimated to be greater than about 50%) as measured by urinary sodium levels among normal and hypertensive individuals in Japan. (Kobayashi Y, et al.: *Jpn Circ J*;47(2):268–75).

Further, the Japanese show two broad groups, salt sensitive and salt insensitive (Preventive nutritional factors in epidemiology: interaction between sodium and calcium. Mizushima S, *Clin Exp Pharmacol Physiol* 1999;26:573). Many Japanese hypertensives are believed to be salt sensitive. Accordingly, members of the Japanese ethnic group who exhibit the combination of salt sensitivity, high sodium intake and failure to voluntarily limit sodium consumption are particularly benefited by the therapy of the present invention.

In another embodiment of the present invention, therefore, the subject in need of treatment is salt sensitive individual who is, in whole or in part, a member of the Japanese ethnic group, and, inter alia, has or is susceptible to hypertension and/or cardiovascular disease, particularly cardiovascular disease selected from one or more members of the group consisting of heart failure, left ventricular diastolic dysfunction, hypertrophic cardiomyopathy, and diastolic heart failure.

Hypertension in Blacks similarly is a significant problem. Many hypertensive and normotensive Blacks are salt sensitive (Svetkey, LP et al.: *Hypertension.* 1996;28:854–8). Accumulated epidemiologic data indicate that the prevalence of hypertension among Blacks is greater than among whites in almost all age- and sex-matched groups. Hypertensive Blacks generally. have a higher incidence of left ventricular dysfunction, stroke, and renal damage (but a lower incidence of ischemic heart disease) than do hypertensive whites. (Eisner, G M. *Am J Kidney Dis* 1990; 16(4 Suppl 1):35–40) The reasons for the epidemic hypertension rates among American Blacks are largely environmental: high sodium and alcohol intake, obesity, physical inactivity, and psychosocial stress have all been identified as causes. (Flack, J M, et al.: *J Assoc Acad Minor Phys* 1991;2:143–50)

The cause of the problem in both Black and white populations is unclear, but it appears that a difference in sodium handling may contribute to the particular hemodynamic and hormonal profile of Black hypertensives. Intrinsic or hypertension-induced renal abnormalities that limit natriuretic capacity, reduced Na+,K(+)-ATPase pump activity, other membrane ion transport disturbances, differential exposure to psychological stressors, greater insulin resistance, and dietary factors (reduced calcium and potassium intake) have been suggested as possibly playing a role. (Flack, J M et al.: *Hypertension*; 1991;17(1 Suppl):I115–21). One study has indicated that genetic differences may also underlie the salt sensitivity in Blacks. (Svetkey, L P, et al.: *Hypertension* 1996; 28:854–8).

Hypertension among Blacks generally is initially managed by restricting sodium intake in the diet. If dietary control is insufficient, administration of an antihypertensive agent with 24-hour efficacy and that lowers vascular peripheral resistance, promotes sodium excretion, and potentially improves renal hemodynamics is recommended. (Eisner, G M. *Am J Kidney Dis* 1990;16(4 Suppl 1):35–40). Blacks, however, generally respond differently to antihypertensive agents as compared to white. In general, beta-adrenergic receptor antagonists or ACE inhibitors monotherapies are less effective in Blacks than in whites. Black males tend to be even less responsive to ACE inhibitors than Black females (Eisner, G M. *Am J Kidney Dis* 1990;16(4 Suppl 1):35–40). Accordingly, members of the Black ethnic group who exhibit the combination of salt sensitivity, high sodium intake and failure to voluntarily limit sodium consumption are particularly benefited by the therapy of the present invention. In another embodiment of the present invention, therefore, the subject in need of treatment is salt sensitive individual who is, in whole or in part, a member of the Black ethnic group, and, inter alia, has or is susceptible to hypertension and/or cardiovascular disease, particularly cardiovascular disease selected from one or more members of the group consisting of heart failure, left ventricular diastolic dysfunction, hypertrophic cardiomyopathy, and diastolic heart failure.

Non-Modulating Individuals

A non-modulating individual demonstrates a blunted positive response in renal blood flow rate and adrenal production of aldosterone to a high sodium intake or angiotensin II administration. Such non-modulating individuals additionally may exhibit increased fasting insulin levels and increased increment in glucose-stimulated insulin levels. (Ferri et al.: *Diabetes* 1999.; 48:1623–30). Insulin resistance is also associated with increased risk of myocardial infarction.

Accordingly, in another embodiment of the present invention the subject in need of treatment is a salt sensitive and non-modulating individual that, inter alia, (i) has or is susceptible to insulin resistance, particularly Type I or Type II diabetes mellitus, and/or glucose resistance, and/or (ii) has or is susceptible to cardiovascular disease.

Aged Individuals

In salt sensitive individuals the incremental blood pressure response to a given increase in dietary intake of sodium increases with age. Similarly, salt sensitivity is more frequently observed in individuals of advanced age. Furthermore, insulin resistance shows a similar increase with age.

Accordingly, in one embodiment of the present invention the subject in need of treatment is a salt sensitive individual at least 55 years of age, preferably at least about 60 years of age, and more preferably at least about 65 years of age, and, inter alia, has or is susceptible to insulin resistance, particularly Type I or Type II diabetes mellitus, and/or glucose resistance.

Detoxified and Recovering Alcoholics

Detoxified and recovering alcoholics also commonly are salt sensitive (Genaro C et al.: *Hypertension* 2000: 869–874). Accordingly, in another embodiment of the present invention the subject in need of treatment is a salt sensitive individual and, inter alia, is a detoxified or recovering alcoholic.

Obesity

Obese individuals are commonly salt sensitive. A study by Bonner (*MMW Fortschr Med* 1999; 14:34–6) estimated that 44% of all hypertensive patients are overweight and further associated with salt sensitivity, elevated intracellular calcium, sodium retention, and increased cardiac output. Furthermore, Dimsdale et al. (*Am J Hypertens* 1990; 3:429–35) reported that obese patients were more likely to increase their systolic pressure in response to salt loading. Additionally, salt sensitive children also have an increased probability of obesity and cardiovascular disease. (Falkner B et al.: *Am J Clin Nutr* 1997; 65:618S–621S). Even in normotensive individuals, sodium-sensitive subjects tend to weigh more than sodium-resistant subjects. (Rocchini A P et al.: *Am J Med Sci* 1994; 307 Suppl 1:S75–80). Accordingly, in another embodiment of the present invention the subject in need of treatment is a salt sensitive individual and, inter alia, is obese.

Biological Evaluation

Human cardiovascular disorders are complex conditions, often initiated by vascular hypertension or a myocardial infarction (MI). In order to determine the probable effectiveness of a therapy for cardiovascular disorders, it is important to determine the potency of components in several assays. Accordingly, in Assay "A", the efficacy of the aldosterone antagonist epeplerenone (epoxymexrenone) was determined in a hypertensive rat model with vascular inflammation, using angiotensin II infusion. In Assay "B" a study is described evaluating the efficacy of the aldosterone antagonist epeplerenone (epoxymexrenone) in a rat model using aldosterone infusion to produce hypertension with vascular inflammation. In Assay "C" a further study is described evaluating the efficacy of the aldosterone antagonist epeplerenone (epoxymexrenone) in a rat model using aldosterone infusion to produce hypertension with vascular inflammation.

In addition, clinical trials can be used to evaluate aldosterone antagonist therapy in humans. Numerous examples of such therapeutic tests have been published, including those of the RALES 003 study described in American Journal of Cardiology 78, 902–907 (1996) or the RALES 004 study described in New England Journal of Medicine 341, 709–717 (1999).

Assay A: In Vivo Angiotensin II Infusion Model
Protocol:
Methods:
Male Wistar rats (n=50, 10/group; BW=200 g)
1% NaCl to drink
Experimental groups
 1. Control
 2. Angiotensin II (25 ng/min, sc via alzet minipump)
 3. Angiotensin II (25 ng/min, sc)+eplerenone 100 mpk
 4. Angiotensin II (25 ng/min, sc)+adrenalectomy+ dexamethasone (12 μg/kg/d, sc)
 5. Angiotensin II (25 ng/min, sc)+adrenalectomy+ dexamethasone (12 μg/kg/d, sc)+aldosterone (40 mg/kg/d, sc via alzet minipump)
SBP measured by tail-cuff every week
24-hours food and fluid intake and urine output measured every day
Urine samples collected every day for determination of urinary electrolytes.
Sacrifice by exanguination after 4 weeks. Blood was be collected in dry tubes for determination of serum electrolytes and in EDTA-containing tubes for measurement of aldosterone and corticosterone levels
Hearts were stained with hematoxylin&eosin and have been analyzed for determination of morphologic abnormalities (i.e. necrosis, vascular injury).

Results
Blood pressure. Systolic blood pressure increased in all animals receiving angiotensin II infusion. Neither eplerenone nor adrenalectomy reduced blood pressure when compared to animals receiving vehicle. Aldosterone infusion increased blood pressure in angiotensin II/salt, adrenalectomized rats. FIG. 23 demonstrates this increase in systolic blood pressure.

Electrolyte excretion. The ratio between daily urinary $Na^+$ excretion and urinary $K^+$ excretion (U $Na^+/K^+$ ratio) was used as an index for natriuresis. Urinary $Na^+/K^+$ ratio was similar in all groups before the start of the treatments, and increased similarly in all animals upon initiation of the high salt diet. Urinary $Na^+/K^+$ ratio was not unchanged in animals receiving angiotensin II infusion until day 17 when it was significantly increased in these animals with respect to the vehicle-infused rats. A similar effect occurred in angiotensin II-infused animals receiving eplerenone, which demonstrated increases in urinary $Na^+/K^+$ ratio from day 14 of infusion. However, at no time-point did eplerenone-treated rats demonstrate higher urinary $Na^+/K^+$ ratio than angiotensin II-infused rats treated with vehicle. In fact, a significant difference was only observed at day 21, when angiotensin II-infused, vehicle treated rats demonstrated higher urinary $Na^+/K^+$ ratio than eplerenone-treated animals indicating that, under these experimental conditions eplerenone did not produce a significant diuretic or natriuretic effect. Adrenalectomized animals with or without aldosterone infusion always demonstrated higher urinary $Na^+/K^+$ ratio than the adrenal-intact animals.

Myocardial injury. Seven out of the ten angiotensin II/salt-treated animals developed vascular inflammatory changes in the coronary arteries. These changes were characterized by leukocyte infiltration of the perivascular space, mainly by macrophages. Fibrinoid necrosis of the media was also observed in some arteries. In some cases, when the lesions were extensive there was cardiomyocyte necrosis associated in the surrounding myocardium. Parenchymal hemorrhages were observed in these cases, consistent with findings of myocardial necrosis. These vascular inflammatory lesions were observed in only one of the ten angiotensin II-infused animals receiving eplerenone, despite the fact that these animals were as hypertensive as the vehicle-treated angiotensin II-infused rats. (See FIG. 24). Similarly, adrenalectomy prevented the vascular inflammatory lesions in the heart. However, aldosterone replacement restored the severe coronary and myocardial inflammation and injury observed in angiotensin-II infused, adrenal-intact, vehicle-treated rats.

Figure 26:
FIG. 26 shows induction of COX-2 expression in heart of Ang II infused rat.
Figure 27:
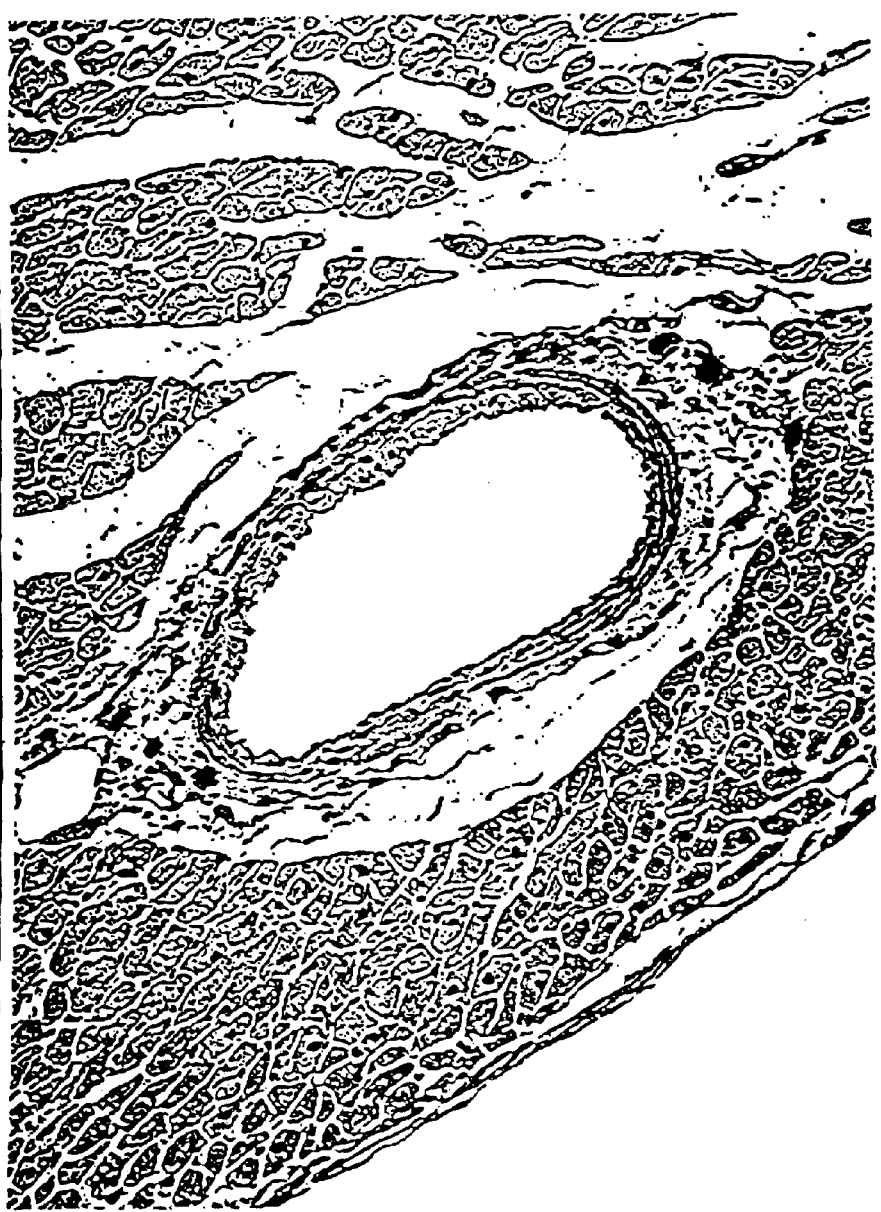
FIG. 27 shows prevention by eplerenone of induction of COX-2 expression in heart of Ang II infused rat.

Immunostaining of the hearts from angiotensin II-infused rats with a cyclooxgenase-2 specific antibody identified the presence of this enzyme in areas of inflammation around the arteries, mainly in monocyte/macrophages. Cycloxygenase-2 staining was also observed in the vascular smooth muscle cells of the media of coronary arteries, even when there was no evidence of morphologic alterations or inflammatory aggregates in the perivascular space (FIG. 26). Eplerenone treatment, as well as adrenalectomy markedly reduced and in most cases completely prevented the expression of cycloxygenase-2 in the hearts from angiotensin II-infused rats (See FIGS. 25 and 27). Replacement of aldosterone in angiotensin-II, adrenalectomized rats restored the presence of cycloxygenase-2 in coronary arteries.

Figure 28:
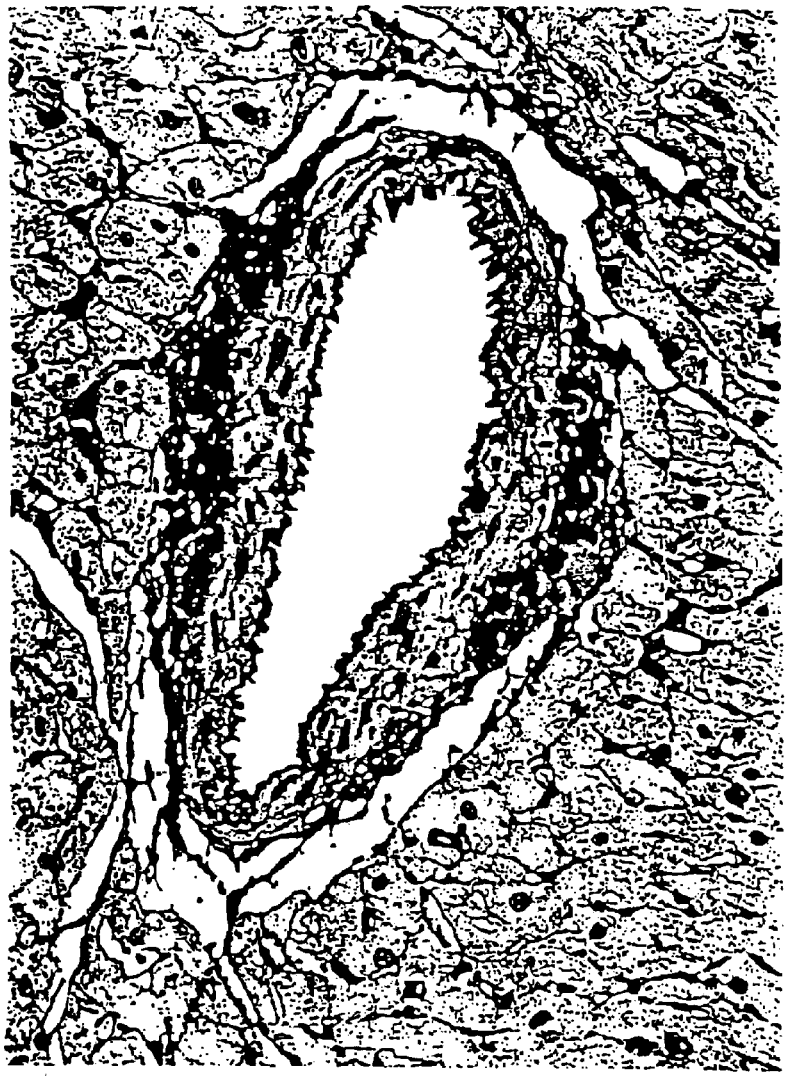
FIG. 28 shows lack of osteopontin expression in the heart of a vehicle infused rat.
Figure 29:
FIG. 29 shows prevention by eplerenone of induction of osteopontin expression in heart of aldosterone infused rat.

Osteopontin (also known as early T-cell activation-1, Eta-1) is a secreted glycoprotein with pro-inflammatory characteristics that mediates chemoattraction, activation and migration of monocytes. Immunostaining of the hearts from angiotensin II-infused, saline-drinking rats with an osteopontin-specific antibody identified the presence of osteopontin in the media of coronary arteries. Both eplerenone treatment and adrenalectomy prevented osteopontin expression in the hearts of angiotensin II-infused, saline-drinking rats (FIGS. 28 and 29). Aldosterone replacement restored osteopontin expression in adrenalectomized animals.

Assay B: In Vivo Aldosterone Infusion Model
Protocol 2:
Methods:
Male Sprague Dawley rats (n=39; BW=250 g)
1% NaCl to drink
Uni-nephrectomy performed during implantation of minipumps
Experimental groups
 1. Control
 2. Aldosterone (0.75 mg/hr, sc via alzet minipump)
 2. Aldosterone (0.75 mg/hr, sc via alzet minipump)+ eplerenone 100 mpk, p.o
 1. Aldosterone (0.75 mg/hr, sc via alzet minipump)+ 0.6% KCl in the drinking fluid
Groups 1, 2 and 3 received only 0.3% KCl in the drinking solution
SBP measured by radio-telemetry probes inserted in the abdominal aorta
Sacrifice after 4 weeks.
Hearts were harvested and divided by half through a transverse section at the mid-ventricles: The upper half was stored into formalin. The bottom part was snap-frozen in liquid nitrogen for biochemical analysis.

Hearts were stained with hematoxylin&eosin and the collagen specific dye picro-sirius red and were analyzed for determination of interstitial collagen volume fraction and morphologic abnormalities (i.e. necrosis, vascular injury).

Hydroxyproline concentration was measured in the frozen hearts.

Determination of osteopontin and COX-2 was performed by quantitative RT-PCR (Taqman). Osteopontin was also identified in the heart by immunohistochemistry.

Results

Figure 43:
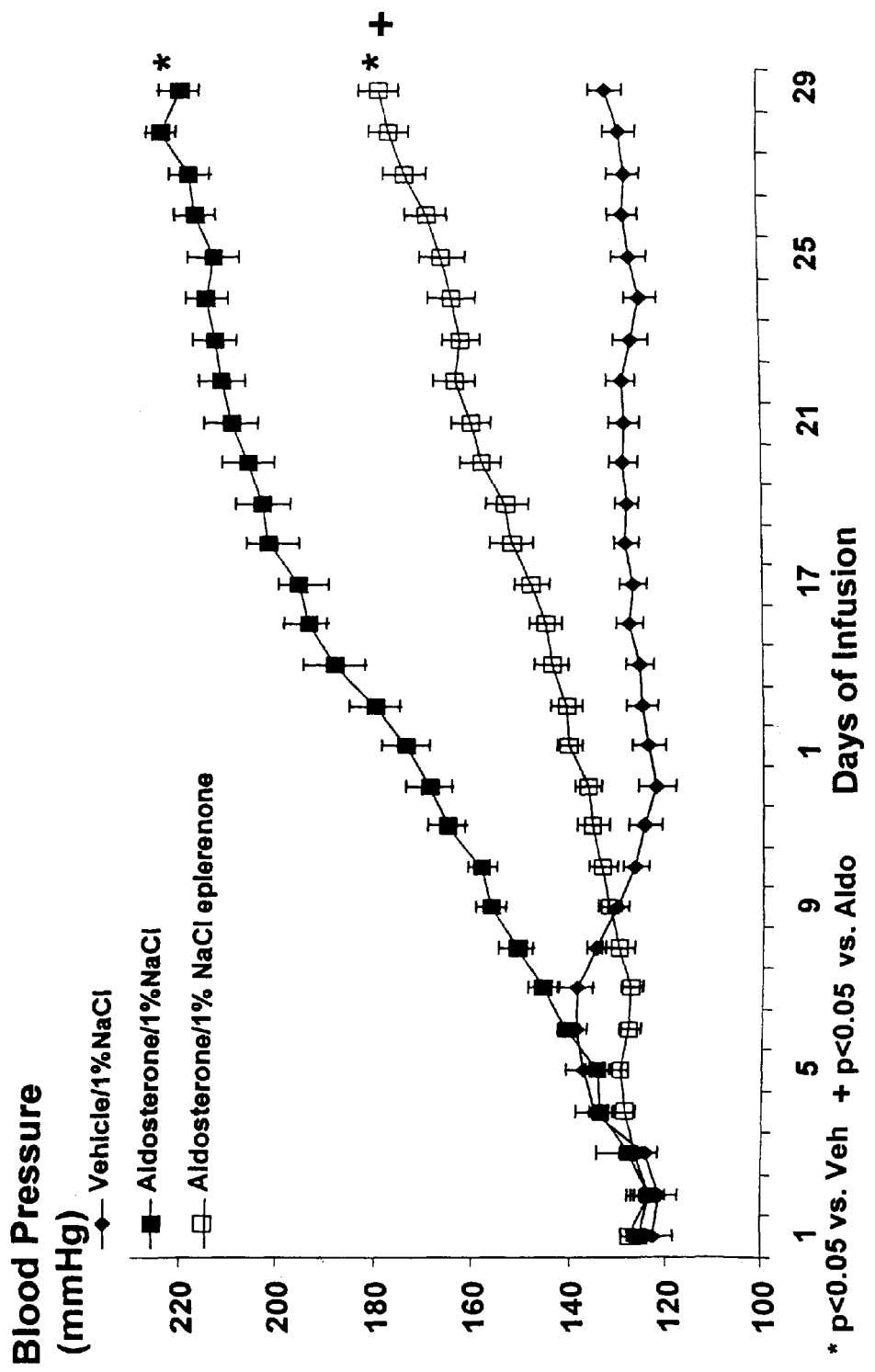
FIG. 43 shows systolic blood pressure elevation with aldosterone infusion, and depression of this elevation with aldosterone infusion and eplerenone treatment.

Blood pressure. Systolic blood pressure increased in all animals receiving aldosterone infusion. Eplerenone treatment significantly reduced, but did not normalize blood pressure. FIG. 43 shows these results graphically.

Figure 32:
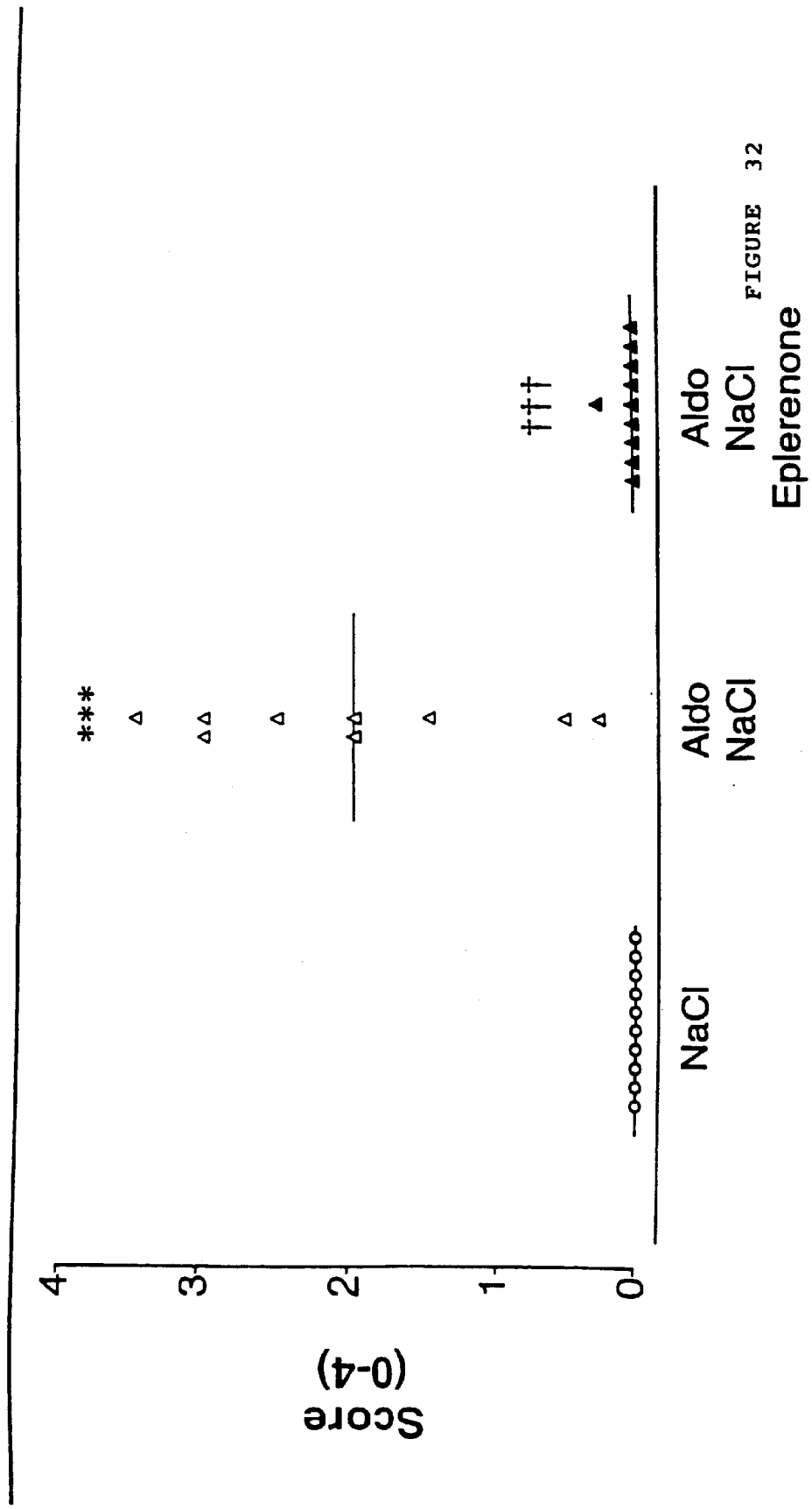
FIG. 32 shows prevention by eplerenone of myocardial injury in aldosterone infused rats.

Myocardial injury. Saline-drinking, uni-nephrectomized rats did not have myocardial injury. Determination of interstitial collagen by histologic determination of interstitial collagen volume fraction or by biochemical determination of hydroxyproline concentration evidenced the absence of myocardial fibrosis in animals receiving aldosterone/salt treatment. However, examination of the hematoxilin-eosin-stained hearts from aldosterone/salt-treated rats evidenced severe vascular inflammatory lesions. These lesions were identical to those described in protocol 1. Administration of eplerenone completely prevented the vascular inflammatory changes in aldosterone-infused, saline-drinking, uni-nephrectomized rats (FIG. 32), even though it did not normalize blood pressure. Elevations of dietary potassium did not have significant effects in the development of aldosterone-induced injury, as these animals demonstrated similar levels of injury as the aldosterone/salt treated rats receiving vehicle.

Figure 45:
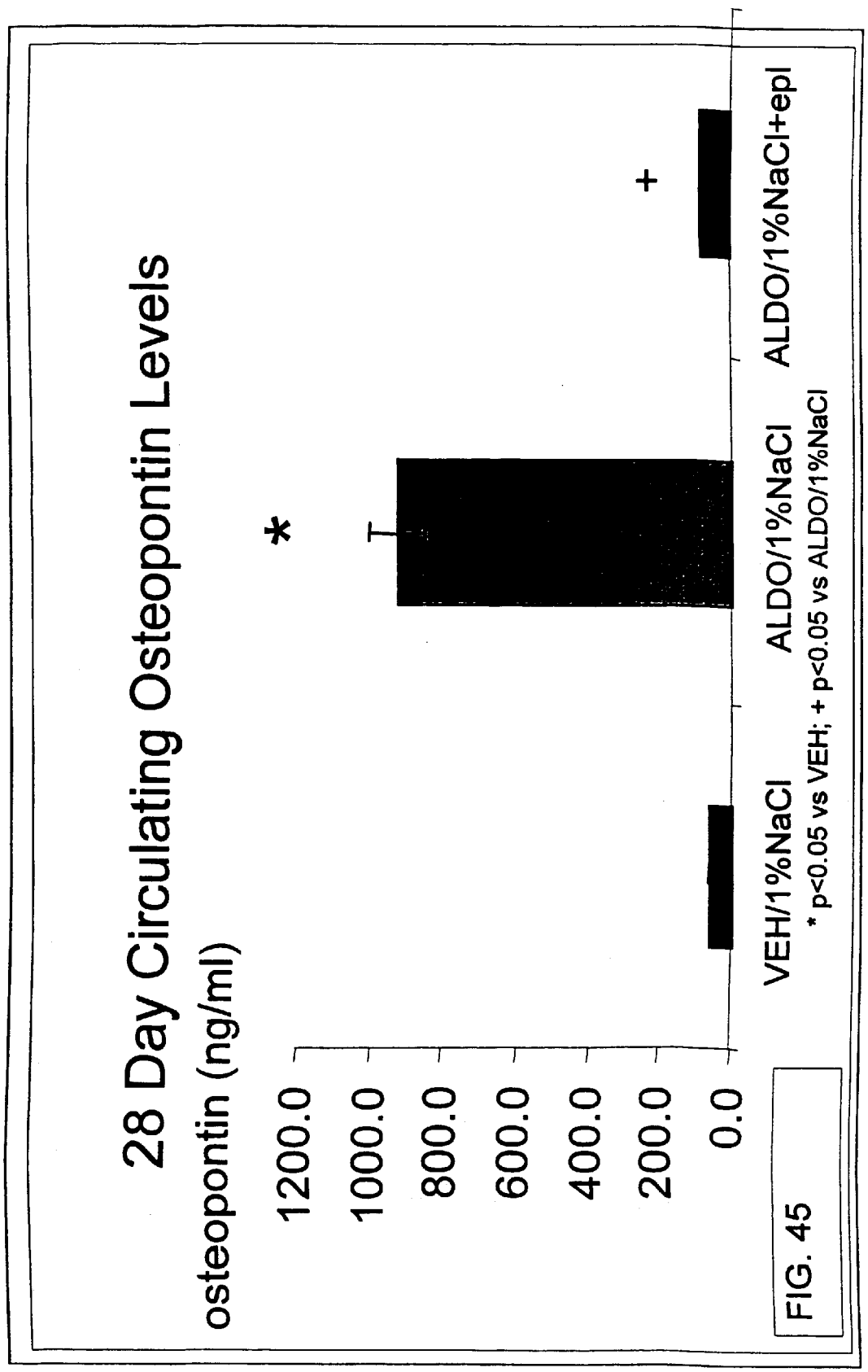
FIG. 45 shows 28 day circulating osteopontin levels for control rats, for rats infused with aldosterone, and for rats infused with aldosterone and treated with eplerenone.

Serum osteopontin levels were determined at 28 days, and measured for each group (NaCl 1% drinking rats, NaCl 1% drinking rats with aldosterone, and NaCl 1% drinking rats with aldosterone and eplerenone). FIG. 45 shows the marked decrease in circulating osteopontin levels in the eplerenone treated rats.

Figure 30:
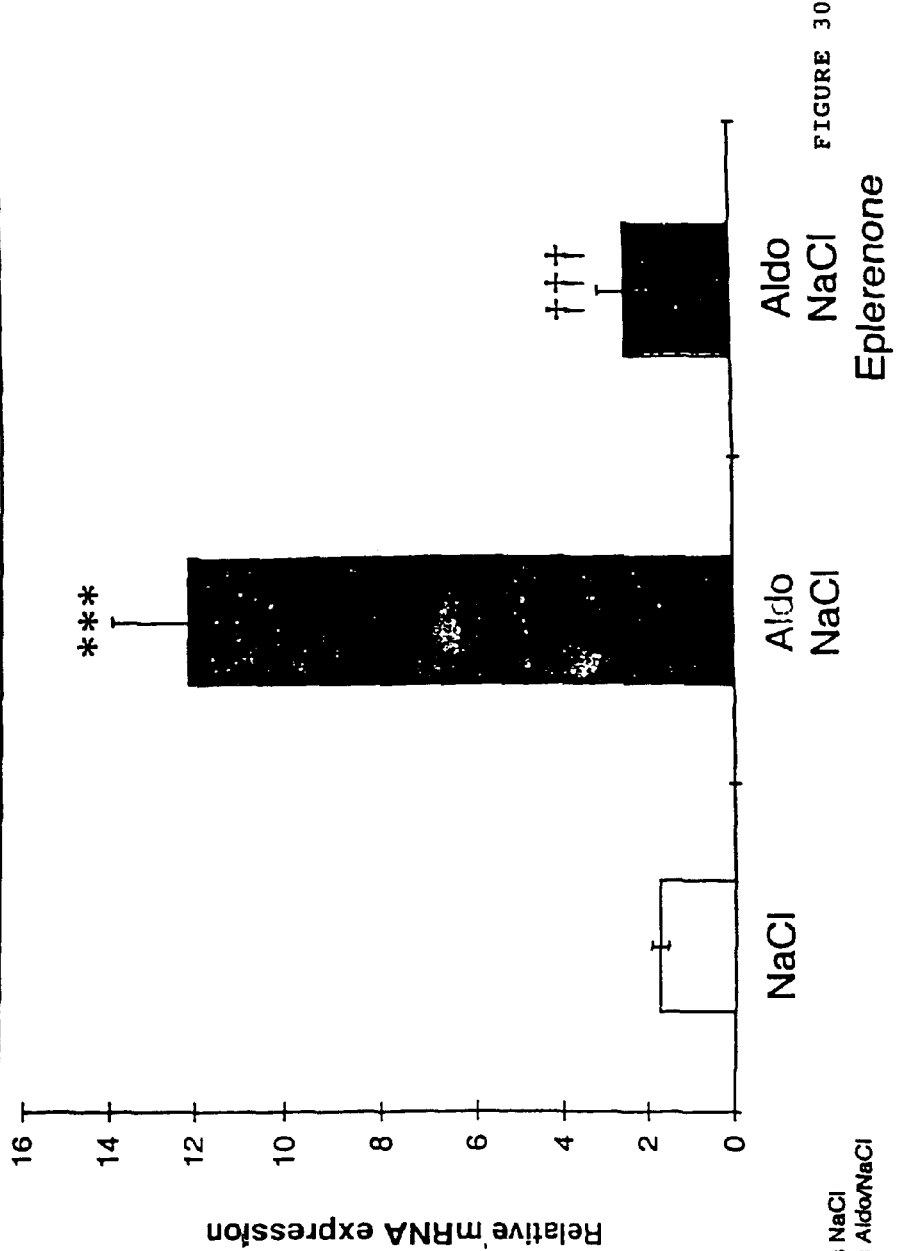
FIG. 30 shows prevention by eplerenone of osteopontin upregulation in myocardium of aldosterone infused rats.
Figure 31:
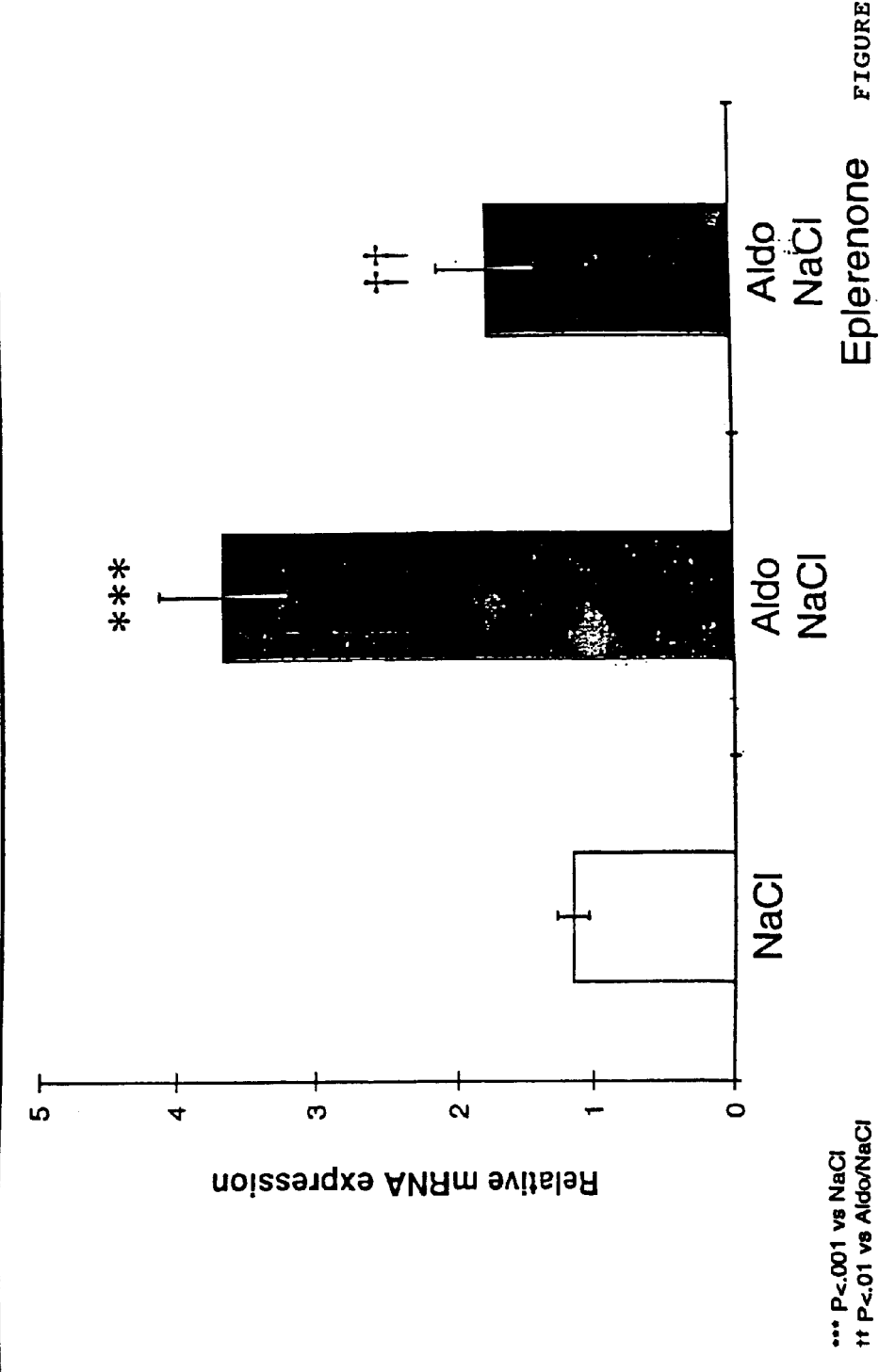
FIG. 31 shows prevention by eplerenone of COX-2 upregulation in myocardium of aldosterone infused rats.
Figure 39:
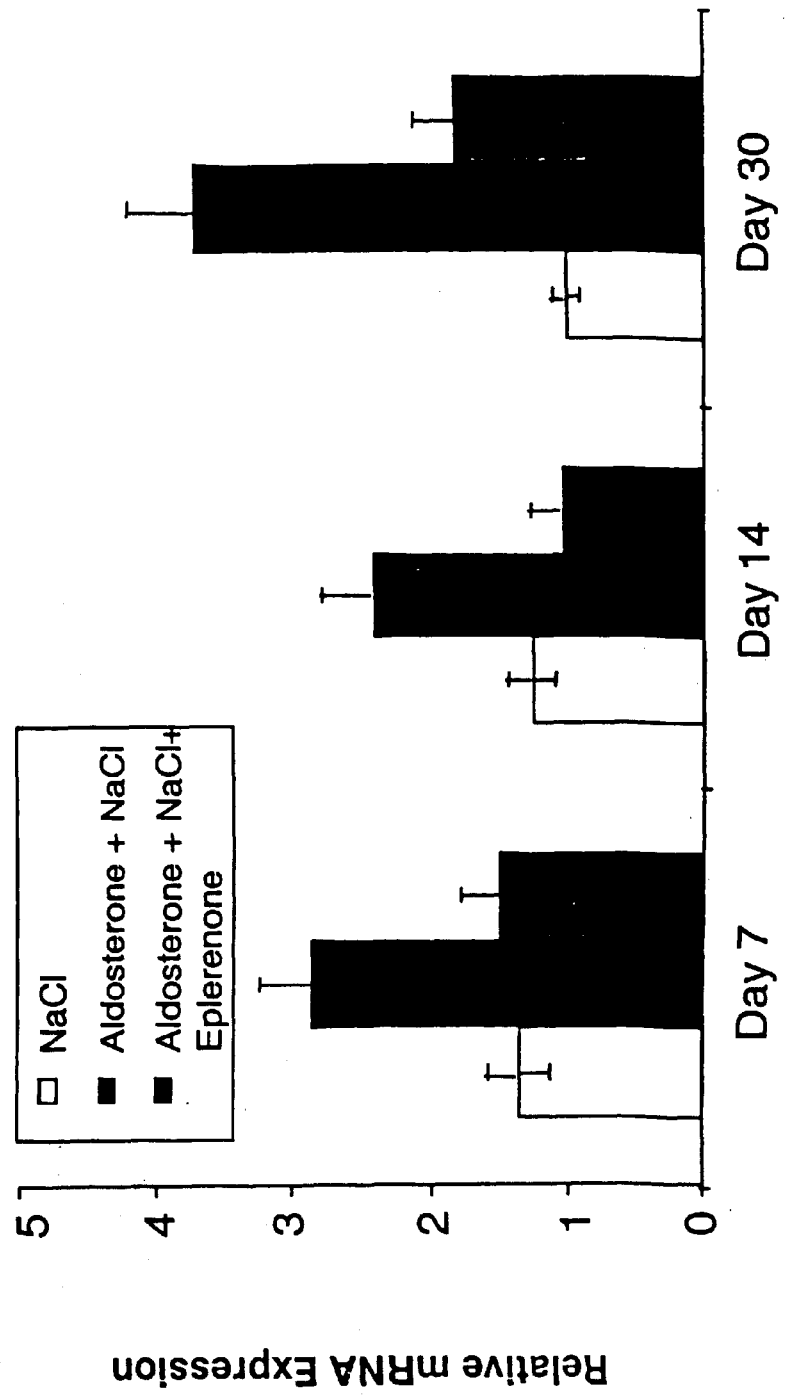
FIG. 39 shows inhibition of early time-course expression of myocardial COX-2 in aldosterone-infused, hypertensive rats treated with eplerenone.
Figure 40:
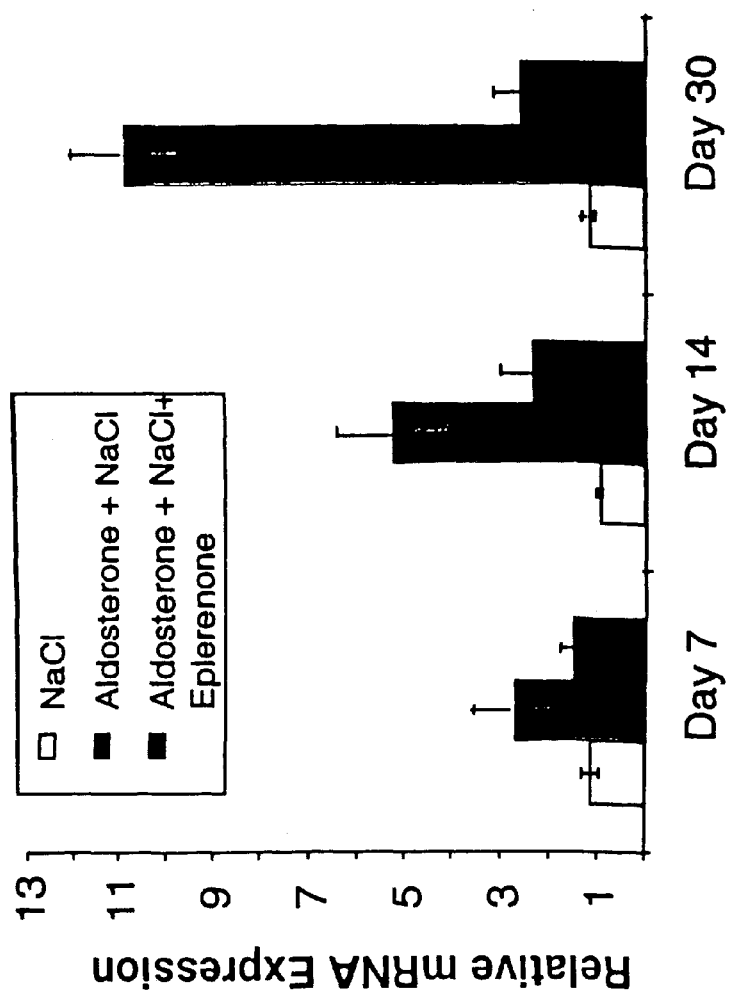
FIG. 40 shows inhibition of early time-course expression of myocardial osteopontin in aldosterone-infused, hypertensive rats treated with eplerenone.
Figure 41:
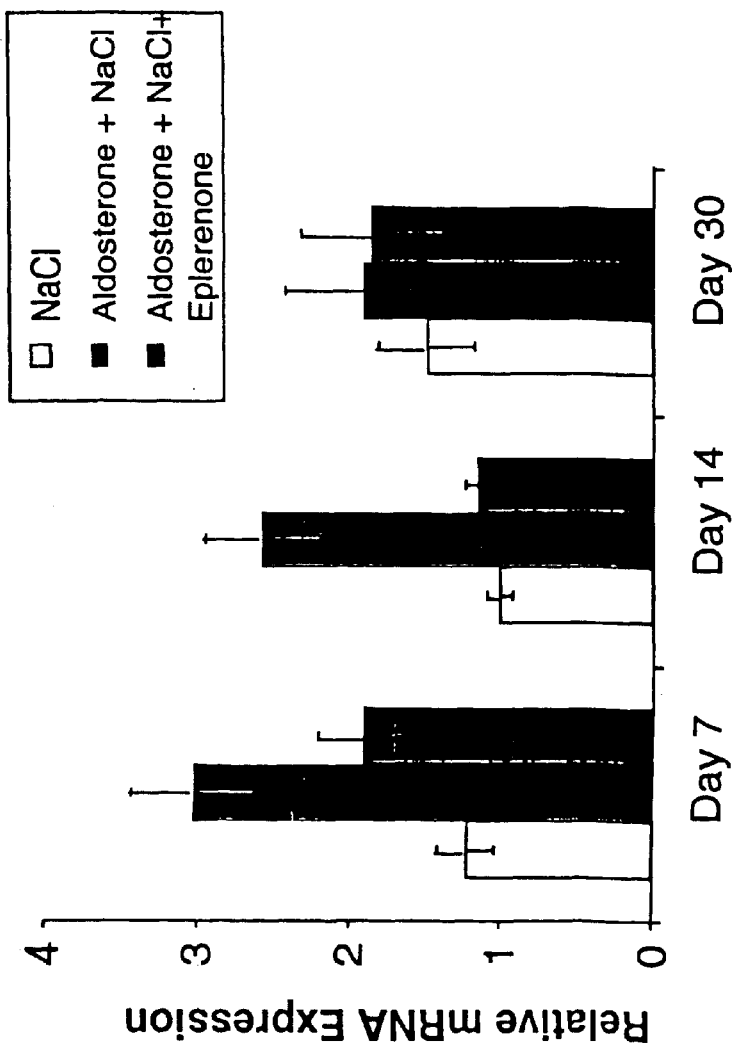
FIG. 41 shows inhibition of early time-course expression of myocardial MCP-1 in aldosterone-infused, hypertensive rats treated with eplerenone.
Figure 42:
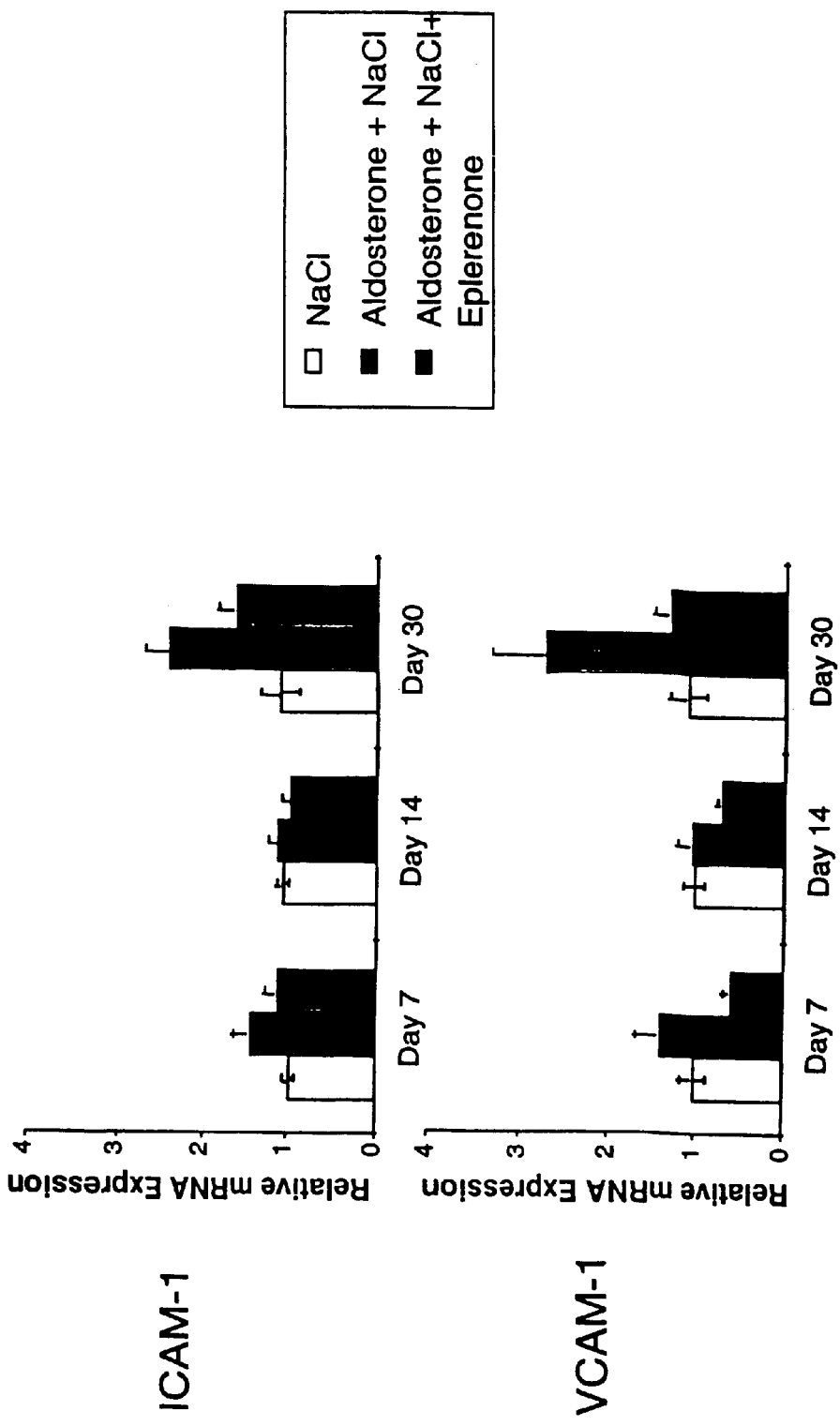
FIG. 42 shows inhibition of early time-course expression of myocardial ICAM-1 and VCAM-1 in aldosterone-infused, hypertensive rats treated with eplerenone.
Figure 46:
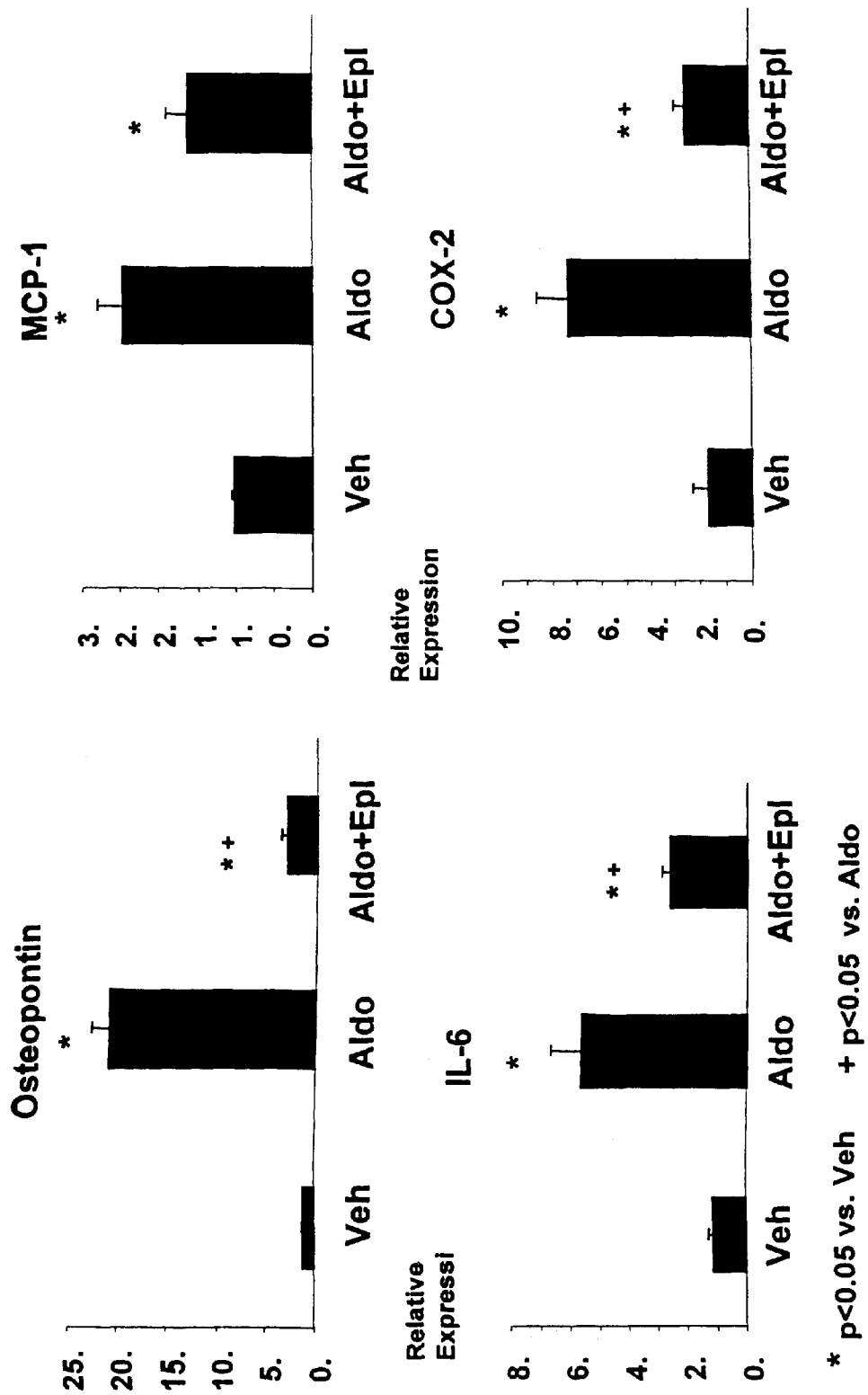
FIG. 46 shows the relative mRNA expression at 28 days for inflammatory cytokines in control rats, in rats infused with aldosterone, and in rats infused with aldosterone and treated with eplerenone.

Osteopontin immunostaining was also performed in the hearts from these animals. Osteopontin was not detected in saline-drinking, uninephrectomized animals receiving no aldosterone. However, osteopontin was clearly identified in the media of coronary arteries in animals receiving aldosterone infusion. Eplerenone treatment, prevented the expression of osteopontin in the hearts from aldosterone-infused rats (FIGS. 30 and 40). Increases in dietary potassium did not reduce osteopontin expression. Determination of osteopontin mRNA by quantitative RT-PCR, demonstrated a marked (7-fold) upregulatoin of this cytokine in the hearts of aldosterone/salt-treated rats receiving vehicle (relative mRNA expression: 1.7±0.2 vs 12.25±1.7, P<0.0001). This effect was prevented by eplerenone (relative mRNA expression: 2.5±0.6, P<0.0001 vs aldosterone/salt+vehicle group). Consistent with a role for cycloxygenase-2 in the development aldosterone-induced vascular inflammation in the heart, COX-2 mRNA expression was 3-fold increased in rats with aldosterone/salt+vehicle treatment (relative MRNA expression: 1.2±0.12 vs 3.7±0.46, P<0.0001). Similar to the effects on osteopontin expression, eplerenone prevented the increase in COX-2 expression in aldosterone/salt-treated rats (relative mRNA expression: 1.8±0.36, P<0.01 vs aldosterone/salt+vehicle group, see FIGS. 31 and 39). In like fashion, MCP-1 expression and IL-6 expression was attenuated by eplerenone treatment (FIG. 46).

Figure 33:
FIG. 33 shows upregulated co-expression of COX-2 and osteopontin in coronary artery media of aldosterone infused rat.

The above data suggest that aldosterone mediates a vascular inflammatory phenotype in the heart of hypertensive rats. This phenotype is associated with up-regulation of the cytokine osteopontin and the enzyme cycloxygenase-2 in vascular smooth muscle cells in the arterial media, which may mediate the perivascular inflammation observed and the consequent ischemic/necrotic injury of coronary arteries and myocardium. Without wishing to be bound by any theory, it is believed that this is the mechanism that mediates the vascular alterations observed in diseases such as heart failure, coronary artery disease, auto-immune or viral myocarditis, periateritis nodosa, stroke, and nephrosclerosis. FIG. 33 reveals that osteopontin and cyclooxygensase-2 are expressed in similar regions of the coronary arterial wall. While theory plays no part in the instant invention, FIG. 34 shows a proposed mechanism for this model. In these examples, eplerenone treatment prevented the vascular inflammation in the heart to an extent similar to that of adrenalectomy, as demonstrated in protocol #1. The effects of eplerenone were largely independent of major reductions in systolic blood pressure as demonstrated in protocol #1. The lack of a diuretic or natriuretic effect of eplerenone in angiotensin II/salt hypertensive rats suggests that the protective effects of the selective aldosterone antagonist were also independent of its potential effects on epithelial tissues. In addition, the fact that an elevated dietary potassium failed to mimic the effects of eplerenone, argue against the possibility that eplerenone provides benefit through its potassium-sparing properties. Thus, we propose that aldosterone may have direct deleterious effects in the coronary vasculature unrelated to the effects of this hormone in electrolyte homeostasis in epithelial tissues or its effects on blood pressure. Administration of eplerenone to humans could provide benefit by its anti-inflammatory effects in vascularized organs, including but not limited to heart, kidney, and brain, as suggested by the present experiment.

Assay C: Further In Vivo Aldosterone Infusion Study

The procedure of Assay B was expanded upon in a further study. Uninephrectomized, Sprague-Dawley rats were given 1% NaCl–0.3% KCl to drink and one of the following treatments: vehicle; aldosterone infusion; or aldosterone infusion in combination with eplerenone (100 mg/kg/day). Aldosterone/salt treatment induced severe hypertension in rats after 30 days, which was significantly reduced by eplerenone. Myocardial tissue from animals in each treatment group was examined after 7, 14, or 30 days of treatment. Histopathologic analysis revealed vascular inflammatory lesions starting at 14 days that extended to surrounding myocardium and resulted in focal ischemic/necrotic changes. Lesions were preceded by the expression and progressive upregulation of proinflammatory molecules. Upregulation of proinflammatory molecules and associated vascular and myocardial damage were markedly attenuated by eplerenone treatment. These data demonstrate that eplerenone is effective in reducing blood pressure and providing end-organ protection against aldosterone-induced vascular inflammatory damage in the heart.

Animals

Male Sprague-Dawley rats, weighing 230 to 250 g, (Harlan Sprague-Dawley Industries, Indianapolis, IN) were housed in a room 12-hours light/12-hours dark daily cycle at an ambient temperature of 22±1° C. (n=96). Animals were allowed one week to adjust after arrival and had free access to TEKLAD 22/5 rodent diet (Harlan TEKLAD, Madison, Wis.) and tap water until the initiation of the experiment.

Experimental Protocol

Prior to surgery the animals were individually weighed and placed in one of the following groups: (I) high salt control (vehicle/normal chow/1% NaCl & 0.3% KCl drinking water, n=31 for 3 time point groups), (II) aldosterone control (aldosterone/normal chow/1% NaCl & 0.3% KCl drinking water, n=28 for 3 time point groups), (III) 100 mg/kg/day eplerenone (aldosterone/eplerenone chow/1% NaCl & 0.3% KCl drinking water, n=30 for 3 time points). Potassium chloride supplementation was added to the saline solution in order to prevent the potential hypokalemia associated with aldosterone excess.

Treatment

At the time of the surgery, an Alzet 2002 osmotic minipump (Alza Corp., Palo Alto, Calif.) containing either vehicle (9% ethanol/87% propylene glycol/4% dH$_2$O) or 1.0 mg/mL d-aldosterone (Sigma Chemical, St. Louis, Mo.) was inserted subcutaneously at the nape of the neck. Aldosterone was administered at a dose of 0.75 □g/hour. Eplerenone was incorporated into TEKLAD 22/5 rodent diet (Harlan TEKLAD, Madison, Wis.) at a concentration of 1 mg/g of chow (calculated to deliver 100 mg/kg/day). Previous analytical work has demonstrated the stability of eplerenone in this diet, as well as the homogeneity obtained after preparation. Animals were sacrificed from each group (n=8–13) after 7, 14, or 30 days of treatment.

Surgical procedure

Animals to be sacrificed after 7 or 14 days of treatment were uninephrectomized and implanted with an Alzet minipump. Animals treated for 30 days were uninephrectomized, fitted for Alzet minipumps, and implanted with radio telemetry units (model #TA11PA-C40, Data Sciences Inc., St. Paul, Minn.) according to the following procedure. Animals were anesthetized with 5% isoflurane (SOLVAY Animal Health Inc., Mendota Heights, Minn.), which was delivered in O$_2$ using a VMS anesthesia instrument (Matrix Medical, Inc., Orchard Park, N.Y.). Anesthesia was maintained with 1–2% isoflurane throughout the surgical procedure. The surgery site was clipped, scrubbed with nolvasan, and sprayed with betadine. A rostral-caudal incision was made through the skin from the base of the rib cage to the pubic region using a #11 scalpel blade. A second incision was made through the muscles of the abdominal wall to expose the peritoneal cavity. The urethra, renal artery and vein of the left kidney were isolated, tied off with 4-0 silk, and the kidney excised and discarded. Organs were carefully displaced with tissue retractors in order to expose the abdominal aorta. A 1.5 cm segment just rostral to the bifurcation of the abdominal aorta into the iliac arteries was cleared of excessive connective tissue and 4-0 silk was used to make an anchor adjacent to the aorta. A microvascular clip was then placed at both ends of the cleaned region to stop excessive blood flow. Using a bent, 21 gauge needle, the abdominal aorta was penetrated. The cannula of the radio telemetry unit was inserted and stabilized in the aorta using the 4-0 silk anchor. Organs were repositioned and the telemetry unit was placed over the organs. Using a non-interrupted suture pattern with 4-0 silk, the abdominal wall was closed, and the skin was subsequently closed using a 4-0 silk in an interrupted suture pattern. Animals were injected around the sutures with 100 µL of the anesthetic Marcaine HCl (Sanofi Winthrop Pharmaceuticals, New York, N.Y.) and given an injection (i.m.) of the antibiotic Mandol (Eli Lilly & Co., Indianapolis, Ind.). Post-operative care included monitoring the animals on a heating pad during recovery from anesthesia until sternal recumbency was reestablished. Animals were monitored daily for signs of distress and infection at the surgical site. Animals displaying continued discomfort after surgery were treated with 0.1–0.5 mg/kg, s.c. Buphrenorphine (Rickett & Colman Pharmaceuticals, Inc. Richmond, Va.). Animals were then placed on tap water and TEKLAD 22/5 rodent diet (Harlan TEKLAD, Madison, Wis.).

Blood Pressure Analysis

Radiotelemetrized arterial blood pressure was calculated with the DATAQUEST A.R.T Version 1.1-Gold software (Data Sciences International, St. Paul, Minn.). Data points were collected over a 24 hour period with the collection rate set for a 10 second reading every 5 min for each animal. The 24 hour period used was from 6:00 a.m. to 6:00 a.m.

Sacrifice

At the cessation of each experimental time point, the animals were anesthetized with pentobarbital (65 mg/kg i.p., Sigma Chemical, St. Louis Mo.) and weighed with a Mettler PM6000 balance (Mettler-Toledo, Inc., Hightstown, N.J.). The abdominal cavity was opened to expose the abdominal aorta. A 16-gauge needle was inserted into the abdominal aorta and the animal was exsanguinated into a 12cc syringe. The blood sample was transferred immediately into glass serum collection tubes (Terumo Medical Corp., Elkton, Md.) for drug level analysis. The samples were placed on wet ice until sample collection was complete and centrifuged for 15 min at 3000 rev/min at 4° C.

Following exsanguination, hearts and kidneys were isolated, removed, rinsed in cold phosphate-buffered saline, and blotted dry. Kidneys were immediately bifurcated through the long axis with a razor blade and placed in 10% neutral buffered formalin (NBF, Richard-Allen Scientific, Kalamazoo, Mich.). For the hearts, the right ventricle (RV) was cut away from the left ventricle (LV), both ventricles were weighed using a Mettler AE163 balance (Mettler-Toledo, Inc., Hightstown, N.J.), and the RV was placed in 10% NBF. A 2 mm coronal slab of the LV apex was removed and frozen with dry ice/isopentane for analysis of gene expression and the remaining portion of the LV was placed in 10% NBF for fixation. Final wet trimming was completed after 3–4 days fixation where a second 2 mm coronal slab was removed for hydroxyproline analysis and a third 2 mm slab was removed from the equatorial region for histology.

Tissue Processing & Staining

The equatorial regions of the heart were routinely processed into paraffin with an automated tissue processor (Hypercenter XP, Shandon/Lipshaw Inc., Pittsburgh, Pa.) and embedded into fresh paraffin apical side down (Shandon Embedding Center, Shandon/Lipshaw Inc.). Five and 10 □m sections were cut from each block of tissue using a Leica RM2035 rotary microtome (Leica Inc., Houston, Tex.) and mounted on Superfrost/Plus microscope slides (Fisher Scientific, Pittsburgh, Pa.). Ten □m sections were stained with the collagen specific stain, Picrosirius Red F3BA (Saturated Picric Acid (Sigma Chemical, St. Louis, Mo.) with 0.1% (w/v) Sirius Red F3BA (C.I. #35780, Pfaltz & Bauer, Inc. Waterbury, Conn.) (6). Mounted tissues were hydrated with water. Slides were subsequently incubated in distilled water with 0.2% (w/v) Phosphomolybdic Acid (Sigma Chemical, St. Louis Mo.) for 15 min, transferred to 0.1% Picrosirius Red F3BA stain for 110 min, placed in 95% ethanol w/1% acetic acid (v/v) for 1 min followed by two, 1-min incubations in 100% ethanol, and cleared in xylene for 1 min. Slides were coverslipped with #1 cover glass using Permount Histological Mounting Media (Fisher Scientific). Two slides mounted with 5 □m sections were cut for each animal. One slide was processed for H&E staining and one for Periodic Acid Schiff (PAS) staining. The H&E and PAS were used for pathological scoring of the hearts.

Histopathologic Analysis

Semi-quantification of myocardial injury was performed as described previously with minor modifications (7). Briefly, a scale from 0 to 4 was used to score the level of myocardial injury. A score of 0 represented no damage. A score of 1 represented the presence of vascular and perivascular inflammatory lesions without cardiomyocyte injury. A score of 2 was given when one clear area of myocardial necrosis was observed. Myocardial necrosis was defined as the presence of necrotic changes in cardiomyocytes such as nuclear pyknosis or karyolysis, non-contracting marginal wavy fibers and hypereosinophilia of the cytoplasm, or clear evidence of destruction of the cardiomyocyte membrane. When two or more separate areas of necrosis were found (implicating the presence of two different infracted regions), hearts received a score of 3. A score of 4 was assigned to hearts that demonstrated extensive areas of necrosis compromising more than 50% of the left ventricle.

Image Analysis

Picrosirius Red F3BA stained slides were used to quantify interstitial collagen with a Videometric 150 Image Analysis System (Oncor Inc., Gaithersburg, Md.). Briefly, images were captured using a Nikon E Plan 10/0.25; 160/- Objective (Nikon Inc. Garden City, N.Y.) attached to a Nikon Optiphot microscope (Nikon Inc.). A Toshiba 3 CCD Color Video Camera (Model#IK-T30T, Toshiba Corp. Japan) relayed the images in RGB format from the microscope to a 386 computer with a V150 video board. The V150 video board/V150 software application (Oncor Inc.) converted RGB images to HIS (Hue, Intensity, Saturation) format for display and analysis on a Sony Trinitron Color Video Monitor (Model#PVM-1342Q, Sony Corp, Tokyo, Japan) at a magnification of 305×. Once the image was displayed on the image monitor; hue, intensity, and saturation of pixels to be measured were defined by a process called thresholding. The V150 application then measured only pixels which fell into thresholding limits. The system was calibrated with a micrometer scale (EM Sciences, FT. Washington, Pa. 19034), which allowed data to be expressed in $mm^2$ or $\square m^2$. After each measurement, data was automatically saved in ASCII file format and transferred to Microsoft Excel version 7.0 for final summation.

Immunohistochemistry

Five $\mu m$ sections were deparaffinized in xylene (two, 5–10 min incubations) and rehydrated by 3 min incubations in ethanol as follows: two incubations in 100% ethanol followed by two incubations in 95% alcohol and one incubation in 70% alcohol. Once hydrated, sections were rinsed in tap water for 1 min and distilled water for 1 min. Endogenous peroxidase activity was blocked by placing slides in 3.0% $H_2O_2$ for 15 min followed by a 5 min rinse in distilled water. Slides were processed for antigen retrieval using citric acid, pH6.0. Slides were heated to boiling, cooled for 20 min at 25° C., and rinsed in distilled water. Slides were stained using a DAKO autostainer (DAKO Corporation, Carpinteria, Calif.). Prior to staining, slides were rinsed and incubated in blocking buffer for 20 min. Blocking buffer is described in the Vectastain ABC kit (Vector Labs, Burlingame, Calif.) and contains 10 mL TNB (NEN TSA Biotin System kit, Cat#NEL700A, NEN Life Science Products, Boston, Mass.) and 3 drops of normal (corresponding to the secondary antibody) serum.

Primary antibodies used for staining include: Osteopontin, diluted at 1:100 (Mouse monoclonal, Cat#MPIIIb10, Developmental Studies Hybridoma Bank, The University of Iowa, Iowa City, Iowa); ED-1 diluted at 1:500 (anti-macrophage glycoprotein, mouse monoclonal, MAB1435, Chemicon International Inc., Temecula, Calif.); CD-3 diluted at 1:300 (anti-T-cell, rabbit polyclonal-affinity purified antibody, A0452, DAKO Corporation, Carpineria, Calif.); ICAM-1 diluted at 1:100 (goat polyclonal-affinity purified, M-19:sc-1511, Santa Cruz Biotechnology, Santa Cruz, Calif); VCAM-1 diluted at 1:100 (goat polyclonal-affinity purified, C-19:sc-1504, Santa Cruz Biotechnology). Slides were incubated with primary antibodies for 60 min, followed by biotinylated antibodies at a final concentration of 5 $\mu L/mL$ for 30 min at 25° C. Staining was visualized with the Vectastain ABC-AP kit (Vector Laboratories) and diaminobenzidine staining (DAKO Corporation, Carpinteria, Calif.). Slides were rinsed in water and counter-stained with hematoxylin for approximately 30 sec. Isotype-matched IgG (Sigma Chemical, St. Louis Mo.) was used as a negative control for the primary antibodies.

In situ Hybridization for Osteopontin mRNA

RNA probes were generated based on a sequence for rat osteopontin (GenBank accession#NM 008608-1). Briefly, a cDNA fragment of rat osteopontin was generated by RT-PCR using the following primers: forward primer, 5'-TGG CAC ATT TGT CTT; reverse primer 3'AGC CCA TCC AGTC. The cDNA fragment was inserted into the PCR II plasmid using the TA cloning kit (Invitrogen Corporation, Carlsbad, Calif.). Probes were labeled in 100 $\mu L$ in vitro transcription reaction containing: rRNasin (2 U), DNase (0.5 U), TE Buffer (1×), rGTP (10 mM), rCTP (10 mM), rATP (10 mM), rUTP (10 mM), (PROMEGA, Madison, Wis.), 5 $\mu L$ (50 $\mu Ci$) $^{33}P$-UTP (Elkin Pelmer, Boston, Mass.) and appropriate RNA polymerases (Sp6 RNA Polymerase (20 U/$\mu L$); T7 RNA Polymerase (15 $\mu L$), PROMEGA) for 60 min at 37° C. Free label was removed from the reaction using Microcon YM-50 Microconcentrators (Amicon, Bedford, Mass.). Sections were deparaffinized in xylene, rehydrated in graded ethanol solutions as described above, and fixed in 4% paraformaldehyde (EMS, Ft. Washington, Pa.) for 10 min at 4° C. Tissues were then digested with Proteinase K (5 mg/mL; 10 min, 37° C., Roche, Indianapolis, Ind.) and washed in 0.5×SSC buffer (Saline-Sodium Citrate buffer) (10 min). Prehybridization was performed after sequential dehydration in graded series of ethanol, the reverse process as described above for rehydration, followed by incubation in hybridization buffer (50% formamide, 2×SSC, 10% dextran sulfate, v/v) for 2 hours at 42° C. Hybridization was performed overnight using hybridization buffer containing tRNA (50 $\mu g/mL$, Sigma, St. Louis, Mo.) and the appropriate labeled probe at 55° C. Hybridized tissues were then washed successively in 2×SSC buffer, 0.1×SSC-EDTA buffer (0.1×SSC, 1 mM EDTA), and 2×SSC buffer for 1 hour 40 min. Slides were finally dehydrated in graded series of ethanol as described above containing $NH_4OAc$ (2 min each) and dried in a vacuum desiccator for 1.5 hours at room temperature. Tissues were exposed overnight to a phosphorus screen. Slides were coated with photographic emulsion (Kodak, Rochester, N.Y.) and exposed at 4° C. for 3–5 weeks prior to development. Developed slides were counterstained with hematoxylin and eosin.

Principles of TagMan Analysis

The fluorogenic 5'-nuclease assay (TaqMan PCR) using Applied Biosystems' 7700 Sequence Detection System (Applied Biosystems, Foster City, Calif.) allowed for real time detection/quantitation of a specific gene by monitoring the increase in fluorescence of a gene-specific, dye-labeled oligonucleotide probe. Probes for target and reference genes were labeled at the 5'-end with a 6-carboxyfluorescein (6FAM) reporter dye and at the 3'-end with a 6-carboxy-N, N,N',N'-tetramethylrhodamine (TAMRA) quencher dye. When the probe was annealed to the target gene, fluorescence of 6FAM was prevented by the close proximity of TAMRA. The exonuclease activity of Taq polymerase released the dyes from the oligonucleotide probe by displacing the probe from the target sequence resulting in fluorescence excitation in direct proportion to the amount of target message present. Data analysis was performed using the Sequence Detection System software from Applied Biosystems.

TaqMan Primers and Probes: TGF□1, ANP, Collagen I, Collagen III

Primers and probes were designed using Oligo Primer Analysis Software, Version 5.0 (National Biosciences Inc. (NBI)-Wojciech Rychlik, Cascade, Colo.). Primers were synthesized by Life Technologies (Grand Island, N.Y.) and probes were synthesized by Applied Biosystems. Primer/probe sets were designed from known sequences of rat genes to be analyzed. All target gene values were normalized to a reference gene, constitutively expressed cyclophilin. Primer/probe sets sequences can be found in Table 8

RNA isolation: TGFβ1, ANP, Collagen I, Collagen III

RNA was extracted from frozen (−70° C.) left ventricle (LV) tissue (approximately 10–20 mg) using 1.5 mL RNA-STAT 60 according to manufacturer's instructions (Leedo Medical Laboratories, Inc., Houston, Tex.). Briefly, tissues were homogenized using a tissue homogenizer equipped with a 5 mm probe (Ultra-Turrax T8 Homogenizer, IKA Works, Inc. Wilmington, N.C.). Following homogenization, an equal volume of molecular grade chloroform (Sigma Chemical Co., St. Louis, Mo.) was incubated with periodic mixing for 10 min at room temperature. Samples were centrifuged at 12,000 g for 10 min and RNA was precipitated from the top layer by adding an equal volume of molecular grade isopropanol (Sigma Chemical Co.) followed by an overnight incubation at −80° C. RNA was pelleted by centrifugation at 12,000 g, washed with 75% ethanol, and solubilized in nuclease-free water (Promega, Madison, Wis.). RNA was diluted and analyzed spectrophotometrically for concentration and purity (A260/A280= 1.9–2.0, with an average yield of 2–5 µg RNA).

Reverse Transcription: TGFβ1, ANP, Collagen I, Collagen III

Double-stranded cDNA was synthesized by adding 400 ng RNA (4 uL) to a final volume of 20 uL containing 15% nuclease-free water (Promega, Madison, Wis.), 1×RT Buffer (Life Technologies, Grand Island, N.Y.), 10 mM DTT (Life Technologies), 0.5 mM each of dATP, dTTP, dGTP, dCTP (PE Biosystems, Foster City, Calif.), 2.5 µM Oligo d(T)15 (Oligo Therapeutics, Inc., Wilsonville, Oreg.), 40 units RNAsin (Promega), and 200 units SuperScript II Reverse Transcriptase (Life Technologies). The reactions were performed in thin-walled reaction tubes with caps (Applied Biosystems) to ensure accurate reaction temperatures. Reactions were performed using a GeneAmp 9600 thermal cycler

TABLE 8

TaqMan RT-PCR Gene Marker Primer/Probe Sets

| Gene | Forward Primer | Reverse Primer | Probe |
| --- | --- | --- | --- |
| Transforming growth factor beta 1 (TGFβ1) | CACCATCCATGACATGAACC | ACCTTGCTGTACTGTGTGTCC | TCAGCTCCACAGAGAAGAACTGC |
| Atrial natriuretic factor (ANP) | TGGGCTCCTTCTCCATCAC | AGCAGAGCCCTCAGTTTG | CCATATTGGAGCAAATCCCGTATAC |
| Collagen I | ACCAAGGCTGCAACCTGGA | GCAGGAAGGTCAGCTGGAT | CCATACTCGAACTGGAATCCATCG |
| Collagen III | GGCTTTCAGTTCAGCTATGG | GACTGTCTTGCTCCATTCAC | CCTGATCTTCCTGAAGATGTCCTTG |
| Cyclophilin | CTTGTCCATGGCAAATGCTG | GTGATCTTCTTGCTGGTCTTGC | CCACAATGCTCATGCCTTCTTTCACC |
| Cyclooxegenase-2 (COX-2) | TCAAAGACACTCAGGTAGACATGATCT | CGGCACCAGACCAAAGACTT | CACGTCCCTGAGCACCTGCGG |
| Osteopontin | CCAGCACACAAGCAGACGTT | TCAGTCCATAAGCCAAGCTATCAC | CAGTCGATGTCCCTGACGGCCG |
| Monocyte Chemoattractant Protein-1 (MCP-1) | GCAGGTCTCTGTCACGCTTCT | GGCTGAGACAGCACGTGGAT | CCTGTTGTTCACAGTTGCTGCCTGTAGC |
| Intercellular Adhesion Molecule-1 (ICAM-1) | ACCTGCAGCCGGAAAGC | CCCGTTTGACAGACTTCACCAT | CCGATAGGCAGCGGGACACCA |
| Vascular Cell Adhesion Molecule-1 (VCAM-1) | GAAGCCGGTCATGGTCAAGT | GGTCACCCTTGAACAGTTCTATCTC | TGGCTCCTGATGTTTACCCAATTGACAGA |
| Cyclophilin | AGAGAAATTTGAGGATGAGAACTTCAT | TTGTGTTTGGTCCAGCATTTG | AAGCATACAGGTCCTGGCATCTTGTCCAT |

All oligonucleotides are written 5'–3'. Primers are unlabeled and all probes are labeled at the 5' end with 6-carboxyfluorescein (6FAM) reporter dye and at the 3' end with 6-carboxy-N,N,N',N'-tetramethylrhodamine (TAMRA) quencher dye (Applied Biosystems) according to the following protocol: 1 hour at 37° C., 5 min at 95° C., and 10 min at 4° C.

TaqMan Analysis: TGFβ1, ANP, Collagen I, Collagen III

Each PCR reaction contained the following: 2.5 μL (50 ng) of each cDNA added to 22.5 μL of a PCR mix containing: 38.5% nuclease-free water (Promega), 1×PCR Buffer II, 2 mM $MgCl_2$, 0.05 U/μL AmpliTaq Gold (PCR Core Reagent Kit, N808-0228, Applied Biosystems), 300 nM each of a forward and a reverse primer (Life Technologies), 200 nM probe (Applied Biosystems) and 200 μM each of DATP, dTTP, dGTP, and dCTP (Applied Biosystems). Single reactions were set up in MicroAmp optical tubes with MicroAmp optical caps (Applied Biosystems) and loaded into the 7700 Sequence Detector. The following protocol was applied to all reactions: 10 min at 95° C. (polymerase activation), 40 cycles of 10 seconds at 95° C. (denaturation) and 1 min at 57° C. (annealing).

TaqMan Primers and Probes: COX-2, Osteopontin, MCP-1, ICAM-1, VCAM-1

All primers and probes were designed using Primer Express software supplied with the 7700 Sequence Detection System and synthesized by Applied Biosystems. Standard curves using 5-fold dilutions of total RNA (from 200 ng to 320 pg) were performed to determine the efficiency of each primer/probe set in the TaqMan reaction prior to the analysis of the experimental samples. Primer/probe sets were designed from known sequences of rat genes to be analyzed. All target gene values were normalized to a reference gene, constitutively expressed cyclophilin. Primer/probe set sequences can be found in Table 8.

RNA isolation: COX-2, Osteopontin, MCP-1, ICAM-1, VCAM-1

RNA was extracted from frozen (−80° C.) rat heart tissue using the Totally RNA Isolation Kit (Ambion, Inc., Austin, Tex.). Tissue was crushed using a stainless steel mortar and pestle, which had been chilled to −80° C. and transferred to a dounce homogenizer (Kontes, Vineland, N.J.) containing 3–10 mL cold denaturation buffer. Tissue was homogenized and transferred to a sterile, 15 mL polypropylene centrifuge tube. An equal volume of phenol:chloroform:isoamyl alcohol (25:24:1) was added, samples were shaken vigorously for 1 min, and incubated on ice for at least 15 min. Samples were centrifuged for 30 min at 10,000g. The aqueous phase was removed, 1/10 volume of a sodium acetate solution (3.0 M NaOAc pH 4.5) was added, samples were shaken or inverted for 10 seconds, and acid-phenol (premixed with isoamyl alcohol):chloroform (5:1, Ambion, Inc.) was added at an volume equivalent to the starting sample volume. Samples were shaken vigorously for 1 min, followed by a 15-min incubation on ice, and centrifuged for 30 min at 10,000 g. The aqueous phase removed and placed in a clean polypropylene tube. An equal volume of isopropanol (Sigma, St. Louis, Mo.) was added and the samples were mixed and incubated overnight at −20° C. The samples were centrifuged for 30 min at 10,000 g, the supernatant was removed and the RNA pellet was resuspended in DNAse/RNAse-free water. Samples were frozen at −80° C. for at least 2 hours, thawed on wet ice, and diluted for quantitation.

All RNA was further purified by DNase digestion to remove genomic DNA and LiCl precipitation to remove carbohydrates. Each RNA (100 μg) was incubated for 45 min at 37° C. with 1 unit of DNAse (Roche Diagnostics, Indianapolis, Ind.) and 10 units RNAse inhibitor (Applied Biosystems, Foster City, Calif.) in a buffer containing 40 mM Tris pH 7.8, 6 mM $MgCl_2$, 10 mM $CaCl_2$. The DNAse and buffer were removed using the RNeasy Mini protocol for RNA. cleanup (Qiagen, Valencia, Calif.). The RNA was then precipitated with 7.5M LiCl/50 mM EDTA (Ambion, Inc., Austin, Tex.) in a volume equal to half the sample volume, incubated overnight at −20° C., and centrifuged for 30 min at 13–16,000g at 4° C. All RNA was frozen for at least 2 hours at −80° C., thawed, diluted, and analyzed spectrophotometrically for concentration and purity.

TaqMan Analysis: COX-2, Osteopontin, MCP-1, ICAM-1, VCAM-1

TaqMan reactions were performed as follows. Ten μL (200 ng) of total RNA (DNAsed and LiCl precipitated) was added to 15 μL of a RT-PCR reaction mix containing: 12.5 μL of 2× One-Step PCR Master Mix without uracil-N-glycosylase (contains AmpliTaq Gold DNA Polymerase, dNTPs with dUTP, passive reference, and optimized buffer components), 0.625 μL of a 40× MultiScribe and RNAse Inhibitor Mix, 0.625 μL of 20 μM forward primer, 0.625 μL of 20 μM reverse primer, 0.5 μL of 5 μM TaqMan probe, and 0.125 μL of DNAse/RNAase-free water. Reactions were set up in duplicate in MicroAmp optical 96-well reaction plates with MicroAmp optical caps or adhesive covers (Applied Biosystems) and loaded into the 7700 Sequence Detector. The following protocol was applied to all reactions: 30 min at 48° C. (reverse transcription), 10 min at 95° C. (inactivation of reverse transcriptase and polymerase activation), 40 cycles of 15 seconds at 95° C. (denaturation), and 1 min at 60° C. (annealing).

Hydroxyproline Assay

Myocardial hydroxyproline concentration was measured by a calorimetric assay that quantifies the reaction between oxidized hydroxyproline, and p-dimethylaminobenzaldehyde as described previously (4). Briefly, tissues (180–250 mg) were dried for 18 hours at 60° C. using a Reacti-Therm heating block (Pierce, Rockford, Ill.) and weighed. Dried tissues and a positive collagen control (Bovine Collagen Type I, Sigma, St. Louis, Mo.) were hydrolyzed with 2 mL 6N HCl for 3 hours at 150° C. in the Reacti-Therm heating block. Acid was evaporated under nitrogen gas, samples were rehydrated in 1 mL of citrate-acetate buffer (0.7 M NaOAc, 0.2 M citrate, 45 mM citric acid, pH 6.0) in the presence of 4 mL isopropanol, and filtered through a 0.45 □m Millex LCR filter (Gelman Sciences, Ann Arbor, Mich.).

Hydroxyproline content was measured by incubating 60 μL of hydrolyzed sample or collagen standard with 350 μL citrate-acetate-isopropanol buffer (citrate-acetate buffer with 40% isopropanol, v/v) and 100 μL of 300 mM Chloramine T (J. T. Baker, Phillipsburg, N.J.) for 5 min at 25° C. Erlich's Reagent (1.25 mL, 3.5 M p-dimethylaminobenzaldehyde in 70% perchloric acid with 80% isopropanol, v/v) was added for visualization and quantitation of hydroxyproline. Samples were incubated at 60° C. for 30 min, cooled to room temperature, and absorbance was monitored at 558 nm. Hydroxyproline content was quantitated from a freshly prepared standard curve of trans-4-hydroxy-L-proline (Sigma, St. Louis, Mo.). All samples and standards were performed in duplicate.

Statistical Analysis

Data were analyzed using one-way analysis of variance (ANOVA). Because the assumptions of normality within groups and equality of variance across groups could not be consistently met, the analysis was performed on the rank transformed values of the raw data (nonparametric analysis). The alpha=0.05 level of significance was used for the planned comparisons between the means. The Least Significant Differences (LSD) method was used for planned comparisons between groups. Data were analyzed using PROC TTEST in the SAS statistical software package (SAS PC, version 6.12, SAS Institute, Cary, N.C.). All data are reported as mean±standard error of the mean (SEM).

Animal Exclusion

Three animals died during the experiment: rat #17 (aldosterone +salt group, found dead after 24 days of infusion), rat #64 (aldosterone +salt group, died following surgery), and rat 5 (vehicle group, died following surgery). Additional animals were excluded if multiple parameters were found not to represent the treatment group to which they were assigned (e.g. more than 3 standard deviations from the mean for that treatment group). Three such animals were excluded from the study: rat #57 (from 7-day protocol, aldosterone +salt group), rat #97 (from 14-day protocol, aldosterone+salt group), and rat 24 (from 30-day protocol, 100 mg/kg/day eplerenone group). These three animals demonstrated expression of inflammatory marker genes (COX-2, Osteopontin, MCP-1, ICAM-1, and VCAM-1) that were greater than 3 standard deviations from the mean for the treatment group. Rat #24 was also excluded as a result of telemetry unit dysfunction. Values generated for these animals are shown in Table 9.10–Table 9.19, separated from the data for the other animals in the data tables.

TABLE 9.10

Individual data used for Table 10

| Day | Systolic Blood Pressure (mmHg) | | | | | | | |
|---|---|---|---|---|---|---|---|---|
| | Control: vehicle + salt | | | | | | | |
| | Rat # | | | | | | | |
| | 1 | 2 | 4 | 6 | 7 | 8 | 9 | 10 |
| 3 | 118 | 130 | 121 | — | — | — | — | 118 |
| 4 | 120 | 122 | 125 | — | — | — | — | 123 |
| 5 | 126 | 123 | 125 | — | — | — | — | 127 |
| 6 | 132 | 129 | 130 | — | — | — | — | 131 |
| 7 | 133 | 132 | 134 | — | — | — | — | 131 |
| 8 | 135 | 133 | 133 | — | — | — | — | 129 |
| 9 | 131 | 131 | 133 | — | — | — | — | 128 |
| 10 | 130 | 132 | 128 | 124 | — | 116 | 135 | 127 |
| 11 | 130 | 130 | 129 | 125 | — | 118 | 138 | 128 |
| 12 | 130 | 128 | 126 | 124 | — | 124 | 143 | 128 |
| 13 | 131 | 127 | 128 | 121 | — | 123 | 143 | 126 |
| 14 | 142 | 122 | 126 | 125 | — | 128 | 148 | 128 |
| 15 | 144 | 128 | 127 | 128 | — | 125 | 134 | 127 |
| 16 | 132 | 133 | 127 | 128 | — | 128 | 134 | 123 |
| 17 | 133 | 133 | 127 | 123 | — | 124 | 140 | 128 |
| 18 | 134 | 133 | 129 | 121 | — | 126 | 143 | 128 |
| 19 | 125 | 129 | 120 | 125 | — | 124 | 140 | 128 |
| 20 | 119 | 131 | 121 | 125 | — | 122 | 139 | 126 |
| 21 | 123 | 131 | 125 | 126 | — | 120 | 136 | 128 |
| 22 | 127 | 128 | 128 | 126 | — | 125 | 133 | 129 |
| 23 | 129 | 133 | 131 | 125 | — | 128 | 138 | 131 |
| 24 | 132 | 134 | 130 | 125 | — | 132 | 140 | 130 |
| 25 | 133 | 131 | 125 | 125 | — | 128 | 136 | 129 |
| 26 | 132 | 131 | 127 | 126 | — | 132 | 141 | 130 |
| | Aldosterone + salt | | | | | | | |
| | Rat # | | | | | | | |
| | 11 | 12 | 13 | 14 | 15 | 16 | 18 | 19 | 20 |
| 3 | 116 | 152 | 115 | 127 | 143 | 122 | — | 124 | 159 |
| 4 | 120 | 149 | 122 | 134 | 129 | 135 | — | 125 | 152 |
| 5 | 126 | 158 | 124 | 142 | 129 | 137 | — | 128 | 151 |
| 6 | 132 | 170 | 136 | 157 | 144 | 149 | — | 135 | 158 |
| 7 | 140 | 179 | 139 | 165 | 153 | 154 | — | 145 | 165 |
| 8 | 145 | 182 | 143 | 160 | 158 | 154 | — | 146 | 163 |
| 9 | 150 | 191 | 148 | 172 | 172 | 159 | — | 151 | 169 |
| 10 | 156 | 196 | 149 | 175 | 175 | 165 | — | 151 | 172 |
| 11 | 154 | 201 | 155 | 178 | 181 | 163 | — | 155 | 175 |
| 12 | 159 | 207 | 161 | 190 | 186 | 170 | — | 163 | 190 |
| 13 | 161 | 210 | 166 | 196 | 191 | 172 | — | 166 | 194 |
| 14 | 164 | 208 | 170 | 204 | 192 | 181 | 159 | 172 | 192 |
| 15 | 171 | 200 | 164 | 205 | 183 | 173 | 160 | 175 | 194 |
| 16 | 179 | 218 | 165 | 200 | 194 | 176 | 166 | 187 | 198 |
| 17 | 174 | 222 | 178 | 209 | 220 | 185 | 170 | 192 | 202 |
| 18 | 181 | 226 | 174 | 212 | 213 | 186 | 175 | 198 | 203 |
| 19 | 189 | 219 | 185 | 208 | 231 | 188 | 177 | 201 | 203 |
| 20 | 192 | 225 | 190 | 220 | 212 | 198 | 180 | 207 | 204 |
| 21 | 197 | 227 | 197 | 218 | 220 | 201 | 186 | 213 | 211 |
| 22 | 198 | 227 | 204 | 213 | 223 | 204 | 190 | 221 | 204 |
| 23 | 200 | 221 | 203 | 223 | 214 | 204 | 187 | 220 | 199 |
| 24 | 204 | 218 | 199 | 222 | 219 | 207 | 194 | 212 | 212 |

TABLE 9.10-continued

Individual data used for Table 10

| Day | Systolic Blood Pressure (mmHg) | | | | | | | | |
|---|---|---|---|---|---|---|---|---|---|
| 25 | 215 | 209 | 205 | 231 | 219 | 210 | 198 | 196 | 210 |
| 26 | 219 | 211 | 215 | 224 | 207 | 202 | 192 | 212 | 205 |

Eplerenone + aldosterone + salt

| | Rat # | | | | | | | | |
|---|---|---|---|---|---|---|---|---|---|
| | 21 | 22 | 23 | 25 | 26 | 27 | 28 | 29 | 30 | 24* |
| 3 | 123 | 126 | 130 | 128 | 119 | 125 | 126 | 125 | 130 | — |
| 4 | 130 | 128 | 131 | 139 | 122 | 126 | 128 | 130 | 134 | — |
| 5 | 132 | 134 | 132 | 143 | 123 | 127 | 127 | 133 | 142 | — |
| 6 | 133 | 142 | 136 | 152 | 126 | 133 | 137 | 140 | 150 | — |
| 7 | 140 | 142 | 143 | 156 | 132 | 140 | 140 | 141 | 156 | — |
| 8 | 142 | 146 | 141 | 156 | 131 | 138 | 138 | 139 | 152 | — |
| 9 | 142 | 146 | 139 | 154 | 130 | 133 | 137 | 141 | 151 | — |
| 10 | 143 | 143 | 138 | 158 | 134 | 136 | 139 | 142 | 149 | — |
| 11 | 145 | 139 | 138 | 160 | 136 | 137 | 140 | 145 | 152 | — |
| 12 | 147 | 140 | 139 | 165 | 137 | 139 | 140 | 148 | 154 | — |
| 13 | 148 | 144 | 137 | 170 | 140 | 140 | 140 | 149 | 153 | — |
| 14 | 146 | 142 | 138 | 178 | 143 | 144 | 143 | 152 | 161 | — |
| 15 | 145 | 143 | 137 | 173 | 143 | 144 | 141 | 149 | 156 | — |
| 16 | 148 | 137 | 137 | 179 | 145 | 145 | 143 | 150 | 164 | — |
| 17 | 148 | 141 | 143 | 182 | 149 | 148 | 143 | 160 | 174 | — |
| 18 | 151 | 146 | 144 | 187 | 152 | 149 | 148 | 162 | 177 | — |
| 19 | 156 | 147 | 145 | 192 | 153 | 154 | 150 | 166 | 177 | — |
| 20 | 159 | 147 | 146 | 192 | 155 | 151 | 151 | 168 | 176 | — |
| 21 | 162 | 148 | 152 | 200 | 159 | 154 | 155 | 175 | 182 | — |
| 22 | 162 | 149 | 153 | 203 | 160 | 158 | 155 | 176 | 185 | — |
| 23 | 169 | 157 | 157 | 209 | 163 | 160 | 159 | 180 | 191 | — |
| 24 | 168 | 164 | 159 | 211 | 163 | 162 | 161 | 180 | 195 | — |
| 25 | 174 | 165 | 161 | 215 | 165 | 161 | 161 | 182 | 198 | — |
| 26 | 178 | 168 | 163 | 223 | 167 | 166 | 162 | 192 | 202 | — |

— No data were collected due to technical difficulties.
*Data from this animal were not considered for statistical analysis and not included in the final results.

TABLE 9.11

Individual data used for Table 11

| Rat # | Final Body Weight (g) | Left Ventricle Weight (mg) | Right Ventricle Weight (mg) | Tibia Length (cm) | Left Ventricle Weight/ Tibia Length (mg/cm) | Right Ventricle Weight/ Tibia Length (mg/cm) | ANP (AU) |
|---|---|---|---|---|---|---|---|
| | | | Control: vehicle + salt | | | | |
| 47 | 291 | 771 | 194 | 3.9 | 198 | 50 | 0.90 |
| 48 | 283 | 699 | 155 | 3.8 | 184 | 41 | 0.70 |
| 49 | 284 | 696 | 166 | 3.8 | 183 | 44 | 3.59 |
| 50 | 267 | 562 | 175 | 3.8 | 148 | 46 | 3.96 |
| 51 | 268 | 636 | 178 | 3.8 | 167 | 47 | 1.11 |
| 52 | 273 | 709 | 185 | 3.7 | 192 | 50 | 0.94 |
| 53 | 269 | 699 | 197 | 3.8 | 184 | 52 | 0.64 |
| 54 | 245 | 612 | 189 | 3.8 | 161 | 50 | 1.06 |
| 55 | 286 | 667 | 190 | 3.8 | 176 | 50 | 0.93 |
| 56 | 245 | 616 | 149 | 3.8 | 162 | 39 | 1.10 |
| Mean | 271 | 667 | 178 | 3.8 | 175 | 47 | 1.49 |
| SEM | 5 | 19 | 5 | 0.01 | 5 | 1 | 0.38 |
| | | | Aldosterone + salt | | | | |
| 58 | 266 | 784 | 183 | 3.8 | 206 | 48 | 11.92 |
| 59 | 271 | 719 | 178 | 3.6 | 200 | 49 | 3.99 |
| 60 | 299 | 719 | 223 | 3.9 | 184 | 57 | 13.41 |
| 61 | 286 | 779 | 185 | 3.9 | 200 | 47 | 3.64 |
| 62 | 274 | 746 | 168 | 3.8 | 196 | 44 | 9.09 |
| 63 | 276 | 620 | 154 | 3.8 | 163 | 41 | 13.13 |

TABLE 9.11-continued

Individual data used for Table 11

| Rat # | Final Body Weight (g) | Left Ventricle Weight (mg) | Right Ventricle Weight (mg) | Tibia Length (cm) | Left Ventricle Weight/ Tibia Length (mg/cm) | Right Ventricle Weight/ Tibia Length (mg/cm) | ANP (AU) |
|---|---|---|---|---|---|---|---|
| 65 | — | 849 | 197 | 3.9 | 218 | 51 | 6.13 |
| 66 | 266 | 674 | 174 | 3.7 | 182 | 47 | 3.88 |
| Mean | 277 | 736 | 183 | 3.8 | 194 | 48 | 8.15 |
| SEM | 5 | 25 | 7 | 0.03 | 6 | 2 | 1.51 |
| 57* | 267 | 778 | 208 | 3.8 | 205 | 55 | 13.32 |
| | Eplerenone + aldosterone + salt |
| 67 | 306 | 859 | 216 | 3.9 | 220 | 55 | 1.26 |
| 68 | 295 | 712 | 181 | 3.8 | 187 | 48 | 1.81 |
| 69 | 286 | 618 | 154 | 3.7 | 167 | 42 | 0.59 |
| 70 | 277 | 658 | 174 | 3.8 | 173 | 46 | 2.58 |
| 71 | 295 | 754 | 192 | 3.8 | 198 | 51 | 4.48 |
| 72 | 281 | 733 | 171 | 3.8 | 193 | 45 | 4.98 |
| 73 | 273 | 726 | 181 | 3.8 | 191 | 48 | 3.82 |
| 74 | 286 | 696 | 190 | 3.8 | 183 | 50 | 3.59 |
| 75 | — | 700 | 170 | 3.8 | 184 | 45 | 0.95 |
| 76 | 276 | 688 | 187 | 3.8 | 181 | 49 | 3.67 |
| Mean | 286 | 714 | 182 | 3.8 | 188 | 48 | 2.77 |
| SEM | 4 | 20 | 5 | 0.01 | 5 | 1 | 0.49 |

— No data were collected due to technical difficulties.
*Data from this animal were not considered for statistical analysis and not included in the final results.

TABLE 9.12

Individual data used for Table 12

| Rat # | Final Body Weight (g) | Left Ventricle Weight (mg) | Right Ventricle Weight (mg) | Tibia Length (cm) | Left Ventricle Weight/ Tibia Length (mg/cm) | Right Ventricle Weight/ Tibia Length (mg/cm) | ANP (AU) |
|---|---|---|---|---|---|---|---|
| | Control: vehicle + salt |
| 87 | 319 | 760 | 188 | 3.9 | 195 | 48 | 0.16 |
| 88 | 337 | 782 | 238 | 3.9 | 201 | 61 | 0.92 |
| 89 | 322 | 665 | 179 | 3.9 | 171 | 46 | 0.36 |
| 90 | 322 | 802 | 208 | 3.8 | 211 | 55 | 0.89 |
| 91 | — | 742 | 174 | 3.8 | 195 | 46 | 7.04 |
| 92 | 327 | 790 | 200 | 3.8 | 208 | 53 | 1.89 |
| 93 | 324 | 747 | 303 | 3.8 | 197 | 80 | 3.33 |
| 94 | 301 | 826 | 184 | 3.80 | 217 | 48 | 1.80 |
| 95 | 303 | 745 | 178 | 3.8 | 196 | 47 | 1.08 |
| 96 | 295 | 756 | 206 | 3.9 | 194 | 53 | 0.17 |
| 127 | 313 | 777 | 174 | 3.9 | 199 | 45 | nd |
| 128 | 295 | 677 | 178 | 3.8 | 178 | 47 | nd |
| 129 | 278 | 657 | 165 | 3.8 | 173 | 43 | nd |
| Mean | 311 | 748 | 198 | 3.8 | 195 | 52 | 1.76 |
| SEM | 5 | 15 | 10 | 0.01 | 4 | 3 | 0.66 |
| | Aldosterone + salt |
| 98 | 298 | 846 | 194 | 3.8 | 223 | 51 | 4.58 |
| 99 | 261 | 784 | 189 | 3.8 | 206 | 50 | 7.75 |
| 100 | 307 | 912 | 208 | 3.9 | 234 | 53 | 7.34 |
| 101 | 242 | 720 | 174 | 3.8 | 189 | 46 | 4.18 |
| 102 | 307 | 923 | 217 | 3.9 | 237 | 56 | 1.59 |
| 103 | 279 | 854 | 186 | 3.80 | 225 | 49 | 17.81 |
| 104 | 308 | 894 | 216 | 3.9 | 229 | 55 | 6.48 |
| 105 | 290 | 859 | 171 | 3.9 | 220 | 44 | 8.08 |
| 106 | 264 | 750 | 153 | 3.8 | 197 | 40 | 2.51 |
| 130 | 275 | 818 | 202 | 3.8 | 215 | 53 | nd |
| 131 | 193 | 746 | 195 | 3.7 | 202 | 53 | nd |
| 132 | 215 | 700 | 172 | 3.6 | 194 | 48 | nd |
| Mean | 270 | 817 | 189 | 3.8 | 214 | 50 | 6.70 |
| SEM | 11 | 22 | 5 | 0.02 | 5 | 1 | 1.59 |
| 97* | 235 | 809 | 178 | 3.9 | 207 | 46 | 5.96 |

TABLE 9.12-continued

Individual data used for Table 12

| Rat # | Final Body Weight (g) | Left Ventricle Weight (mg) | Right Ventricle Weight (mg) | Tibia Length (cm) | Left Ventricle Weight/ Tibia Length (mg/cm) | Right Ventricle Weight/ Tibia Length (mg/cm) | ANP (AU) |
|---|---|---|---|---|---|---|---|
| | Eplerenone + aldosterone + salt | | | | | | |
| 133 | 281 | 804 | 182 | 3.8 | 212 | 48 | nd |
| 134 | 304 | 898 | 188 | 3.8 | 236 | 49 | 2.84 |
| 135 | 293 | 789 | 176 | 3.8 | 208 | 46 | 3.22 |
| 136 | 268 | 851 | 189 | 3.9 | 221 | 49 | 6.39 |
| 137 | 267 | 668 | 139 | 3.8 | 176 | 37 | 4.04 |
| 138 | 247 | 833 | 371 | 3.7 | 225 | 100 | 25.90 |
| 139 | 296 | 886 | 193 | 3.8 | 233 | 51 | 5.52 |
| 140 | 291 | 756 | 188 | 3.8 | 199 | 49 | 3.57 |
| 141 | 297 | 751 | 158 | 3.8 | 198 | 42 | 2.29 |
| 142 | 264 | 795 | 155 | 3.7 | 215 | 42 | 8.37 |
| 143 | 302 | 915 | 225 | 3.9 | 235 | 58 | 4.24 |
| Mean | 283 | 813 | 197 | 3.8 | 214 | 52 | 6.64 |
| SEM | 6 | 22 | 19 | 0.02 | 6 | 5 | 2.22 |

— No data were collected due to technical difficulties.
nd No data were reported due to insufficient mRNA sample.
*Data from this animal were not considered for statistical analysis and not included in the final results.

TABLE 9.13

Individual data used for Table 13

| Rat # | Final Body Weight (g) | Left Ventricle Weight (mg) | Right Ventricle Weight (mg) | Tibia Length (cm) | Left Ventricle Weight/ Tibia Length (mg/cm) | Right Ventricle Weight/ Tibia Length (mg/cm) | ANP (AU) |
|---|---|---|---|---|---|---|---|
| | Control: vehicle + salt | | | | | | |
| 1 | 308 | 686 | 160 | 4.0 | 172 | 40 | 0.95 |
| 2 | 337 | 763 | 194 | 4.1 | 186 | 47 | 0.30 |
| 4 | 316 | 728 | 162 | 4.0 | 182 | 41 | 0.12 |
| 6 | 343 | 721 | 162 | 4.1 | 176 | 40 | 1.06 |
| 7 | 291 | 664 | 153 | 4.0 | 166 | 38 | 1.93 |
| 8 | 294 | 612 | 180 | 4.1 | 149 | 44 | 0.24 |
| 9 | 291 | 613 | 141 | 4.0 | 153 | 35 | 1.17 |
| 10 | 332 | 812 | 184 | 4.2 | 193 | 44 | 0.11 |
| Mean | 314 | 700 | 167 | 4.1 | 172 | 41 | 0.74 |
| SEM | 8 | 25 | 6 | 0.03 | 5 | 1 | 0.23 |
| | Aldosterone + salt | | | | | | |
| 11 | 289 | 934 | 196 | 4.0 | 234 | 49 | 23.59 |
| 12 | 219 | 726 | 148 | 3.8 | 191 | 39 | 43.11 |
| 13 | 289 | 963 | 215 | 3.9 | 247 | 55 | 14.83 |
| 14 | 282 | 942 | 176 | 3.9 | 242 | 45 | 18.90 |
| 15 | 290 | 1030 | 224 | 3.9 | 264 | 57 | 14.83 |
| 16 | 267 | 837 | 173 | 3.9 | 215 | 44 | 23.43 |
| 18 | 319 | 962 | 220 | 3.9 | 247 | 56 | 15.14 |
| 19 | 263 | 873 | 187 | 4.0 | 218 | 47 | 6.77 |
| 20 | 234 | 919 | 185 | 3.8 | 242 | 49 | 20.97 |
| Mean | 272 | 910 | 192 | 3.9 | 233 | 49 | 20.17 |
| SEM | 10 | 29 | 8 | 0.02 | 7 | 2 | 3.36 |
| | Eplerenone + aldosterone + salt | | | | | | |
| 21 | 310 | 873 | 177 | 3.9 | 224 | 45 | 1.93 |
| 22 | 343 | 908 | 202 | 4.1 | 233 | 52 | 1.15 |
| 23 | 334 | 899 | 200 | 3.9 | 231 | 51 | 4.89 |
| 25 | 299 | 1063 | 209 | 3.9 | 273 | 54 | 21.26 |
| 26 | 361 | 958 | 187 | 3.9 | 246 | 48 | 10.63 |
| 27 | 351 | 1129 | 242 | 3.9 | 289 | 62 | 20.25 |
| 28 | 316 | 929 | 189 | 3.9 | 238 | 48 | 10.20 |
| 29 | 352 | 805 | 181 | 4.0 | 206 | 46 | 4.82 |
| 30 | 317 | 861 | 195 | 3.9 | 221 | 50 | 7.67 |

TABLE 9.13-continued

Individual data used for Table 13

| Rat # | Final Body Weight (g) | Left Ventricle Weight (mg) | Right Ventricle Weight (mg) | Tibia Length (cm) | Left Ventricle Weight/ Tibia Length (mg/cm) | Right Ventricle Weight/ Tibia Length (mg/cm) | ANP (AU) |
|---|---|---|---|---|---|---|---|
| Mean | 331 | 936 | 198 | 3.9 | 240 | 51 | 9.20 |
| SEM | 7 | 34 | 6 | 0.00 | 9 | 2 | 2.44 |
| 24* | 273 | 822 | 178 | 3.9 | 211 | 46 | 13.45 |

*Data from this animal were not considered for statistical analysis and not included in the final results.

TABLE 9.14

Individual data used for Table 14

| Rat # | Myocardial Necrosis (0–4) | Interstitial Collagen Volume Fraction (%) | Hydroxy-proline (µg/mg) | Collagen-I mRNA (AU) | Collagen-III mRNA (AU) |
|---|---|---|---|---|---|
| Control: vehicle + salt | | | | | |
| 47 | 0.0 | 2.9 | 5.11 | 1.72 | 1.39 |
| 48 | 0.0 | 7.1 | 5.72 | 0.63 | 0.80 |
| 49 | 0.0 | 3.1 | 3.15 | 1.97 | 2.00 |
| 50 | 0.0 | 4.1 | 2.37 | 1.08 | 1.19 |
| 51 | 0.0 | 3.4 | 2.23 | 1.40 | 1.09 |
| 52 | 0.0 | 4.5 | 2.48 | 0.73 | 0.92 |
| 53 | 0.0 | 2.3 | 2.35 | 1.22 | 1.27 |
| 54 | 0.0 | 6.6 | 2.42 | 0.78 | 0.91 |
| 55 | 0.0 | 4.1 | 4.68 | 0.54 | 0.70 |
| 56 | 0.0 | 6.3 | 5.21 | 0.93 | 0.61 |
| Mean | 0.0 | 4.4 | 3.57 | 1.10 | 1.09 |
| SEM | 0.0 | 0.5 | 0.45 | 0.15 | 0.13 |
| Aldosterone + salt | | | | | |
| 58 | 0.0 | nd | 4.48 | 0.84 | 0.65 |
| 59 | 0.0 | 3.2 | 4.06 | 1.40 | 1.29 |
| 60 | 0.0 | 6.5 | 2.32 | 1.97 | 1.67 |
| 61 | 0.0 | nd | 2.14 | 1.89 | 1.67 |
| 62 | 0.0 | 6.1 | 2.18 | 1.36 | 1.59 |
| 63 | 0.0 | 6.9 | 2.31 | 1.05 | 1.59 |
| 65 | 0.0 | 6.5 | 2.10 | 1.33 | 1.58 |
| 66 | 0.0 | 4.4 | 2.22 | 1.07 | 1.30 |
| Mean | 0.0 | 5.6 | 2.73 | 1.36 | 1.42 |
| SEM | 0.0 | 0.6 | 0.34 | 0.14 | 0.12 |
| 57* | 0.0 | 3.1 | 3.86 | 1.71 | 1.15 |
| Eplerenone + aldosterone + salt | | | | | |
| 67 | 0.0 | 4.3 | 2.02 | 0.62 | 0.93 |
| 68 | 0.0 | 7.2 | 4.18 | 0.92 | 0.95 |
| 69 | 0.0 | 2.9 | 4.08 | 0.29 | 0.43 |
| 70 | 0.0 | 3.3 | 3.96 | 1.79 | 1.25 |
| 71 | 0.0 | 4.2 | 4.26 | 0.78 | 1.03 |
| 72 | 0.0 | 6.6 | 4.17 | 0.85 | 1.14 |
| 73 | 0.0 | 4.4 | 1.90 | 0.29 | 0.45 |
| 74 | 0.0 | 4.9 | 1.53 | 0.42 | 0.64 |
| 75 | 0.0 | 8.8 | 2.08 | 1.28 | 1.33 |
| 76 | 0.0 | 6.9 | 2.41 | 1.21 | 2.71 |
| Mean | 0.0 | 5.4 | 3.06 | 0.85 | 1.09 |
| SEM | 0.0 | 0.6 | 0.36 | 0.15 | 0.21 | nd = No data were reported due to insufficient mRNA sample.
*Data from this animal were not considered for statistical analysis and not included in the final results.

TABLE 9.15

Individual data used for Table 15

| Rat # | Myocardial Necrosis (0–4) | Collagen Volume Fraction (%) | Hydroxy-proline (µg/mg) | Collagen-I mRNA (AU) | Collagen-III mRNA (AU) |
|---|---|---|---|---|---|
| Control: vehicle + salt | | | | | |
| 87 | 0.0 | 4.6 | 2.03 | 0.90 | 0.96 |
| 88 | 0.0 | 3.9 | 2.20 | 1.60 | 1.60 |
| 89 | 0.0 | 6.5 | 4.51 | 0.92 | 0.80 |
| 90 | 0.0 | 4.4 | 4.07 | 0.58 | 0.65 |
| 91 | 0.0 | 6.3 | 4.93 | 1.28 | 1.42 |
| 92 | 0.0 | 3.1 | 4.00 | 0.94 | 1.05 |
| 93 | 0.0 | 4.9 | 2.89 | 1.14 | 1.00 |
| 94 | 0.0 | 3.9 | 3.24 | 1.07 | 1.02 |
| 95 | 0.0 | 3.2 | 3.21 | 1.56 | 1.00 |
| 96 | 0.0 | 3.7 | 3.16 | 0.80 | 0.56 |
| 127 | 0.0 | 4.9 | 2.66 | nd | nd |
| 128 | 0.0 | 6.0 | 2.70 | nd | nd |
| 129 | 0.0 | 6.1 | 2.84 | nd | nd |
| Mean | 0.0 | 4.7 | 3.26 | 1.08 | 1.01 |
| SEM | 0.0 | 0.4 | 0.24 | 0.10 | 0.10 |
| Aldosterone + salt | | | | | |
| 98 | 0.0 | 4.4 | 2.89 | 1.15 | 0.76 |
| 99 | 1.0 | 5.4 | 2.91 | 2.31 | 1.80 |
| 100 | 0.0 | 3.2 | 6.28 | 0.25 | 0.44 |
| 101 | 0.0 | 5.9 | 5.63 | 1.89 | 1.39 |
| 102 | 0.0 | 4.6 | 4.83 | 2.03 | 1.17 |
| 103 | 1.0 | 3.9 | 5.64 | 1.00 | 1.24 |
| 104 | 0.0 | 4.8 | 5.29 | 1.20 | 1.06 |
| 105 | 0.0 | 4.6 | 2.76 | 1.70 | 1.31 |
| 106 | 1.0 | 5.9 | 2.68 | 0.43 | 0.59 |
| 130 | 0.0 | 3.4 | 2.60 | nd | nd |
| 131 | 3.0 | 6.4 | 3.00 | nd | nd |
| 132 | 3.0 | 9.0 | 3.99 | nd | nd |
| Mean | 0.8 | 5.1 | 4.04 | 1.33 | 1.08 |
| SEM | 0.3 | 0.5 | 0.40 | 0.24 | 0.14 |
| 97* | 3.0 | 3.2 | 2.73 | 2.69 | 1.22 |
| Eplerenone + aldosterone + salt | | | | | |
| 133 | 1.0 | 4.1 | 2.95 | 0.86 | 0.60 |
| 134 | 0.0 | 6.2 | 5.97 | 0.86 | 1.19 |
| 135 | 1.0 | 3.9 | 6.52 | 0.90 | 1.16 |
| 136 | 0.0 | 3.7 | 5.35 | 1.65 | 1.24 |
| 137 | 0.0 | 4.2 | 6.80 | 1.14 | 1.70 |
| 138 | 0.0 | 3.5 | 5.32 | 1.44 | 1.81 |
| 139 | 1.0 | 3.3 | 2.72 | 0.50 | 0.60 |
| 140 | 0.0 | 3.7 | 3.13 | 1.24 | 1.61 |
| 141 | 0.0 | 5.2 | 2.41 | 1.69 | 2.21 |
| 142 | 2.0 | 5.6 | 2.81 | 2.03 | 1.80 |
| 143 | 0.0 | 6.0 | 5.03 | 3.02 | 3.77 |

TABLE 9.15-continued

Individual data used for Table 15

| Rat # | Myocardial Necrosis (0–4) | Collagen Volume Fraction (%) | Hydroxy-proline (μg/mg) | Collagen-I mRNA (AU) | Collagen-III mRNA (AU) |
|---|---|---|---|---|---|
| Mean | 0.5 | 4.5 | 4.46 | 1.39 | 1.61 |
| SEM | 0.2 | 0.3 | 0.50 | 0.21 | 0.26 | nd = No data were reported due to insufficient mRNA sample.

*Data from this animal were not considered for statistical analysis and not included in the final results.

TABLE 9.16

Individual data used for Table 16

| Rat # | Myocardial Necrosis (0–4) | Collagen Volume Fraction (%) | Hydroxy-proline (μg/mg) | Collagen-I mRNA (AU) | Collagen-III mRNA (AU) |
|---|---|---|---|---|---|
| Control: vehicle + salt | | | | | |
| 1 | 0.0 | 4.3 | 2.00 | 1.69 | 1.43 |
| 2 | 0.0 | 4.1 | 2.71 | 0.90 | 0.98 |
| 4 | 0.0 | 6.4 | 2.95 | 1.65 | 1.02 |
| 6 | 0.0 | 7.9 | 3.02 | 0.90 | 1.28 |
| 7 | 0.0 | 5.8 | 2.81 | 0.97 | 0.62 |
| 8 | 0.0 | 7.7 | 5.84 | 1.03 | 0.54 |
| 9 | 0.0 | 6.0 | 5.45 | 0.69 | 0.94 |
| 10 | 0.0 | 7.1 | 7.03 | 0.92 | 0.48 |
| Mean | 0.0 | 6.2 | 3.98 | 1.09 | 0.91 |
| SEM | 0.0 | 0.5 | 0.65 | 0.13 | 0.12 |
| Aldosterone + salt | | | | | |
| 11 | 1.5 | 6.6 | 7.24 | 2.20 | 0.75 |
| 12 | 2.5 | 8.8 | 8.01 | 2.02 | 0.58 |
| 13 | 3.0 | 7.2 | 3.62 | 5.88 | 1.99 |
| 14 | 2.0 | 7.1 | 3.69 | 1.05 | 0.72 |
| 15 | 3.0 | 9.3 | 4.00 | 1.32 | 2.04 |
| 16 | 0.5 | 6.8 | 3.54 | 2.02 | 1.43 |
| 18 | 2.0 | 4.0 | 3.07 | 1.98 | 1.82 |
| 19 | 0.3 | 7.2 | 3.25 | 1.63 | 1.89 |
| 20 | 3.5 | 14.5 | 3.09 | 2.54 | 1.28 |
| Mean | 2.0 | 7.9 | 4.39 | 2.29 | 1.39 |
| SEM | 0.4 | 1.0 | 0.62 | 0.47 | 0.20 |
| Eplerenone + aldosterone + salt | | | | | |
| 21 | 0.0 | 3.4 | 5.18 | 1.89 | 0.95 |
| 22 | 0.0 | 5.0 | 6.11 | 1.54 | 0.72 |
| 23 | 0.0 | 6.5 | 5.17 | 2.65 | 1.37 |
| 25 | 0.0 | 7.9 | 6.40 | 1.97 | 0.89 |
| 26 | 0.0 | 7.1 | 2.73 | 2.98 | 1.26 |
| 27 | 0.0 | 6.3 | 2.84 | 2.65 | 1.87 |
| 28 | 0.0 | 6.1 | 2.97 | 2.90 | 1.66 |
| 29 | 0.0 | 5.4 | 2.82 | 2.88 | 2.89 |
| 30 | 0.0 | 7.8 | 2.72 | 3.35 | 2.16 |
| Mean | 0.0 | 6.2 | 4.10 | 2.53 | 1.53 |
| SEM | 0.0 | 0.5 | 0.53 | 0.20 | 0.23 |
| 24* | 0.0 | 4.4 | 5.75 | 2.01 | 0.73 |

*Data from this animal were not considered for statistical analysis and not included in the final results.

TABLE 9.17

Individual data used for Table 17

| Rat # | COX-2 (AU) | Osteopontin (AU) | MCP1 (AU) | TGF-β (AU) | ICAM (AU) | VCAM (AU) |
|---|---|---|---|---|---|---|
| Control: vehicle + salt | | | | | | |
| 47 | nd | nd | nd | 1.32 | nd | nd |
| 48 | nd | nd | nd | 0.66 | nd | nd |
| 49 | nd | nd | nd | 1.46 | nd | nd |
| 50 | 0.57 | 1.28 | 1.13 | 0.72 | 1.15 | 1.19 |
| 51 | 1.04 | 0.94 | 1.00 | 1.17 | 0.94 | nd |
| 52 | 0.99 | 0.73 | 0.71 | 0.80 | 1.17 | 1.17 |
| 53 | 0.87 | 1.00 | 0.84 | 1.11 | 0.82 | 0.60 |
| 54 | 1.88 | nd | nd | 0.90 | nd | nd |
| 55 | 1.01 | nd | nd | 0.52 | nd | nd |
| 56 | nd | 1.66 | 1.67 | 1.50 | 1.00 | 0.86 |
| Mean | 1.06 | 1.12 | 1.07 | 0.98 | 1.02 | 0.96 |
| SEM | 0.18 | 0.16 | 0.17 | 0.12 | 0.07 | 0.14 |
| Aldosterone + salt | | | | | | |
| 58 | 2.10 | 1.84 | 2.05 | 1.23 | 1.39 | 3.49 |
| 59 | 0.70 | 0.84 | 1.78 | 0.98 | 0.80 | 0.85 |
| 60 | 2.01 | 0.95 | 3.06 | 1.31 | 1.09 | 2.06 |
| 61 | 2.95 | 1.05 | 2.36 | 1.89 | 1.61 | 2.51 |
| 62 | 2.05 | 1.08 | 1.95 | 1.22 | 1.11 | 1.65 |
| 63 | 1.94 | 4.92 | 2.33 | 1.45 | 1.15 | 0.61 |
| 65 | 3.54 | 3.29 | 3.14 | 1.47 | 1.56 | 0.94 |
| 66 | 2.45 | 1.32 | 2.40 | 1.21 | 1.06 | 0.27 |
| Mean | 2.22 | 1.91 | 2.38 | 1.35 | 1.22 | 1.55 |
| SEM | 0.29 | 0.51 | 0.17 | 0.09 | 0.10 | 0.39 |
| 57* | 0.82 | 28.64 | 5.17 | 1.35 | 1.68 | 5.23 |
| Eplerenone + aldosterone + salt | | | | | | |
| 67 | 1.19 | 0.54 | 2.35 | 0.80 | 0.91 | 0.67 |
| 68 | 2.85 | 1.24 | 1.60 | 0.81 | 0.89 | 0.58 |
| 69 | 0.60 | 0.52 | 0.85 | 0.51 | 0.89 | 0.22 |
| 70 | nd | nd | nd | 1.31 | nd | nd |
| 71 | 1.16 | 0.27 | 0.83 | 0.80 | 0.40 | 0.57 |
| 72 | 0.82 | 0.60 | 1.74 | 1.02 | 1.23 | nd |
| 73 | 1.86 | 1.13 | 2.38 | 0.61 | nd | nd |
| 74 | nd | nd | nd | 0.84 | nd | nd |
| 75 | 0.60 | 0.96 | 0.67 | 1.51 | 0.58 | 0.53 |
| 76 | 0.91 | 0.75 | 2.03 | 1.64 | 1.00 | 1.00 |
| Mean | 1.25 | 0.75 | 1.56 | 0.99 | 0.83 | 0.56 |
| SEM | 0.29 | 0.12 | 0.25 | 0.12 | 0.10 | 0.08 | nd = No data was reported due to insufficient mRNA sample.

*Data from this animal were not considered for statistical analysis and not included in the final results.

TABLE 9.18

Individual data used for Table 18

| Rat # | COX-2 (AU) | Osteopontin (AU) | MCP1 (AU) | TGF-β (AU) | ICAM (AU) | VCAM (AU) |
|---|---|---|---|---|---|---|
| Control: vehicle + salt | | | | | | |
| 87 | 1.69 | 1.28 | 1.28 | 1.21 | 1.45 | 0.92 |
| 88 | 0.74 | 1.13 | 0.94 | 1.19 | 1.11 | 0.64 |
| 89 | nd | nd | nd | 1.00 | nd | nd |
| 90 | 1.00 | 0.94 | 0.73 | 0.84 | 1.14 | nd |
| 91 | 1.43 | 1.00 | 1.38 | 1.32 | 1.23 | 0.93 |
| 92 | 0.61 | 1.28 | 0.91 | 1.26 | 0.98 | 1.00 |
| 93 | 0.84 | 1.40 | 1.00 | 0.86 | 0.94 | 1.35 |
| 94 | 1.18 | 0.87 | 1.05 | 0.82 | 1.00 | nd |
| 95 | nd | nd | nd | 1.00 | nd | nd |
| 96 | nd | nd | nd | 0.74 | nd | nd |
| 127 | nd | nd | nd | nd | nd | nd |
| 128 | nd | nd | nd | nd | nd | nd |
| 129 | nd | nd | nd | nd | nd | nd |
| Mean | 1.07 | 1.13 | 1.04 | 1.02 | 1.12 | 0.97 |
| SEM | 0.15 | 0.08 | 0.08 | 0.07 | 0.07 | 0.11 |

TABLE 9.18-continued

Individual data used for Table 18

| Rat # | COX-2 (AU) | Osteopontin (AU) | MCP1 (AU) | TGF-β (AU) | ICAM (AU) | VCAM (AU) |
|---|---|---|---|---|---|---|
| Aldosterone + salt | | | | | | |
| 98 | nd | nd | nd | 1.26 | nd | nd |
| 99 | 7.39 | 8.14 | 2.42 | 1.85 | 1.16 | 0.89 |
| 100 | 1.83 | 1.02 | 1.87 | 0.55 | 1.18 | 0.69 |
| 101 | 5.80 | 6.19 | 4.59 | 1.91 | 1.75 | 0.84 |
| 102 | 2.59 | 4.06 | 3.19 | 1.49 | 1.15 | 0.72 |
| 103 | 6.63 | 12.04 | 3.34 | 1.18 | 1.91 | 2.23 |
| 104 | 4.18 | 2.35 | 1.91 | 1.32 | 1.19 | 1.03 |
| 105 | 3.71 | 8.25 | 2.50 | 1.27 | 1.82 | 1.65 |
| 106 | 2.62 | 10.41 | 2.22 | 0.56 | 1.57 | 1.24 |
| 130 | nd | nd | nd | nd | nd | nd |
| 131 | nd | nd | nd | nd | nd | nd |
| 132 | nd | nd | nd | nd | nd | nd |
| Mean | 4.34 | 6.56 | 2.76 | 1.27 | 1.47 | 1.16 |
| SEM | 0.72 | 1.37 | 0.32 | 0.16 | 0.12 | 0.19 |
| 97* | 23.34 | 81.29 | 5.88 | 1.29 | 1.84 | 1.75 |
| Eplerenone + aldosterone + salt | | | | | | |
| 133 | 1.56 | 4.03 | 1.78 | 0.58 | 1.20 | 0.54 |
| 134 | 1.04 | 1.00 | 1.37 | 0.62 | 1.36 | 0.66 |
| 135 | 0.70 | 0.77 | 1.27 | 1.04 | 0.95 | 0.61 |
| 136 | 1.41 | 8.43 | 1.75 | 1.42 | 1.26 | 0.61 |
| 137 | 3.78 | 1.59 | 1.60 | 1.29 | 1.56 | 0.67 |
| 138 | 1.86 | 3.97 | 1.24 | 1.49 | 0.98 | 0.86 |
| 139 | 6.19 | 3.93 | 1.92 | 0.71 | 1.51 | 1.21 |
| 140 | 1.87 | 2.13 | 1.24 | 1.21 | 0.79 | 1.00 |
| 141 | 0.99 | 0.72 | 1.89 | 1.44 | 0.98 | 0.68 |
| 142 | 1.92 | 4.76 | 2.21 | 1.69 | 1.72 | 1.60 |
| 143 | 0.86 | 0.99 | 1.20 | 2.41 | 0.83 | 0.68 |
| Mean | 2.02 | 2.94 | 1.59 | 1.26 | 1.19 | 0.83 |
| SEM | 0.49 | 0.72 | 0.10 | 0.16 | 0.09 | 0.10 | nd = No data were reported due to insufficient mRNA sample.
*Data from this animal were not considered for statistical analysis and not included in the final results.

TABLE 2.19

Individual data used for Table 19

| Rat # | COX-2 (AU) | Osteopontin (AU) | MCP1 (AU) | TGF-β (AU) | ICAM (AU) | VCAM (AU) |
|---|---|---|---|---|---|---|
| Control: vehicle + salt | | | | | | |
| 1 | 1.15 | 0.81 | 2.39 | 0.53 | 1.01 | 0.96 |
| 2 | 1.75 | 1.46 | 1.79 | 0.52 | 2.29 | 1.93 |
| 4 | 0.96 | 0.57 | 1.00 | 1.00 | 0.99 | nd |
| 6 | 0.95 | 0.82 | 0.81 | 1.19 | 1.60 | 1.38 |
| 7 | 0.86 | 1.13 | 0.52 | 1.00 | nd | nd |
| 8 | 1.07 | 1.16 | 0.53 | 1.68 | 0.55 | 0.45 |
| 9 | 1.00 | 1.00 | 1.52 | 0.90 | 0.96 | 1.00 |
| 10 | nd | nd | nd | 1.24 | nd | nd |
| Mean | 1.11 | 0.99 | 1.22 | 1.01 | 1.23 | 1.14 |
| SEM | 0.11 | 0.11 | 0.27 | 0.13 | 0.25 | 0.25 |
| Aldosterone + salt | | | | | | |
| 11 | nd | nd | nd | 1.41 | nd | nd |
| 12 | 4.26 | 13.13 | 3.94 | 1.27 | nd | nd |
| 13 | 4.81 | 11.43 | 7.19 | 2.11 | 2.67 | 3.48 |
| 14 | nd | nd | nd | 1.20 | nd | nd |
| 15 | 1.54 | 13.78 | 1.61 | 1.95 | 1.63 | 1.87 |
| 16 | nd | nd | nd | 1.49 | nd | nd |
| 18 | 3.10 | 7.97 | 9.35 | 0.83 | 1.69 | 2.99 |
| 19 | 5.28 | 18.44 | 2.30 | 0.54 | 1.50 | 1.64 |
| 20 | 8.20 | 14.88 | 2.86 | 1.21 | 1.54 | 0.72 |
| Mean | 4.53 | 13.27 | 4.54 | 1.33 | 1.81 | 2.14 |
| SEM | 0.92 | 1.43 | 1.25 | 0.16 | 0.22 | 0.49 |

TABLE 2.19-continued

Individual data used for Table 19

| Rat # | COX-2 (AU) | Osteopontin (AU) | MCP1 (AU) | TGF-β (AU) | ICAM (AU) | VCAM (AU) |
|---|---|---|---|---|---|---|
| Eplerenone + aldosterone + salt | | | | | | |
| 21 | 2.44 | 1.53 | 2.11 | 1.00 | 1.54 | 1.42 |
| 22 | 0.55 | 3.28 | 1.70 | 1.49 | 2.06 | 1.29 |
| 23 | 1.97 | 1.98 | 2.21 | 1.40 | 1.01 | 1.49 |
| 25 | 3.41 | 8.91 | 1.38 | 1.31 | 1.21 | 1.27 |
| 26 | 3.71 | 1.88 | 2.10 | 0.96 | 1.26 | 0.79 |
| 27 | 3.04 | 1.97 | 2.02 | 1.93 | 1.06 | 0.52 |
| 28 | 2.11 | 1.28 | 1.43 | 1.54 | 0.60 | 0.57 |
| 29 | 1.34 | 1.43 | 5.58 | 1.32 | 0.99 | 0.61 |
| 30 | 1.92 | 1.01 | 2.11 | 0.89 | nd | 1.42 |
| Mean | 2.28 | 2.59 | 2.29 | 1.32 | 1.22 | 1.04 |
| SEM | 0.33 | 0.82 | 0.42 | 0.11 | 0.15 | 0.14 |
| 24* | 12.21 | 54.57 | 8.14 | 1.35 | 2.92 | 4.01 | nd = No data were reported due to insufficient mRNA sample.
*Data from this animal were not considered for statistical analysis and not included in the final results Results Blood Pressure Blood pressure remained normal in vehicle+salt controls throughout the experiment (Table 10). Aldosterone+salt induced a progressive increase in blood pressure with time. In animals receiving eplerenone+aldosterone+salt, systolic blood pressure was significantly reduced at days 8–30. However, blood pressure remained elevated compared to vehicle+salt controls.

TABLE 10

Effects of aldosterone + salt treatment alone or in combination with eplerenone on blood pressure over time
Systolic Blood Pressure (mmHg)

| Day | Vehicle + salt | n | Aldosterone + salt | n | Eplerenone + aldosterone + salt | n |
|---|---|---|---|---|---|---|
| 3 | 122 ± 3 | 4 | 132 ± 6 | 8 | 126 ± 1 | 9 |
| 4 | 123 ± 1 | 4 | 133 ± 4* | 8 | 130 ± 2* | 9 |
| 5 | 125 ± 1 | 4 | 137 ± 4* | 8 | 132 ± 2* | 9 |
| 6 | 130 ± 1 | 4 | 148 ± 5* | 8 | 139 ± 3* | 9 |
| 7 | 132 ± 1 | 4 | 155 ± 5* | 8 | 143 ± 3* | 9 |
| 8 | 132 ± 1 | 4 | 156 ± 4* | 8 | 142 ± 3*# | 9 |
| 9 | 131 ± 1 | 4 | 164 ± 5* | 8 | 142 ± 3*# | 9 |
| 10 | 127 ± 2 | 7 | 168 ± 6* | 8 | 142 ± 2*# | 9 |
| 11 | 128 ± 2 | 7 | 171 ± 6* | 8 | 143 ± 3*# | 9 |
| 12 | 129 ± 2 | 7 | 178 ± 6* | 8 | 145 ± 3*# | 9 |
| 13 | 128 ± 3 | 7 | 182 ± 6* | 8 | 147 ± 3*# | 9 |
| 14 | 131 ± 4 | 7 | 182 ± 6* | 9 | 150 ± 4*# | 9 |
| 15 | 130 ± 2 | 7 | 181 ± 5* | 9 | 148 ± 4*# | 9 |
| 16 | 129 ± 2 | 7 | 187 ± 6* | 9 | 150 ± 4*# | 9 |
| 17 | 130 ± 2 | 7 | 195 ± 7* | 9 | 154 ± 5*# | 9 |
| 18 | 131 ± 3 | 7 | 196 ± 6* | 9 | 157 ± 5*# | 9 |
| 19 | 127 ± 2 | 7 | 200 ± 6* | 9 | 160 ± 5*# | 9 |
| 20 | 126 ± 3 | 7 | 203 ± 5* | 9 | 160 ± 5*# | 9 |
| 21 | 127 ± 2 | 7 | 208 ± 4* | 9 | 165 ± 6*# | 9 |
| 22 | 128 ± 1 | 7 | 209 ± 4* | 9 | 167 ± 6*# | 9 |
| 23 | 131 ± 2 | 7 | 208 ± 4* | 9 | 172 ± 6*# | 9 |
| 24 | 132 ± 2 | 7 | 210 ± 3* | 9 | 174 ± 6*# | 9 |
| 25 | 130 ± 2 | 7 | 210 ± 4* | 9 | 176 ± 6*# | 9 |
| 26 | 131 ± 2 | 7 | 210 ± 3* | 9 | 180 ± 7*# | 9 |

These data are expressed graphically in FIG. 1.
Values are mean ± SEM of values obtained every 5 min over 24-hour period.
*Significantly different from vehicle + salt, p < 0.05.
Significantly different from aldosterone + salt, p < 0.05.

Body weight, Myocardial Hypertrophy and ANP

Body weights were significantly lower in animals receiving aldosterone+salt treatment at days 7, 14, and 30 compared to vehicle+salt normotensive controls (Tables 11–13). The decrease in body weight induced by aldosterone+salt treatment was significantly attenuated by administration of eplerenone at day 30 (Table 11). Significant left and right ventricular hypertrophy occurred in response to aldosterone+salt treatment. Left ventricular hypertrophy was evident after 7 days of aldosterone+salt treatment (Table 11) whereas right ventricular hypertrophy was only evident after 30 days of aldosterone+salt treatment (Table 13). Eplerenone did not impact absolute ventricular weights or ventricular weight to tibia length ratios induced by aldosterone+salt treatment (Tables 11–13). Significant elevations in atrial natiuretic peptide (ANP) mRNA levels were also observed in animals treated with aldosterone+salt (Tables 11–13). The ANP mRNA upregulation was significantly reduced by eplerenone after 30 days of treatment but not after 14 days (Table 13).

TABLE 11

Effects of aldosterone + salt treatment alone or in combination with eplerenone in rats after 7 days of treatment

| Group | Final Body Weight (g) | Left Ventricle Weight (mg) | Right Ventricle Weight (mg) | Tibia Length (cm) | Left Ventricle Weight/ Tibia Length (mg/mm) | Right Ventricle Weight/ Tibia Length (mg/mm) | ANP mRNA (AU) |
|---|---|---|---|---|---|---|---|
| Vehicle + salt | 271 ± 5 (n = 10) | 667 ± 19 (n = 10) | 178 ± 5 (n = 10) | 3.8 ± 0.01 (n = 10) | 175 ± 5 (n = 10) | 47 ± 1 (n = 10) | 1.49 ± 0.38 (n = 10) |
| Aldosterone + salt | 277 ± 5 (n = 7) | 736 ± 25* (n = 8) | 183 ± 7 (n = 8) | 3.8 ± 0.03 (n = 8) | 194 ± 6* (n = 8) | 48 ± 2 (n = 8) | 8.72 ± 1.51* (n = 8) |
| Eplerenone + aldosterone + salt | 287 ± 4* (n = 9) | 714 ± 20 (n = 10) | 182 ± 5 (n = 10) | 3.8 ± 0.01 (n = 10) | 188 ± 5 (n = 10) | 48 ± 1 (n = 10) | 2.77 ± 0.49*# (n = 10) |

Values are mean ± SEM measured after 7 days of treatment.
*Significantly different from vehicle + salt control, p < 0.05.
Significantly different from aldosterone + salt, p < 0.05.
Eplerenone dose was 100 mg/kg/day.
ANP = atrial natiuretic peptide.
AU = arbitrary units, measured relative to cyclophilin expression.

TABLE 12

Effects of aldosterone + salt treatment alone or in combination with eplerenone in rats after 14 days of treatment

| Group | Final Body Weight (g) | Left Ventricle Weight (mg) | Right Ventricle Weight (mg) | Tibia Length (cm) | Left Ventricle Weight/ Tibia Length (mg/mm) | Right Ventricle Weight/ Tibia Length (mg/mm) | ANP mRNA (AU) |
|---|---|---|---|---|---|---|---|
| Vehicle + salt | 311 ± 5 (n = 12) | 748 ± 25 (n = 13) | 198 ± 10 (n = 13) | 3.8 ± 0.01 (n = 13) | 195 ± 4 (n = 13) | 52 ± 3 (n = 13) | 1.76 ± 0.66 (n = 10) |
| Aldosterone + salt | 270 ± 11* (n = 12) | 817 ± 22* (n = 12) | 189 ± 5 (n = 12) | 3.8 ± 0.02 (n = 12) | 214 ± 5* (n = 12) | 50 ± 1 (n = 12) | 6.70 ± 1.59* (n = 9) |
| Eplerenone + aldosterone + salt | 283 ± 6* (n = 11) | 813 ± 22* (n = 11) | 197 ± 19 (n = 11) | 3.8 ± 0.02 (n = 11) | 214 ± 6* (n = 11) | 52 ± 5 (n = 11) | 6.64 ± 2.22* (n = 10) |

Values are mean ± SEM measured after 14 days of treatment.
*Significantly different from vehicle + salt, p < 0.05.
Eplerenone dose was 100 mg/kg/day.
ANP = atrial natiuretic peptide.
AU = arbitrary units, measured relative to cyclophilin expression.

TABLE 13

Effects of aldosterone + salt treatment alone or in combination with eplerenone in rats after 30 days of treatment

| Group | Final Body Weight (g) | Left Ventricle Weight (mg) | Right Ventricle Weight (mg) | Tibia Length (cm) | Left Ventricle Weight/ Tibia Length (mg/mm) | Right Ventricle Weight/ Tibia Length (mg/mm) | ANP mRNA (AU) |
|---|---|---|---|---|---|---|---|
| Vehicle + salt (n = 8) | 314 ± 8 | 700 ± 25 | 167 ± 6 | 4.1 ± 0.03 | 172 ± 5 | 41 ± 1 | 0.74 ± 0.23 |
| Aldosterone + salt (n = 9) | 272 ± 10* | 910 ± 29* | 192 ± 8* | 3.9 ± 0.02* | 233 ± 7* | 49 ± 2* | 20.17 ± 3.36* |
| Eplerenone + aldosterone + salt (n = 9) | 331 ± 7# | 936 ± 34* | 198 ± 6* | 3.9 ± 0.00* | 240 ± 9* | 51 ± 2* | 9.20 ± 2.44*# |

Values are mean ± SEM measured after 30 days of treatment.
*Significantly different from vehicle + salt, $p < 0.05$.
Significantly different from aldosterone + salt, $p < 0.05$.
Eplerenone dose was 100 mg/kg/day.
ANP = atrial natiuretic peptide.
AU = arbitrary units, measured relative to cyclophilin expression.

Myocardial Fibrosis

Interstitial collagen volume fraction and hydroxyproline levels were not statistically different at any time point among the experimental groups (Tables 14–16). A modest increase in collagen type-I message was detected in aldosterone+salt and aldosterone+eplerenone+salt treatment at 30 days, compared to vehicle+salt controls (Table 16). Collagen type III mRNA levels were not significantly increased at any time point (Tables 14–16).

TABLE 14

Effects of aldosterone + salt treatment alone or in combination with eplerenone on myocardial injury and fibrosis in rats after 7 days of treatment

| Group | Myocardial Necrosis (0–4) | ICVF (%) | Hydroxyproline (μg/mg) | Collagen-I (AU) | Collagen-III (AU) |
|---|---|---|---|---|---|
| Vehicle + salt | 0.0 ± 0.0 (n = 10) | 4.4 ± 0.5 (n = 10) | 3.57 ± 0.45 (n = 10) | 1.10 ± 0.15 (n = 10) | 1.09 ± 0.13 (n = 10) |
| Aldosterone + salt | 0.0 ± 0.0 (n = 8) | 5.6 ± 0.6 (n = 6) | 2.73 ± 0.34 (n = 8) | 1.36 ± 0.14 (n = 8) | 1.42 ± 0.12 (n = 8) |
| Eplerenone + aldosterone + salt | 0.0 ± 0.0 (n = 10) | 5.4 ± 0.6 (n = 10) | 3.06 ± 0.36 (n = 10) | 0.85 ± 0.15 (n = 10) | 1.09 ± 0.21 (n = 10) |

Values are mean ± SEM measured after 7 days of treatment.
Eplerenone dose was 100 mg/kg/day.
ICVF = interstitial collagen volume fraction.
Collagen-I = Collagen type I mRNA.
Collagen-III = Collagen type III mRNA.
AU = arbitrary units, measured relative to cyclophilin expression.

TABLE 15

Effects of aldosterone + salt treatment alone or in combination with eplerenone on myocardial injury and fibrosis in rats after 14 days of treatment

| Group | Myocardial Necrosis (0–4) | ICVF (%) | Hydroxyproline (μg/mg) | Collagen-I (AU) | Collagen-III (AU) |
|---|---|---|---|---|---|
| Vehicle + salt | 0.0 ± 0.0 (n = 13) | 4.7 ± 0.4 (n = 13) | 3.26 ± 0.24 (n = 13) | 1.08 ± 0.10 (n = 10) | 1.01 ± 0.10 (n = 10) |
| Aldosterone + salt | 0.8 ± 0.3 (n = 12) | 5.1 ±0.5 (n = 12) | 4.04 ± 0.40 (n = 12) | 1.33 ± 0.24 (n = 9) | 1.08 ± 0.14 (n = 9) |
| Eplerenone + aldosterone + salt | 0.5 ± 0.2 (n = 11) | 4.5 ± 0.3 (n = 11) | 4.46 ± 0.50 (n = 11) | 1.39 ± 0.21 (n = 11) | 1.61 ± 0.26 (n = 11) |

Values are mean ± SEM measured after 14 days of treatment.
Eplerenone dose was 100 mg/kg/day.
ICVF = interstitial collagen volume fraction.
Collagen-I = collagen type I mRNA.
Collagen-III = collagen type III mRNA.
AU = arbitrary units, measured relative to cyclophilin expression.

TABLE 16

Effects of aldosterone + salt treatment alone or in combination with eplerenone on myocardial injury and fibrosis in rats after 30 days of treatment

| Group | Myocardial Necrosis (0–4) | ICVF (%) | Hydroxyproline (μg/mg) | Collagen-I (AU) | Collagen-III (AU) |
|---|---|---|---|---|---|
| Vehicle + salt (n = 8) | 0.0 ± 0.0 | 6.2 ± 0.5 | 3.98 ± 0.65 | 1.09 ± 0.13 | 0.91 ± 0.12 |

TABLE 16-continued

Effects of aldosterone + salt treatment alone or in combination with eplerenone on myocardial injury and fibrosis in rats after 30 days of treatment

| Group | Myocardial Necrosis (0–4) | ICVF (%) | Hydroxyproline (μg/mg) | Collagen-I (AU) | Collagen-III (AU) |
|---|---|---|---|---|---|
| Aldosterone + salt (n = 9) | 2.0 ± 0.4* | 7.9 ± 1.0 | 4.39 ± 0.62 | 2.29 ± 0.47* | 1.39 ± 0.20 |
| Eplerenone + Aldosterone + salt (n = 9) | 0.0 ± 0.0# | 6.2 ± 0.5 | 4.10 ± 0.53 | 2.53 ± 0.20* | 1.53 ± 0.23 |

Data are mean ± SEM measured after 30 days of treatment.
*Significantly different from vehicle, $p < 0.05$.
Significantly different from aldosterone + salt, $p < 0.05$.
Eplerenone dose was 100 mg/kg/day.
ICVF = interstitial collagen volume fraction
Collagen-I = collagen type I mRNA.
Collagen-III = collagen type III mRNA.
AU = arbitrary units, measured relative to cyclophilin expression.

Myocardial Histopathology

Figure 44:
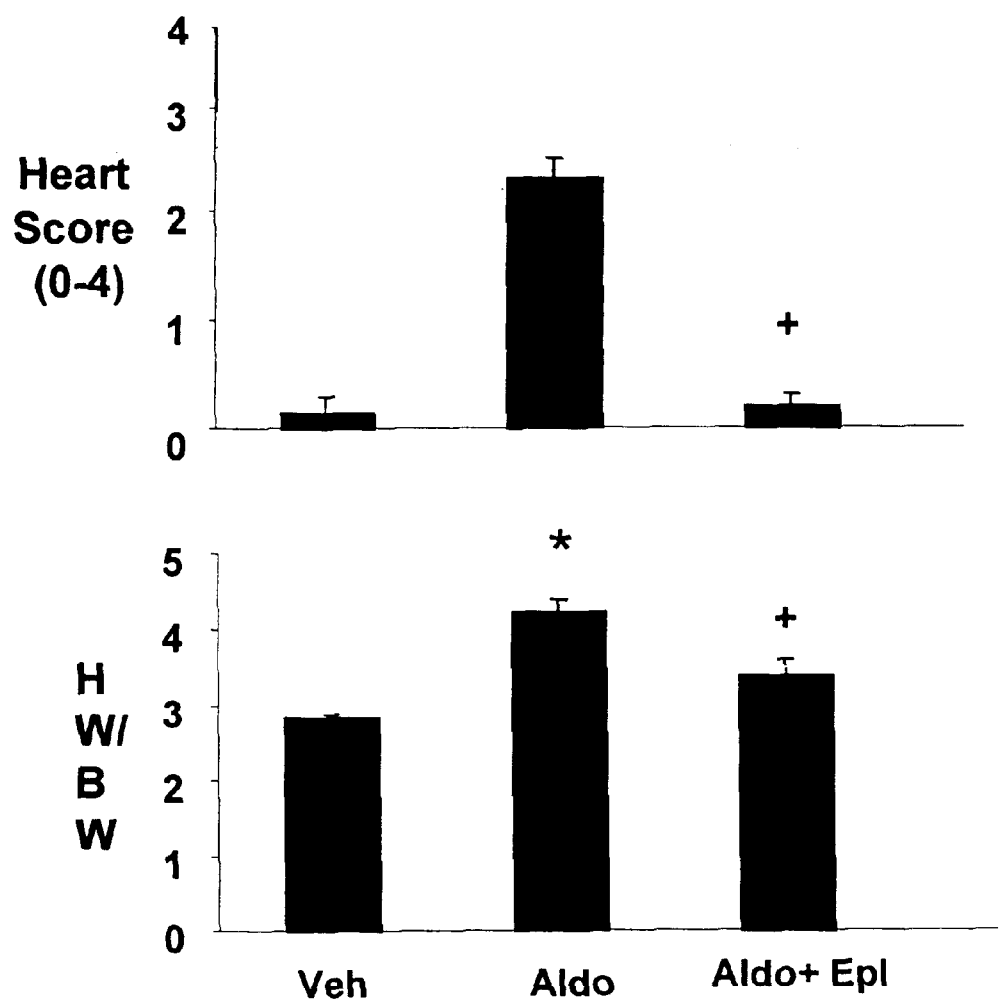
FIG. 44 shows myocardial histopathology scores at 28 days for control rats, for rats infused with aldosterone, and for rats infused with aldosterone and treated with eplerenone, and the ratio of heart weight to body weight for rats infused with aldosterone, and for rats infused with aldosterone and treated with eplerenone.

Myocardial tissue damage was evaluated after 7, 14, and 30 days of treatment using a semi-quantitative scoring system. Hearts from vehicle+salt controls were histologically normal at all timepoints. No vascular or myocardial lesions were identified in hearts from rats receiving aldosterone+salt after 7 days of treatment (Table 14). In contrast, focal arterial and myocardial alterations were observed starting at 14 days of treatment (Tables 15 and 16). Qualitative changes in the arteries and myocardium were similar after 14 days and 30 days of aldosterone+salt treatment, but the frequency and severity increased with time. Administration of eplerenone markedly attenuated myocardial injury at all time points (Tables 14–16; FIG. 44).

Gene Expression of Inflammatory Mediators

The expression levels of multiple proinflammatory molecules were assessed using quantitative Taqman PCR analysis (Tables 17–19). Expression levels of cyclooxygenase-2 (COX-2) and monocyte chemoattractant protein-1 (MCP-1) were similarly and significantly increased by aldosterone+salt treatment at all time points. Osteopontin expression was also markedly upregulated after 14 days (~6-fold) and 30 days (~13-fold) of aldosterone+salt treatment (Tables 18–19). Transforming growth factor beta one (TGF-$\beta_1$. mRNA levels were not upregulated at any of the time points examined. Intracellular adhesion molecule-1 (ICAM-1) mRNA expression was upregulated at day 14 and 30 of aldosterone+salt treatment, although increases were modest (Tables 9–10). Gene expression for vascular cell adhesion molecule-1 (VCAM-1) was increased two-fold at day 30 of aldosterone+salt treatment, however this increase did not reach statistical significance (Table 19). Expression of all marker genes was significantly reduced by eplerenone compared to gene expression in animals treated with aldosterone+salt.

TABLE 17

Effects of aldosterone + salt treatment alone or in combination with eplerenone on the relative mRNA expression of the inflammatory markers in rats after 7 days of treatment

| Group | COX-2 mRNA (AU) | Osteopontin mRNA (AU) | MCP-1 mRNA (AU) | TGF-β1 mRNA (AU) | ICAM mRNA (AU) | VCAM mRNA (AU) |
|---|---|---|---|---|---|---|
| Vehicle + salt | 1.06 ± 0.18 (n = 6) | 1.12 ± 0.16 (n = 5) | 1.07 ± 0.17 (n = 5) | 0.98 ± 0.12 (n = 10) | 1.02 ± 0.12 (n = 5) | 0.96 ± 0.14 (n = 5) |
| Aldosterone + salt | 2.22 ± 0.29* (n = 8) | 1.91 ± 0.51 (n = 8) | 2.38 ± 0.17* (n = 8) | 1.35 ± 0.09 (n = 8) | 1.22 ± 0.10 (n = 8) | 1.55 ± 0.39 (n = 8) |
| Eplerenone + aldosterone + salt | 1.25 ± .27# (n = 8) | 0.75 ± 0.12 (n = 8) | 1.56 ± 0.25# (n = 8) | 0.99 ± 0.12 (n = 10) | 0.83 ± 0.10 (n = 7) | 0.56 ± 0.08 (n = 6) |

Values are mRNA expression means in arbitrary units ± SEM after 7 days of treatment (relative to cyclophilin expression)
*Significantly different from vehicle + salt, $p < 0.05$.
Significantly different from aldosterone + salt, $p < 0.05$.
Eplerenone dose was 100 mg/kg/day.
COX-2 = cyclooxygenase-2.
MCP-1 = monocyte chemoattractant protein-1.
TGF-1 = transforming growth factor beta 1.
ICAM = intracellular adhesion molecule-1.
VCAM = vascular cell adhesion molecule-1.

TABLE 18

Effects of aldosterone + salt treatment alone or in combination with eplerenone on the relative mRNA expression of the inflammatory markers in rats after 14 days of treatment

| Group | COX-2 mRNA (AU) | Osteopontin mRNA (AU) | MCP-1 mRNA (AU) | TGF-β1 mRNA (AU) | ICAM mRNA (AU) | VCAM mRNA (AU) |
|---|---|---|---|---|---|---|
| Vehicle + salt | 1.07 ± 0.15 (n = 7) | 1.13 ± 0.08 (n = 7) | 1.04 ± 0.08 (n = 7) | 1.02 ± 0.07 (n = 10) | 1.12 ± 0.07 (n = 7) | 0.97 ± 0.11 (n = 5) |
| Aldosterone + salt | 4.34 ± 0.72* (n = 8) | 6.56 ± 1.37* (n = 8) | 2.76 ± 0.32* (n = 8) | 1.27 ± 0.16 (n = 9) | 1.47 ± 0.12* (n = 8) | 1.16 ± 0.19 (n = 8) |
| Eplerenone + aldosterone + salt | 2.02 ± 0.49*# (n = 11) | 2.94 ± 0.72#* (n = 11) | 1.59 ± 0.10*# (n = 11) | 1.26 ± 0.16 (n = 11) | 1.19 ± 0.09* (n = 11) | 0.83 ± 0.10 (n = 11 |

Values are mRNA expression means in arbitrary units ± SEM after 14 days of treatment (relative to cyclophilin expression)
*Significantly different from vehicle + salt, $p < 0.05$.
Significantly different from aldosterone + salt, $p < 0.05$.
Eplerenone dose was 100 mg/kg/day.
COX-2 = cyclooxygenase-2.
MCP-1 = monocyte chemoattractant protein-1.
TGF-1 = transforming growth factor beta 1.
ICAM = intracellular adhesion molecule-1.
VCAM = vascular cell adhesion molecule-1.

TABLE 19

Effects of aldosterone + salt treatment alone or in combination with eplerenone on the relative mRNA expression of the inflammatory markers in rats after 30 days of treatment

| Group | COX-2 mRNA (AU) | Osteopontin mRNA (AU) | MCP-1 mRNA (AU) | TGF-β1 mRNA (AU) | ICAM mRNA (AU) | VCAM mRNA (AU) |
|---|---|---|---|---|---|---|
| Vehicle + salt | 1.11 ± 0.11 (n = 7) | 0.99 ± 0.11 (n = 7) | 1.22 ± 0.27 (n = 7) | 1.01 ± 0.13 (n = 8) | 1.23 ± 0.25 (n = 6) | 1.14 ± 0.25 (n = 5) |
| Aldosterone + salt | 4.53 ± 0.92* (n = 6) | 13.27 ± 1.43* (n = 6) | 4.54 ± 1.25* (n = 6) | 1.33 ± 0.16 (n = 9) | 1.81 ± 0.22* (n = 5) | 2.14 ± 0.49 (n = 5) |
| Eplerenone + aldosterone + salt | 2.28 ± 0.33*# (n = 9) | 2.59 ± 0.82*# (n = 9) | 2.29 ± 0.42*# (n = 9) | 1.32 ± 0.11 (n = 9) | 1.22 ± 0.15# (n = 8) | 1.04 ± 0.14# (n = 9) |

Values are mRNA expression means in arbitrary units ± SEM after 30 days of treatment (relative to cyclophilin expression)
*Significantly different from vehicle + salt, $p < 0.05$.
Significantly different from aldosterone + salt, $p < 0.05$.
Eplerenone dose was 100 mg/kg/day.
COX-2 = cyclooxygenase-2.
MCP-1 = monocyte chemoattractant protein-1.
TGF-1 = transforming growth factor beta 1.
ICAM = intracellular adhesion molecule-1.
VCAM = vascular cell adhesion molecule-1.

Immunohistochemistry

The molecular analysis of the aldosterone+salt-induced proinflammatory response was further characterized using immunohistochemical analysis. The majority of cells adhering to the endothelium and infiltrating the perivascular space stained positive for a monocyte/macrophage antibody (ED-1) and negative for a T-cell antibody (CD-3). Significant expression of osteopontin was evident in hearts from aldosterone+salt treated rats, compared with the absence of osteopontin staining in hearts from vehicle+salt controls. Osteopontin expression was primarily localized to medial cells of affected and some unaffected coronary arteries, but was also present in some macrophages in the perivascular space and areas of myocardial necrosis. No evidence of significant osteopontin expression was found in cardiomyocytes. ICAM-1 staining was identified in endothelial cells and in the perivascular space; however, VCAM-1 was primarily expressed in endothelial cells. Administration of eplerenone markedly blunted the aldosterone+salt treatment induced staining in myocardial tissue for all marker proteins evaluated.

In-situ Hybridization for Osteopontin mRNA

In-situ hybridization was performed to localize osteopontin expression in myocardial tissue. The majority of osteopontin mRNA was found in the medial cells of coronary arteries (FIG. 3); however, osteopontin message was also identified in perivascular cells and cells infiltrating ischemic and necrotic areas. Osteopontin mRNA was not evident in cardiomyocytes or in unaffected interstitial areas.

CONCLUSION

Treatment of rats with aldosterone in the presence of salt induced vascular inflammation and cardiac tissue damage. This damage induced by aldosterone+salt treatment was preceded by an inflammatory response that was characterized by the upregulation of proinflammatory molecules. Eplerenone markedly attenuated this initial vascular inflammatory response and subsequent myocardial injury.

Renal Hypertensive Rat Model

A combination therapy of an aldosterone inhibitor and a cyclooxygenase-2 selective inhibitor may be evaluated for blood pressure lowering activity in the renal-artery ligated hypertensive rat, a model of high renin hypertension. In this model, six days after litigation of the left renal artery, both plasma renin activity and blood pressure are elevated significantly (J. L. Cangiano et al, *J. Pharmacol. Exp. Ther.*, 206, 310–313 (1979)). Male Sprague-Dawley rats are instrumented with a radiotelemetry blood pressure transmitter for continuous monitoring of blood pressure. The rats are anesthetized with a mixture of ketamine-HCl (100 mg/kg) and acepromazine maleate (2.2 mg/kg). The abdominal aorta is exposed via a midline incision. Microvascular clamps are placed on the aorta distal to the renal arteries and the iliac bifurcation. The aorta is punctured with a 22-gauge needle and the tip of a catheter is introduced. The catheter, which is held in place by a ligature in the psoas muscle, is connected to a radiotelemetry blood pressure transmitter (Mini-Mitter Co., Inc., Sunriver, Oreg.). The transmitter is placed in the peritoneal cavity and sutured to abdominal muscle upon closing of the incision. Rats are housed singly above a radiotelemetry receiver and are allowed standard rat cho and water ad libitum. At least five days are allowed for recovery from surgery. Mean arterial pressure and heart rate are measured on a data recorder as is appropriate, such as a mini-computer. Data Data are sampled for 10 seconds at 200–500 Hz at 2.5 to 10 min intervals 24 hours per day. After collecting control data for 24 hours, the rats are anesthetized with methohexital (30 mg/kg, i.p.) and supplemented as needed. A midline abdominal incision is made, approximately 2 cm in length to expose the left kidney. The renal artery is separated from the vein near the aorta, with care taken not to tramatize the vein. The artery is completely ligated with sterile 4-O silk. The incision is closed by careful suturing of the muscle layer and skin. Six days later, when MAP is typically elevated by 50–70 mmHg, an aldosterone antagonist or a combination with one or more Cyclooxygenase-2 selective inhibitors are administerd by gavage each day for about 8 weeks. Single drug dosing is carried out using 20 and 200 mg/kg/day of the aldosterone inhibitor (for example, eplerenone) and 1, 3, 10, 30, and 100 mg/kg/day of the cycloogenase-2 selective inhibitor. Drug mixtures are obtained by administering a combination of a dose of 1, 3, 10, 30, or 100 mg/kg/day of the cycloogenase-2 selective inhibitor with a dose of either 20 or 200 mg/kg/day of the aldosterone inhibitor. Blood pressure lowering is monitored by the radiotelemetry system and responses with the compounds are compared to a response obtained in vehicle-treated animals. Plasma and urinary sodium and potassium levels are monitored as a measure of the effectiveness of the aldosterone blockade. Urine samples are collected overnight using metabolic cages to isolate the samples. Plasma samples are obtained by venous catheterization. Sodium and potassium are measured by flame photometry. Cardic fibrosis is determined by histological and chemical measurements of the excised hearts following perfusion fixation. Left and right ventricles are weighed, embedded, and sectioned. Subsequently, sections are stained with picrosirius red and the red staining collagen areas are quantitated by computerized image analysis. The apex of the heart is acid digested and the free hydroxyproline measured colorimetrically. It is expected that MAP will be significantly lowered toward normal pressures in the test animals, treated with the combination therapy and that the condition of myocardial fibrosis will be arrested or avoided.

Several other animal models are available which are appropriate for evaluation of prevention of cardiovascular conditions including the prevention of atherosclerosis. See Stehbens, *Prog. Card. Dis.*, XXIX, 1007–28 (1986) and Zhang et al., *Science*, 258, 468–71 (1992).

An APOe mouse model for atherosclerosis has been described by Roselear et al. (Arterioscle. *Thromb. Vasc. Biol.*, 16, 1013–18 (1996)). The aldosterone blocker should be active in preventing atherosclerotic lesions.

Although this invention has been described with respect to specific embodiments, the details of these embodiments are not to be construed as limitations.

All patent documents referenced herein are incorporated by reference.

What is claimed is:

1. A method for preventing or treating an inflammation-related cardiovascular disorder in a subject in need thereof, which method comprises treating the subject with a therapeutically effective amount of an aldosterone antagonist and cyclooxygenase-2 inhibitor combination or pharmaceutically-acceptable salts thereof.

2. The method of claim 1 wherein the cardiovascular disorder is selected from coronary artery disease, aneurysm, arteriosclerosis, atherosclerosis, myocardial infarction, embolism, stroke, thrombosis, angina, vascular plaque inflammation, vascular plaque rupture, Kawasaki disease, calcification and inflammation.

3. The method of claim 2 wherein said calcification is selected from the group consisting of vascular calcification and valvar calcification.

4. The method of claim 2 wherein said inflammation is selected from the group consisting of trauma-induced inflammation, surgically-induced inflammation, bacterial-induced inflammation and viral induced inflammation.

5. The method of claim 2 wherein the cardiovascular disorder is atherosclerosis.

6. The method of claim 2 wherein the cardiovascular disorder is thrombosis.

7. The method of claim 2 wherein the cardiovascular disorder occurs, in whole or in part, in the brain.

8. The method of claim 2 wherein the cardiovascular disorder occurs, in whole or in-part, in the heart.

9. The method of claim 1 wherein said aldosterone antagonist is an aldosterone receptor antagonist.

10. The method of claim 1 wherein said aldosterone antagonist is a spirolactone-type compound.

11. The method of claim 1 wherein said aldosterone antagonist is spironolactone.

12. The method of claim 1 wherein said aldosterone antagonist is an epoxy-steroidal aldosterone antagonist.

13. The method of claim 12 wherein said epoxy-steroidal compound has an epoxy moiety fused to the "C" ring of the steroidal nucleus of a 20-spiroxane compound.

14. The method of claim 13 wherein said 20-spiroxane compound is characterized by the presence of a 9-alpha,11-beta-substituted epoxy moiety.

15. The method of claim 12 wherein said epoxy-steroidal compound is selected from the group consisting of:
Pregn-4-ene-7,21-dicarboxylic acid, 9,11-epoxy-17-hydroxy-3-oxo-,γ-lactone, methyl ester, (7α,11α,17α)-;
Pregn-4-ene-7,21-dicarboxylic acid, 9,11-epoxy-17-hydroxy-3-oxo-dimethyl ester, (7α,11α,17α)-;
3'H-cyclopropa[6,7]pregna-4,6-diene-21-carboxylic acid, 9,11-epoxy-6,7-dihydro-17-hydroxy-3-oxo-, γ-lactone, (6β,7β,11β,17β)-;
Pregn-4-ene-7,21-dicarboxylic acid, 9,11-epoxy-17-hydroxy-3-oxo, 7-(1-methylethyl)ester, monopotassium salt, (7α,11α,17α)-;
Pregn-4-ene-7,21-dicarboxylic acid, 9,11-epoxy-17-hydroxy-3-oxo-, 7-methyl ester, monopotassium salt, (7α,11α,17α)-;
3'H-cyclopropa[6,7]pregna-1,4,6-triene-21-carboxylic acid, 9,11-epoxy-6,7-dihydro-17-hydroxy-3-oxo-, γ-lactone, (6α,7α,11α)-;
3'H-cyclopropa[6,7]pregna-4,6-diene-21-carboxylic acid, 9,11-epoxy-6,7-dihydro-17-hydroxy-3-oxo-, methyl ester, (6α,7α,11α,17α)-;
3'H-cyclopropa[6,7]pregna-4,6-diene-21-carboxylic acid, 9,11-epoxy-6,7-dihydro-17-hydroxy-3-oxo-, monopotassium salt, (6α,7α,11α,17α)-;
3'H-cyclopropa[6,7]pregna-4,6-diene-21-carboxylic acid, 9,11-epoxy-6,7-dihydro-17-hydroxy-3-oxo-, γ-lactone, (6α,7α,11α,17α)-;
Pregn-4-ene-7,21-dicarboxylic acid, 9,11-epoxy-17-hydroxy-3-oxo-, γ-lactone, ethyl ester, (7α,11α,17α)-; and
Pregn-4-ene-7,21-dicarboxylic acid, 9,11-epoxy-17-hydroxy-3-oxo-, γ-lactone, 1-methylethyl ester, (7α, 11α,17α)-.

16. The method of claim 1 wherein said aldosterone antagonist is eplerenone.

17. The method of claim 1 wherein the selective cyclooxygenase-2 inhibiting agent is selected from compounds of Formula 1:

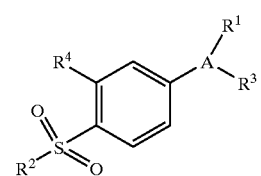

wherein
A is a 5- or 6-member ring substituent selected from partially unsaturated or unsaturated heterocyclo and carboxcyclic rings, wherein A is optionally substituted with one or more radicals selected from the group consisting of alkyl, halo, oxo, and alkoxy;
$R^1$ is selected from the group consisting of cyclohexyl, pyridinyl, and phenyl, wherein cyclohexyl, pyridinyl, or phenyl are optionally substituted with one or more radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, halo, alkoxy, and alkylthio;
$R^2$ is selected from the group consisting of alkyl and amino;
$R^3$ is a radical selected from the group consisting of halo, alkyl, alkenyl, alkynyl, aryl, heteroaryl, oxo, cyano, carboxyl, cyanoalkyl, heterocyclyloxy, alkyloxy, alkylthio, alkylcarbonyl, cycloalkyl, phenyl, haloalkyl, heterocyclo, cycloalkenyl, phenylalkyl, heterocyclylalkyl, alkylthioalkyl, hydroxyalkyl, alkoxycarbonyl, phenylcarbonyl, phenylalkylcarbonyl, phenylalkenyl, alkoxyalkyl, phenylthioalkyl, phenyloxyalkyl, alkoxyphenylalkoxyalkyl, alkoxycarbonylalkyl, aminocarbonyl, aminocarbonylalkyl, alkylaminocarbonyl, N-phenylaminocarbonyl, N-alkyl-N-phenylaminocarbonyl, alkylaminocarbonylalkyl, carboxyalkyl, alkylamino, N-arylamino, N-arylkylamino, N-alkyl-N-arylkylamino, N-alkyl-N- arylamino, aminoalkyl, alkylaminoalkyl, N-phenylaminoalkyl, N-phenylalkylaminoalkyl, N-alkyl-N-phenylalkylaminoalkyl, N-alkyl-N-phenylaminoalkyl, phenyloxy, phenylalkoxy, phenylthio, phenylalkylthio, alkylsulfinyl, alkylsulfonyl, aminosulfonyl, alkylaminosulfonyl, N-phenylaminosulfonyl, phenylsulfonyl, and N-alkyl-N-phenylaminosulfonyl; and $R^4$ is selected from the group consisting of hydrido and halo;

or a pharmaceutically-acceptable salt thereof.

18. The method of claim 17 wherein A is selected from the group consisting of thienyl, oxazolyl, furyl, furanone, pyrrolyl, thiazolyl, imidazolyl, benzofuryl, indenyl, benzithienyl, isoxazolyl, pyrazolyl, cyclopentenyl, cyclopentadienyl, benzindazolyl, cyclopentenone, benzopyranopyrazolyl, phenyl, and pyridyl.

19. The method of claim 18 wherein A is substituted with one or more radicals selected from the group consisting of alkyl, halo, oxo, and alkoxy.

20. The method of claim 19 wherein A is substituted with one or more halo radical.

21. The method of claim 20 wherein the halo is choro.

22. The method of claim 19 wherein A is substituted by one or more alkyl radical.

23. The method of claim 22 wherein the alkyl is methyl.

24. The method of claim 19 wherein A is substituted with one or more oxo moiety.

25. The method of claim 17 wherein A is substituted with one or more alkoxy radical.

26. The method of claim 17 wherein $R^1$ is selected from the group consisting of cyclohexyl, pyridinyl, and phenyl, wherein cyclohexyl, pyridinyl, or phenyl is optionally substituted with one or more radicals selected from $C_{1-2}$ alkyl, $C_{1-2}$ haloalkyl, cyano, carboxyl, $C_{1-2}$ alkoxycarbonyl, hydroxyl, $C_{1-2}$ hydroxyalkyl, $C_{1-2}$ haloalkoxy, amino, $C_{1-2}$ alkylamino, phenylamino, nitro, $C_{1-2}$ alkoxy-$C_{1-2}$-alkyl, $C_{1-2}$ alkylsulfinyl, $C_{1-2}$ alkoxy, halo, alkoxy, and $C_{1-2}$ alkylthio.

27. The method of claim 17 wherein $R^1$ is selected from the group consisting of pyridyl, cyclohexyl, and phenyl, wherein pyridyl, cyclohexyl, or phenyl is optionally substituted with one or more radicals selected from the group consisting of alkyl, halo, and alkoxy.

28. The method of claim 27 wherein $R^1$ is pyridyl.

29. The method of claim 28 wherein pyridyl is substituted with one or more radicals selected from the group consisting of alkyl, halo, and alkoxy.

30. The method of claim 29 wherein the pyridyl is substituted with alkyl.

31. The method of claim 30 wherein alkyl is $C_{1-2}$ alkyl.

32. The method of claim 31 wherein alkyl is methyl.

33. The method of claim 29 wherein the pyridyl is substituted with halo.

34. The method of claim 33 wherein the halo is chloro.

35. The method of claim 27 wherein $R^1$ is cyclohexyl.

36. The method of claim 35 wherein the cyclohexyl is substituted with one or more radicals selected from the group consisting of alkyl, halo, and alkoxy.

37. The method of claim 35 wherein the cyclohexyl is substituted with alkyl.

38. The method of claim 37 wherein the alkyl is $C_{1-2}$ alkyl.

39. The method of claim 37 wherein the alkyl is methyl.

40. The method of claim 35 wherein the pyridyl is substituted with halo.

41. The method of claim 40 wherein the halo is chloro.

42. The method of claim 27 wherein $R^1$ is phenyl optionally substituted with one or more radicals selected from the group consisting of alkyl, halo, and alkoxy.

43. The method of claim 42 wherein the phenyl is substituted with one or more radicals selected from the group consisting of alkyl, halo, and alkoxy.

44. The method of claim 43 wherein the phenyl is substituted with alkyl.

45. The method of claim 44 wherein the alkyl is $C_{1-2}$ alkyl.

46. The method of claim 45 wherein the alkyl is methyl.

47. The method of claim 17 wherein $R^2$ is alkyl or amino.

48. The method of claim 47 wherein the alkyl is $C_{1-2}$ alkyl.

49. The method of claim 48 wherein the alkyl is methyl.

50. The method of claim 17 wherein $R^3$ is a radical selected from the group consisting of halo, $C_{1-2}$ alkyl, $C_{2-3}$ alkenyl, $C_{2-3}$ alkynyl, aryl, heteroaryl, oxo, cyano, carboxyl, cyano-$C_{1-3}$-alkyl, heterocyclyloxy, $C_{1-3}$ alkyloxy, alkylthio, alkylcarbonyl, cycloalkyl, phenyl, $C_{1-3}$ haloalkyl, heterocyclo, cycloalkenyl, phenyl-$C_{1-3}$-alkyl, heterocyclyl-$C_{1-3}$-alkyl, $C_{1-3}$ alkylthio-$C_{1-3}$-alkyl, $C_{1-3}$ hydroxyalkyl, $C_{1-3}$ alkoxycarbonyl, phenylcarbonyl, phenyl-$C_{1-3}$-alkylcarbonyl, phenyl-$C_{2-3}$-alkenyl, $C_{1-3}$ alkoxy-$C_{1-3}$-alkyl, phenylthio-$C_{1-3}$-alkyl, phenylyloxyalkyl, alkoxyphenylalkoxyalkyl, alkoxycarbonylalkyl, aminocarbonyl, aminocarbonyl-$C_{1-3}$-alkyl, $C_{1-3}$ alkylaminocarbonyl, N-phenylaminocarbonyl, N—$C_{1-3}$ alkyl-N-phenylaminocarbonyl, $C_{1-3}$ alkylaminocarbonyl-$C_{1-3}$-alkyl, carboxy-$C_{1-3}$-alkyl, $C_{1-3}$ alkylamino, N-arylamino, N-arylkylamino, N—$C_{1-3}$ alkyl-N-arylkylamino, N—$C_{1-3}$ alkyl-N-arylamino, amino-$C_{1-3}$-alkyl, $C_{1-3}$ alkylaminoalkyl, N-phenylamino-$C_{1-3}$-alkyl, N-phenyl-$C_{1-3}$-alkylaminoalkyl, N—$C_{1-3}$ alkyl-N-phenyl-$C_{1-3}$-alkylamino-$C_{1-3}$-alkyl, N—$C_{1-3}$ alkyl-N-phenylamino-$C_{1-3}$-alkyl, phenyloxy, phenylalkoxy, phenylthio, phenyl-$C_{1-3}$-alkylthio, $C_{1-3}$ alkylsulfinyl, $C_{1-3}$ alkylsulfonyl, aminosulfonyl, $C_{1-3}$ alkylaminosulfonyl, N-phenylaminosulfonyl, phenylsulfonyl, and N—$C_{1-3}$ alkyl-N-phenylaminosulfonyl.

51. The method of claim 50 wherein $R^3$ is a radical selected from the group consisting of halo, $C_{1-2}$ alkyl, cyano, carboxyl, $C_{1-2}$ alkyloxy, phenyl, $C_{1-2}$ haloalkyl, and $C_{1-2}$ hydroxyalkyl.

52. The method of claim 17 wherein $R^4$ is hydrido.

53. The method of claim 17 wherein $R^4$ is halo.

54. The method of claim 53 wherein the halo is fluoro.

55. The method of claim 17 wherein the selective cyclooxygenase-2 inhibiting agent is 4-(4-cyclohexyl-2-methyloxazol-5-yl)-2-fluorobenzenesulfonamide.

56. The method of claim 17 wherein the selective cyclooxygenase-2 inhibiting agent is 4-(4-(methylsulfonyl)phenyl]-3-phenyl-2(5H)-furanone.

57. The method of claim 17 wherein the selective cyclooxygenase-2 inhibiting agent is 2-(6-methylpyrid-3-yl)-3-(4-methylsulfinylphenyl)-5-chloropyridine.

58. The method of claim 17 wherein the selective cyclooxygenase-2 inhibiting agent is 4-[5-(4-methylphenyl)-3-(trifluoromethyl)-1H-pyrazol-1-yl]-benzenesulfonamide.

59. The method of claim 17 wherein the selective cyclooxygenase-2 inhibiting agent is 4-(4-(methylsulfonyl)phenyl]-3-phenyl-2(5H)-furanone.

60. The method of claim 17 wherein the selective cyclooxygenase-2 inhibiting agent is 4-[5-(4-chorophenyl)-3-(trifluoromethyl)-1H-pyrazole-1-yl]benzenesulfonamide.

61. The method of claim 17 wherein the selective cyclooxygenase-2 inhibiting agent is 4-(4-cyclohexyl-2-methyloxazol-5-yl)-2-fluorobenzenesulfonamide.

62. The method of claim 17 wherein the selective cyclooxygenase-2 inhibiting agent is 5-chloro-3-(4-(methylsulfonyl)phenyl)-2-(methyl-5-pyridinyl)pyridine.

63. The method of claim 17 wherein the selective cyclooxygenase-2 inhibiting agent is 2-(3,5-difluorophenyl)-3-4-(methylsulfonyl)phenyl)-2-cyclopenten-1-one.

64. The method of claim 17 wherein the selective cyclooxygenase-2 inhibiting agent is 4-(4-(methylsulfonyl)phenyl]-3-phenyl-2(5H)-furanone.

65. The method of claim 17 wherein the selective cyclooxygenase-2 inhibiting agent is 4-[5-methyl-3-phenyl-isoxazol-4-yl]benzenesulfonamide.

66. The method of claim 17 wherein the selective cyclooxygenase-2 inhibiting agent is N-[[4-(5-methyl-3-phenylisoxazol-4-yl]phenyl]sulfonyl]propanamide.

67. The method of claim 1 wherein the agents are administered in a sequential manner.

68. The method of claim 1 wherein the agents are administered in a substantially simultaneous manner.

* * * * *